(12) United States Patent
Zhang et al.

(10) Patent No.: US 10,047,084 B2
(45) Date of Patent: Aug. 14, 2018

(54) IMIDAZOLONE DERIVATIVES, PHARMACEUTICAL COMPOSITIONS AND USES THEREOF

(71) Applicant: BEIJING FORELANDPHARMA CO. LTD., Beijing (CN)

(72) Inventors: Xingmin Zhang, Beijing (CN); Qi Ji, Beijing (CN); Lei Wang, Beijing (CN); Congmin Gao, Beijing (CN); Ensi Wang, Beijing (CN); Zhenjian Du, Beijing (CN); Longlong Gong, Beijing (CN); Bo Chen, Beijing (CN)

(73) Assignee: BEIJING FORELANDPHARMA CO. LTD., Beijing (CN)

( * ) Notice: Subject to any disclaimer, the term of this patent is extended or adjusted under 35 U.S.C. 154(b) by 0 days.

(21) Appl. No.: 15/037,466

(22) PCT Filed: Nov. 14, 2014

(86) PCT No.: PCT/CN2014/091138
§ 371 (c)(1),
(2) Date: May 18, 2016

(87) PCT Pub. No.: WO2015/074516
PCT Pub. Date: May 28, 2015

(65) Prior Publication Data
US 2016/0304510 A1    Oct. 20, 2016

(30) Foreign Application Priority Data
Nov. 20, 2013  (CN) .......................... 2013 1 0589080

(51) Int. Cl.
| | |
|---|---|
| *C07D 471/04* | (2006.01) |
| *C07D 471/14* | (2006.01) |
| *A61K 31/4375* | (2006.01) |
| *C07D 519/00* | (2006.01) |

(52) U.S. Cl.
CPC ........ *C07D 471/04* (2013.01); *A61K 31/4375* (2013.01); *C07D 471/14* (2013.01); *C07D 519/00* (2013.01)

(58) Field of Classification Search
CPC .. C07D 471/04; C07D 471/14; C07D 519/00; A61K 31/4375
See application file for complete search history.

(56) References Cited

U.S. PATENT DOCUMENTS

| | | | |
|---|---|---|---|
| 2010/0105696 A1 | 4/2010 | Garcia-Echeverria et al. | |
| 2011/0230476 A1 | 9/2011 | Niu et al. | |

FOREIGN PATENT DOCUMENTS

| | | | | |
|---|---|---|---|---|
| CA | 2 931 147 | | 5/2015 | |
| CN | 101616672 A | | 12/2009 | |
| CN | 102372711 | * | 3/2012 | |
| CN | 102372711 A | | 3/2012 | |
| CN | 102399218 A | | 4/2012 | |
| CN | 103833752 A | | 6/2014 | |
| EP | 3 072 893 | | 9/2016 | |
| JP | 2010-519309 A | | 6/2010 | |
| JP | 2012-504119 A | | 2/2012 | |
| JP | 2012-528828 A | | 11/2012 | |
| WO | WO 2010/038165 A1 | | 4/2010 | |
| WO | WO2010139731 | * | 12/2010 | ........... C07D 471/04 |
| WO | WO 2012/077031 A1 | | 6/2012 | |
| WO | WO 2014/079364 A1 | | 5/2014 | |
| WO | WO 2015/074516 A1 | | 5/2015 | |

OTHER PUBLICATIONS

Ma et al. (Bioorg. Med. Chem. 23 (2015) 7585-7596).*
Kubinyi (3D QSAR in Drug Design: Ligand-Protein Interactions and Molecular Similarity, vol. 2-3, Springer, 1998, 800 pages). p. 243-44 provided.*
Wermuth, The Practice of Medicinal Chemsitry, 2d ed. (2003), 768 pages. Chs. 9-10 provided.*
Machine translation of CN102372711 (Mar. 2012).*
International Search Report dated Feb. 17, 2015 issued in PCT/CN2014/091138.
Canadian Office Action dated May 25, 2017 issued in CA 2,931,147.
Supplementary European Search Report dated May 18, 2017 issued in EP 14863847.1.
Australian Office Action dated May 10, 2017 issued in corresponding Australian Patent Application No. 2014352463.

* cited by examiner

*Primary Examiner* — Robert Havlin
(74) *Attorney, Agent, or Firm* — Scully Scott Murphy & Presser

(57) ABSTRACT

This application relates to imidazolone compounds, pharmaceutically acceptable salts, solvents, polymorphs or prodrugs thereof, and further relates to pharmaceutical combinations comprising the foregoing substances and uses for preventing and treating protein kinase related diseases such as cancer, metabolic diseases, and cardiovascular diseases.

8 Claims, No Drawings

IMIDAZOLONE DERIVATIVES, PHARMACEUTICAL COMPOSITIONS AND USES THEREOF

TECHNICAL FIELD

The present invention pertains to the pharmaceutical field, and relates to a series of imidazolone compounds, pharmaceutically acceptable salts, stereoisomers, isotopic labels, solvates, polymorphs or prodrugs thereof, pharmaceutical compositions comprising said compounds, and use of the compounds for treating diseases associated with the activities of protein kinases, for example, cancers, metabolic diseases, cardiovascular diseases, and so on.

BACKGROUND ART

Mammalian target of Rapamycin (mTOR) is an atypical serine/threonine protein kinase, is a member of the phosphoinositide 3-kinase (PI3K) related kinase family, and is a main signaling molecule of cell functions such as intracellular synthesis and catabolism. The mTOR signaling pathway has a close relationship with nutrition, energy states and growth factors, and modulates many cellular processes including autophagy, protein, lipids and lysosomes synthesis, and energy metabolism, cytoskeleton organization, cell survival, and so on. Under the changing periphery nutritional conditions in mammalian cells, mTOR regulates the conversion between synthesis and degradation metabolism to enable the cells to grow and survive under different nutritional conditions. Because of the important role of mTOR in cells, aberrant or deregulated mTOR signaling can lead to human diseases (such as cancer and other diseases). Therefore, mTOR signaling pathway is becoming an important target for the design of anticancer drugs.

The activation of the PI3K/Akt/mTOR signaling pathway is closely related to a variety of tumorigenesis. mTOR can accelerate cell cycles, reduce apoptosis and promote tumor cell migration in brain glioma, breast cancer, and ovarian cancer. Activation of mTOR begins at several ligand-activated growth factor receptors on the cell surface, such as epidermal growth factor receptor and insulin-like growth factor 1 and -2 (IGF-1 and IGF-2). The activation of the receptors leads to the activation of the PI3K kinase, thereby resulting in the activation of the downstream effector Akt protein. Akt is a regulatory factor that can regulate cell survival in multiple levels. After phosphorylation, Akt inhibits the downstream TSC1/2 complex, and thus mTOR is activated by Rheb. In the downstream of the PI3K/Akt and PEN/Akt and Ras/Erk1/2 signaling pathways, the TSC1/2 complex plays a vital role in the regulation of mTOR activation.

It has been found two different mTOR protein complexes, mTORC1 and mTORC2, in a cell. Both of the protein complexes contain a unique protein interacting with mTOR, and are regulated by different mechanisms, respectively. Great progress has been made in the research and development of mTOR inhibitor drugs. Rapamycin is the first discovered mTOR inhibitor and has been shown a good tumor-inhibiting effect in a variety of cancer models. Although rapamycin analogues with better pharmacological properties have been developed, however, the rapamycin analogues available in clinically are only confined to a few cancers. The important discovery that Akt is an important kinase in the survival of cancer cells and mTORC2 can directly phosphorylate Akt provides a new way of thinking in the research of anti-cancer with mTORC2, but also contributes to the research and development of the second-generation anti-cancer drugs which act on both mTORC1 and mTORC2 targets simultaneously. Simultaneous inhibition of the activities of both mTOR complexes (mTORC1 and mTORC2) in cancer cells provides a wider and more effective anti-cancer effect.

mTORC1 has six subunits, and mTORC2 is composed of seven subunits. Among them, mTOR, mLST8, DEPTOR and Tti1/Tel2 catalytic subunits are present in mTORC1 complex and mTORC2 complex. The two complexes have different regulatory proteins, Raptor and PRAS40 present in the mTORC1, rictor, mSin and protor1/2 present in the mTORC2. Upstream signals of mTORC1 are mainly from the intracellular and extracellular pathways, including growth factors, cell stress, energy status, oxygen and amino acids. These signals control many of the major processes in the cell including autophagy and synthesis of proteins, mRNA, and lipid. Heterodimer (TSC1/TSC2) is a key upstream regulatory factor of mTORC1, with a function of being an activating protein of the Rheb GTPase. Rheb coupled to GTP directly interacts with mTORC1 and activates its enzymatic activity. As a GTPase activating protein of Rheb, TSC1/2 converts Rheb to a status without activity and coupled to GDP by a negative regulation. mTORC1, after phosphorylation, activates its downstream factors 4E-BP1 and S6K1 to promote protein expression and to increase the generation of mRNA. Furthermore, mTORC1 controls cellular metabolism and ATP generation in combination with the SREBP1/2 transcription factor and HIF1-alpha. In addition to the role in anabolism, mTORC1 can also modulate autophagy by negative regulations in order to promote cell growth. In mammals, mTORC1 directly phosphorylates the ULK1/Atg13/FIP20 kinase complex and inhibits the initiation of autophagy. mTORC1 can also affect the autophagy by other mechanisms, such as modulating the inhibiting factor of autophagy, DAP1, and promoting the formation of the lysates.

Compared with mTORC1, people have a less knowledge of the mTORC2 signaling pathway. mTORC2 signaling is not sensitive to nutrient conditions but has a response to some growth factors. mTORC2 regulates several members in the AGC kinase subfamily, such as Akt, SGK1 and PKC-α. Akt activates the downstream signaling proteins to regulate cell metabolism, survival, apoptosis, growth and proliferation. mTORC2 directly phosphorylates the Akt (Ser473) site to activate its function. But in the absence of mTORC2, the phosphorylations of TSC2 and GSK3-β are not affected. mTORC2 can also directly activate the SGK1 kinase to regulate ion transfer and cell growth. However, compared with Akt, the function of SGK1 is completely inhibited in the absence of mTORC2. mTORC2 activated PKC-α can affect the formation of the actin cytoskeleton.

Many studies have shown that mTOR signaling pathway is related to the development of cancers. Many components between the downstream of PI3K and the upstream of mTOR mutate in cancers, including Tsc1/2, Lkb1, Pten and Nf1. The activation of oncogenes of mTOR can induce the growth, survival and proliferation processes of several cancer cells. More and more researches show that uncontrolled protein expression is related to mTORC1. Because 4E-BP1/eIF4m at downstream of TORC1 plays a key role in tumor formation. 4E-BP1/eIF4 transfers the oncogenic signals from the mRNA expression by Akt. These signals lead to the expression of several special oncogenic proteins, and finally the oncogenic proteins regulate the cell survival, cell cycle, neovascularization, energy metabolism and tumor metastasis. In addition, ribosome biogenesis associated with the mTOR activation may be related to the high levels of cell growth.

The increase of the lipid synthesis is an important sign of tumor cell proliferation. This is because that the new cells need to generate fatty acids to synthesize the cell membranes. PI3K signaling pathway activates the lipotropic synthesis factor (SREBP1), while mTORC1 is a signaling factor for the activation of SREBP1 by PI3K. Meanwhile SREBP1 also drives the expression of some pentose phosphate oxidative constituent factors. The pentose phosphate oxidative pathway controls the lipid synthesis and nucleic acid synthesis.

Autophagy can be very strongly suppressed by the continuous activation of PI3K/mTORC1 signaling. To tumor cells, the disadvantage of suppressing autophagy is the reduced survival ability of tumor cells under conditions of lack of nutrition and energy, thereby affecting the formation of tumor.

mTORC2 has been confirmed to have the potential to control the formation of the vascular system and immune chemokines. This indicates that the inhibition of mTORC2 can impair the formation and sustainable growth of tumors by preventing angiogenesis or reducing invasion of immune cells. In some tumors, the high expression of mTORC2 is associated with the high expression of its subunits rictor. The deletion of PTEN, a tumor suppressor gene, leads to an enhanced function of TORC2 in mice. These results support that mTORC2 plays an important role in tumorigenesis, and meanwhile show that reducing of mTORC2 vitality may potentially have an important significance in the anticancer therapy.

SUMMARY OF THE INVENTION

The invention provides a series of imidazolone derivatives for use in the preparation of a medicament for treating diseases associated with the activities of protein kinases.

According to one aspect of the invention, the invention provides a compound represented by formula I:

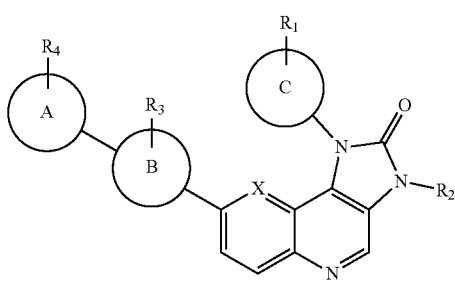

I wherein,

Rings A and B are independently selected from the group consisting of aryl and heteroaryl, wherein the heteroaryl contains at least one heteroatom selected from the group consisting of N, O and S;

Ring C is a saturated carbocycle attaching with one heteroatom or a saturated heterocycle containing at least one heteroatom, wherein the heteroatom is selected from the group consisting of N, O and S;

$R_1$ is at least one group attached to Ring C (Ring C is a saturated heterocycle), which is selected from H; $C_{1-6}$ alkyl, $C_{1-6}$ alkoxyl, $C_{2-6}$ alkenyl or $C_{2-6}$ alkynyl, optionally substituted by at least one group selected from the group consisting of halogen, cyano, amino, hydroxy, carboxyl, trifluoromethyl, and monocyclic or bicyclic aryl; or selected from $R_6CO$, $R_6SO_2$ or $R_6SO$, wherein $R_6$ is selected from $NH_2$, $NHR_7$; $C_{1-6}$ alkyl, $C_{1-6}$ alkoxyl, $C_{2-6}$ alkenyl or $C_{2-6}$ alkynyl, optionally substituted by at least one of hydroxy, mercapto, amino, trifluoromethyl and halogen; monocyclic or bicyclic cycloalkyl (e.g., $C_{1-6}$ cycloalkyl); saturated or unsaturated monocyclic heterocyclyl or bicyclic heterocyclyl containing at least one heteroatom selected from the group consisting of N, O and S; monocyclic or bicyclic aryl; or monocyclic or bicyclic heteroaryl containing at least one heteroatom selected from the group consisting of N, O and S atoms (e.g., monocyclic heteroaryl containing from one to three nitrogen atoms); said aryl or heteroaryl are optionally substituted by halogen or $C_{1-6}$ alkyl; and $R_7$ is selected from $C_{1-6}$ alkyl, $C_{2-6}$ alkenyl or $C_{2-6}$ alkynyl, monocyclic or bicyclic aryl or heteroaryl;

Ring C is "a saturated carbocycle attaching with a heteroatom", which means that the saturated carbocycle is substituted by a substitutent containing one heteroatom. The substitutent containing one heteroatom is selected from hydroxy, mercapto, amino, $C_{1-6}$ alkyl, $C_{2-6}$ alkenyl or $C_{2-6}$ alkynyl attaching with one N, O or S atom (such as alkoxyl, monoalkylamino, dialkylamino, alkylthiol), aryl (monocyclic or bicyclic aryl), carbocycle ($C_{3-6}$ cycloalkyl), heteroaryl (monocyclic or bicyclic heteroaryl), heterocyclyl (monocyclic or bicyclic heterocyclyl); and the saturated carbocycle is also optionally substituted by other groups selected from the group consisting of $C_{1-6}$ alkyl, $C_{1-6}$ alkoxyl, $C_{2-6}$ alkenyl and $C_{2-6}$ alkynyl which are optionally substituted by at least one group selected from the group consisting of halogen, cyano, amino, hydroxy, carboxyl, trifluoromethyl, and monocyclic or bicyclic aryl;

$R_2$ is selected from the group consisting of H, $C_{1-6}$ alkyl, $C_{1-6}$ alkoxyl, $C_{2-6}$ alkenyl and $C_{2-6}$ alkynyl;

$R_3$ is at least one group attached to Ring B, each independently selected from at least one of H, $C_{1-6}$ alkyl, halogen and $C_{1-6}$ alkoxyl;

$R_4$ is at least one group attached to Ring A, each independently selected from H; halogen; hydroxy; amino; cyano; $C_{1-6}$ alkyl, $C_{1-6}$ alkoxyl, $C_{2-6}$ alkenyl or $C_{2-6}$ alkynyl, optionally substituted by halogen; and monocyclic or bicyclic aryl or heteroaryl optionally substituted by halogen;

X is selected from the group consisting of CH and N, or pharmaceutically acceptable salts, stereoisomers, isotopical labels, solvates, polymorphs or prodrugs thereof.

In some embodiments, in the Formula I, Rings A and B are independently selected from monocyclic or bicyclic aryl or heteroaryl; and Ring C is selected from a saturated monocyclic or biscyclic heterocycle containing from 4 to 8 ring atoms (the heteroatom on the heterocycle is, for example, one N atom), or a saturated monocyclic carbocycle containing from 4 to 7 ring atoms and attaching with one heteroatom (for example, the heteroatom is O or N).

In some embodiments, in the Formula I, Rings A and B are independently monocyclic heteroaryl wherein the heteroatom is a nitrogen atom, and Ring C is selected from the group consisting of a saturated monocyclic carbocycle containing from 4 to 7 ring atoms and attaching with one heteroatom which is O or N and a saturated monocyclic heterocycle containing from 4 to 7 ring atoms wherein the heteroatom is a nitrogen atom.

In some embodiments, in the Formula I, wherein Ring C is selected from the group consisting of a saturated carbocycle and a saturated monocyclic heterocycle containing from 5 to 6 ring atoms wherein the heteroatom is a nitrogen atom.

In some embodiments, in the Formula I, Rings A and B are independently selected from the group consisting of pyridyl, pyrimidinyl, pyrazinyl, pyridazinyl, triazinyl, imidazole, pyrrole, pyrazole, triazole, tetrazole and phenyl; and Ring C is selected from the group consisting of azetidinyl, 3-piperidyl, 4-piperidyl, 2-piperidyl, 2-pyrrolinyl, 3-pyrrolinyl, indolinyl and pyrazolinyl. For example, Ring A is one of the following structures:

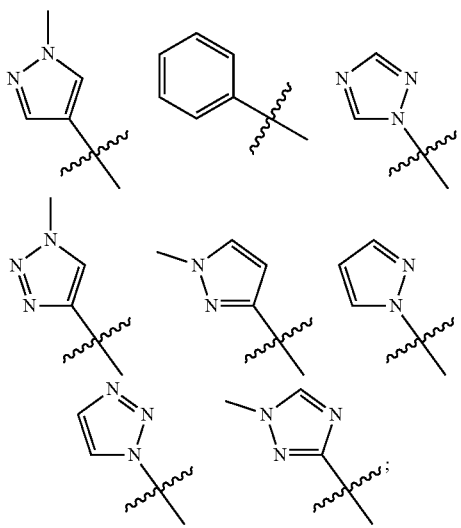

and Ring B is pyridyl.

In some embodiments, in the Formula I, in the $R_1$ group, the heteroaryl is selected from the group consisting of monocyclic heteroaryl containing at least one N atom; $C_{5-10}$ monocyclic or bicyclic aryl optionally substituted by halogen or $C_{1-6}$ alkyl; a 4- to 7-membered saturated monocyclic carbocycle; amino optionally substituted by at least one $C_{1-6}$ alkyl; and $C_{1-6}$ alkyl optionally substituted by at least one halogen, hydroxyl or amino.

In some embodiments, in the Formula I, when Ring C is heterocyclyl wherein the heteroatom is N, $R_1$ is attached to one N atom; or when Ring C is a saturated carbocycle attaching with one heteroatom which is N, $R_1$ is attached to one N atom.

In some embodiments, in the Formula I, the compound is the following compound:
1-(1-(2-hydroxyacetyl)piperidin-3-yl)-3-methyl-8-(6-(1-methyl-1H-pyrazol-4-yl)pyridin-3-yl)-1H-imidazo[4,5-c]quinolin-2(3H)-one;
1-(1-(1H-1,2,4-triazole-3-carbonyl)piperidin-3-yl)-3-methyl-8-(6-(1-methyl-1H-pyrazol-4-yl)pyridin-3-yl)-1H-imidazo[4,5-c]quinolin-2(3H)-one;
3-methyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one;
1-(1-((S)-2-hydroxypropionyl)piperidin-3-yl)-3-methyl-8-(6-(1-methyl-1H-pyrazol-4-yl)pyridin-3-yl)-1H-imidazo[4,5-c]quinolin-2(3H)-one;
1-(1-((R)-2-hydroxypropionyl)piperidin-3-yl)-3-methyl-8-(6-(1-methyl-1H-pyrazol-4-yl)pyridin-3-yl)-1H-imidazo[4,5-c]quinolin-2(3H)-one;
3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one;
1-(1-(2-hydroxyacetyl)pyrrolidin-3-yl)-3-methyl-8-(6-(1-methyl-1H-pyrazol-4-yl)pyridin-3-yl)-1H-imidazo[4,5-c]quinolin-2(3H)-one;
1-(1-(1H-1,2,4-triazole-3-carbonyl)pyrrolidin-3-yl)-3-methyl-8-(6-(1-methyl-1H-pyrazol-4-yl)pyridin-3-yl)-1H-imidazo[4,5-c]quinolin-2(3H)-one;
3-methyl-8-(6-(1-methyl-1H-pyrazol-4-yl)pyridin-3-yl)-1-(1-methylpyrrolidin-3-yl)-1H-imidazo[4,5-c]quinolin-2(3H)-one;
1-(1-ethylpyrrolidin-3-yl)-3-methyl-8-(6-(1-methyl-1H-pyrazol-4-yl)pyridin-3-yl)-1H-imidazo[4,5-c]quinolin-2(3H)-one;
1-(1-acetylpyrrolidin-3-yl)-3-methyl-8-(6-(1-methyl-1H-pyrazol-4-yl)pyridin-3-yl)-1H-imidazo[4,5-c]quinolin-2(3H)-one;
1-(1-benzylpyrrolidin-3-yl)-3-methyl-8-(6-(1-methyl-H-pyrazol-4-yl)pyridin-3-yl)-1H-imidazo[4,5-c]quinolin-2(3H)-one;
1-(1-((4-chlorphenyl)sulfonyl)pyrrolidin-3-yl)-3-methyl-8-(6-(1-methyl-1H-pyrazol-4-yl)pyridin-3-yl)-1H-imidazo[4,5-c]quinolin-2(3H)-one;
3-methyl-8-(6-(1-methyl-1H-pyrazol-4-yl)pyridin-3-yl)-1-(1-p-toluenesulfonylpyrrolidin-3-yl)-1H-imidazo[4,5-c]quinolin-2(3H)-one;
3-(3-methyl-8-(6-(1-methyl-1H-pyrazol-4-yl)pyridin-3-yl)-2-oxo-2,3-dihydro-1H-imidazo[4,5-c]quinolin-1-yl)pyrrolidine-1-sulfamide;
3-methyl-8-(6-(1-methyl-1H-pyrazol-4-yl)pyridin-3-yl)-1-(1-(2,2,2-trifluoroacetyl)pyrrolidin-3-yl)-1H-imidazo[4,5-c]quinolin-2(3H)-one;
1-((1r,4r)-4-hydroxycyclohexyl)-3-methyl-8-(6-(1-methyl-1H-pyrazol-4-yl)pyridin-3-yl)-1H-imidazo[4,5-c]quinolin-2(3H)-one;
1-((1s,4s)-4-hydroxycyclohexyl)-3-methyl-8-(6-(1-methyl-1H-pyrazol-4-yl)pyridin-3-yl)-1H-imidazo[4,5-c]quinolin-2(3H)-one;
1-((1s,4s)-4-hydroxycyclohexyl)-3-methyl-8-(6-phenylpyridin-3-yl)-1H-imidazo[4,5-c]quinolin-2(3H)-one;
1-((1s,4s)-4-hydroxycyclohexyl)-8-(6-methoxyl-5-methylpyridin-3-yl)-3-methyl-1H-imidazo[4,5-c]quinolin-2(3H)-one;
1-((1s,4s)-4-hydroxycyclohexyl)-3-methyl-8-(1-phenyl-1H-pyrazol-4-yl)-1H-imidazo[4,5-c]quinolin-2(3H)-one;
1-((1s,4s)-4-hydroxycyclohexyl)-3-methyl-8-(6-methylpyridin-3-yl)-1H-imidazo[4,5-c]quinolin-2(3H)-one;
1-((1r,4r)-4-hydroxycyclohexyl)-3-methyl-8-(1-phenyl-1H-pyrazol-4-yl)-1H-imidazo[4,5-c]quinolin-2(3H)-one;
1-((1r,4r)-4-hydroxycyclohexyl)-8-(6-methoxyl-5-methylpyridin-3-yl)-3-methyl-1H-imidazo[4,5-c]quinolin-2(3H)-one;
1-((1r,4r)-4-hydroxycyclohexyl)-3-methyl-8-(6-phenylpyridin-3-yl)-1H-imidazo[4,5-c]quinolin-2(3H)-one;
8-(6-aminopyridin-3-yl)1-((1s,4s)-4-hydroxycyclohexyl)-3-methyl-1H-imidazo[4,5-c]quinolin-2(3H)-one;
(R)-3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one;
(S)-3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one;
(S)-1-(1-(ethylsulfonyl)pyrrolidin-3-yl)-3-methyl-8-(6-(1-methyl-1H-pyrazol-4-yl)pyridin-3-yl)-1H-imidazo[4,5-c]quinolin-2(3H)-one;

(S)-3-methyl-1-(1-(methanesulfonyl)pyrrolidin-3-yl)-8-(6-phenylpyridin-3-yl)-1H-imidazo[4,5-c]quinolin-2(3H)-one;

(R)-3-methyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one;

1-(3-hydroxycyclohexyl)-3-methyl-8-(6-(1-methyl-1H-pyrazol-4-yl)pyridin-3-yl)-1H-imidazo[4,5-c]quinolin-2(3H)-one;

N-((1s,4s)-4-(3-methyl-8-(6-(1-methyl-1H-pyrazol-4-yl)pyridin-3-yl)-2-oxo-2,3-dihydro-1H-imidazo[4,5-c]quinolin-1-yl)cyclohexyl)acetamide;

N-((1s,4s)-4-(3-methyl-8-(6-(1-methyl-1H-pyrazol-4-yl)pyridin-3-yl)-2-oxo-2,3-dihydro-1H-imidazo[4,5-c]quinolin-1-yl)cyclohexyl)methanesulfonamide;

(1s,4s)-4-(3-methyl-8-(6-(1-methyl-1H-pyrazol-4-yl)pyridin-3-yl)-2-oxo-2,3-dihydro-1H-imidazo[4,5-c]quinolin-1-yl)cyclohexanecarboxylic acid;

3-deuteromethyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one;

3-methyl-8-(6-(1-methyl-1H-pyrazol-4-yl)pyridin-3-yl)-1-(1-(methanesulfonyl)piperidin-3-yl)-1H-imidazo[4,5-c][1,5]naphthyridin-2(3H)-one;

(S)-3-methyl-8-(6-(1-methyl-1H-pyrazol-4-yl)pyridin-3-yl)-1-(1-(methanesulfonyl)pyrrolidin-3-yl)-1H-imidazo[4,5-c][1,5]naphthyridin-2(3H)-one;

(S)-3-methyl-1-(1-(methanesulfonyl)pyrrolidin-3-yl)-8-(6-phenylpyridin-3-yl)-1H-imidazo[4,5-c][1,5]naphthyridin-2(3H)-one;

2-methyl-2-(4-(3-methyl-8-(6-(1-methyl-1H-pyrazol-4-yl)pyridin-3-yl)-2-oxo-2,3-dihydro-1H-imidazo[4,5-c]quinolin-1-yl)phenyl)propionamide;

2-methyl-2-(4-(3-methyl-8-(6-(1-methyl-1H-pyrazol-4-yl)pyridin-3-yl)-2-oxo-2,3-dihydro-1H-imidazo[4,5-c]quinolin-1-yl)phenyl)propionic acid;

1-(3-hydroxycyclopentyl)-3-methyl-8-(6-(1-methyl-1H-pyrazol-4-yl)pyridin-3-yl)-1H-imidazo[4,5-c]quinolin-2(3H)-one;

(S)-8-(6-(1H-1,2,4-triazol-1-yl)pyridin-3-yl)-3-methyl-1-(1-(methanesulfonyl)pyrrolidin-3-yl)-1H-imidazo[4,5-c]quinolin-2(3H)-one;

(S)-8-(6-(1H-pyrazol-1-yl)pyridin-3-yl)-3-methyl-1-(1-(methanesulfonyl)pyrrolidin-3-yl)-1H-imidazo[4,5-c]quinolin-2(3H)-one;

(S)-3-methyl-8-(6-(1-methyl-1H-1,2,3-triazol-4-yl)pyridin-3-yl)-1-(1-(methanesulfonyl)pyrrolidin-3-yl)-1H-imidazo[4,5-c]quinolin-2(3H)-one;

(S)-8-(6-(1H-1,2,3-triazol-1-yl)pyridin-3-yl)-3-methyl-1-(1-(methanesulfonyl)pyrrolidin-3-yl)-1H-imidazo[4,5-c]quinolin-2(3H)-one;

(S)-3-methyl-8-(6-(1-methyl-1H-pyrazol-3-yl)pyridin-3-yl)-1-(1-(methanesulfonyl)pyrrolidin-3-yl)-1H-imidazo[4,5-c]quinolin-2(3H)-one;

(S)-3-methyl-8-(6-(1-methyl-1H-1,2,4-triazol-3-yl)pyridin-3-yl)-1-(1-(methanesulfonyl)pyrrolidin-3-yl)-1H-imidazo[4,5-c]quinolin-2(3H)-one;

(R)-3-methyl-8-(6-(1-methyl-1H-pyrazol-4-yl)pyridin-3-yl)-1-(1-(methanesulfonyl)piperidin-3-yl)-1H-imidazo[4,5-c][1,5]naphthyridin-2(3H)-one;

(S)-3-methyl-8-(6-(1-methyl-1H-1,2,3-triazol-4-yl)pyridin-3-yl)-1-(1-(methanesulfonyl)pyrrolidin-3-yl)-1H-imidazo[4,5-c][1,5]naphthyridin-2(3H)-one;

1-((1s,4s)-4-hydroxycyclohexyl)-3-methyl-8-(6-(1-methyl-1H-1,2,3-triazol-4-yl)pyridin-3-yl)-1H-imidazo[4,5-c]quinolin-2(3H)-one;

(R)-1-(1-(ethylsulfonyl)piperidin-3-yl)-3-methyl-8-(6-(1-methyl-H-pyrazol-4-yl)pyridin-3-yl)-1H-imidazo[4,5-c]quinolin-2(3H)-one;

(R)-1-(1-(cyclopropylsulfonyl)piperidin-3-yl)-3-methyl-8-(6-(1-methyl-1H-pyrazol-4-yl)pyridin-3-yl)-1H-imidazo[4,5-c]quinolin-2(3H)-one;

(R)-3-(3-methyl-8-(6-(1-methyl-1H-pyrazol-4-yl)pyridin-3-yl)-2-oxo-2,3-dihydro-1H-imidazo[4,5-c]quinolin-1-yl)piperidine-1-sulfamide;

(R)—N-ethyl-3-(3-methyl-8-(6-(1-methyl-1H-pyrazol-4-yl)pyridin-3-yl)-2-oxo-2,3-dihydro-1H-imidazo[4,5-c]quinolin-1-yl)piperidine-1-formamide;

(R)-3-methyl-8-(6-(1-methyl-1H-pyrazol-4-yl)pyridin-3-yl)-1-(1-(((trifluoromethyl)sulfonyl)piperidin-3-yl)-1H-imidazo[4,5-c]quinolin-2(3H)-one;

1-(4-hydroxy-4-methylcyclohexyl)-3-methyl-8-(6-(1-methyl-1H-pyrazol-4-yl)pyridin-3-yl)-1H-imidazo[4,5-c]quinolin-2(3H)-one;

(R)-3-methyl-8-(6-(1-methyl-1H-1,2,3-triazol-4-yl)pyridin-3-yl)-1-(1-(methanesulfonyl)piperidin-3-yl)-1H-imidazo[4,5-c]quinolin-2(3H)-one;

3-methyl-8-(6-(1-methyl-1H-pyrazol-4-yl)pyridin-3-yl)-1-(1-(methanesulfonyl)piperidin-4-yl)-1H-imidazo[4,5-c]quinolin-2(3H)-one;

3-methyl-8-(6-(1-methyl-1H-1,2,3-triazol-4-yl)pyridin-3-yl)-1-(1-(methanesulfonyl)piperidin-4-yl)-1H-imidazo[4,5-c]quinolin-2(3H)-one;

3-methyl-8-(6-(1-methyl-1H-1,2,3-triazol-4-yl)pyridin-3-yl)-1-(8-(methanesulfonyl)-8-azabicyclo[3.2.1]octan-3-yl)-1H-imidazo[4,5-c]quinolin-2(3H)-one;

3-methyl-8-(6-(1-methyl-1H-pyrazol-4-yl)pyridin-3-yl)-1-(8-(methanesulfonyl)-8-azabicyclo[3.2.1]octan-3-yl)-1H-imidazo[4,5-c]quinolin-2(3H)-one;

N-(2-(3-methyl-8-(6-(1-methyl-1H-pyrazol-4-yl)pyridin-3-yl)-2-oxo-2,3-dihydro-1H-imidazo[4,5-c]quinolin-1-yl)ethyl)methanesulfonamide; and 3-methyl-8-(6-(1-methyl-1H-pyrazol-4-yl)pyridin-3-yl)-1-(1-(methanesulfonyl)azetidin-3-yl)-1H-imidazo[4,5-c]quinolin-2(3H)-one.

According to another aspect of the invention, the invention provides a pharmaceutical composition comprising the above compound of the invention, or pharmaceutically acceptable salts, stereoisomers, isotopical labels, solvates, polymorphs or prodrugs thereof, as well as pharmaceutically acceptable carriers. The pharmaceutical composition includes, but not limited to, oral, parenteral, topical and rectal dosage forms. In some embodiments, the pharmaceutical composition may be in the form of a tablet, capsule, pill, powder, sustained release preparation, solution or suspension for oral administration; a sterile solution, suspension or emulsion for parenteral injection; an ointment or a cream for topical administration; or a suppository for rectal administration. In further or additional embodiments, the pharmaceutical composition is in unit dosage forms suitable for single administration of precise dosages. In further or additional embodiments, the amount of the compound is in a range of about 0.001 to about 1000 mg/kg body weight/day. In further or additional embodiments, the amount of the compound is in a range of about 0.5 to about 50 mg/kg body weight/day. In some embodiments, the amount of the compound is about 0.001 to about 7 g/day. In further or additional embodiments, the amount of the compound is about 0.002 to about 6 g/day. In further or additional embodiments, the amount of the compound is about 0.005 to about 5 g/day. In further or additional embodiments, the amount of the compound is about 0.01 to about 5 g/day. In further or additional embodiments, the amount of the compound is about 0.02 to about 5 g/day. In further or additional embodiments, the amount of the compound is about 0.05 to about 2.5 g/day. In further or additional embodiments, the amount of the compound is about 0.1 to about 1 g/day. In further or additional embodiments, dosage levels below the lower limit of the aforesaid range may be more than adequate. In further or additional embodiments, dosage levels above the upper limit of the aforesaid range may be required. In further or additional embodiments, the compound is administered in a single dose, once daily. In further or additional embodiments, the compound is administered in multiple doses, more than once per day. In further or additional embodiments, the compound is administered twice daily. In further or additional embodiments, the compound is administered three times per day. In further or additional embodiments, the compound is administered four times per day. In further or additional embodiments, the compound is administered more than four times per day. In some embodiments, the individual to which the pharmaceutical composition is administrated is a mammal. In further or additional embodiments, the mammal is human. In further or additional embodiments, the pharmaceutical composition further comprises at least one therapeutic agent (i.e., into a single dosage form). In some embodiments, the pharmaceutical composition and the at least one therapeutic agent, respectively, in a separate dosage form, are combined into a combination product such as a kit of part.

According to a further aspect of the invention, the invention provides use of the aforesaid compound of the invention, or pharmaceutically acceptable salts, stereoisomers, isotopical labels, solvates, polymorphs or prodrugs thereof in the preparation of a medicament for inhibiting one or both of the mTOR and PI3K kinases.

According to a yet other aspect of the invention, the invention provides a compound as aforesaid, or pharmaceutically acceptable salts, stereoisomers, isotopical labels, solvates, polymorphs or prodrugs thereof, for use in the inhibition of one or both of the mTOR and PI3K kinases.

According to another aspect of the invention, the invention provides use of the compound of the invention, or pharmaceutically acceptable salts, stereoisomers, isotopical labels, solvates, polymorphs or prodrugs thereof in the preparation of a medicament for treating or preventing a disease associated with the activity of a protein kinase (e.g., by inhibiting one or both of the mTOR and PI3K kinases).

According to a further aspect of the invention, the invention provides a compound as aforesaid, or pharmaceutically acceptable salts, stereoisomers, isotopical labels, solvates, polymorphs or prodrugs thereof, for use in the treatment or prophylaxis of a disease associated with the activity of a protein kinase.

According to another aspect of the invention, the invention provides a method for modulating (e.g., down-regulating) the activity of a protein kinase, comprising bringing the protein kinases into contact with an effective amount of the aforesaid compound or pharmaceutically acceptable salts, stereoisomers, isotopical labels, solvates, polymorphs or prodrugs thereof. The method may be used in vivo, or may be also used in vitro. Preferably, the protein kinase is at least one selected from the group consisting of mTOR and PI3K.

According to another aspect of the invention, the invention provides a method for treating a disease associated with the activity of a protein kinase, comprising administrating an effective amount of the compound of the invention or pharmaceutically acceptable salts, stereoisomers, isotopical labels, solvates, polymorphs or prodrugs thereof to an individual in need thereof. The individual may be a mammal, such as a human.

According to some embodiments of the invention, the disease associated with the activity of a protein kinase of the invention (e.g., the disease treated or prevented by inhibiting one or both of the mTOR and PI3K kinases) may be a tumor, for example, leukemia, malignant lymphoma, multiple myeloma, gastrointestinal stromal tumor, colon cancer, rectal cancer, breast cancer, liver cancer, stomach cancer, ovarian cancer, uterine cancer, cervical cancer, vaginal cancer, choriocarcinoma, lung cancer, kidney cancer, prostate cancer, bladder cancer, pancreatic cancer, glioblastoma, mast cell tumor, cerebroma, germ cell tumor, melanoma, or sarcoma including dermatofibrosarcoma protuberans and osteosarcoma. The disease associated with the activity of a protein kinase of the invention may also be a metabolic disease (e.g., diabetes mellitus, obesity) and a cardiovascular disease (e.g., atherosclerosis).

DETAILED DESCRIPTION OF THE INVENTION

The section headings used herein are for organizational purposes only and are not to be construed as limiting the subject matter described. All documents, whole or portions, cited in the application are hereby expressly incorporated by reference in their entirety, including but not limited to patents, patent applications, articles, books, manuals, and treatises.

Chemical Terminology

Unless defined otherwise, all technical and scientific terms used herein have the same meaning as that commonly understood by one of skill in the art to which the claimed subject matter belongs. All patents, patent applications, published materials referred to throughout the entire disclosure herein, unless noted otherwise, are incorporated by reference in their entirety. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It should also be noted that use of "or" means "and/or" unless stated otherwise. Furthermore, use of the term "including" as well as other forms, such as "include", "includes", and "included" is not limiting. Likewise, use of the term "comprising" as well as other forms, such as "comprise", "comprises", and "comprised" is not limiting.

Definition of standard chemistry terms may be found in reference works, including Carey and Sundberg "ADVANCED ORGANIC CHEMISTRY $4^{th}$ ED." Vols. A (2000) and B (2001), Plenum Press, New York. Unless otherwise indicated, conventional methods such as MS, NMR, IR and UV/Vis spectroscopy and pharmacology methods, within the skill of the art are employed. Unless specific definitions are provided, the nomenclature employed in connection with the analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed by conventional methods well known in the art and as described in various general and more specific references that are cited and discussed throughout the present specification. Throughout the specification, groups and substituents thereof can be chosen by one skilled in the art to provide stable moieties and compounds.

Wherein substituent groups are specified by their conventional chemical formulas, written from left to right, they equally encompass the chemically identical substituents that would result from writing the structure from right to left. As a non-limiting example, $CH_2O$ is equivalent to $OCH_2$.

Unless otherwise noted, the use of general chemical terms, such as but not limited to "alkyl," "amine," "aryl," are equivalent to their optionally substituted forms. For example, "alkyl," as used herein, includes optionally substituted alkyl.

The term "optional" or "optionally" means that the subsequently described event or circumstance may or may not occur, and that the description includes instances wherein said event or circumstance occurs and instances in which it does not. For example, "optionally substituted alkyl" means either "unsubstituted alkyl" (alkyl that is unsubstituted) or "substituted alkyl" (alkyl that is substituted by a substituent) as defined below.

As used herein, $C_1$-$C_n$, includes $C_1$-$C_2$, $C_1$-$C_3$ ... $C_1$-$C_n$. By way of example, a group designated as "$C_1$-$C_4$" indicates that there are one to four carbon atoms in the moiety, i.e. the group containing 1 carbon atom, 2 carbon atoms, 3 carbon atoms or 4 carbon atoms. Thus, by way of example, "$C_1$-$C_4$ alkyl" indicates that there are one to four carbon atoms in the alkyl group, i.e., the alkyl group is selected from among methyl, ethyl, propyl, iso-propyl, n-butyl, isobutyl, sec-butyl, and tert-butyl. Whenever it appears herein, a numerical range such as "1 to 10" refers to each integer in the given range; e.g., "1 to 10 carbon atoms" means that the group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms, or 10 carbon atoms.

The term "alkyl" as used herein, alone or in combination, refers to an optionally substituted straight-chain or optionally substituted branched-chain saturated aliphatic hydrocarbon radical. The "alkyl" radical herein may have preferably from 1 to about 20 carbon atoms, for example, from 1 to about 10 carbon atoms, from 1 to about 8 carbon atoms, or from 1 to about 6 carbon atoms, or from 1 to about 4 carbon atoms, or from 1 to about 3 carbon atoms. Examples of the alkyl radical herein include but not limited to methyl, ethyl, n-propyl, isopropyl, 2-methyl-1-propyl, 2-methyl-2-propyl, 2 methyl 1 butyl, 3 methyl 1 butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2 ethyl 1 butyl, n-butyl, isobutyl, sec-butyl, tert-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl" or "$C_{1-6}$ alkyl", means that the alkyl group may consist of 1 carbon atom, 2 carbon atoms, 3 carbon atoms, 4 carbon atoms, 5 carbon atoms or 6 carbon atoms. The present definition also covers the occurrence of the term "alkyl" where no numerical range is designated.

The "alkyl" as used in combination herein refers to an alkyl linked with other groups, for example, the alkyl of alkoxyl, the alkyl of alkylthiol, the "alkyl" of hydroxyalkyl, haloalkyl, cyanoalkyl, monoalkylamino, and dialkylamino, etc.

The term "alkoxy" as used herein, alone or in combination, refers to an alkyl ether radical (O-alkyl). Non-limiting examples of alkoxy radicals include methoxy, ethoxy, n-propoxy, isopropoxy, n-butoxy, isobutoxy, sec-butoxy, tert-butoxy and the like.

The term "alkylene" as used herein, alone or in combination, refers to an optionally substituted straight-chain or optionally substituted branched-chain hydrocarbon monoradical containing at least one carbon-carbon double bond. The alkylene has, but not limited to, from 2 to about 18 carbon atoms, for example, from 2 to about 10 carbon atoms, or from 2 to about 8 carbon atoms, from 2 to about 6 carbon atoms, or from 2 to about 4 carbon atoms. The group may be in either cis or trans conformation about the double bond(s), and should be understood to include both isomers. Examples include, but are not limited to ethenyl ($CH=CH_2$), 1-propenyl ($CH_2CH=CH_2$), isopropenyl ($C(CH_3)=CH_2$), butenyl, 1,3-butadienyl and the like. Whenever it appears herein, a numerical range such as "$C_2$-$C_6$ alkenyl" or "$C_{2-6}$ alkenyl", means that the alkenyl group may consist of 2 carbon atoms, 3 carbon atoms, 4 carbon atoms, 5 carbon atoms or 6 carbon atoms. The present definition also covers the occurrence of the term "alkenyl" where no numerical range is designated.

The term "alkynyl" as used herein, alone or in combination, refers to an optionally substituted straight- or branched-chain hydrocarbon monoradical having at least one carbon-carbon triple-bond. The alkynyl has from 2 to about 18 carbon atoms, for example, from 2 to about 10 carbon atoms, from 2 to about 8 carbon atoms, from 2 to about 6 carbon atoms, or from 2 to about 4 carbon atoms. Examples of the alkynyl radical herein include, but are not limited to ethynyl, 2-propynyl, 2-butynyl, 1,3-butadiynyl, and the like. Whenever it appears herein, a numerical range such as "$C_2$-$C_6$ alkynyl" or "$C_{2-6}$ alkynyl", means that the alkynyl group may consist of 2 carbon atoms, 3 carbon atoms, 4 carbon atoms, 5 carbon atoms or 6 carbon atoms. The present definition also covers the occurrence of the term "alkynyl" where no numerical range is designated.

The term "halo" or "halogen-substituted" as used herein, alone or in combination, refers to an optionally substituted group (such as alkyl, alkenyl and alkynyl) in which at least one hydrogen atom is replaced with a halogen atom (such as fluorine, chlorine, bromine, iodine, or a combination thereof). In some embodiments, two or more hydrogen atoms are replaced with halogen atoms that are the same as each other (e.g., difluoromethyl, trifluoromethyl); in other embodiments, two or more hydrogens are replaced with halogen atoms that are not all the same as each other (e.g., 1-chloro-1-fluoro-1-iodo-ethyl). Non-limiting examples of haloalkyl group are fluoromethyl and bromoethyl. A non-limiting example of haloalkenyl group is bromoethenyl. A non-limiting example of haloalkynyl group is chloroethynyl.

The term "aryl" as used herein, alone or in combination, refers to an optionally substituted aromatic hydrocarbon radical having 6 to about 20, for example, 6 to 12 or 6 to 10 ring-forming carbon atoms, which may be monocyclic aryl, bicyclic aryl or polycyclic aryl. The bicyclic aryl or polycyclic aryl may be fused through a monocyclic aryl with other independent rings, such as alicyclic, heterocyclic, aromatic, heteroaromatic rings. Non-limiting examples of the monocyclic aryl group include monocyclic aryl having from 6 to about 12, from 6 to about 10, or from 6 to about 8 ring-forming carbon atoms, for example, phenyl; bicyclic aryl, for example, naphthyl; and polycyclic aryl, for example, phenanthrenyl, anthracenyl, and azulenyl.

The term "heteroaryl" as used herein, alone or in combination, refers to an optionally substituted heteroaryl containing from about 5 to about 20, for example, from 5 to 12, or from 5 to 10 skeletal ring atoms, wherein at least one (for example, 1 to 4, 1 to 3, or 1 to 2) ring atom is a heteroatom independently selected from among oxygen, nitrogen, sulfur, phosphorous, silicon, selenium and tin but not limited to these atoms. The ring of said group does not contain two adjacent O or S atoms. Heteroaryl includes monocyclic heteroaryl (containing one ring), bicyclic heteroaryl (containing two rings) or polycyclic heteroaryl (containing more than two rings). In embodiments in which two or more heteroatoms are present in the ring, the two or more heteroatoms can be the same as each another, or some or all of the two or more heteroatoms can each be different from the others. The bicyclic heteroaryl or polycyclic heteroaryl may be fused through a monocyclic heteroaryl with other independent rings such as alicyclic, heterocyclic, aromatic, heteroaromatic rings (which may be collectively known as fused ring heteroaryl). Non-limiting examples of monocyclic heteroaryl group include monocyclic heteroaryl having from 5 to about 12, from 5 to about 10, from 5 to about 7 or 6 skeletal ring atoms, for example, a non-limiting example is pyridyl; fused ring heteroaryl groups include benzimidazolyl, quinolinyl, acridinyl. Further examples of heteroaryl include but not limited to pyridine, pyrimidine, pyrazine, pyridazine, triazine, furan, thiophene, imidazole, triazole, tetrazole, thiazole, isothiazole, 1,2,4-thiadiazole, pyrrole, pyrazole, oxazole, isoxazole, oxadiazole, benzofuran, benzothiophene, benzothiazole, indole, indazole, quinoline, isoquinoline, purine, carbazole, benzimidazole, pyrrolopyridine, pyrroloprimidine, pyrazolopyridine, pyrazolopyrimidine and the like, acridinyl, phenazinyl, benzoxazolyl, benzothiadiazolyl, benzoxadiazolyl, benzotriazolyl, isoquinolinyl, indolizinyl, isothiazolyl, isoindolyl, oxadiazolyl, purinyl, phthalazinyl, pteridinyl, quinazolinyl, quinoxalinyl, triazinyl, thiadiazolyl and the like, and their oxides, for example, pyridyl-N-oxide and the like.

The term "heterocycle" or "heterocyclyl" as used herein, alone or in combination, refers to a non-aromatic heterocycle radical, and includes a saturated heterocycle or an unsaturated heterocycle (containing an unsaturated bond), wherein one or more (e.g., 1 to 4, 1 to 3, or 1 to 2) ring atoms are heteroatoms such as oxygen, nitrogen or sulfur atoms. The heterocycle may include mono-heterocycle (containing one ring) or bis-heterocycle (containing two bridged rings) or poly-heterocycle (containing more than two bridged rings); and also include sprio rings. Heterocyclyl may have from 3 to about 20, for example, from 3 to about 10, from 3 to about 8, from 4 to 8, from 4 to 7, from 5 to about 8, or from 5 to about 6 ring atoms. Non-limiting examples of heterocyclyl include azinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexyl, 3-azabicyclo[4.1.0]heptyl, 3H-indolyl, quinolizinyl and the like. The terms also include all ring forms of the carbohydrates, including but not limited to the monosaccharides, the disaccharides and the oligosaccharides. Examples also include, but not limited to, aziridinyl, tetrahydrofuranyl, tetrahydrothiophenyl, pyrrolidinyl, oxazolidinyl, thiazolidinyl, imidazolidinyl, isoxazolidinyl, isothiazolidinyl, pyrazolidinyl, morpholinyl, thiomorpholinyl, piperazinyl, piperidyl, and the like. Heterocyclyl also includes one or more aromatic rings fused (i.e., having a common bond) heterocycle, for example, 2,3-dihydrobenzofuran, 1,3-benzodioxolane, benzo-1,4-dioxane, phthalimide, naphthalimide. The heterocyclyl having one or more fused aromatic rings may be attached to other groups via the aromatic or non-aromatic ring moiety. Other groups may bond to a heterocycle via a heteroatom or a carbon atom (i.e., the heterocycle is attached to a parent molecule or is further substituted).

The term "carbocycle" or "carbocyclyl" as used herein, alone or in combination, refers to a non-aromatic carbon-containing ring radical, and includes a saturated carbocycle (e.g., cycloalkyl) or a unsaturated carbocycle (e.g., cycloalkenyl). The carbocycle includes a monocyclic carbocycle (containing one ring), which may be, for example, monocyclic cycloalkyl; a bicyclic carbocycle (containing two rings), which may be, for example, bicyclic cycloalkyl; and a polycyclic carbocycle (containing more than two rings). The carbocycle (e.g., cycloalkyl or cycloalkenyl) may have from 3 to 20 carbon atoms, for example, from 3 to about 15 ring carbon atoms, or from 3 to about 10 ring carbon atoms, or from 3 to 6 ring carbon atoms. Examples include cyclopropyl, cyclobutyl, cyclopentyl, cyclohexyl, cycloheptyl, cyclopentenyl, cyclohexadienyl, cycloheptatrienyl, adamantyl, and the like.

The term "halogen" refers to fluorine, chlorine, bromine and iodine, preferably fluorine, chlorine, and bromine. Cyano refers to "—CN"; hydroxyl refers to "—OH"; mercapto refers to "—SH"; and amino refers to "—NH$_2$".

The term "substituted" means that one or more hydrogens on a given atom are replaced with a specified group. If the normal valency of the given atom is not exceeded in the current case, then the substitution results in a stable compound.

Pharmaceutical Terminology

The term "subject", "patient" or "individual" as used herein in reference to individuals suffering from a disease, a disorder, a condition, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treat," "treating" or "treatment," and other grammatical equivalents as used herein, include alleviating, abating or ameliorating disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving the symptoms caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

The terms "administer", "administering", "administration", and the like, as used herein, refer to the methods that may be used to enable delivery of compounds or compositions to the desired site of biological action. These methods include, but not limited to oral routes, intraduodenal routes, parenteral injection (including intravenous, subcutaneous, intraperitoneal, intramuscular, intraarterial injection or infusion), topical and rectal administration. Those of skill in the art are familiar with administration techniques that can be employed with the compounds and methods described herein, e.g., as discussed in Goodman and Gilman, The Pharmacological Basis of Therapeutics, current ed.; Pergamon; and Remington's, Pharmaceutical Sciences (current edition), Mack Publishing Co., Easton, Pa. In preferred embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not affect the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, but not limited to carriers, stabilizers, diluents, dispersing agents, suspending agents, thickening agents, and/or excipients.

The term "carrier" as used herein, refers to relatively nontoxic chemical compounds or agents that facilitate the incorporation of a compound into cells or tissues.

The term "pharmaceutically acceptable salt" as used herein, refers to salts that retain the biological effectiveness of the free acids and bases of the specified compound and that are not biologically or otherwise undesirable. The compound of the invention also includes a pharmaceutically acceptable salt. The pharmaceutically acceptable salt refers to those formed by converting basic groups in the parent compound into a salt form. The pharmaceutically acceptable salt includes, but not limited to, inorganic or organic acid salts of the basic groups such as amine (amino) groups. The pharmaceutically acceptable salt of the invention may be synthesized from the parent compound, i.e., by reaction of the basic groups in the parent compound with 1-4 equivalents of an acid in a solvent system. Suitable salts are listed in Remingtong's Pharmaceutical Sciences, $17^{th}$ ed., Mack Publishing Company, Easton, Pa., 1985, p. 1418 and Journal of Pharmaceutical Science, 66, 2(1977).

Unless indicated specifically, the salt of the invention refers to acidic salts formed by organic/inorganic acids, and basic salts formed by organic/inorganic bases. In addition, when the basic functional group in the compound of formula I is (but not limited to) pyridine or imidazole, and the acidic function group is (but not limited to) carboxylic acid, an amphoteric ion (an inner-salt) will be formed. The inner-salts are also encompassed in the salts of the invention.

The term "solvate" as used herein refers to a combination of a compound of this invention with a solvent molecule formed by solvation. In some embodiments, the solvate refers to a hydrate, i.e., the solvent molecule is water molecule, and the combination of a compound of this invention and water forms a hydrate. One or more compounds of the invention may exist in the form of a solvate, just like the solvates formed with the pharmaceutically acceptable solvents such as water, ethanol, and the like. Therefore, the invention includes both solvated and non-solvated forms. "Solvate" refers to a physical aggregate formed with a compound of the invention and one or more solvent molecules. This physical aggregate includes different degrees of ions and covalent bonds, for example, hydrogen bonds. It has been confirmed that this solvate may be separated off, for example, when the lattice of a crystal has one or more solvent molecules. "Solvate" includes both parts of solvent phase and separable solvate. There are many examples of the corresponding solvates, including ethanol solvate, methanol solvate, and the like. "Hydrate" is a solvate in which the solvent is water ($H_2O$) molecule.

One or more compounds of the invention may be arbitrary prepared into a solvate. The preparation of a solvate is well known in the art. For example, the preparation of a solvate of the antifungal drug, fluconazole, i.e., with ethyl acetate and water, is described in M. Caira et al, J. Pharmaceutical Sci., 93(3), 601-611 (2004). Similar preparation methods of solvates and hydrates are also described in E. C. van Tonder et al, AAPS PharmSciTech., 5(1), article 12 (2004); and A. L. Bingham et al, Chem. Commun., 603-604 (2001). A typical, non-limiting preparation process is to dissolve the compound of the invention in a desired amount of an ideal solvent (organic solvent or water or a mixture thereof) at a temperature higher than normal temperature, cool, stand and crystallize, and then separate off the crystals using a standard method. The presence of the solvent (water) in the solvate (hydrate) formed during the crystallization can be confirmed by an I. R. spectroscopic analysis technology.

The term "polymorph" or "polymorphism" as used herein refers to a compound of this invention present in different crystal lattice forms.

The term "an isotopic label" as used herein, refers to a compound of the invention labelled by an isotope. For example, the isotopes in the compound of the invention include various isotopes of H, C, N, O, P, F, and S, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}S$.

The term "pharmaceutically acceptable prodrug" as used herein, refers to any pharmaceutically acceptable salt, ester, salt of an ester or other derivative of a compound of this invention, which, upon administration to a recipient, is capable of providing, either directly or indirectly, a compound of this invention or a pharmaceutically active metabolite or residue thereof. Particularly preferred derivatives or prodrugs are those that increase the bioavailability of the compounds of this invention when such compounds are administered to a patient (e.g., by allowing orally administered compound to be more readily absorbed into blood), or those that enhance delivery of the parent compound to a biological organ or action site (e.g., the brain or lymphatic system).

Various forms of prodrugs are well known in the art. See, T. Higuchi and V. Stella, Pro-drugs as Novel Delivery Systems (1987) Vol. 14 of the A.C.S. Symposium Series, Bioreversible Carriers in Drug Design, (1987) Edward B. Roche, ed., American Pharmaceutical Association and in Pergamon Press for discussion concerning prodrugs. *Design of Prodrugs*, Bundgaard, A. Ed., Elseview, 1985 and *Method in Enzymology*, Widder, K. et al., Ed.; Academic, 1985, vol. 42, p. 309-396; Bundgaard, H. "Design and Application of Prodrugs" in *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38, each of which is incorporated herein by reference.

"Stereoisomer" as used herein, refers to isomers produced from different arrangements of atoms in molecules in space. The compound of formula I possess asymmetric or chiral centers, and thus different stereoisomeric forms exist. All stereostructures of molecular formula I, like a mixture, include racemic mixtures, as a part of the present invention. Diastereomer isomers can be separated into individual diastereomers, depending on their different physicochemical properties, by using the well-known means. For example, the resolution of individual enantiomers may be achieved by reacting with suitable optically active substance (for example, chiral alcohol or Mosher's acyl chloride) to convert into diastereoisomers, and then separating them and converting (such as hydrolyzing) into the corresponding individual isomers. Some compounds of formula 1 may be atropisomers (such as substituted aryl), which is also a part of the invention. Enantiomers may be isolated by using a chiral chromatographic column. The compound of formula I may exist different tautomeric forms, which are encompassed in the scope of the invention, for example, compounds in keto-enol and imine-enamine forms.

The term "metabolic disease" as used herein, refers to a disease caused by metabolic problems including dysmetabolish, exuberant metabolism, and others. The metabolic disease mainly includes the following diseases: diabetes mellitus, diabetic ketoacidosis, hyperglycosemia hyperosmolality syndrome, hypoglycemia, gout, protein-calorie malnutrition, vitamin A deficiency, scurvy, vitamin D deficiency, osteoporosis, and the like.

The term "cardiovascular disease" as used herein, also known as circulatory disease, is a series of diseases concerning the circulatory system. The circulatory system refers to organs and tissues carrying blood within the human body, mainly including heart, blood vessels (artery, vein, capillary). The cardiovascular disease can be subdivided into acute and chronic, and generally associating with arteriosclerosis. The cardiovascular diseases include heart diseases, hypotension, hypertension, hyperglycemia, stroke, myocardial infarction, thrombus, arteriosclerosis, and the like.

DETAILED DESCRIPTION OF THE INVENTION

The novel features of the invention are set forth with particularity in the appended claims. A better understanding of the features and advantages of the present invention will be obtained by reference to the following detailed description that sets forth illustrative embodiments, in which the principles of the invention are utilized.

While preferred embodiments of the present invention have been shown and described herein, such embodiments are provided by way of example only. It should be understood that various alternatives to the embodiments of the invention described herein may be employed in practicing the invention. Those ordinary skilled in the art will appreciate that numerous variations, changes, and substitutions are possible without departing from the invention. It should be understood that the following claims define the scope of aspects of the invention and that methods and structures within the scope of these claims and their equivalents be covered thereby.

Synthetic Schemes

Methods for synthesizing the compounds of the invention include, but not limited to, the following reaction formulas and reaction steps:

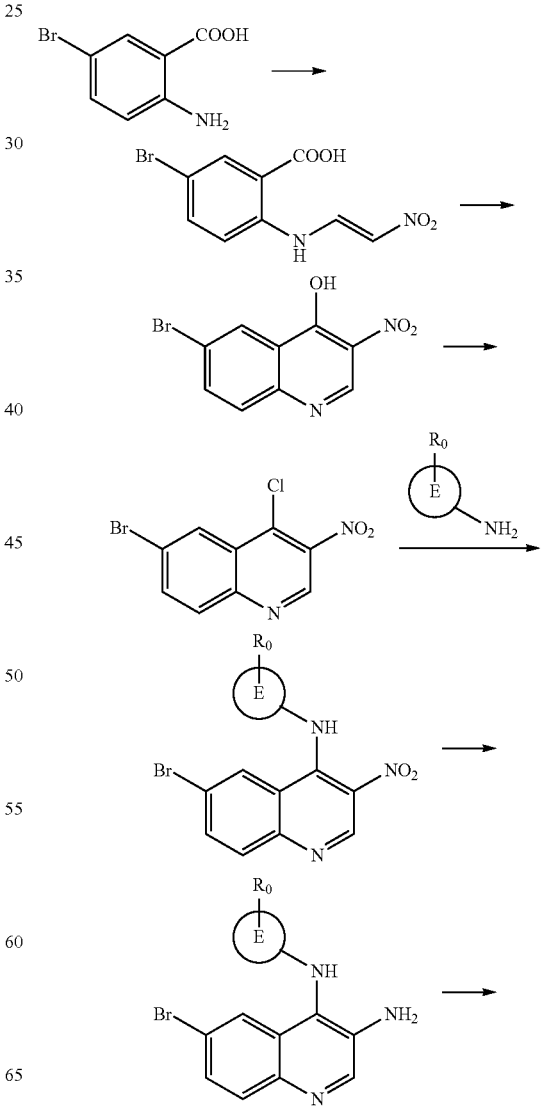

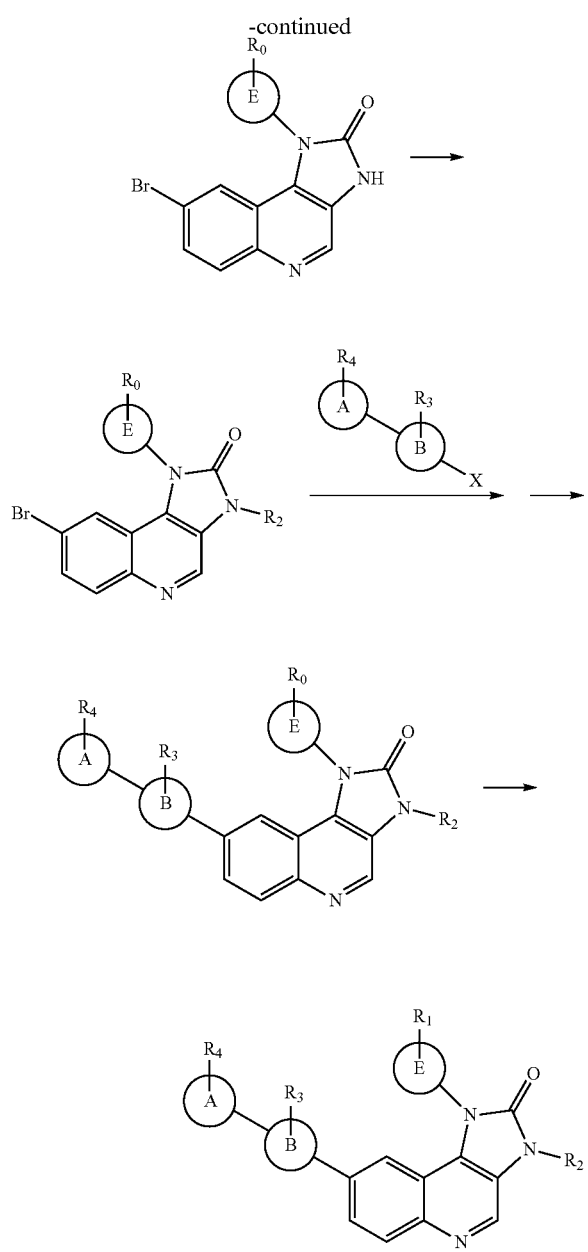

The conditions for LC-MS analysis in the synthesis process are as follows:
Instrument: Agilent LCMS1260/MSD6120
Chromatographic column. Agilent SB-C18, 2.1*50 mm, 1.8 μm, SN: USWEY07289
Mobile phase: A: H2O (0.1% FA) 90%, B: ACN 10%, 0.400 mL/min, 45.00° C.
Schedule

| Time | Function | Parameters | | |
|------|----------|------------|---|---|
| 2.24 | Changing solvent components | Solvent components | A: 0.0% | B: 100.0% |
| 3.00 | Changing solvent components | Solvent components | A: 0.0% | B: 100.0% |
| 3.01 | Changing flow rate | Flow rate: 0.5 mL/min | | |
| 3.01 | Changing solvent components | Solvent components | A: 90.0% | B: 10.0% |
| 5.00 | Changing solvent components | Solvent components | A: 90.0% | B: 10.0% |
| 5.01 | Changing flow rate | Flow rate: 0.4 mL/min | | |
| 5.01 | Changing solvent components | Solvent components | A: 90.0% | B: 10.0% |

Instrument Parameters:
Ionization Mode: API-ES
Polarity: Positive
Collision-induced dissociations ascending order: Disabled
Percentage of cycle time: 50.00%
(I) Scheme I:

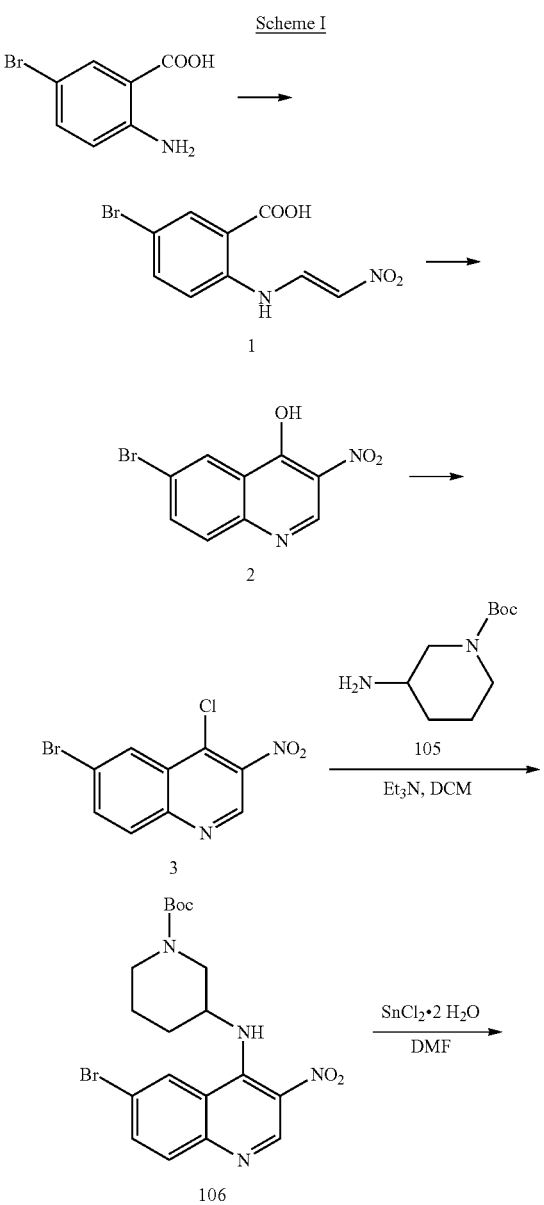

-continued

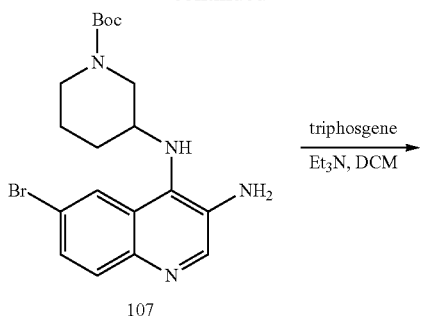

107

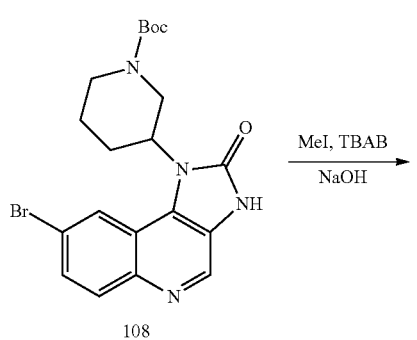

108

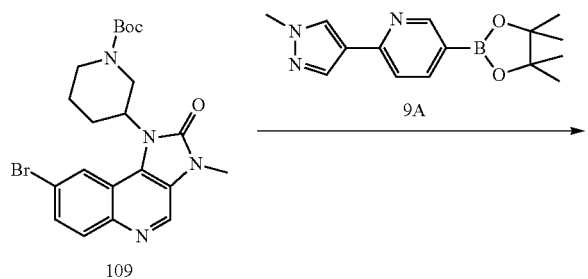

109

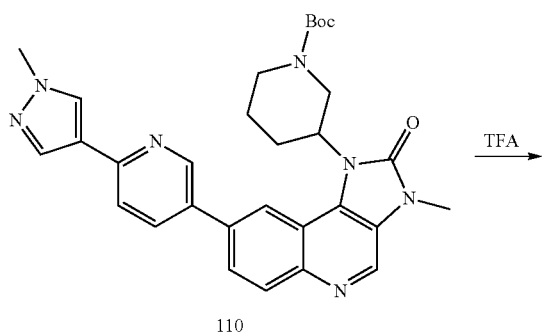

110

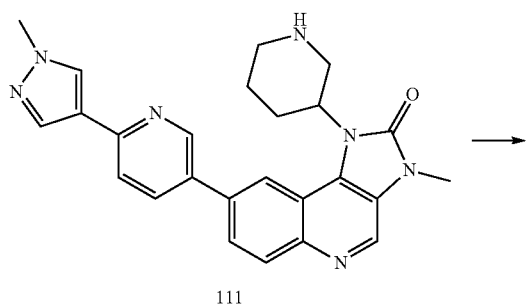

111

-continued

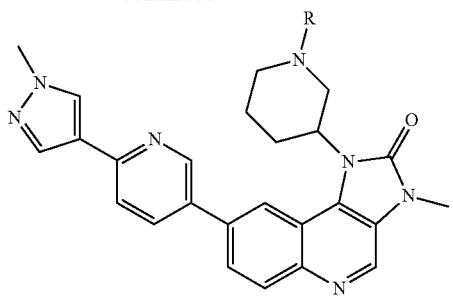

Synthesis of Intermediate 1

70 g of ice and 32 g of NaOH are mixed, slowly added with 15.4 ml of nitromethane under stirring, stirred at 0° C. for 1 h and then poured into a mixture of 70 g of ice and 72 ml of 37% HCl, as a stock solution. 50 g of 2-amino-5-bromobenzoic acid, 300 ml of water, and 300 ml of acetone were charged into a 2000-ml single-necked flask, stirred, added with the stock solution, and reacted at room temperature. The reaction was monitored by TLC. After the reaction was completed, the solution was filtered and drained to yield 50.25 g of intermediate 1 as a yellow solid. Yield: 76%.

Synthesis of Intermediate 2

50.25 g (0.175 mole) of Intermediate 1 was placed in a 500-ml single-necked flask, added with 250 ml of acetic anhydride, heated to 60° C., followed by the addition of 18.2 g (0.23 mol) of potassium acetate. Then the temperature was raised to 110° C., and the mixture was reacted. The reaction was monitored by TLC. After 4 h, the mixture was allowed to cool to room temperature, filtered, and washed with acetic acid to be colorless, to give 26.8 g of Intermediate 2 as a white solid. Yield: 56%.

Synthesis of Intermediate 3

26.8 g (99 mmol) of Intermediate 2 was placed in a 500-ml single-necked flask, added with 200 ml of phosphorus oxychloride, and refluxed at 120° C. for 1 h. The reaction was monitored by TLC. After the reaction was completed, the reaction mixture was poured into a large amount of ice water and stirred, leading to formation of precipitates. The reaction mixture was filtered, and the filter cake was washed with ice water, and then dissolved in methylene chloride. The organic phase was washed with brine three times, dried by anhydrous magnesium sulfate, and rotary evaporated to dryness to afford 16.1 g of Intermediate 3. Yield: 53%.

INTERMEDIATE 106 tert-butyl 3-((6-bromo-3-nitroquinolin-4-yl)amino)piperidine-1-carboxylate

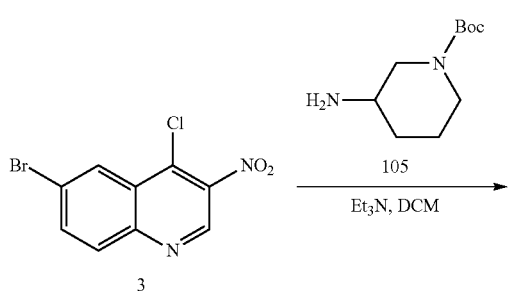

9.8 g (34.1 mmol) of Compound 3 and 11.3 g (56.4 mmol) of Compound 105 were dissolved in 100 ml of DCM, stirred until the solid was dissolved, then added with 8.6 ml (61.7 mmol) of triethylamine, and stirred at room temperature for 2 h, and TLC (PE:EA=3:1) showed that the reaction was completed. The reaction solution was purified on a silica gel column (petroleum ether:ethyl acetate=1:1 to ethyl acetate) to afford a yellow powder (13.7 g). Yield: 88.5%. LC-MS: 451,453 [M+1]$^+$, $t_R$=2.696 min.

INTERMEDIATE 107 tert-butyl 3-((3-amino-6-bromoquinolin-4-yl)amino)piperidine-1-carboxylate

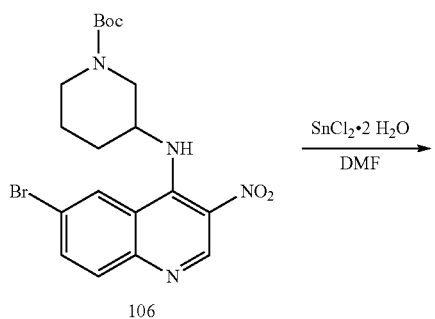

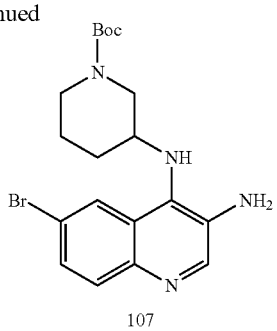

12.3 g (27.25 mmol) of Intermediate 106 was suspended in 123 ml of DMF, and added with 30.75 g (136.27 mmol) of stannous chloride dihydrate in batches under cooling in an ice bath. Then the ice bath was removed. The reaction solution was stirred at room temperature for 1 h, and TLC (ethyl acetate+triethylamine) showed that the raw materials were reacted completely. The reaction solution was poured into 820 ml of saturated sodium bicarbonate solution and stirred to quench the reaction, and extracted with 400 ml of ethyl acetate. The two phases were filtered by suction and separated off. The aqueous phase was extracted with 2×200 ml of ethyl acetate, and the solid obtained by suction filtration was stirred with 2×200 ml of ethyl acetate, and filtered by suction. The filtrate was combined with the organic phases, and washed with 200 ml of saturated saline solution, dried, filtered, and evaporated to dryness, to afford a yellow crude solid (13.3 g). Crude yield: >100%. LC-MS: 421,423 [M+1]$^+$, $t_R$=1.743 min.

INTERMEDIATE 108 tert-butyl 3-(8-bromo-2-oxo-2,3-dihydro-1H-imidazo[4,5-c]quinolin-1-yl)piperidine-1-carboxylate

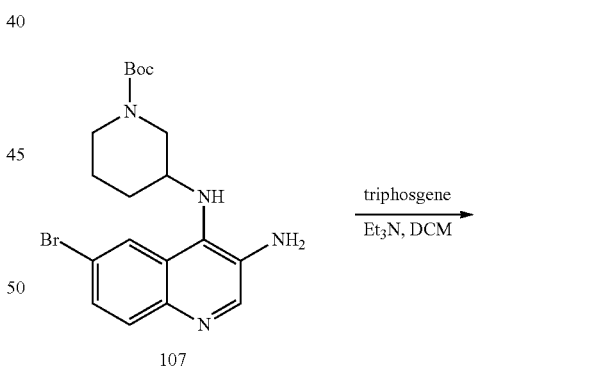

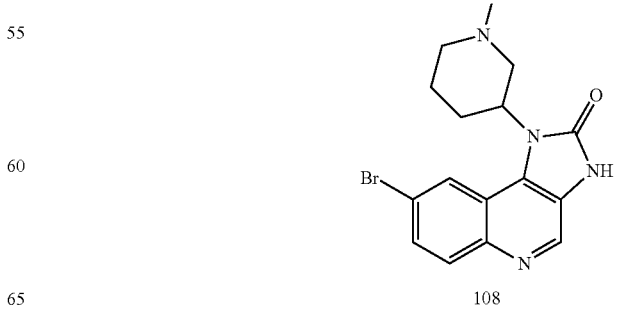

2.09 g of crude Compound 107 (about 3.3 mmol) was dissolved in 10 ml of dichloromethane, cooled to 0° C., added with 1.5 ml (10.8 mmol) of triethylamine, and then added dropwise with a solution of 0.49 g (1.65 mmol) of triphosgene in 10 ml of dichloromethane under stirring. The reaction mixture was stirred at 0-5° C. for 2 h. TLC (ethyl acetate) showed almost no raw materials were present. 25 mL of saturated sodium bicarbonate solution were added to quench the reaction at 0° C., and stirred for 10 min. The organic phase was separated off, and the aqueous phase was extracted with 3×20 ml of dichloromethane. The organic phases were combined, dried, filtered and evaporated to dryness, and purified on a silica gel column (ethyl acetate to ethyl acetate: methanol=10:1) to afford a yellow powder (1.29 g). Yield: 87.4%. LC-MS: 447,449 [M+1]$^+$, $t_R$=2.203 min.

INTERMEDIATE 109 tert-butyl 3-(8-bromo-3-methyl-2-oxo-2,3-dihydro-1H-imidazo[4,5-c]quinolin-1-yl)piperidine-1-carboxylate

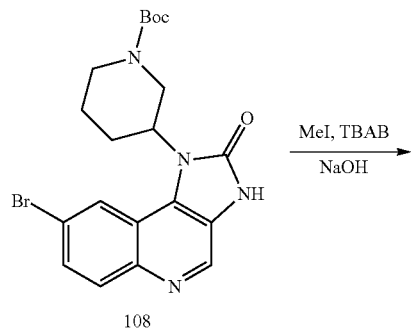

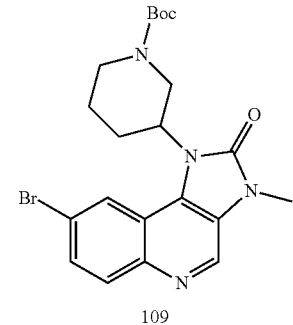

2 g (4.47 mmol) of Intermediate 108 was suspended in 50 ml of dichloromethane, added with 0.15 g of TBAB (0.45 mmol) and 40 ml of 10% sodium hydroxide solution, followed by the addition of 0.7 ml (11.2 mmol) of methyl iodide under stirring, and stirred at room temperature for 20 h. TLC (DCM:MeOH=10:1) showed no raw material present. The solution was separated into two layers, the aqueous layer was extracted with 2×20 ml of dichloromethane, and the organic phases were combined, dried, filtered, and evaporated to dryness, to afford a crude product, which was purified by silica gel column chromatography (dichloromethane:methanol=50:1 to 30:1) to afford a yellow powder (2.0 g). Yield: 97%. LC-MS: 461,463 [M+1]$^+$, $t_R$=2.365 min.

INTERMEDIATE 110 tert-butyl 3-(3-methyl-8-(6-(1-methyl-1H-pyrazol-4-yl)pyridin-3-yl)-2-oxo-2,3-hydro-1H-imidazo[4,5-c]quinolin-1-yl)piperidine-1-carboxylate

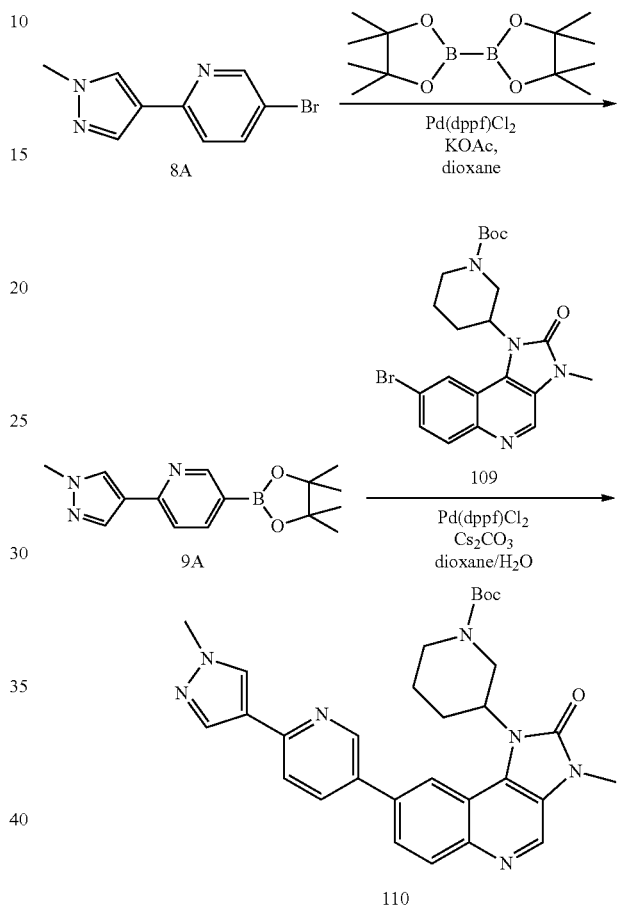

Under the protection of nitrogen, 1.55 g (6.5 mmol) of Compound 8A, 1.98 g (7.8 mmol) of bis(pinacolato)diboron, 1.91 g (19.5 mmol) of potassium acetate and 0.212 g (0.26 mmol) of Pd(dppf)Cl$_2$·CH$_2$Cl$_2$ were suspended in 30 ml of dioxane, heated to 95° C. and stirred for 2 h, TLC (ethyl acetate) showed that the reaction was completed. The crude reaction solution was allowed to cool to room temperature, and added with 2 g (4.34 mmol) of Intermediate 109, 5.66 g (17.36 mmol) of cesium carbonate, 10 ml of dioxane, 10 ml of 2M sodium carbonate solution and 0.177 g (0.22 mmol) of Pd(dppf)Cl$_2$·CH$_2$Cl$_2$, heated to 110° C. and stirred for 5 h. TLC (DCM:MeOH=10:1) showed that the reaction was completed. The reaction solution was allowed to cool, evaporated to remove dioxane, dissolved in 60 ml of dichloromethane and 60 ml of water. The organic phase was separated off, and the aqueous phase was extracted with 60 ml of dichloromethane, and the organic phases were combined, dried, evaporated to dryness, and purified on a silica gel column (dichloromethane:methanol=30:1 to 10:1) to afford a terreous powder (2 g). Yield: 85%. LC-MS: 540 [M+1]$^+$, $t_R$=2.148 min.

INTERMEDIATE 111

3-methyl-8-(6-(1-methyl-1H-pyrazol-4-yl)pyridin-3-yl)-1-(piperidin-3-yl)-1H-imidazo[4,5-c]quinolin-2(3H)-one

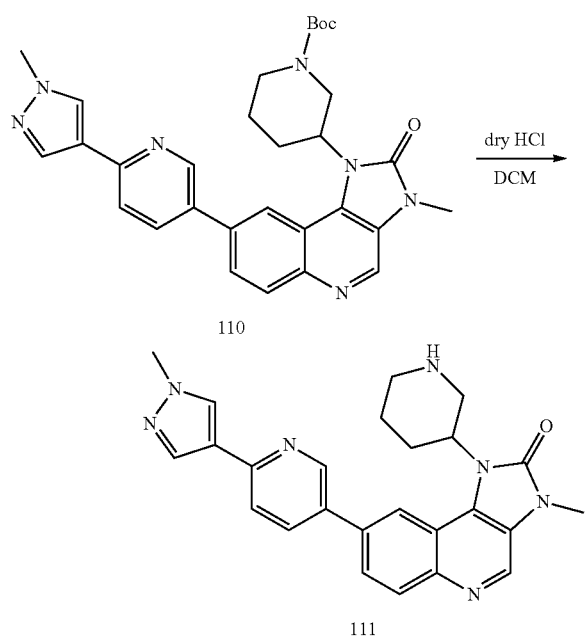

1 g (1.87 mmol) of Compound 110 was dissolved in 30 ml of dichloromethane, and purged with dry hydrogen chloride gas for 5 h under stirring, forming a large number of precipitates. TLC (DCM:MeOH=10:1) showed that the reaction was completed. The reaction solution was filtered by suction, and dried in vacuo to afford a crude hydrochloride (1.34 g). Curde yield: >100%. LC-MS: 440 [M+1]$^+$, $t_R$=1.427 min.

EXAMPLE 1

1-(1-(2-hydroxyacetyl)piperidin-3-yl)-3-methyl-8-(6-(1-methyl-1H-pyrazol-4-yl)pyridin-3-yl)-1H-imidazo[4,5-c]quinolin-2(3H)-one

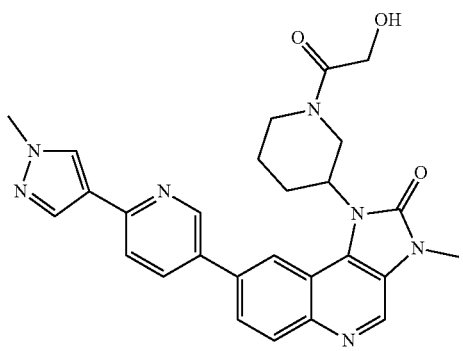

20 mg (0.0455 mmol) of Compound 111, 4.15 mg (0.0546 mmol) of hydroxyacetic acid, 9.23 mg (0.0683 mmol) of HOBt and 13.09 mg (0.0683 mmol) of EDCI were suspended in 2 ml of dichloromethane, added with 13.9 mg (0.137 mmol) of triethylamine, and stirred at room temperature for 5 h. TLC (DCM:MeOH=10:1) showed that the raw materials were reacted completely. 5 mL of saturated sodium bicarbonate solution was added and stirred for 0.5 h. The organic phase was separated off, and the aqueous phase was extracted with 2×5 ml of dichloromethane, and the organic phases were combined, dried, evaporated to dryness, and purified by preparative TLC (dichloromethane:methanol=10:1) to afford the target compound of Example 1 (14 mg), as a light yellow powder. Yield: 61.8%. LC-MS: 498 [M+1]$^+$, $t_R$=1.436 min $^1$H NMR (400 MHz, CDCl$_3$) δ 8.93 (d, J=53.4 Hz, 1H), 8.77 (d, J=8.6 Hz, 1H), 8.39 (s, 1H), 8.31 (d, J=8.8 Hz, 1H), 8.19-8.11 (m, 3H), 7.92 (d, J=8.5 Hz, 1H), 7.65 (d, J=8.5 Hz, 1H), 5.12-4.81 (m, 2H), 4.35 (m, J=15.4 Hz, 2H), 4.02 (s, 3H), 3.78-3.55 (m, 5H), 3.23 (t, J=12.1 Hz, 2H), 2.32-1.94 (m, 3H).

EXAMPLE 2

1-(1-(1H-1,2,4-triazole-3-carbonyl)piperidin-3-yl)-3-methyl-8-(6-(1-methyl-1H-pyrazol-4-yl)pyridin-3-yl)-1H-imidazo[4,5-c]quinolin-2(3H)-one

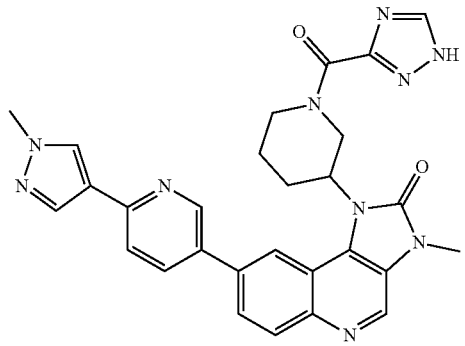

20 mg (0.0455 mmol) of Compound 111, 6.2 mg (0.0546 mmol) of 1H-1,2,4-triazole-3-carboxylic acid, 9.23 mg (0.0683 mmol) of HOBt and 13.09 mg of EDCI were suspended in 2 ml of dichloromethane, added with 13.9 mg (0.137 mmol) of triethylamine, and stirred at room temperature for 4 h. TLC (DCM:MeOH=10:1) showed that most of the raw materials were not reacted. 9.3 mg of 1H-1,2,4-triazole-3-carboxylic acid, 26 mg of HATU and 15 mg of triethylamine were supplemented, and stirred at room temperature overnight. TLC (DCM:MeOH=10:1) showed that most of the raw materials were reacted completely. 10 mL of saturated sodium bicarbonate solution was added and stirred for 1 h. The organic phase was separated off, and the aqueous phase was extracted with 2×5 ml of dichloromethane. The organic phases were combined, dried, evaporated to dryness, and purified by preparative TLC (dichloromethane:methanol=10:1) to afford the target compound of Example 2 (17.8 mg), as a light yellow powder. Yield: 73%. LC-MS: 535 [M+1]$^+$, $t_R$=1.463 min $^1$H NMR (400 MHz, DMSO+D$_2$O) δ 9.41 (d, J=7.9 Hz, 1H), 9.14 (d, J=6.0 Hz, 1H), 9.00-8.91 (m, 1H), 8.87-8.79 (m, 1H), 8.78-8.65 (m, 2H), 8.64-8.44 (m, 2H), 8.39 (s, 1H), 8.22-7.96 (m, 1H), 5.56-4.07 (m, 3H), 4.00 (d, J=16.3 Hz, 3H), 3.60 (d, J=13.2 Hz, 3H), 3.44-3.17 (m, 2H), 3.00-2.82 (m, 1H), 2.31-2.14 (m, 1H).

EXAMPLE 3

3-methyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one

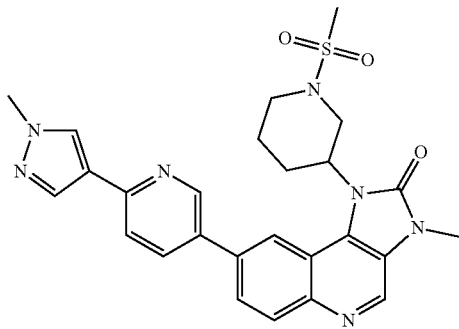

20 mg (0.0455 mmol) of Compound 111 was dissolved in 2 ml of dichloromethane, added with 6.9 mg (0.0683 mmol) of triethylamine and 6.35 mg (0.0546 mmol) of methanesulfonyl chloride, and stirred at room temperature overnight. TLC (DCM:MeOH=10:1) showed that the reaction was completed. 5 mL of saturated sodium bicarbonate solution was added and stirred for 20 minutes. The organic phase was separated off, and the aqueous phase was extracted with 2×5 ml of dichloromethane. The organic phases were combined, dried, evaporated to dryness, and purified by preparative TLC (dichloromethane:methanol=10:1) to afford the target compound of Example 3 (10 mg), as a light yellow powder. Yield: 42.5%. LC-MS: 518 [M+1]$^+$, $t_R$=1.551 min $^1$H NMR (400 MHz, CDCl$_3$) δ 8.95 (d, J=2.0 Hz, 1H), 8.76 (s, 1H), 8.44-8.00 (m, 5H), 7.95 (d, J=8.9 Hz, 1H), 7.69 (d, J=7.8 Hz, 1H), 5.15-5.03 (m, 1H), 4.21 (d, J=8.9 Hz, 1H), 4.02 (s, 3H), 4.00-3.80 (m, 2H), 3.62 (s, 3H), 3.02-2.75 (m, 5H), 2.34-1.83 (m, 3H).

EXAMPLE 4

1-(1-((S)-2-hydroxypropionyl)piperidin-3-yl)-3-methyl-8-(6-(1-methyl-1H-pyrazol-4-yl)pyridin-3-yl)-1H-imidazo[4,5-c]quinolin-2(3H)-one

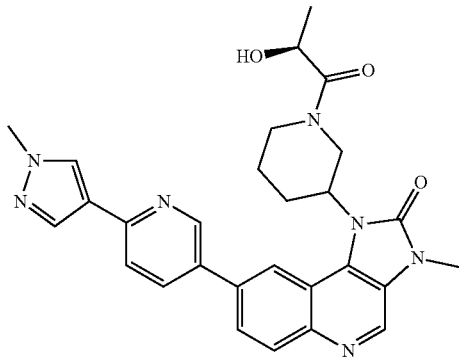

80 mg (0.156 mmol) of the hydrochloride of Compound 111, 21.1 mg (0.234 mmol) of L-lactic acid, 31.6 mg (0.234 mmol) of HOBt and 44.9 mg (0.234 mmol) of EDCI were suspended in 5 ml of dichloromethane, added with 0.153 ml (1.1 mmol) of triethylamine under stirring, stirred at room temperature overnight. TLC (DCM:MeOH=10:1) showed that the raw materials were reacted completely. 15 mL of saturated sodium bicarbonate solution was added and stirred for 0.5 h. The organic phase was separated off, and the aqueous phase was extracted with 2×15 ml of dichloromethane. The organic phases were combined, dried, filtered, evaporated to dryness, and purified by preparative TLC (dichloromethane:methanol=10:1) to afford the target compound of Example 4 (45 mg), as a light yellow powder. The product was dissolved in 75% ethanol, adjusted pH to 1 with 1 M HCl, stirred for 0.5 h, and evaporated to dryness to afford a hydrochloride salt. LC-MS: 512 [M+1]$^+$, $t_R$=1.472 min $^1$H NMR (400 MHz, DMSO+D$_2$O) δ 9.27-9.19 (m, 1H), 9.16-8.98 (m, 1H), 8.70-8.32 (m, 5H), 8.19 (d, J=11.1 Hz, 1H), 8.00 (dd, J=15.9, 8.4 Hz, 1H), 5.63-4.31 (m, 3H), 4.24-4.05 (m, 2H), 3.96 (s, 3H), 3.77-3.70 (m, 1H), 3.58 (s, 3H), 3.47-3.22 (m, 1H), 2.97-2.64 (m, 1H), 2.43-1.89 (m, 2H), 1.33-1.26 (m, 3H).

EXAMPLE 5

1-(1-((R)-2-hydroxypropionyl)piperidin-3-yl)-3-methyl-8-(6-(1-methyl-1H-pyrazol-4-yl)pyridin-3-yl)-1H-imidazo[4,5-c]quinolin-2(3H)-one

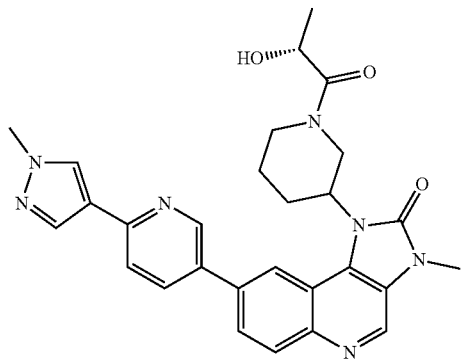

80 mg (0.156 mmol) of the hydrochloride of Compound 111, 21.1 mg (0.234 mmol) of L-lactic acid, 31.6 mg (0.234 mmol) of HOBt and 44.9 mg (0.234 mmol) of EDCI were suspended in 5 ml of dichloromethane, added with 0.153 ml (1.1 mmol) of triethylamine under stirring, and stirred at room temperature overnight. TLC (DCM:MeOH=10:1) showed that the raw materials were reacted completely. 15 mL of saturated sodium bicarbonate solution was added and stirred for 0.5 h. The organic phase was separated off, and the aqueous phase was extracted with 2×10 ml of dichloromethane. The organic phases were combined, dried, filtered, evaporated to dryness, and purified by preparative TLC (dichloromethane:methanol=10:1) to afford the target compound of Example 5 (45 mg), as a light yellow powder. LC-MS: 512[M+1]$^+$, $t_R$=1.476 min $^1$H NMR (400 MHz, CDCl$_3$) δ 9.09-8.63 (m, 2H), 8.43-8.18 (m, 2H), 8.11-7.83 (m, 4H), 7.67-7.49 (m, 1H), 5.10-4.48 (m, 3H), 3.99 (d, J=2.1 Hz, 3H), 3.59 (s, 3H), 3.34-1.51 (m, 6H), 1.47-1.14 (m, 4H).

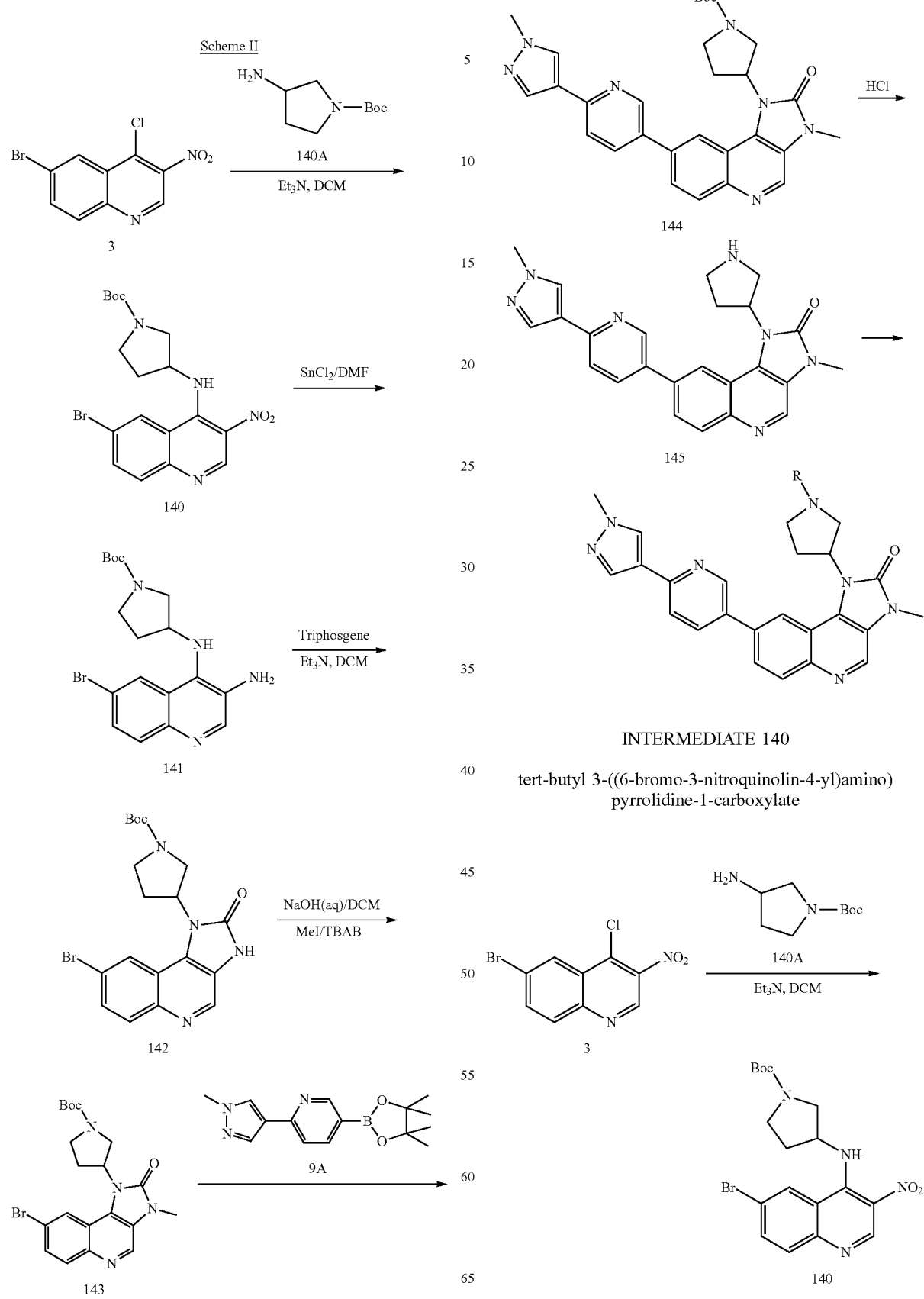
(II) Scheme II:
INTERMEDIATE 140
tert-butyl 3-((6-bromo-3-nitroquinolin-4-yl)amino)pyrrolidine-1-carboxylate 10 g (34.3 mmol) of Compound 3 and 11.3 g (63.36 mmol) of Compound 140A were dissolved in 100 mL of dichloromethane, added with 8.76 mL (62.8 mmol) of triethylamine, and stirred at room temperature overnight. The reaction was monitored by TLC. After the reaction is completed, the solvent was rotary evaporated to dryness to obtain a crude product, which was purified by silica gel column chromatography (eluent: petroleum ether/ethyl acetate=1/1, V/V) to afford a product (13 g) as a yellow powder. Yield: 85%. LC-MS: 437,439 [M+1]$^+$, $t_R$=2.489 min.

INTERMEDIATE 141 tert-butyl 3-((3-amino-6-bromoquinolin-4-yl)amino)pyrrolidine-1-carboxylate

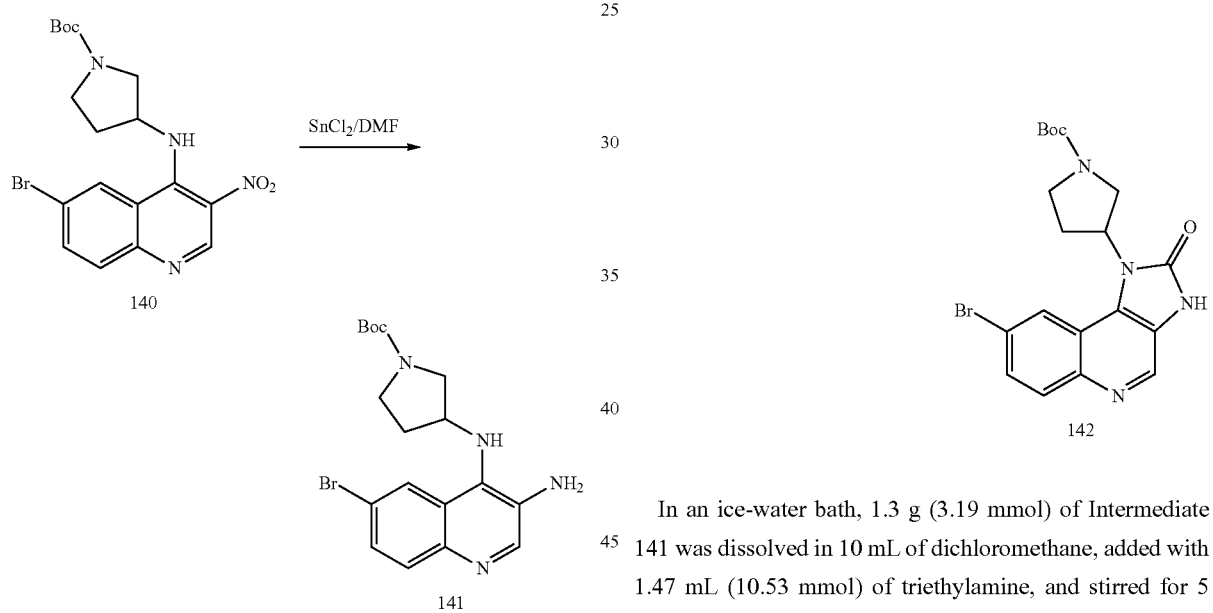

13 g (29.7 mmol) of Intermediate 140 was dissolved in 100 mL of N,N-dimethylformamide in an ice bath. 33.5 g (148.5 mmol) of stannous chloride dihydrate was added in batches over a period of 30 minutes, and stirred at room temperature for 2 h. The reaction was monitored by TLC. After the reaction was completed, to the reaction solution, 10% aqueous sodium hydroxide solution was added dropwise to pH 8-9, and filtered. The filtrate was extracted with dichloromethane, and the filter cake was washed with dichloromethane. The organic phases were combined, washed with water and then with brine, dried, rotary dried to afford a product (11.9 g) as deep yellow oil. Yield: 99%. LC-MS: 407,409 [M+1]$^+$, $t_R$=1.710 min.

INTERMEDIATE 142 tert-butyl 3-(8-bromo-2-oxo-2,3-dihydro-1H-imidazo[4,5-c]quinolin-1-yl)pyrrolidine-1-carboxylate

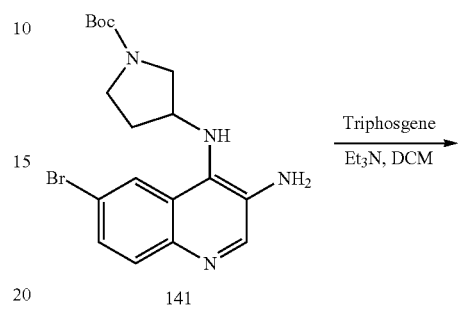

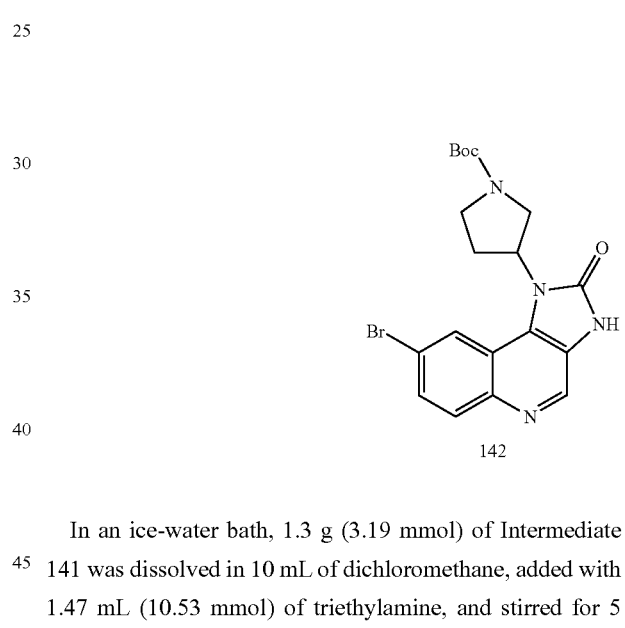

In an ice-water bath, 1.3 g (3.19 mmol) of Intermediate 141 was dissolved in 10 mL of dichloromethane, added with 1.47 mL (10.53 mmol) of triethylamine, and stirred for 5 minutes. A solution of 0.47 g (1.6 mmol) of triphosgene dissolved in 10 mL of dichloromethane was added dropwise and stirred at 0° C. for 4 h. The reaction was monitored by TLC. After the reaction was completed, to the reaction solution 25 mL of saturated sodium bicarbonate solution was dropwise added to quench the reaction, and stirred for 10 minutes. The organic phase was separated off, and the aqueous phase was extracted with dichloromethane. The organic phases were combined, dried, and rotary evaporated to dryness, to afford a crude product. The crude product was purified by silica gel column chromatography (eluent: dichloromethane/methanol=10/1, V/V) to afford a product (0.7 g) as a yellow powder. Yield: 50.7%. LC-MS: 433,435 [M+1]$^+$, $t_R$=1.973 min.

INTERMEDIATE 143 tert-butyl 3-(8-bromo-3-methyl-2-oxo-2,3-dihydro-1H-imidazo[4,5-c]quinolin-1-yl)pyrrolidine-1-carboxylate

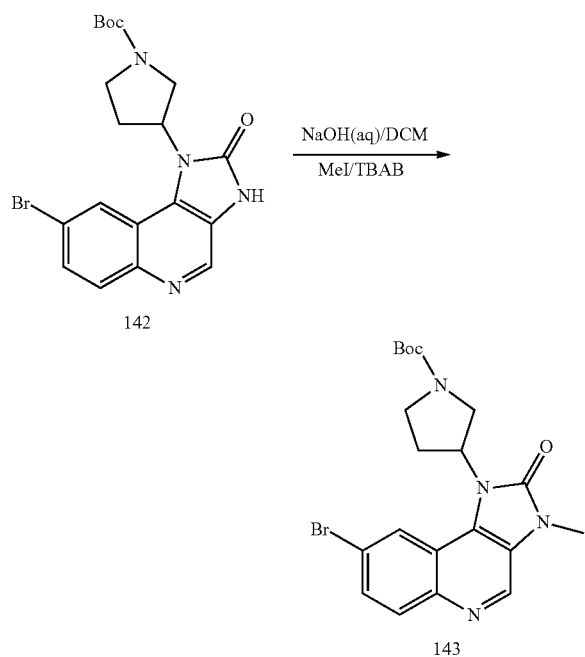

5 g (11.3 mmol) of Intermediate 142 was dissolved in 100 mL of dichloromethane, added with 0.42 g (1.13 mmol) of tetrabutylammonium bromide and 100 mL of 10% aqueous sodium hydroxide solution, stirred for 10 minutes, then added with 2.1 mL (33.8 mmol) of methyl iodide, and stirred for 4 h. The reaction was monitored by TLC. After the reaction was completed, the solution was allowed to stand and separated into layers. The organic phase was separated off, and the aqueous phase was extracted with dichloromethane. The organic phases were combined, dried, and rotary evaporated to dryness, to afford a product (4.9 g), as a yellow solid. Yield: 95%. LC-MS: 447,449 [M+1]$^+$, $t_R$=2.170 min.

INTERMEDIATE 144 tert-butyl 3-(3-methyl-8-(6-(1-methyl-1H-pyrazol-4-yl)piperidin-3-yl)-2-oxo-2,3-dihydro-1H-imidazo[4,5-c]quinolin-1-yl)pyrrolidine-1-carboxylate

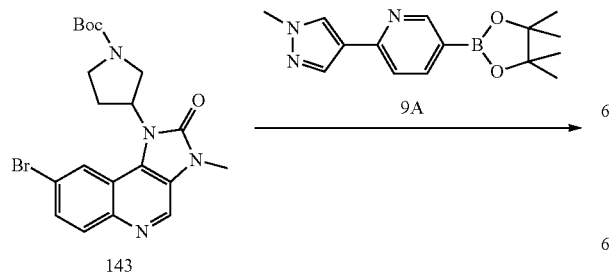

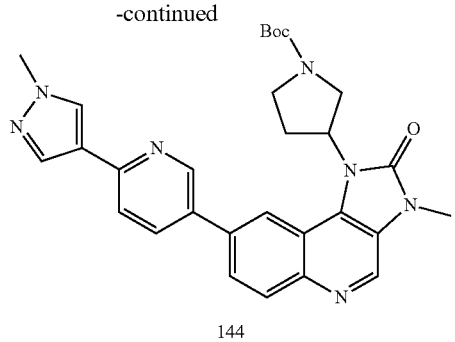

144

Under the protection of nitrogen, 1.2 g (2.68 mmol) of Intermediate 143 and 1.44 g (5.04 mmol) of Intermediate 9A were dissolved in 40 mL of dioxane, added with 5.16 g (15.8 mmol) of cesium carbonate and 10.5 mL of 2M aqueous sodium carbonate solution, then added with 0.22 g (0.268 mmol) of [1,1-bis(diphenylphosphino)ferrocene]palladium chloride, and heated at 110° C. for 5 h. The reaction was monitored by TLC. After the reaction was completed, most of dioxane was removed by rotary evaporation, and the residue was added with water and extracted with dichloromethane. The organic phases were combined, dried, and rotary evaporated to dryness to afford a crude product. The crude product was purified by silica gel column chromatography (dichloromethane/methanol=20/1, V:V) to afford a product (1.3 g), as an earthy red solid. Yield: 92.8%. LC-MS: 526 [M+1]$^+$, $t_R$=1.812 min.

INTERMEDIATE 145

3-methyl-8-(6-(1-methyl-1H-pyrazol-4-yl)pyridin-3-yl)-1-(pyrrolidin-3-yl)-1H-imidazo[4,5-c]quinolin-2(3H)-one hydrochloride

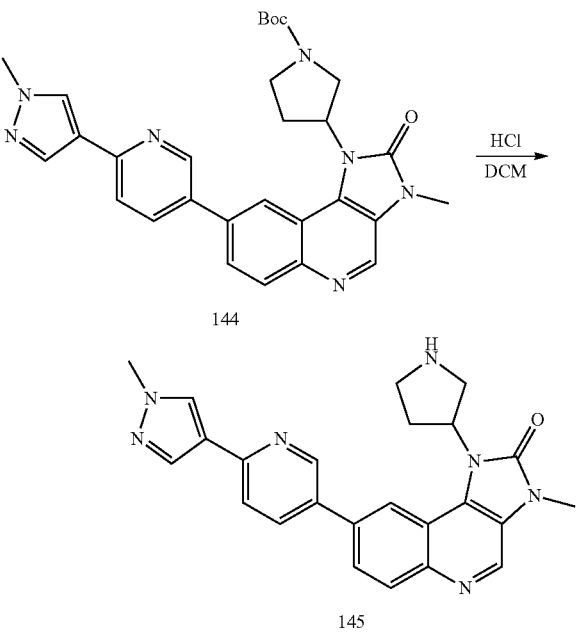

In an ice-water bath, 1.3 g of Intermediate 144 was dissolved in 30 mL of dichloromethane, and hydrogen chloride gas was purged through the reaction solution for 30 minutes. The reaction was monitored by TLC. After the reaction was completed, the solution was filtered, and the solid was washed with dichloromethane, and pumped to dryness under reduced pressure, to afford a crude hydrochloride product (1.3 g), as an earthy yellow solid. Crude yield: >100%. LC-MS: 426 [M+1]$^+$, $t_R$=1.274 min.

EXAMPLE 6

3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2 (3H)-one

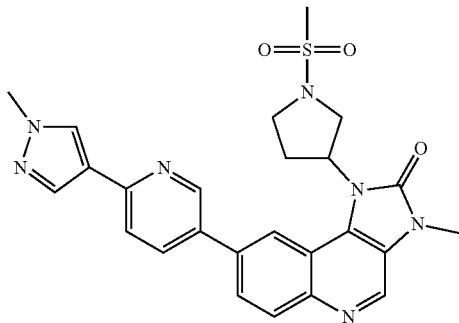

100 mg (0.194 mmol) of Intermediate 145 was dissolved in 5 mL of dichloromethane, added with 29.4 mg (0.291 mmol) of triethylamine, then added with 26.7 mg (0.233 mmol) of methanesulfonyl chloride, and stirred at room temperature overnight. The reaction was monitored by TLC. After the reaction was completed, 10 mL of saturated sodium bicarbonate aqueous solution was added, stirred for 20 minutes, and separated into layers. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 6 (53 mg), as a white solid. Yield: 44.9%. LC-MS: 504 [M+1]$^+$, $t_R$=1.499 min $^1$H NMR (400 MHz, CDCl$_3$) δ 8.91 (s, 1H), 8.78 (s, 1H), 8.34 (s, 1H), 8.29 (d, J=8.9 Hz, 1H), 8.10 (s, 1H), 8.04 (s, 2H), 7.93 (d, J=8.6 Hz, 1H), 7.65 (d, J=8.0 Hz, 1H), 5.87-5.72 (m, 1H), 4.11-4.02 (m, 1H), 4.00 (s, 3H), 3.97 3.92 (m, 1H), 3.86-3.81 (m, 1H), 3.63 (s, 3H), 3.61-3.57 (m, 1H), 2.97 (s, 3H), 2.91-2.82 (m, 1H), 2.58-2.44 (m, 1H).

EXAMPLE 7

1-(1-(2-hydroxyacetyl)pyrrolidin-3-yl)-3-methyl-8-(6-(1-methyl-1H-pyrazol-4-yl)pyridin-3-yl)-1H-imidazo[4,5-c]quinolin-2(3H)-one

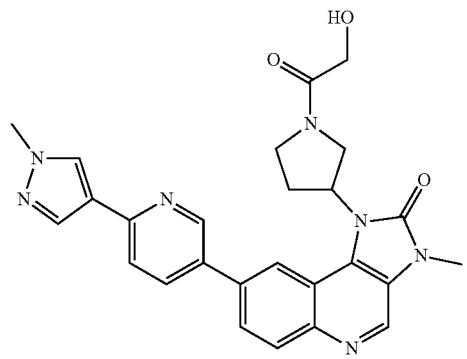

100 mg (0.194 mmol) of Intermediate 145, 69 mg (0.36 mmol) of 1-(3-dimethylaminopropyl)-3-ethyl carbodiimide hydrochloride, 48.6 mg (0.36 mmol) of 1-hydroxybenzotriazole and 21.9 mg (0.288 mmol) of hydroxyacetic acid were dissolved in 5 mL of dichloromethane, then added with 72.8 mg (0.72 mmol) of triethylamine, and stirred at room temperature overnight. The reaction was monitored by TLC. After the reaction was completed, 10 mL of saturated sodium bicarbonate aqueous solution was added, and stirred for 20 minutes, and separated into layers. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 7 (30 mg) as a light yellow solid. Yield: 26.1%. LC-MS: 484 [M+1]$^+$, $t_R$=1.33 min $^1$H NMR (400 MHz, CDCl$_3$) δ 8.88-8.79 (m, 2H), 8.31 (d, J=8.9 Hz, 1H), 8.23-7.96 (m, 3H), 7.94-7.86 (m, 2H), 7.66-7.60 (m, 1H), 5.86-5.62 (m, 1H), 4.43-4.06 (m, 3H), 4.00 (s, 3H), 3.97-3.89 (m, 1H), 3.83-3.73 (m, 1H), 3.63 (d, J=8.9 Hz, 2H), 3.61-3.51 (m, 1H), 3.22-3.05 (m, 3H), 2.89-2.80 (m, 1H), 2.61-2.43 (m, 1H).

EXAMPLE 8

1-(1-(1H-1,2,4-triazole-3-carbonyl)pyrrolidin-3-yl)-3-methyl-8-(6-(1-methyl-1H-pyrazol-4-yl)pyridin-3-yl)-1H-imidazo[4,5-c]quinolin-2(3H)-one

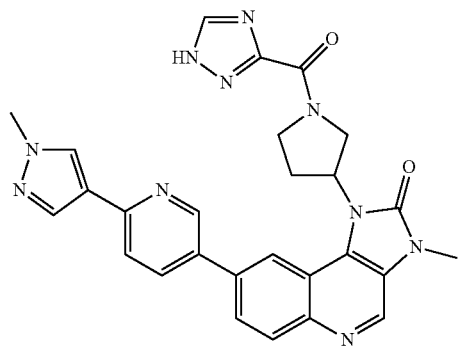

In an ice-water bath, 48.8 mg (0.43 mmol) of 1,2,4-triazole-3-carboxylic acid and 200.76 mg (0.528 mmol) of 2-(7-azabenzotriazole)-N,N,N',N'-tetramethyluronium hexafluorophosphate were dissolved in 5 mL of dichloromethane, added with 97 mg (0.96 mmol) of triethylamine and stirred at 0° C. for 30 minutes, then added with 100 mg (0.24 mmol) of Intermediate 145 and stirred at room temperature overnight. The reaction was monitored by TLC. After the reaction was completed, 10 mL of saturated sodium bicarbonate aqueous solution was added, stirred for 20 minutes, and separated into layers. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 8 (40 mg), as a white solid. Yield: 32%. This product was dissolved in 75% ethanol, adjusted pH to 1 with 1 M HCl, stirred for 0.5 h, and evaporated to dryness to afford a hydrochloride salt. LC-MS: 521 [M+1]$^+$, $t_R$=1.337 min $^1$H NMR (400 MHz, DMSO+D$_2$O) δ 9.33 (d, J=6.6 Hz, 1H), 9.11 (d, J=3.2 Hz, 1H), 8.87-8.71 (m, 2H), 8.68-8.58 (m, 2H), 8.55-8.37 (m, 3H), 8.30 (d, J=8.9 Hz, 1H), 8.11 (dd, J=23.7, 8.5 Hz, 1H), 6.14-6.02 (s, 1H), 4.84-4.10 (m, 3H), 3.97 (s, 3H), 3.57 (d, J=11.5 Hz, 3H), 3.50-3.23 (m, 1H), 2.96-2.61 (m, 2H).

EXAMPLE 9

3-methyl-8-(6-(1-methyl-1H-pyrazol-4-yl)pyridin-3-yl)-1-(1-methylpyrrolidin-3-yl)-1H-imidazo[4,5-c]quinolin-2(3H)-one

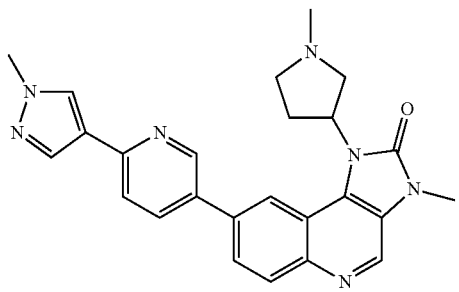

In an ice-water bath, 20 mg (0.5 mmol) of 60% sodium hydride was suspended in 5 mL of tetrahydrofuran and stirred for 5 minutes, added with 50 mg (0.1 mmol) of Intermediate 145 and stirred for 10 minutes, then added dropwise with 7 μL (0.1 mmol) of methyl iodide and stirred at room temperature for 2 h. The reaction was monitored by TLC. After the reaction was completed, 10 mL of water was added dropwise, and extracted with dichloromethane. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 9 (35 mg), as a white solid. Yield: 79.1%. LC-MS: 440 [M+1]$^+$, $t_R$=1.250 min $^1$H NMR (400 MHz, CDCl$_3$+ MeOD) δ 9.52-9.04 (m, 3H), 8.92-8.68 (m, 2H), 8.51-8.48 (m, 1H), 8.31-8.21 (m, 3H), 4.29-3.95 (m, 3H), 3.71 (s, 4H), 3.14 (s, 3H), 3.00-2.82 (m, 1H), 2.64-1.57 (m, 2H).

EXAMPLE 10

1-(1-ethylpyrrolidin-3-yl)-3-methyl-8-(6-(1-methyl-1H-pyrazol-4-yl)pyridin-3-yl)-1H-imidazo[4,5-c]quinolin-2(3H)-one

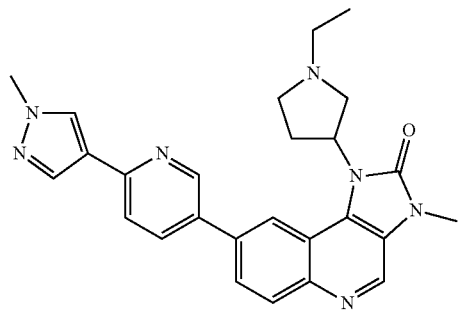

In an ice-water bath, 40 mg (1 mmol) of 60% sodium hydride was suspended in 5 mL of tetrahydrofuran and stirred for 5 minutes, added with 100 mg (0.2 mmol) of Intermediate 145 and stirred for 10 minutes, then added with 31.2 mg (0.2 mmol) of ethyl iodide dropwise and stirred at room temperature for 2 h. The reaction was monitored by TLC. After the reaction was completed, 10 mL of water was added dropwise, and extracted with dichloromethane. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 10 (20 mg), as a white solid. Yield: 22.1%. This product was dissolved in 75% ethanol, adjusted pH to 1 with 1 M HCl, stirred for 0.5 h, and evaporated to dryness to afford a hydrochloride salt. LC-MS: 454 [M+1]$^+$, $t_R$=1.305 min $^1$H NMR (400 MHz, DMSO+D$_2$O) δ 9.34 (d, J=7.2 Hz, 1H), 9.23-9.12 (m, 1H), 8.84-8.71 (m, 2H), 8.59 (s, 1H), 8.42 (q, J=9.2 Hz, 2H), 8.28 (s, 1H), 8.12 (dd, J=8.4, 3.5 Hz, 1H), 6.36-6.13 (m, 1H), 4.45-4.13 (m, 1H), 3.96 (s, 4H), 3.79-3.68 (m, 1H), 3.61 (d, J=8.6 Hz, 3H), 3.57-3.13 (m, 3H), 3.04-2.65 (m, 2H), 1.42-1.29 (m, 3H).

EXAMPLE 11

1-(1-acetylpyrrolidin-3-yl)-3-methyl-8-(6-(1-methyl-1H-pyrazol-4-yl)pyridin-3-yl)-1H-imidazo[4,5-c]quinolin-2(3H)-one

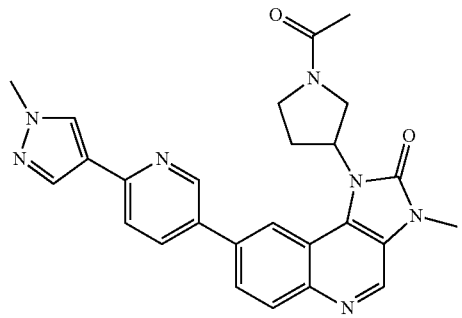

50 mg (0.1 mmol) of Intermediate 145 was suspended in 5 mL of dichloromethane, added with 50 mg (0.5 mmol) of triethylamine dropwise and stirred for 5 minutes, then added with 15 mg (0.15 mmol) of acetic anhydride and stirred at room temperature for 2 h. The reaction was monitored by TLC. After the reaction was completed, the reaction solution was rotary evaporated to dryness to afford a crude product. The crude product was purified with preparative silica gel plate (dichloromethane/methanol=10/1, V/V) to afford the target compound of Example 11 (43 mg), as a white-yellow solid. Yield: 92.1%. This product was dissolved in 75% ethanol, adjusted pH to 1 with 1 M HCl, stirred for 0.5 h, and evaporated to dryness to afford a hydrochloride salt. LC-MS: 468 [M+1]$^+$, $t_R$=1.407 min $^1$H NMR (400 MHz, DMSO) δ 9.39 (d, J=4.4 Hz, 1H), 9.17 (d, J=14.9 Hz, 1H), 8.94-8.69 (m, 3H), 8.60-8.40 (m, 3H), 8.31 (dd, J=8.6, 4.4 Hz, 1H), 6.16-5.83 (m, 1H), 4.33-4.05 (m, 2H), 3.99 (s, 3H), 3.79-3.49 (m, 2H), 3.61 (s, 3H), 2.88-2.58 (m, 2H), 2.02 (d, J=15.3 Hz, 1H).

EXAMPLE 12

1-(1-benzylpyrrolidin-3-yl)-3-methyl-8-(6-(1-methyl-1H-pyrazol-4-yl)pyridin-3-yl)-1H-imidazo[4,5-c]quinolin-2(3H)-one

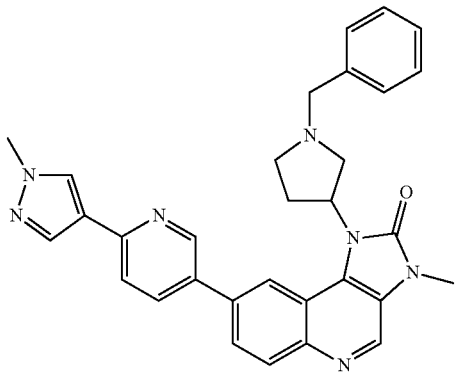

In an ice-water bath, 20 mg (0.5 mmol) of 60% sodium hydride was suspended in 5 mL of tetrahydrofuran and stirred for 5 minutes, then added with 50 mg (0.1 mmol) of Intermediate 145 and stirred for 10 minutes, followed by the dropwise addition of 17.14 mg (0.1 mmol) of benzyl bromide, and stirred at room temperature for 2 h. The reaction was monitored by TLC. After the reaction was completed, 10 mL of water was added dropwise, and extracted with dichloromethane. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 12 (18 mg), as a white solid. Yield: 35.3%. LC-MS: 516 [M+1]$^+$, $t_R$=1.486 min $^1$H NMR (400 MHz, DMSO+D$_2$O) δ 9.39 (s, 1H), 9.19 (d, J=26.9 Hz, 1H), 8.92-8.70 (m, 2H), 8.68-8.57 (m, 1H), 8.48 (d, J=9.0 Hz, 1H), 8.42 (d, J=9.0 Hz, 1H), 8.38-8.26 (m, 1H), 8.13 (dd, J=17.1, 8.3 Hz, 1H), 7.76-7.22 (m, 5H), 6.42-6.16 (m, 1H), 4.82-4.32 (m, 2H), 4.10-3.87 (m, 6H), 3.64-3.37 (m, 4H), 3.11-2.67 (m, 2H).

EXAMPLE 13

1-(1-((4-chlorphenyl)sulfonyl)pyrrolidin-3-yl)-3-methyl-8-(6-(1-methyl-1H-pyrazol-4-yl)pyridin-3-yl)-1H-imidazo[4,5-c]quinolin-2(3H)-one

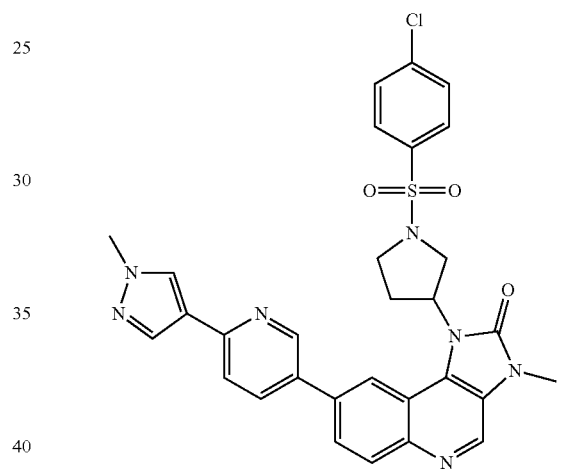

100 mg (0.2 mmol) of Intermediate 145 was suspended in 5 mL of dichloromethane, added with 100 mg (1 mmol) of triethylamine dropwise and stirred for 5 minutes, followed by the addition of 63.3 mg (0.3 mmol) of 4-chlorobenzenesulfonyl chloride, and stirred at room temperature overnight. The reaction was monitored by TLC. After the reaction was completed, 10 mL of saturated sodium bicarbonate aqueous solution was added, stirred for 20 minutes, and separated into layers. The aqueous phase was extracted with dichloromethane, and the organic phases were combined, dried, and rotary evaporated to dryness to afford a crude product. The crude product was purified by silica gel column chromatography (dichloromethane/methanol=20/1, V:V) to afford 50 mg of the target compound of Example 13, as a white solid. Yield: 41.7%. LC-MS: 600 [M+1]$^+$, $t_R$=1.860 min $^1$H NMR (400 MHz, CDCl$_3$) δ 8.92 (d, J=2.0 Hz, 1H), 8.77 (s, 1H), 8.41-8.17 (m, 4H), 8.07 (s, 1H), 7.95 (dd, J=8.8, 1.6 Hz, 1H), 7.79 (d, J=8.5 Hz, 3H), 7.54 (d, J=8.5 Hz, 2H), 5.73-5.50 (m, 1H), 4.00 (s, 3H), 3.97-3.80 (m, 2H), 3.71 (t, J=10.3 Hz, 1H), 3.59 (s, 3H), 3.34-3.22 (m, 1H), 2.97-2.69 (m, 1H), 2.45-2.25 (m, 1H).

EXAMPLE 14

3-methyl-8-(6-(1-methyl-1H-pyrazol-4-yl)pyridin-3-yl)-1-(1-p-toluenesulfonylpyrrolidin-3-yl)-1H-imidazo[4,5-c]quinolin-2(3H)-one

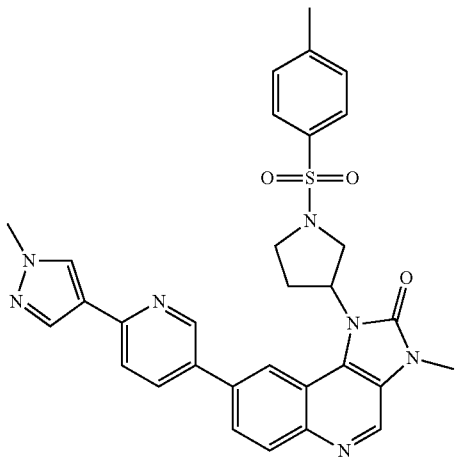

50 mg (0.1 mmol) of Intermediate 145 was suspended in 5 mL of dichloromethane, added with 50 mg (0.5 mmol) of triethylamine dropwise and stirred for 5 minutes, followed by the addition of 30 mg (0.15 mmol) of p-toluenesulfonyl chloride, and stirred at room temperature for 2 h. The reaction was monitored by TLC. After the reaction was completed, 10 mL of saturated sodium bicarbonate aqueous solution was added, stirred for 20 minutes, and separated into layers. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 14 (40 mg), as a white solid. Yield: 69.1%. LC-MS: 580 [M+1]$^+$, $t_R$=1.792 min. $^1$H NMR (400 MHz, CDCl$_3$) δ 8.94 (d, J=2.1 Hz, 1H), 8.76 (s, 1H), 8.49 (br s, 2H), 8.30 (d, J=8.8 Hz, 1H), 8.22 (br s, 1H), 8.08 (s, 1H), 7.97 (dd, J=8.9, 1.6 Hz, 1H), 7.81 (d, J=7.8 Hz, 1H), 7.75 (d, J=8.2 Hz, 2H), 7.38 (d, J=8.0 Hz, 2H), 5.69-5.43 (m, 1H), 4.00 (s, 3H), 3.96-3.81 (m, 2H), 3.67 (t, J=10.7 Hz, 1H), 3.60 (s, 3H), 3.20 (q, J=6.3 Hz, 1H), 2.86-2.68 (m, 1H), 2.48 (s, 3H), 2.34-2.19 (m, 1H).

EXAMPLE 15

3-(3-methyl-8-(6-(1-methyl-1H-pyrazol-4-yl)pyridin-3-yl)-2-oxo-2,3-dihydro-1H-imidazo[4,5-c]quinolin-1-yl)pyrrolidine-1-sulfamide

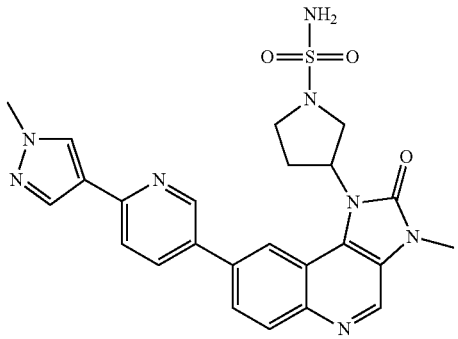

100 mg (0.2 mmol) of Intermediate 145 was suspended in 10 mL of dioxane, added dropwise with 100 mg (1 mmol) of triethylamine, and then added with 57.6 mg (0.6 mmol) of sulfamide, and heated under reflux for 8 h. The reaction was monitored by TLC. After the reaction was completed, the reaction solution was rotary evaporated to dryness, added with water, and extracted with dichloromethane. The organic phases were combined, dried, and rotary evaporated to dryness to afford a crude product. The crude product was purified with preparative silica gel plate (dichloromethane/methanol=10/1, V/V) to afford the target compound of Example 15 (18 mg), as a terreous solid. Yield: 17.8%. LC-MS: 505 [M+1]$^+$, $t_R$=1.409 min $^1$H NMR (400 MHz, CDCl$_3$+MeOD) δ 8.96 (d, J=2.1 Hz, 1H), 8.85 (s, 1H), 8.68 (s, 1H), 8.40 (d, J=6.8 Hz, 1H), 8.31 (d, J=8.9 Hz, 1H), 8.19 (s, 1H), 8.12-7.99 (m, 2H), 7.81 (d, J=8.3 Hz, 1H), 5.92-5.84 (m, 1H), 4.01 (s, 3H), 3.97-3.79 (m, 3H), 3.69 (s, 3H), 3.52-3.43 (m, 1H), 2.88-2.69 (m, 1H), 2.51-2.43 (m, 1H).

EXAMPLE 16

3-methyl-8-(6-(1-methyl-1H-pyrazol-4-yl)pyridin-3-yl)-1-(1-(2,2,2-trifluoroacetyl)pyrrolidin-3-yl)-1H-imidazo[4,5-c]quinolin-2(3H)-one

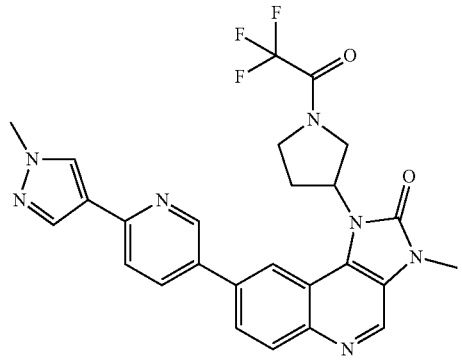

100 mg (0.194 mmol) of Intermediate 145 (in which a portion of trifluoroacetate was included), 69 mg (0.36 mmol) of 1-(3-dimethylaminopropyl)-3-ethylcarbodiimide hydrochloride, 48.6 mg (0.36 mmol) of 1-hydroxybenzotriazole and 40.7 mg (0.36 mmol) of 1,2,4-triazole-3-carboxylic acid were dissolved in 5 mL of dichloromethane, followed by the addition of 72.8 mg (0.72 mmol) of triethylamine, and stirred at room temperature overnight. The reaction was monitored by TLC. After the reaction was completed, 10 mL of saturated sodium bicarbonate aqueous solution was added, and stirred for 20 minutes. Then the reaction solution was separated into layers. The aqueous phase was extracted with dichloromethane, and the organic phases were combined, dried, and rotary evaporated to dryness to afford a crude product. The crude product was purified with preparative silica gel plate (dichloromethane/methanol=10/1, V/V) to afford the target compound of Example 16 (30 mg), as a light yellow solid. Yield: 26.1%. LC-MS: 522 [M+1]$^+$, $t_R$=1.690 min $^1$H NMR (400 MHz, CDCl$_3$) δ 8.86 (s, 1H), 8.78 (s, 1H), 8.30 (d, J=9.1 Hz, 1H), 8.16 (d, J=11.8 Hz, 1H), 8.02 (s, 2H), 7.89 (dd, J=16.4, 7.4 Hz, 2H), 7.60 (d, J=8.1 Hz, 1H), 5.91-5.62 (m, 1H), 4.74-4.37 (m, 1H), 4.31-4.06 (m, 2H), 4.00 (s, 3H), 3.97-3.78 (m, 2H), 3.62 (s, 3H), 3.15-2.89 (m, 1H), 2.70-2.37 (m, 1H).

(III) Scheme III:

Scheme III

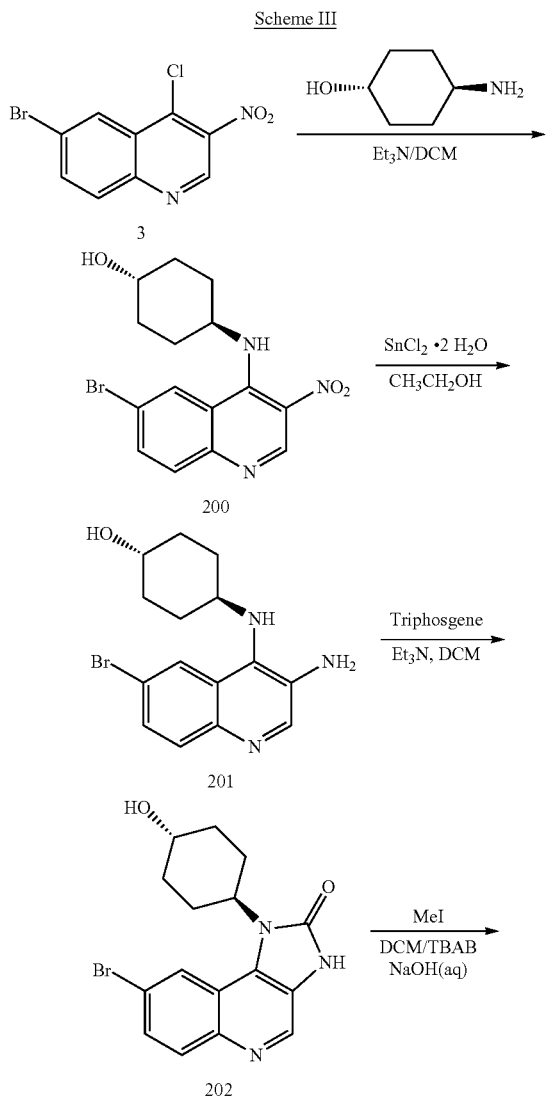

INTERMEDIATE 200

(1r,4r)-4-((6-bromo-3-nitroquinolin-4-yl)amino)cyclohexanol

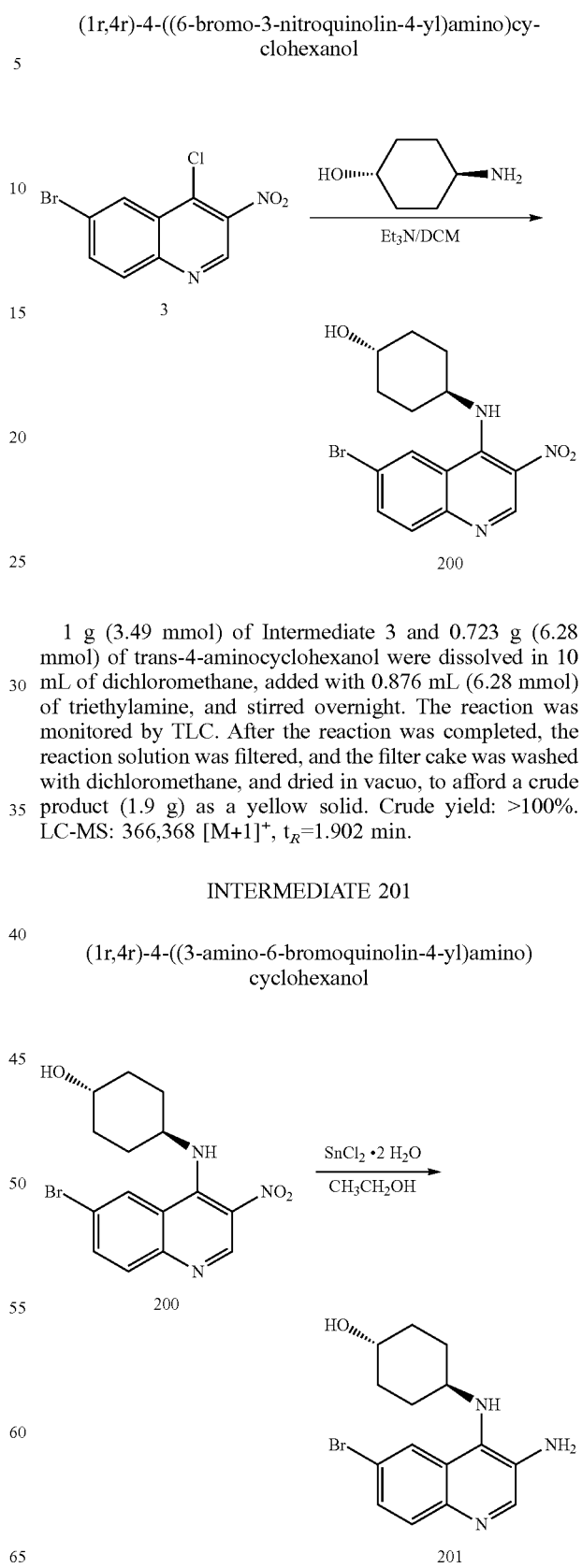

1 g (3.49 mmol) of Intermediate 3 and 0.723 g (6.28 mmol) of trans-4-aminocyclohexanol were dissolved in 10 mL of dichloromethane, added with 0.876 mL (6.28 mmol) of triethylamine, and stirred overnight. The reaction was monitored by TLC. After the reaction was completed, the reaction solution was filtered, and the filter cake was washed with dichloromethane, and dried in vacuo, to afford a crude product (1.9 g) as a yellow solid. Crude yield: >100%. LC-MS: 366,368 [M+1]$^+$, $t_R$=1.902 min.

INTERMEDIATE 201

(1r,4r)-4-((3-amino-6-bromoquinolin-4-yl)amino)cyclohexanol 1.9 g (3.49 mmol) of Intermediate 200 was dissolved in 20 mL of ethanol, added with 3.9 g (17.45 mmol) of stannous chloride in batches, and stirred at room temperature for 2 h. The reaction was monitored by TLC. After the reaction was completed, ethanol was rotary evaporated to dryness, and the residue was added with saturated sodium bicarbonate solution. The aqueous layer was extracted with ethyl acetate, and the organic phases were combined, dried, and rotary evaporated to dryness, to afford a crude product (1.2 g) as a yellow solid. Crude yield: >100%. LC-MS: 336,338 [M+1]$^+$, $t_R$=1.351 min.

INTERMEDIATE 202

8-bromo-1-((1r,4r)-4-hydroxycyclohexyl)-1H-imidazo[4,5-c]quinolin-2(3H)-one

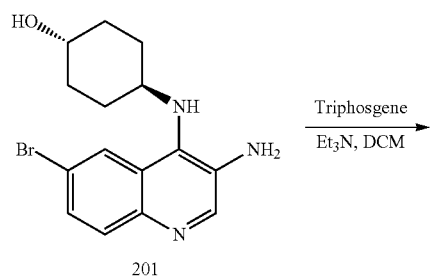

201

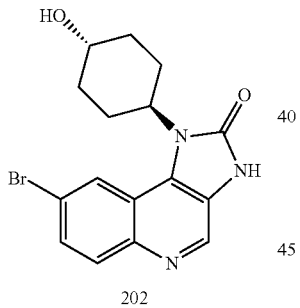

202

At 0° C., 1.2 g (3.49 mmol) of Intermediate 201 was suspended in 20 mL of dichloromethane, added with 1.7 mL (12.22 mmol) of triethylamine, then added with a solution of 0.52 g (1.75 mmol) of triphosgene dissolved in 20 mL of dichloromethane dropwise, and stirred for 5 h. The reaction was monitored by TLC. After the reaction was completed, a saturated sodium bicarbonate solution was added, stirred for 30 minutes, and separated into layers. The aqueous phase was extracted with dichloromethane, and the organic phases were combined, dried, and rotary evaporated to dryness to afford a crude product (1 g). This crude product had an extremely high polarity and was used directly in the next step without further purification.

INTERMEDIATE 203

8-bromo-1-((1r,4r)-4-hydroxycyclohexyl)-3-methyl-1H-imidazo[4,5-c]quinolin-2(3H)-one

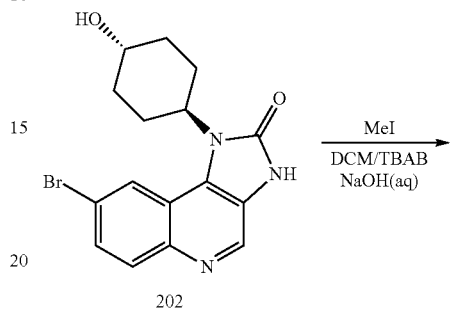

202

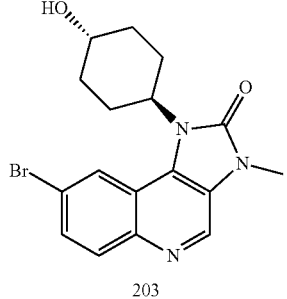

203

1 g (3.49 mmol) of Intermediate 202 was suspended in 30 mL of dichloromethane, added with 0.11 g (0.349 mmol) of tetrabutylammonium bromide and 30 mL of 10% sodium hydroxide solution, stirred for 10 minutes, followed by the addition of 1.5 g (10.47 mmol) of methyl iodide, and stirred at room temperature for 7 h. The reaction was monitored by TLC. After the reaction was completed, the reaction solution was allowed to stand and separated into layers. The organic phase was separated off, and the aqueous phase was extracted with dichloromethane. The organic phases were combined, dried, and rotary evaporated to dryness, to afford a crude product. The crude product was purified by silica gel column chromatography (eluent: ethyl acetate/methanol=20/1, V:V) to afford a product (0.4 g) as a deep yellow solid. Yield: 38.8%. LC-MS: 376,378 [M+1]$^+$, $t_R$=1.541 min.

EXAMPLE 17

1-((1r,4r)-4-hydroxycyclohexyl)-3-methyl-8-(6-(1-methyl-1H-pyrazol-4-yl)pyridin-3-yl)-1H-imidazo[4,5-c]quinolin-2(3H)-one

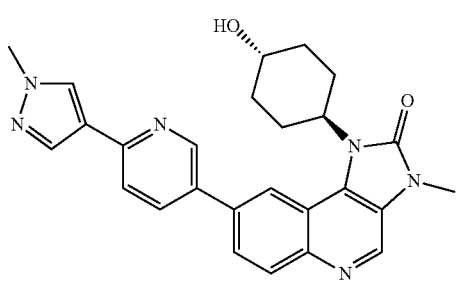

204

Under the protection of nitrogen, 0.1 g (0.36 mmol) of Intermediate 203 and 0.15 g (0.54 mmol) of Intermediate 9A were dissolved in 15 mL of dioxane, added with 0.469 g (1.44 mmol) of cesium carbonate and 15 mL of 2M aqueous sodium carbonate solution, followed by the addition of 0.029 g (0.036 mmol) of [1,1-bis(diphenylphosphino)ferrocene]palladium chloride, and heated at 110° C. for 5 h. The reaction was monitored by TLC. After the reaction was completed, most of dioxane was removed by rotary evaporation, and the residue was added with water and extracted with dichloromethane. The organic phases were combined, dried, and rotary evaporated to dryness to afford a crude product. The crude product was purified with preparative silica gel plate (dichloromethane/methanol=10/1, V/V) to afford the target compound of Example 17 (0.032 g), as a terreous powder. This product was dissolved in 75% ethanol, adjusted pH to 1 with 1 M HCl, stirred for 0.5 h, and evaporated to dryness to afford a hydrochloride salt. LC-MS: 455 [M+1]$^+$, $t_R$=1.420 min $^1$H NMR (400 MHz, DMSO+D$_2$O) δ 9.24 (s, 1H), 9.07 (s, 1H), 8.59 (s, 1H), 8.49 (d, J=9.6 Hz, 2H), 8.40 (s, 2H), 8.22 (s, 1H), 8.06 (d, J=8.4 Hz, 1H), 5.03 (t, J=11.8 Hz, 1H), 3.95 (s, 3H), 3.66-3.59 (m, 1H), 3.56 (s, 3H), 2.39-2.16 (m, 1H), 2.07 (t, J=12.5 Hz, 4H), 1.62-1.41 (m, 3H).

(IV) Scheme IV:

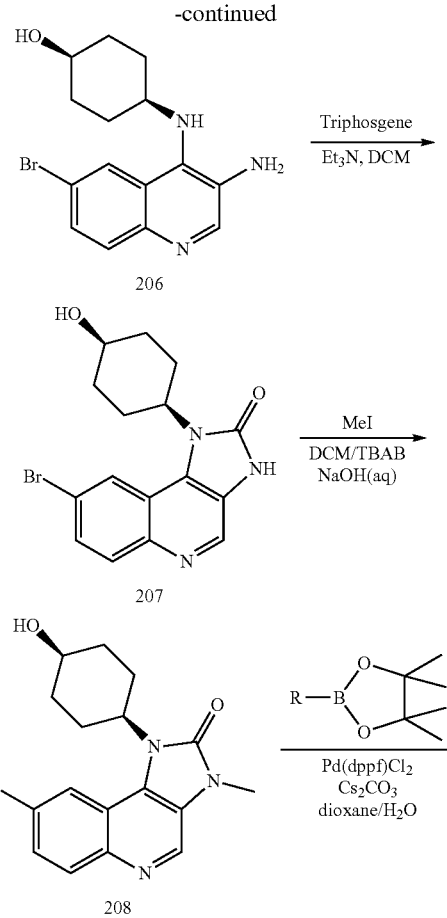

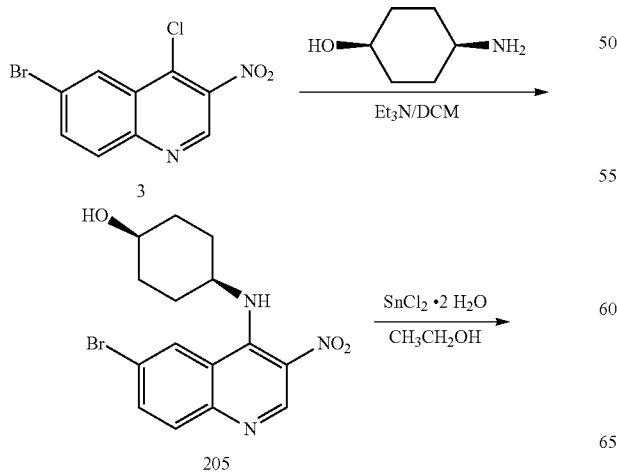

INTERMEDIATE 205

(1s,4s)-4-((6-bromo-3-nitro-4-yl)amino)cyclohexanol

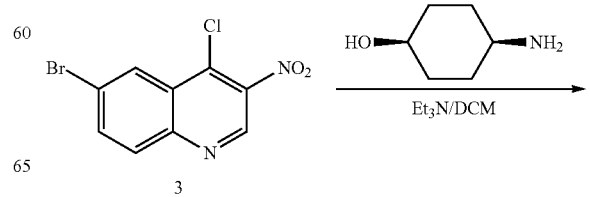

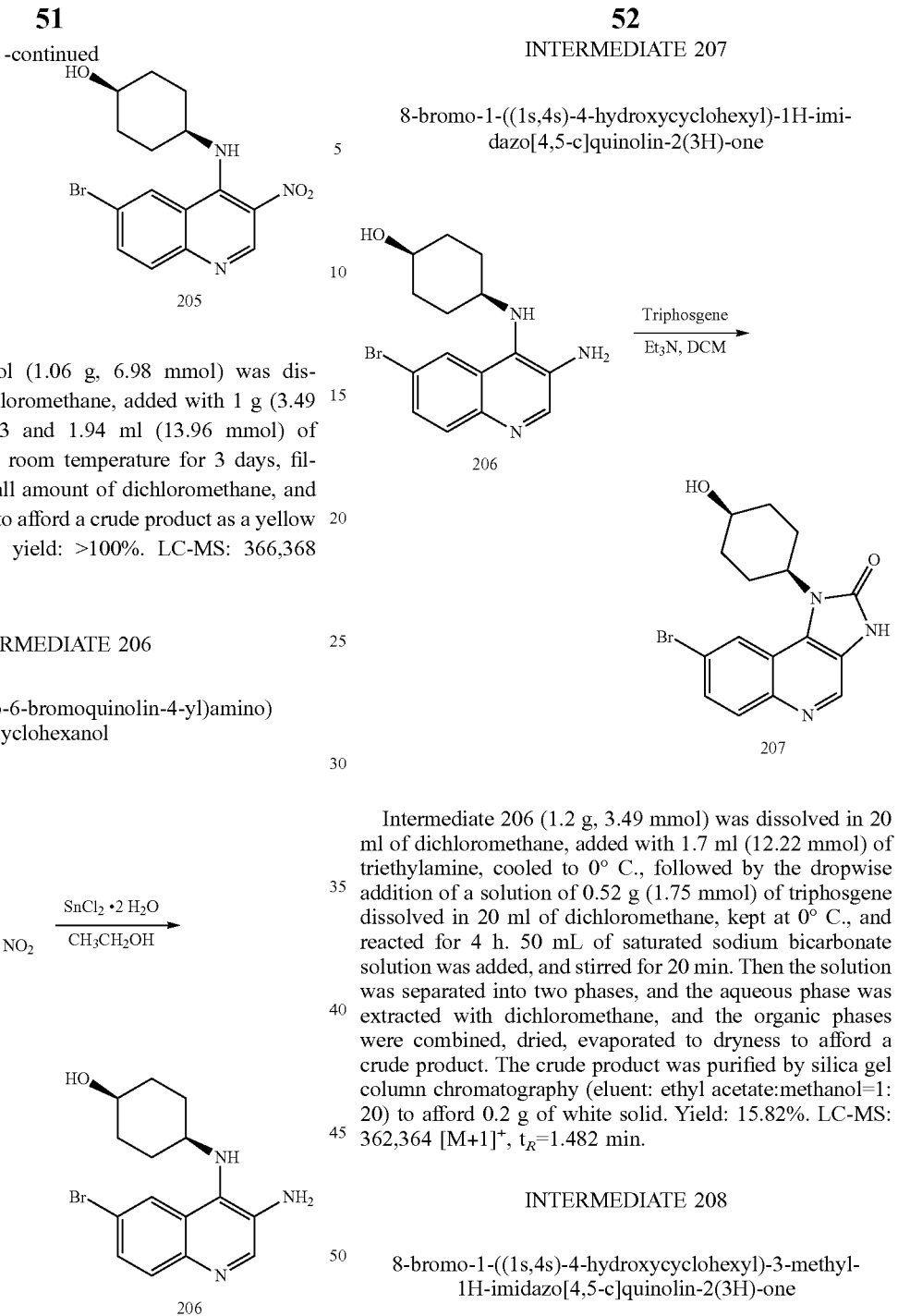

Cis-4-aminocyclohexanol (1.06 g, 6.98 mmol) was dissolved in 10 ml of dichloromethane, added with 1 g (3.49 mmol) of Compound 3 and 1.94 ml (13.96 mmol) of triethylamine, stirred at room temperature for 3 days, filtered, rinsed with a small amount of dichloromethane, and was pumped to dryness to afford a crude product as a yellow solid (1.945 g). Crude yield: >100%. LC-MS: 366,368 $[M+1]^+$, $t_R$=1.913 min.

INTERMEDIATE 206

(1s,4s)-4-((3-amino-6-bromoquinolin-4-yl)amino)cyclohexanol

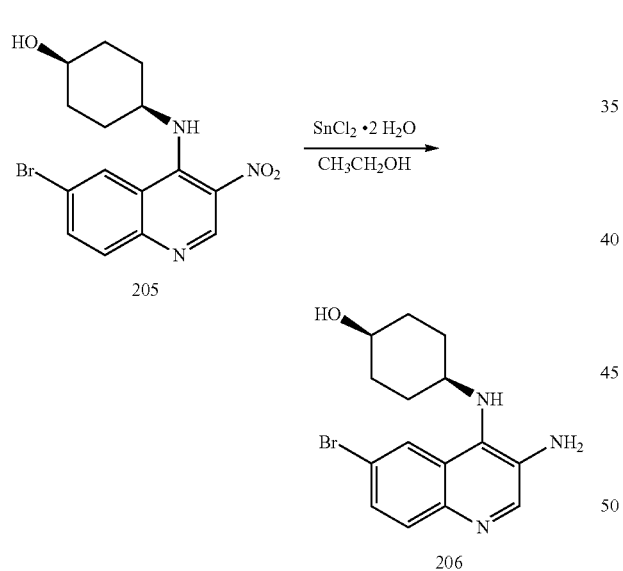

Intermediate 205 (1.945 g, 3.49 mmol) was dissolved in 20 ml of ethanol, added with 3.937 g (17.45 mmol) of water and stannous chloride in batches, stirred at room temperature overnight, evaporated ethanol to dryness, added with 50 ml of ethyl acetate, and adjusted pH to 9 with 10% sodium hydroxide solution. Then the solution was separated into two phases, the aqueous phase was extracted with ethyl acetate, and the organic phases were combined, dried, evaporated to dryness to afford a crude product (1.2 g), as a yellow solid. Crude yield: >100%. LC-MS: 336,338 $[M+1]^+$, $t_R$=1.447 min.

INTERMEDIATE 207

8-bromo-1-((1s,4s)-4-hydroxycyclohexyl)-1H-imidazo[4,5-c]quinolin-2(3H)-one

Intermediate 206 (1.2 g, 3.49 mmol) was dissolved in 20 ml of dichloromethane, added with 1.7 ml (12.22 mmol) of triethylamine, cooled to 0° C., followed by the dropwise addition of a solution of 0.52 g (1.75 mmol) of triphosgene dissolved in 20 ml of dichloromethane, kept at 0° C., and reacted for 4 h. 50 mL of saturated sodium bicarbonate solution was added, and stirred for 20 min. Then the solution was separated into two phases, and the aqueous phase was extracted with dichloromethane, and the organic phases were combined, dried, evaporated to dryness to afford a crude product. The crude product was purified by silica gel column chromatography (eluent: ethyl acetate:methanol=1: 20) to afford 0.2 g of white solid. Yield: 15.82%. LC-MS: 362,364 $[M+1]^+$, $t_R$=1.482 min.

INTERMEDIATE 208

8-bromo-1-((1s,4s)-4-hydroxycyclohexyl)-3-methyl-1H-imidazo[4,5-c]quinolin-2(3H)-one

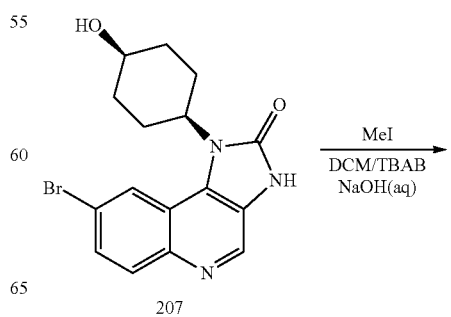

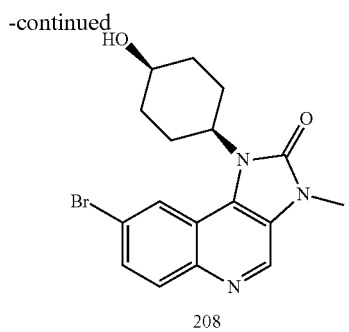

208

Intermediate 207 (200 mg, 0.55 mmol) was dissolved in 10 ml of dichloromethane, added with 18 mg (0.055 mmol) of tetrabutylammonium bromide and 10 ml of 10% sodium hydroxide solution, stirred for 5 min, followed by the addition of 234 mg (1.65 mmol) of methyl iodide, stirred at room temperature for 7.5 h, and allowed to stand and separated into two phases. The aqueous phase was extracted with dichloromethane, and the organic phases were combined, dried, evaporated to dryness to afford a crude product. The crude product was purified by silica gel column chromatography (methanol:dichloromethane=1:10) to afford 120 mg of white solid. Yield: 57.97%.

EXAMPLE 18

1-((1s,4s)-4-hydroxycyclohexyl)-3-methyl-8-(6-(1-methyl-1H-pyrazol-4-yl)pyridin-3-yl)-1H-imidazo[4,5-c]quinolin-2(3H)-one

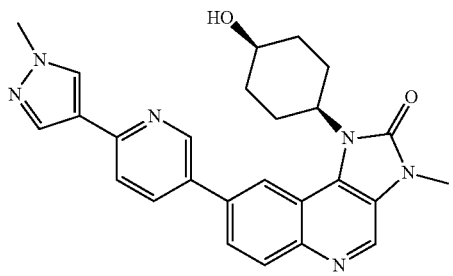 [SMILES: Cn1cc(-c2ccc(-c3ccc4ncc5c(c4c3)n([C@H]3CC[C@@H](O)CC3)c(=O)n5C)cn2)cn1]

Intermediate 208 (120 mg, 0.32 mmol) was dissolved in 3 ml of dioxane, added with 137 mg (0.48 mmol) of Intermediate 9A, 417 mg (1.28 mmol) of cesium carbonate, and 2 ml of 2M aqueous sodium carbonate solution, followed by the addition of 12 mg (0.016 mmol) [1,1-bis(diphenylphosphino)ferrocene]palladium chloride under the protection of nitrogen, and heated at 110° C. for 8 h. Then the reaction solution was cooled to room temperature, evaporated dioxane to dryness, added with 10 ml of water and 10 ml of dichloromethane, and separated into two phases. The aqueous phase was extracted with dichloromethane, and the organic phases were combined, dried, evaporated to dryness to afford a crude product. The crude product was purified by silica gel column chromatography (methanol:dichloromethane=1:10) to afford the target compound of Example 18 (125 mg), as an orange-yellow solid. Yield: 85.94%. LC-MS: 455 [M+1]$^+$, $t_R$=1.600 min $^1$H NMR (400 MHz, DMSO) δ 8.99 (s, 1H), 8.89 (s, 1H), 8.78-8.20 (m, 3H), 8.15 (d, J=8.8 Hz, 1H), 8.07 (s, 1H), 8.00 (d, J=8.7 Hz, 1H), 7.77 (d, J=8.0 Hz, 1H), 4.95-4.76 (m, 1H), 4.65 (br s, 1H), 3.98 (s, 1H), 3.92 (s, 3H), 3.52 (s, 3H), 2.81 (s, 2H), 1.91 (d, J=9.2 Hz, 2H), 1.69 (t, J=11.3 Hz, 4H). This product was dissolved in 75% ethanol, adjusted to pH 1 with 1 M HCl, stirred for 0.5 h, and evaporated to dryness to afford a hydrochloride salt.

EXAMPLE 19

1-((1s,4s)-4-hydroxycyclohexyl)-3-methyl-8-(6-phenylpyridin-3-yl)-1H-imidazo[4,5-c]quinolin-2(3H)-one

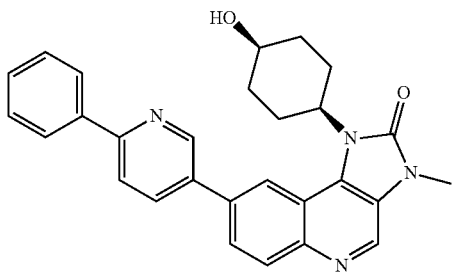 [SMILES: Cn1c(=O)n([C@H]2CC[C@@H](O)CC2)c2c3cc(-c4ccc(-c5ccccc5)nc4)ccc3ncc21]

Under the protection of nitrogen, 74.7 mg (0.32 mmol) of 5-bromo-2-phenylpyridine, 97.5 mg (0.384 mmol) of bis(pinacolato)diboron, 94.2 mg (0.96 mmol) of potassium acetate and 10.6 mg (0.013 mmol) of Pd(dppf)Cl$_2$.CH$_2$Cl$_2$ were suspended in 3 ml of 1,4-dioxane, heated to 95° C. and stirred for 2 h. The resulting reaction solution was cooled for later use. To the above reaction solution, Intermediate 208 (80 mg, 0.213 mmol), 278 mg (0.852 mmol) of cesium carbonate, 1 ml of 2M aqueous sodium carbonate solution, and 3 ml of 1,4-dioxane were added, and then 7 mg (0.0085 mmol) of Pd(dppf)Cl$_2$.CH$_2$Cl$_2$ was added under the protection of nitrogen. The reaction mixture was stirred at 110° C. for 4.5 h, cooled to room temperature, evaporated dioxane to dryness, added with 10 ml of water and 10 ml of dichloromethane, and separated into two phases. The aqueous phase was extracted with dichloromethane, and the organic phases were combined, dried, evaporated to dryness to afford a crude product. The crude product was purified by silica gel column chromatography (methanol:dichloromethane=1:10) to afford the target compound of Example 19 (20 mg), as a light yellow powder. Yield: 21%. LC-MS: 451 [M+1]$^+$, $t_R$=1.913 min $^1$H NMR (400 MHz, DMSO) δ 9.19 (s, 1H), 8.94 (s, 1H), 8.45 (s, 1H), 8.20 (dd, J=8.0, 4.8 Hz, 4H), 8.10 (dd, J=17.4, 8.4 Hz, 2H), 7.60-7.45 (m, 3H), 4.89 (t, J=12.7 Hz, 1H), 4.72 (s, 1H), 4.00 (s, 1H), 3.55 (s, 3H), 2.84 (s, 2H), 1.92 (d, J=12.1 Hz, 2H), 1.71 (t, J=11.3 Hz, 4H).

EXAMPLE 20

1-((1s,4s)-4-hydroxycyclohexyl)-8-(6-methoxyl-5-methylpyridin-3-yl)-3-methyl-1H-imidazo[4,5-c]quinolin-2(3H)-one

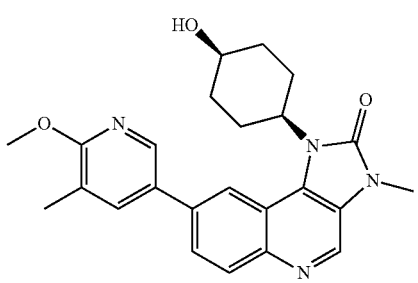

Under the protection of nitrogen, 0.1 g (0.27 mmol) of Intermediate 208 and 0.134 g (0.54 mmol) of 6-methoxyl-5-methylpyridine-3-boric acid pinacol ester (Intermediate 4a) were dissolved in 15 mL of dioxane, added with 0.351 g (1.08 mmol) of cesium carbonate, 15 mL of 2M aqueous sodium carbonate solution, followed by the addition of 0.022 g (0.027 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution by rotary evaporation, and the residue was added with water and extracted with dichloromethane. The organic phases were combined, dried, and rotary evaporated to dryness to afford a crude product. The crude product was purified with preparative silica gel plate (dichloromethane/methanol=10/1, V/V) to afford the target compound of Example 20 (50 mg), as a white solid. Yield: 44.6%. LC-MS: 419 [M+1]$^+$, $t_R$=1.759 min $^1$H NMR (400 MHz, DMSO) δ 8.89 (s, 1H), 8.51 (s, 2H), 8.13 (d, J=8.8 Hz, 1H), 8.08 (s, 1H), 7.99-7.87 (m, 1H), 4.84 (t, J=12.8 Hz, 1H), 4.58 (s, 1H), 3.97 (s, 3H), 3.53 (s, 3H), 2.80 (s, 2H), 2.26 (s, 3H), 1.92 (d, J=12.4 Hz, 2H), 1.68 (t, J=11.4 Hz, 4H).

EXAMPLE 21

1-((1s,4s)-4-hydroxycyclohexyl)-3-methyl-8-(1-phenyl-1H-pyrazol-4-yl)-1H-imidazo[4,5-c]quinolin-2(3H)-one

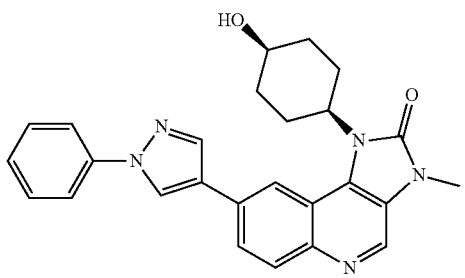 [SMILES: Cn1c(=O)n([C@H]2CC[C@@H](O)CC2)c2c3cc(-c4cnn(-c5ccccc5)c4)ccc3ncc21]

Under the protection of nitrogen, 0.1 g (0.27 mmol) of Intermediate 208 and 0.108 g (0.4 mmol) of 1-phenyl-1H-pyrazole-4-boronic acid pinacol ester (Intermediate 4b) were dissolved in 15 mL of dioxane, added with 0.351 g (1.08 mmol) of cesium carbonate and 15 mL of 2M aqueous sodium carbonate solution, followed by the addition of 0.022 g (0.027 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution by rotary evaporation, and the residue was added with water and extracted with dichloromethane. The organic phases were combined, dried, and rotary evaporated to dryness to afford a crude product. The crude product was purified by preparative silica gel plate (dichloromethane/methanol=10/1, V/V) to afford the target compound of Example 21 (60 mg) as a yellowish white solid. Yield: 50.8%. LC-MS: 440 [M+1]$^+$, $t_R$=1.822 min $^1$H NMR (400 MHz, DMSO) δ 9.22 (s, 1H), 8.87 (s, 1H), 8.61 (s, 2H), 8.11 (d, J=8.7 Hz, 1H), 8.06 (d, J=9.1 Hz, 1H), 7.95 (d, J=8.3 Hz, 2H), 7.57 (t, J=7.8 Hz, 2H), 7.37 (t, J=7.2 Hz, 1H), 4.93-4.79 (m, 1H), 4.07 (s, 1H), 3.94 (s, 1H), 3.55 (s, 4H), 2.93 2.68 (m, 2H), 2.08-1.86 (m, 2H), 1.85-1.50 (m, 4H).

EXAMPLE 22

1-((1s,4s)-4-hydroxycyclohexyl)-3-methyl-8-(6-methylpyridin-3-yl)-1H-imidazo[4,5-c]quinolin-2(3H)-one

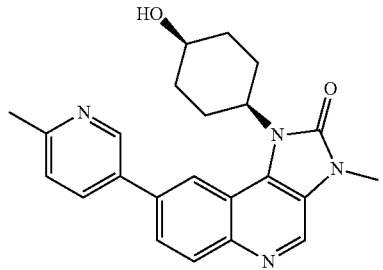

Under the protection of nitrogen, 0.1 g (0.27 mmol) of Intermediate 208 and 0.055 g (0.4 mmol) of 6-methylpyridine-3-boric acid (Intermediate 4c) were dissolved in 15 mL of dioxane, added with 0.351 g (1.08 mmol) of cesium carbonate and 15 mL of 2M aqueous sodium carbonate solution and with 0.022 g (0.027 mmol) [1,1-bis(di-phenylphosphino)ferrocene]palladium chloride, and heated at 110° C. for 5 h. The reaction was monitored by TLC. After the reaction was completed, most of dioxane was removed from the reaction solution by rotary evaporation, and the residue was added with water and extracted with dichloromethane. The organic phases were combined, dried, and rotary evaporated to dryness to afford a crude product. The crude product was purified with preparative silica gel plate (dichloromethane/methanol=10/1, V/V) to afford the target compound of Example 22 (68 mg), as a light yellow solid. Yield: 65.38%. LC-MS: 389 [M+1]$^+$, $t_R$=1.29 min H NMR (400 MHz, DMSO) δ 8.92 (d, J=13.8 Hz, 2H), 8.75-8.05 (m, 3H), 7.96 (d, J=8.8 Hz, 1H), 7.40 (d, J=8.0 Hz, 1H), 4.83 (t, J=12.7 Hz, 1H), 4.64 (s, 1H), 3.97 (s, 1H), 3.53 (s, 3H), 3.23-3.08 (m, 1H), 2.79 (s, 2H), 2.55 (s, 3H), 1.90 (d, J=12.9 Hz, 2H), 1.80-1.47 (m, 5H).

(V) Scheme V:

Scheme V

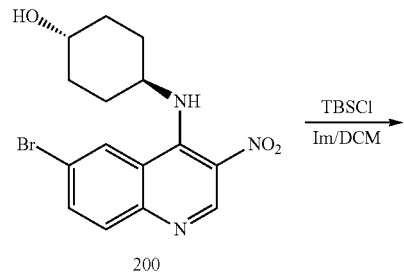
200

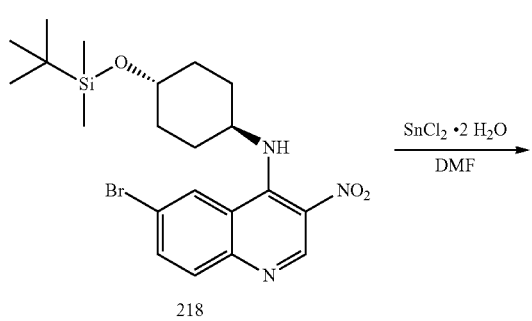
218

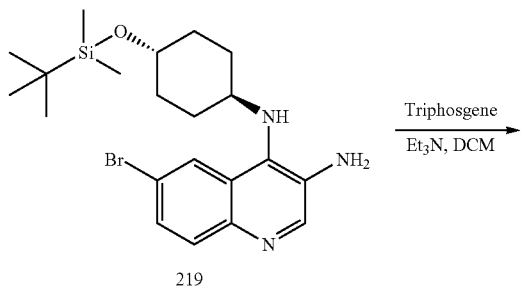
219

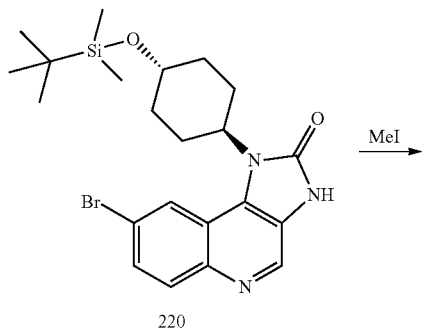
220

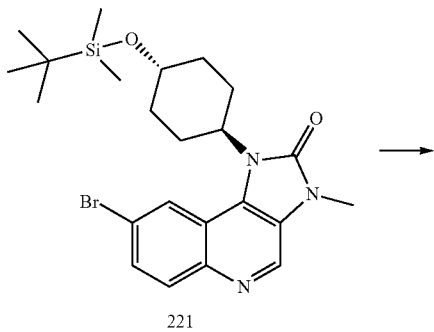
221

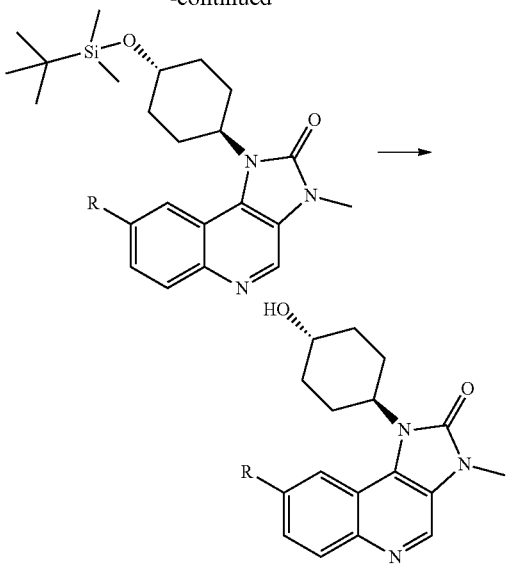

INTERMEDIATE 218

6-bromo-N-((1r,4r)-4-((tert-butyldimethylsilyl)oxy)cyclohexyl)-3-nitroquinoline-4-amine 2.5 g (7 mmol) of Intermediate 200 and 1.58 g (10.5 mmol) of tert-butyldimethylchlorosilane was dissolved in 50 mL of dichloromethane, added with 0.76 g (11.2 mmol) of imidazole, and stirred at room temperature for 24 h. The reaction was monitored by TLC. After the reaction was completed, the reaction solution was rotary evaporated to dryness, added with water and ethyl acetate, and separated into two layers. The aqueous layer was extracted with ethyl acetate, and the organic phases were combined, dried, and rotary evaporated to dryness to afford 3 g of yellow solid. $^1$H NMR (400 MHz, CDCl$_3$) δ 9.53 (d, J=8.4 Hz, 1H), 9.34 (s, 1H), 8.32 (d, J=1.8 Hz, 1H), 7.96-7.72 (m, 2H), 4.18 (dd, J=8.7, 3.8 Hz, 1H), 4.01-3.66 (m, 1H), 2.36-2.15 (m, 2H), 1.98 (dd, J=9.9, 3.8 Hz, 2H), 1.70-1.47 (m, 4H), 0.90 (s, 9H), 0.07 (d, J=3.0 Hz, 6H).

INTERMEDIATE 219

6-bromo-N-((1r,4r)-4-((tert-butyldimethylsilyl)oxy)cyclohexyl)quinoline-3,4-diamine

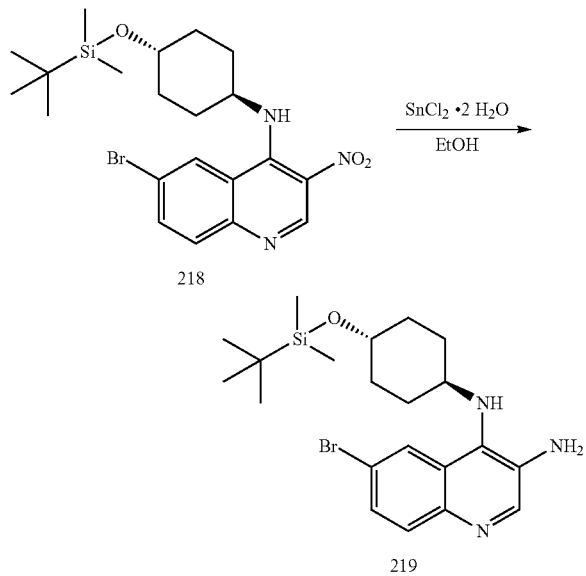

In an ice-water bath, 4.8 g (10 mmol) of Intermediate 218 was suspended in 100 mL of ethanol, added with 11.28 g (50 mmol) of stannous chloride dihydrate in batches over a period of 30 minutes, and stirred at room temperature for 2 h. The reaction was monitored by TLC. After the reaction was completed, to the reaction solution, 10% aqueous sodium hydroxide solution was added dropwise to pH 8-9. The reaction solution was filtered, and the filtrate was extracted with dichloromethane, and the filter cake was washed with dichloromethane. The organic phases were combined, washed with water and with brine, dried, rotary evaporated to dryness to afford a crude product (6 g) as a brownish red solid, which is used directly in the next step.

INTERMEDIATE 220

8-bromo-1-((1r,4r)-4-((tert-butyldimethylsilyl)oxy)cyclohexyl)-1H-imidazo[4,5-c]quinolin-2(3H)-one

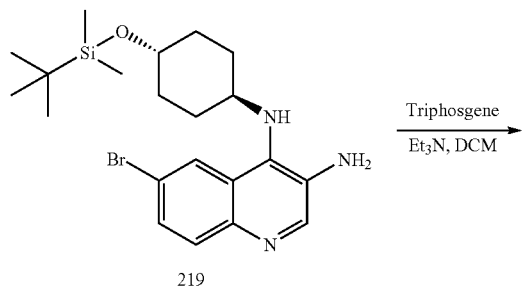

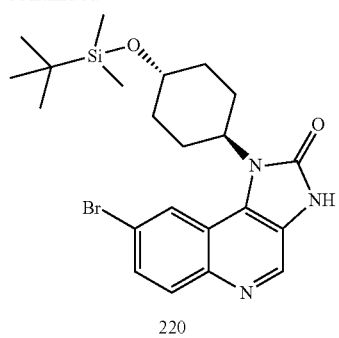

In an ice-water bath, 6 g (10 mmol) of Intermediate 219 was dissolved in 80 mL of dichloromethane, added with 3.5 g (35 mmol) of triethylamine, and stirred for 5 minutes. A solution of 1.5 g (5 mmol) of triphosgene dissolved in 60 mL of dichloromethane was added dropwise, and stirred at 0° C. for 4 h. The reaction was monitored by TLC. After the reaction was completed, to the reaction solution, 100 mL of saturated sodium bicarbonate solution was added dropwise to quench the reaction, and stirred for 10 minutes. The organic phase was separated off, and the aqueous phase was extracted with dichloromethane, and the organic phases were combined, dried, and rotary evaporated to dryness to afford a crude product. The crude product was purified by silica gel column chromatography (eluent: ethyl acetate/petroleum ether=1/1, V/V) to afford a product (1.1 g) as a yellow solid. Yield: 23.1%. $^1$H NMR (400 MHz, CDCl$_3$) δ 9.53 (s, 1H), 8.30 (s, 1H), 8.12 (s, 1H), 7.80 (d, J=9.0 Hz, 1H), 3.88-3.75 (m, 1H), 2.76 (q, J=14.8 Hz, 2H), 2.19-2.09 (m, 2H), 2.08-1.95 (m, 3H), 1.71-1.58 (m, 3H), 0.95 (s, 9H), 0.14 (s, 6H).

INTERMEDIATE 221

8-bromo-1-((1r,4r)-4-((tert)-butyldimethylsilyl)oxy)cyclohexyl)-3-methyl-1H-imidazo[4,5-c]quinolin-2(3H)-one

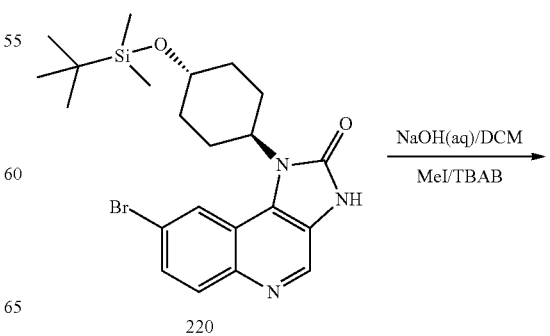

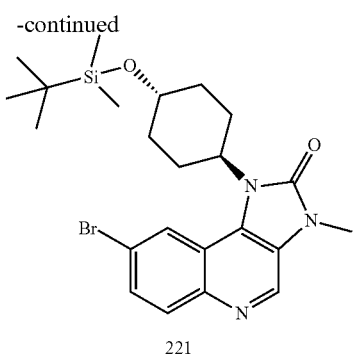

1.1 g (2.3 mmol) of Intermediate 210 was dissolved in 50 mL of dichloromethane, added with 0.074 g (0.23 mmol) of tetrabutylammonium bromide and 50 mL of 10% aqueous sodium hydroxide solution, stirred for 10 minutes, then added with 0.98 g (6.9 mmol) of methyl iodide, and stirred overnight. The reaction was monitored by TLC. After the reaction was completed, the organic phase was separated off, and the aqueous phase was extracted with dichloromethane. The organic phases were combined, dried, and rotary evaporated to dryness to afford a crude product. The crude product was purified by silica gel column chromatography (eluent: ethyl acetate/petroleum ether=1/1, V/V) to afford a product (0.4 g) as a yellow solid. Yield: 36.4%.

INTERMEDIATE 222

1-((1r,4r)-4-((tert-butyldimethylsilyl)oxy)cyclohexyl)-3-methyl-8-(1-phenyl-1H-pyrazol-4-yl)-1H-imidazo[4,5-c]quinolin-2(3H)-one

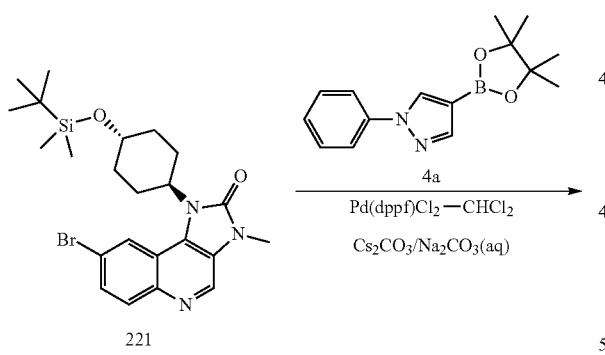

Under the protection of nitrogen, 0.1 g (0.2 mmol) of Intermediate 221 and 0.081 g (0.3 mmol) of Intermediate 4a were dissolved in 10 mL of dioxane, added with 0.26 g (15.8 mmol) of cesium carbonate and 10 mL of 2M aqueous sodium carbonate solution, then added with 0.016 g (0.02 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution. The residue was added with water, and extracted with dichloromethane. The organic phases were combined, dried, and rotary evaporated to dryness to afford a crude product. The crude product was purified by preparative silica gel plate (dichloromethane/methanol=10/1, V/V) to afford a product (50 mg) as a yellow solid. Yield: 45.9%.

| Batch No. | Amount of Raw Material (g) | Amount of Product (g) | Yield: (%) |
|---|---|---|---|
| 022-023 | 0.1 | 0.05 | 45.9 |

EXAMPLE 23

1-((1r,4r)-4-hydroxycyclohexyl)-3-methyl-8-(1-phenyl-1H-pyrazol-4-yl)-1H-imidazo[4,5-c]quinolin-2(3H)-one

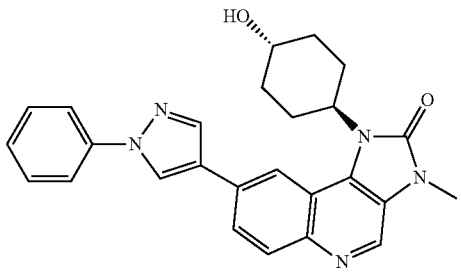 [SMILES: Cn1c(=O)n([C@H]2CC[C@H](O)CC2)c2c3cc(-c4cnn(-c5ccccc5)c4)ccc3ncc21]

50 mg (0.09 mmol) of Intermediate 222 was dissolved in 20 mL of 9% solution of hydrogen chloride in methanol, and stirred at room temperature for 2 h. The reaction was monitored by TLC. After the reaction was completed, the reaction solution was rotary evaporated to dryness, added with 20 mL of dichloromethane and 20 mL of saturated sodium bicarbonate solution, stirred for 30 minutes, allowed to stand and separated into layers. The aqueous phase was extracted with dichloromethane, and the organic phases were combined, dried, and rotary evaporated to dryness to afford a crude product. The crude product was purified by preparative silica gel plate (dichloromethane/methanol=10/1, V/V) to afford the target compound of Example 23 (20 mg), as a white solid. Yield: 50.5%. LC-MS: 440 [M+1]$^+$, $t_R$=1.674 min. $^1$H NMR (400 MHz, DMSO) δ 9.12 (s, 1H), 8.82 (s, 1H), 8.35 (s, 1H), 8.28 (s, 1H), 8.09 (d, J=8.8 Hz, 1H), 8.00 (d, J=9.0 Hz, 1H), 7.92 (d, J=7.7 Hz, 2H), 7.56 (t, J=8.0 Hz, 2H), 7.36 (t, J=7.0 Hz, 1H), 4.96-4.67 (m, 2H), 3.57 (s, 2H), 3.47 (s, 4H), 1.97 (t, J=15.8 Hz, 5H), 1.61-1.42 (m, 3H).

INTERMEDIATE 214

1-((1r,4r)-4-((tert-butyldimethylsilyl)oxy)cyclohexyl)-8-(6-methoxyl-5-methylpyridin-3-yl)-3-methyl-1H-imidazo[4,5-c]quinolin-2(3H)-one

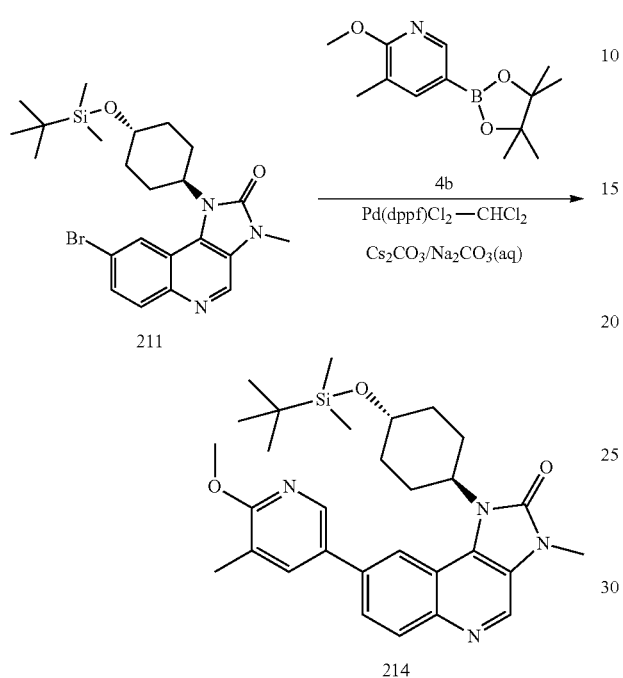

Under the protection of nitrogen, 0.1 g (0.2 mmol) of Intermediate 211 and 0.075 g (0.3 mmol) of Intermediate 4b were dissolved in 10 mL of dioxane, added with 0.26 g (15.8 mmol) of cesium carbonate and 10 mL of 2M aqueous sodium carbonate solution, then added with 0.016 g (0.02 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution. The residue was added with water, and extracted with dichloromethane. The organic phases were combined, dried, and rotary evaporated to dryness to afford a crude product. The crude product was purified by preparative silica gel plate (dichloromethane/methanol=10/1, V/V) to afford a product (70 mg) as a grey brown solid. Yield: 66.0%.

EXAMPLE 24

1-((1r,4r)-4-hydroxycyclohexyl)-8-(6-methoxyl-5-methylpyridin-3-yl)-3-methyl-1H-imidazo[4,5-c]quinolin-2(3H)-one

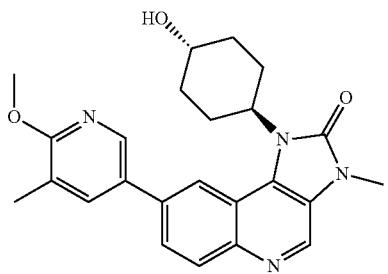 [SMILES: COc1ncc(-c2ccc3ncc4c(c3c2)n([C@H]2CC[C@H](O)CC2)c(=O)n4C)cc1C]

70 mg (0.13 mmol) of Intermediate 214 was dissolved in 20 mL of 9% solution of hydrogen chloride in methanol, and stirred at room temperature for 2 h. The reaction was monitored by TLC. After the reaction was completed, the reaction solution was rotary evaporated to dryness, added with 20 mL of dichloromethane and 20 mL of saturated sodium bicarbonate solution, stirred for 30 minutes, allowed to stand and separated into layers. The aqueous phase was extracted with dichloromethane, and the organic phases were combined, dried, and rotary evaporated to dryness to afford a crude product. The crude product was purified by preparative silica gel plate (dichloromethane/methanol=10/1, V/V) to afford the target compound of Example 24 (35 mg) as a white solid. Yield: 64.8%. LC-MS: 419 [M+1]$^+$, $t_R$=1.628 min $^1$H NMR (400 MHz, DMSO) δ 8.87 (s, 1H), 8.49 (d, J=2.3 Hz, 1H), 8.32 (s, 1H), 8.13 (d, J=8.8 Hz, 1H), 8.01 (s, 1H), 7.94 (d, J=8.8 Hz, 1H), 4.87-4.78 (m, 2H), 3.98 (s, 3H), 3.58 (s, 1H), 3.50 (s, 3H), 2.66-2.55 (m, 2H), 2.28 (s, 3H), 2.02 (t, J=14.7 Hz, 4H), 1.47 (q, J=10.4 Hz, 2H).

INTERMEDIATE 216

1-((1r,4r)-4-((tert-butyldimethylsilyl)oxy)cyclohexyl)-3-methyl-8-(6-phenylpyridin-3-yl)-1H-imidazo[4,5-c]quinolin-2(3H)-one

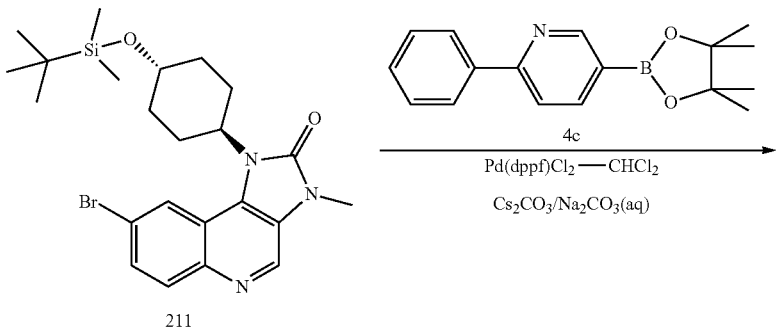

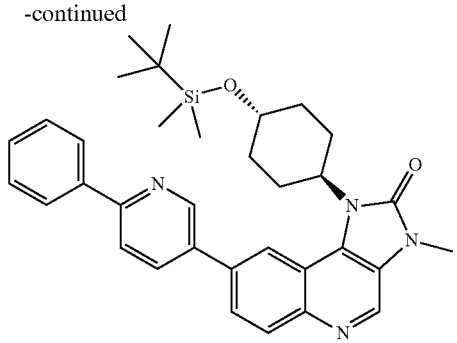

216

Under the protection of nitrogen, 0.1 g (0.1 mmol) of Intermediate 211 and 0.042 g (0.15 mmol) of Intermediate 4c were dissolved in 10 mL of dioxane, added with 0.131 g (15.8 mmol) of cesium carbonate and 10 mL of 2M aqueous sodium carbonate solution, then added with 0.008 g (0.02 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution. The residue was added with water, and extracted with dichloromethane. The organic phases were combined, dried, and rotary evaporated to dryness to afford a crude product. The crude product was purified by preparative silica gel plate (dichloromethane/methanol=10/1, V/V) to afford a product (20 mg) as a yellow solid. Yield: 35.9%.

EXAMPLE 25

1-((1r,4r)-4-hydroxycyclohexyl)-3-methyl-8-(6-phenylpyridin-3-yl)-1H-imidazo[4,5-c]quinolin-2(3H)-one

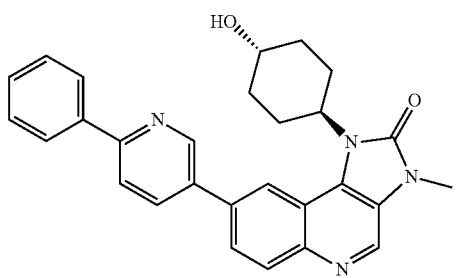 [SMILES: Cn1c(=O)n([C@H]2CC[C@H](O)CC2)c2c3cc(-c4ccc(-c5ccccc5)nc4)ccc3ncc21]

20 mg (0.035 mmol) of Intermediate 216 was dissolved in 20 mL of 9% solution of hydrogen chloride in methanol, and stirred at room temperature for 2 h. The reaction was monitored by TLC. After the reaction was completed, the reaction solution was rotary evaporated to dryness, added with 20 mL of dichloromethane and 20 mL of saturated sodium bicarbonate solution, stirred for 30 minutes, and allowed to be separated into layers. The aqueous phase was extracted with dichloromethane, and the organic phases were combined, dried, and rotary evaporated to dryness to afford a crude product. The crude product was purified by preparative silica gel plate (dichloromethane/methanol=10/1, V/V) to afford the target compound of Example 25 (18 mg) as a grey white solid. Yield: >100%. LC-MS: 452 $t_R$=1.758 min $^1$H NMR (400 MHz, DMSO) δ 9.18 (s, 1H), 8.92 (s, 1H), 8.49 (s, 1H), 8.36 (d, J=8.3 Hz, 1H), 8.30-8.15 (m, 5H), 8.08 (d, J=9.0 Hz, 1H), 7.52 (dt, J=24.9, 7.0 Hz, 3H), 5.04-4.71 (m, 1H), 3.64-3.43 (m, 5H), 2.70-2.55 (m, 3H), 2.02 (s, 4H), 1.58-1.39 (m, J=12.8 Hz, 1H).

(VI) Scheme VI:

Scheme VI

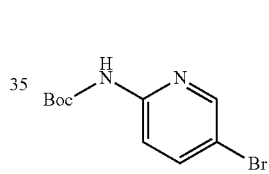

38

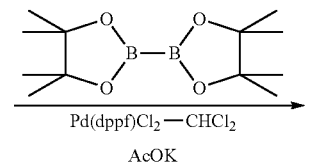

Pd(dppf)Cl$_2$—CHCl$_3$
AcOK

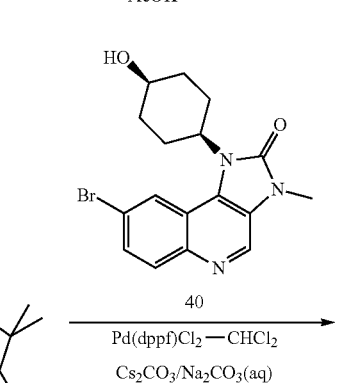

40

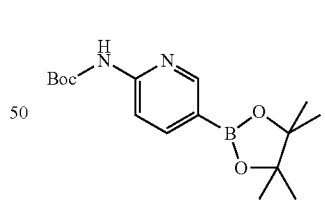

39

Pd(dppf)Cl$_2$—CHCl$_3$
Cs$_2$CO$_3$/Na$_2$CO$_3$(aq)

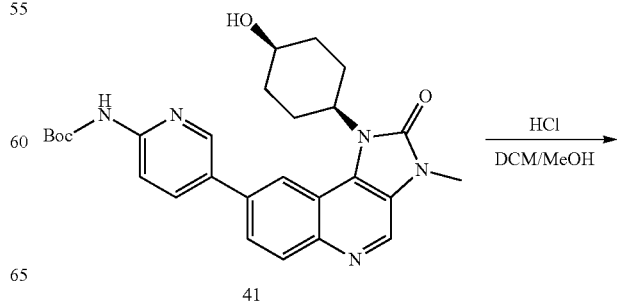

41

HCl
DCM/MeOH

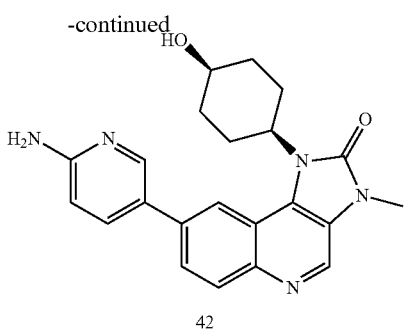

42

INTERMEDIATE 41 tert-butyl (5-(1-((1s,4s)-4-hydroxycyclohexyl)-3-methyl-2-oxo-2,3-dihydro-1H-imidazo[4,5-c]quinolin-8-yl)pyridin-2-yl)carbamate

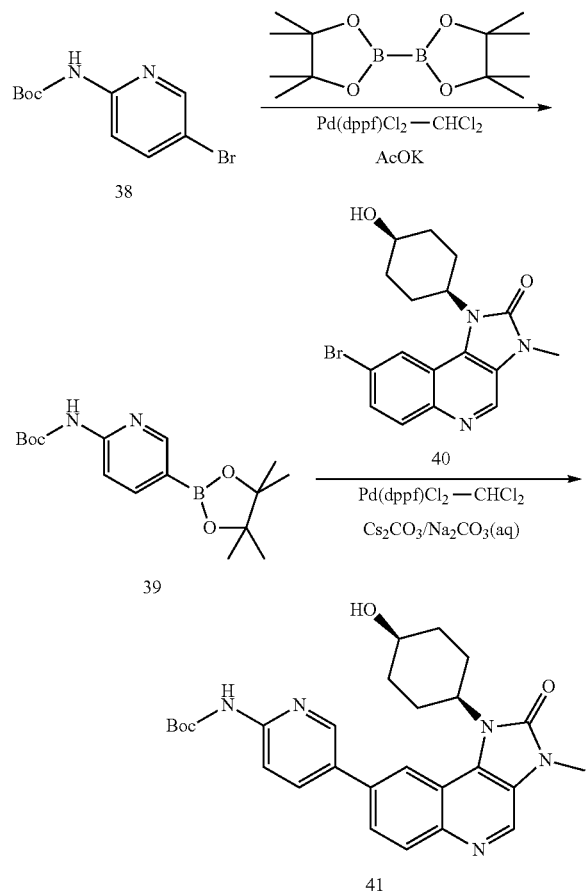

Under the protection of nitrogen, 0.218 g (0.8 mmol) of tert-butyl 2-carbamate-5-bromopyridine (Intermediate 38), 0.244 g (0.96 mmol) of bis(pinacolato)diboron, 0.234 g (2.4 mmol) of potassium acetate and 0.052 g (0.064 mmol) of [1,1-bis(di-phenylphosphino)ferrocene]palladium chloride were suspended in 15 ml of dioxane, and heated at 100° C. for 2 h. The reaction was monitored by TLC. After the reaction was completed, the crude reaction solution was cooled to room temperature, added with 0.2 g (0.54 mmol) of Intermediate 40, 0.9 g (2.7 mmol) of cesium carbonate, 10 ml of dioxane, 10 ml of 2M sodium carbonate solution and 0.044 g (0.054 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by preparative silica gel plate (dichloromethane/methanol=10/1, V/V) to afford a product (240 mg) as a reddish brown solid. Yield: 90.9%.

EXAMPLE 26

8-(6-aminopyridin-3-yl)1-((1s,4s)-4-hydroxycyclohexyl)-3-methyl-1H-imidazo[4,5-c]quinolin-2(3H)-one

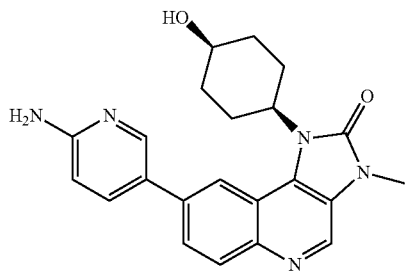 [SMILES: Cn1c(=O)n([C@H]2CC[C@@H](O)CC2)c2c3cc(-c4ccc(N)nc4)ccc3ncc21]

In an ice-water bath, 0.24 g (0.49 mmol) of Intermediate 41 was dissolved in 10 mL of a solvent mixture of dichloromethane/methanol, and hydrogen chloride gas was purged to the reaction solution for 30 minutes. The reaction was monitored by TLC. After the reaction was completed, the reaction solution was rotary evaporated to dryness, and adjusted pH to 8-9 by adding a saturated sodium bicarbonate solution. The aqueous phase was extracted with dichloromethane, and the organic phases were combined, dried, and rotary evaporated to dryness to afford a crude product. The crude product was purified by preparative silica gel plate (dichloromethane/methanol=10/1, V:V) to afford the target compound of Example 26 (0.08 g) as a grey white solid. Yield: 42.1%. LC-MS: 390 [M+1]$^+$, $t_R$=1.166 min.

(VII) Scheme VII:

Scheme VII

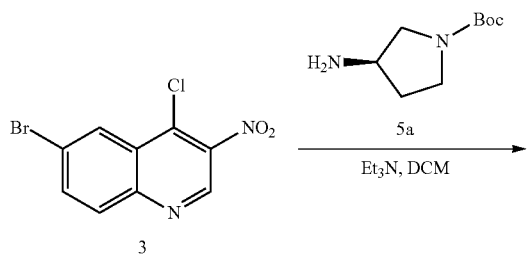

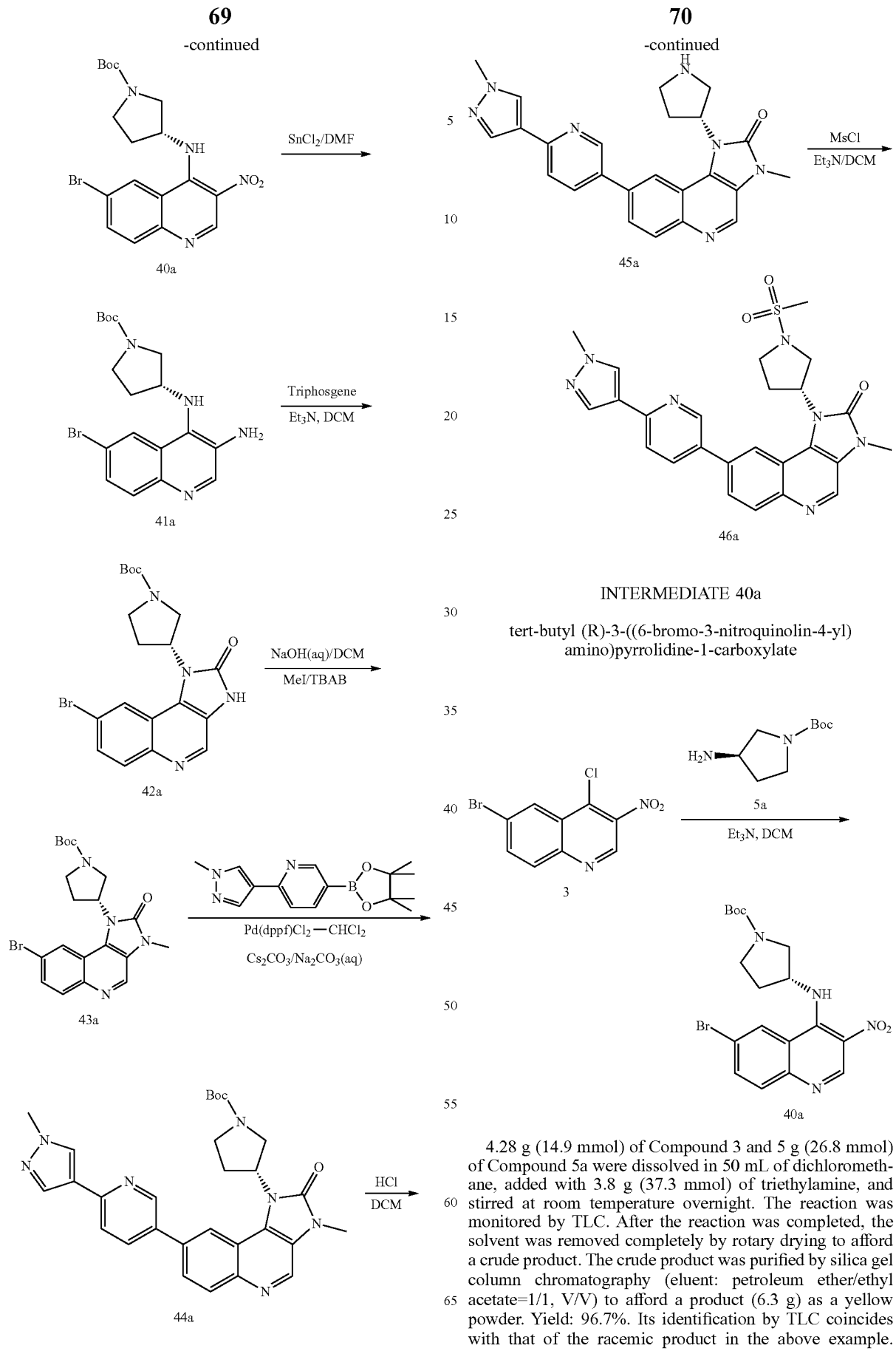

INTERMEDIATE 40a tert-butyl (R)-3-((6-bromo-3-nitroquinolin-4-yl)amino)pyrrolidine-1-carboxylate 4.28 g (14.9 mmol) of Compound 3 and 5 g (26.8 mmol) of Compound 5a were dissolved in 50 mL of dichloromethane, added with 3.8 g (37.3 mmol) of triethylamine, and stirred at room temperature overnight. The reaction was monitored by TLC. After the reaction was completed, the solvent was removed completely by rotary drying to afford a crude product. The crude product was purified by silica gel column chromatography (eluent: petroleum ether/ethyl acetate=1/1, V/V) to afford a product (6.3 g) as a yellow powder. Yield: 96.7%. Its identification by TLC coincides with that of the racemic product in the above example.

INTERMEDIATE 41a tert-butyl (R)-3-((3-amino-6-bromoquinolin-4-yl)amino)pyrrolidine-1-carboxylate

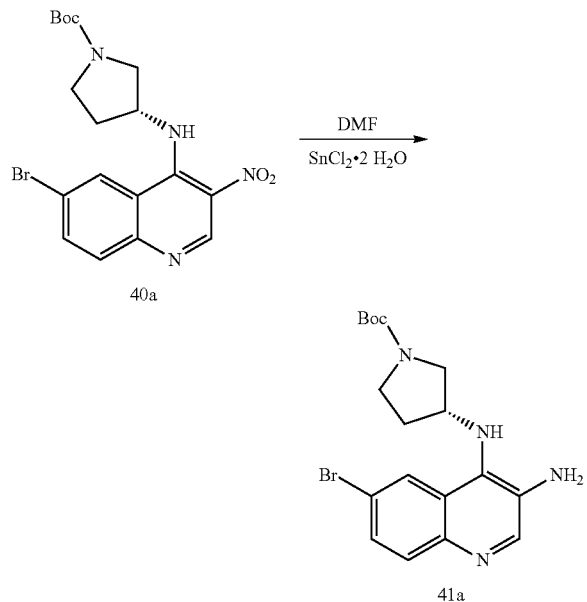

In an ice-water bath, 6.3 g (14.4 mmol) of Intermediate 40a was dissolved in 50 mL of N,N-dimethylformamide 16.3 g (72 mmol) of stannous chloride dihydrate was added in batches over a period of 30 minutes, and stirred at room temperature for 2 h. The reaction was monitored by TLC. After the reaction was completed, to the reaction solution, 10% of aqueous sodium hydroxide solution was added dropwise to pH 8-9. The reaction solution was filtered, the filtrate was extracted with dichloromethane, and the filter cake was washed with dichloromethane. The organic phases were combined, washed with water and with brine, dried, and rotary evaporated to dryness to afford a product (8 g) as reddish brown oil. Crude yield: 100%. Its identification by TLC coincides with that of the racemic product in the above example.

INTERMEDIATE 42a tert-butyl (R)-3-(8-bromo-2-oxo-2,3-dihydro-1H-imidazo[4,5-c]quinolin-1-yl)pyrrolidine-1-carboxylate

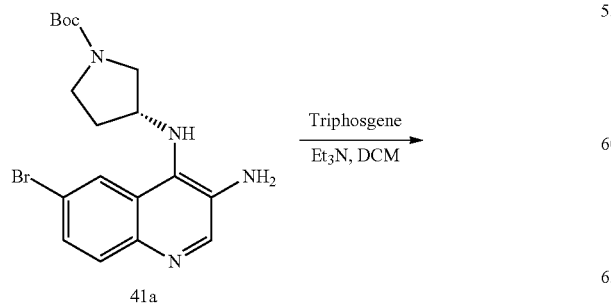

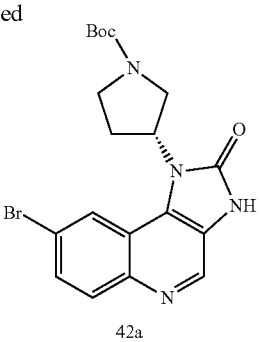

In an ice-water bath, 8 g (14.4 mmol) of Intermediate 41a was dissolved in 50 mL of dichloromethane, added with 5.8 g (57.6 mmol) of triethylamine, and stirred for 10 minutes. A solution of 2.6 g (8.64 mmol) of triphosgene dissolved in 50 mL of dichloromethane was added dropwise, and stirred at 0° C. for 4 h. The reaction was monitored by TLC. After the reaction was completed, 150 mL of saturated sodium bicarbonate solution was added dropwise to the reaction solution to quench the reaction, and stirred for 10 minutes. The organic phase was separated off, and the aqueous phase was extracted with dichloromethane. The organic phases were combined, dried, and rotary evaporated to dryness to afford a crude product. The crude product was purified by silica gel column chromatography (eluent: dichloromethane/methanol=10/1, V/V) to afford a product (0.9 g) as a brown solid. Yield: 14.2%. Its identification by TLC coincides with that of the racemic product in the above example.

INTERMEDIATE 43a tert-butyl (R)-3-(8-bromo-3-methyl-2-oxo-2,3-dihydro-1H-imidazo[4,5-c]quinolin-1-yl)pyrrolidine-1-carboxylate

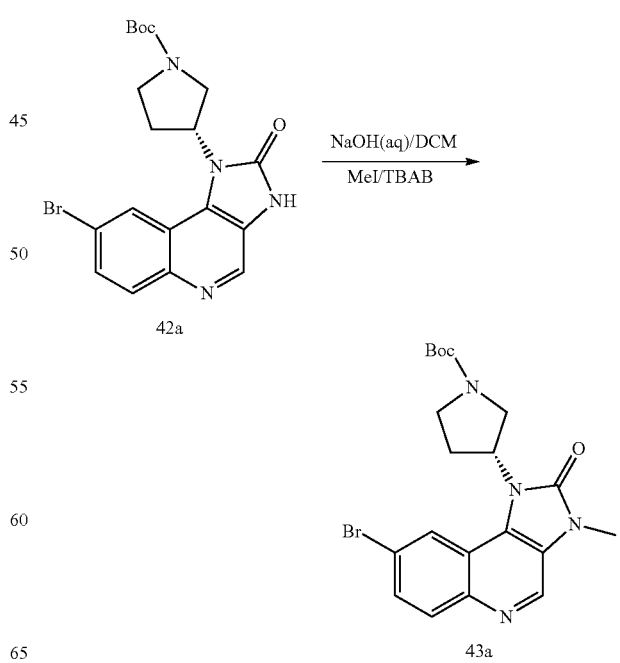

0.9 g (2 mmol) of Intermediate 42a was dissolved in 50 mL of dichloromethane, added with 0.064 g (0.2 mmol) of tetrabutylammonium bromide and 50 mL of 10% aqueous sodium hydroxide solution, stirred for 10 minutes, then added with 0.86 g (6 mmol) of methyl iodide, and stirred for 4 h. The reaction was monitored by TLC. After the reaction was completed, the reaction solution was allowed to be separated into layers. The organic phase was separated off, and the aqueous phase was extracted with dichloromethane. The organic phases were combined, dried, and rotary evaporated to dryness, to afford a product (0.9 g) as a yellow solid. Yield: 99.2%. Its identification by TLC coincides with that of the racemic product in the above example.

INTERMEDIATE 44a tert-butyl (R)-3-(3-methyl-8-(6-(1-methyl-1H-pyrazol-4-yl)piperidin-3-yl)-2-oxo-2,3-dihydro-1H-imidazo[4,5-c]quinolin-1-yl)pyrrolidine-1-carboxylate

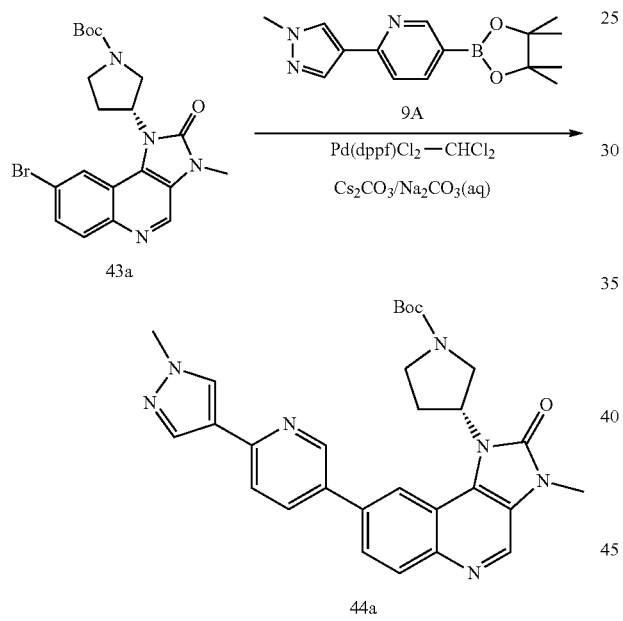

Under the protection of nitrogen, 0.9 g (2 mmol) of Intermediate 43a and 1 g (3.6 mmol) of Intermediate 9A were dissolved in 40 mL of dioxane, added with 3.25 g (10 mmol) of cesium carbonate and 10 mL of 2M aqueous sodium carbonate solution, then added with 0.16 g (0.2 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=20/1, V:V) to afford 1 g of the product as an earthy red solid. Yield: 95.2%. Its identification by TLC coincides with that of the racemic product in the above example.

INTERMEDIATE 45a (R)-3-methyl-8-(6-(1-methyl-1H-pyrazol-4-yl)pyridin-3-yl)-1-(pyrrolidin-3-yl)-1H-imidazo[4,5-c]quinolin-2(3H)-one hydrochloride

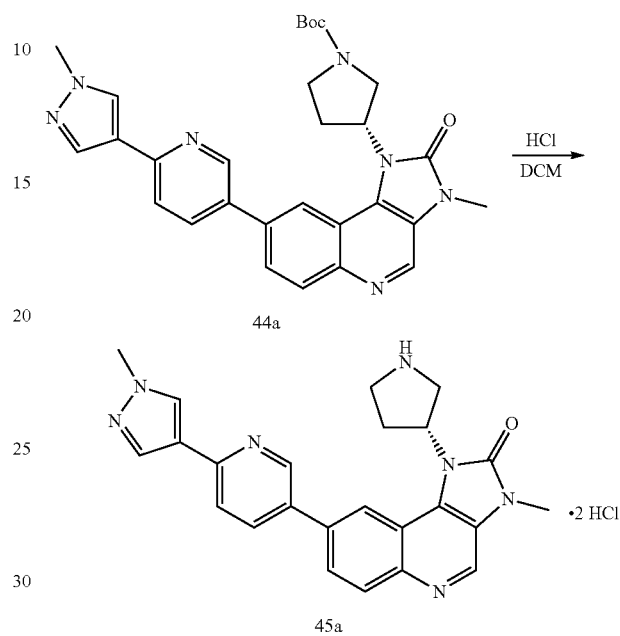

In an ice-water bath, 1 g of Intermediate 44a was dissolved in 30 mL of dichloromethane, and hydrogen chloride gas was purged through the reaction solution for 30 minutes. The reaction was monitored by TLC. After the reaction was completed, the reaction solution was filtered, and the solid was washed with dichloromethane, and pumped to dryness under reduced pressure, to afford a product (0.7 g) as a dark brown solid. Yield: 77.7%. Its identification by TLC coincides with that of the racemic product in the above example.

EXAMPLE 27

(R)-3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one

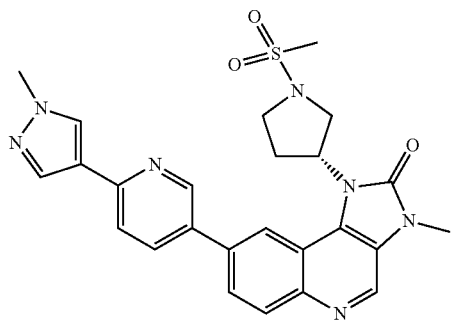 [SMILES: Cn1cc(-c2ccc(-c3ccc4ncc5c(c4c3)n([C@@H]3CCN(S(C)(=O)=O)C3)c(=O)n5C)cn2)cn1]

150 mg (0.3 mmol) of Intermediate 45a was dissolved in 10 mL of dichloromethane, added with 152 mg (1.5 mmol)

of triethylamine, then added with 51.5 mg (0.45 mmol) of methanesulfonyl chloride, and stirred at room temperature overnight. The reaction was monitored by TLC. After the reaction was completed, 20 mL of saturated sodium bicarbonate aqueous solution was added and stirred for 20 minutes. Then the reaction solution was separated into layers, and the aqueous phase was extracted with dichloromethane. The organic phases were combined, dried, and rotary evaporated to dryness to afford a crude product. The crude product was purified by preparative silica gel plate (dichloromethane/methanol=10/1, V/V) to afford the target compound of Example 27 (50 mg), as a yellow-white solid. Yield: 33.5%. Its identifications by TLC and HPLC coincide with those of the racemic product in the above example. LC-MS: 504 [M+1]$^+$, $t_R$=1.460 min.

(VIII) Scheme VIII:

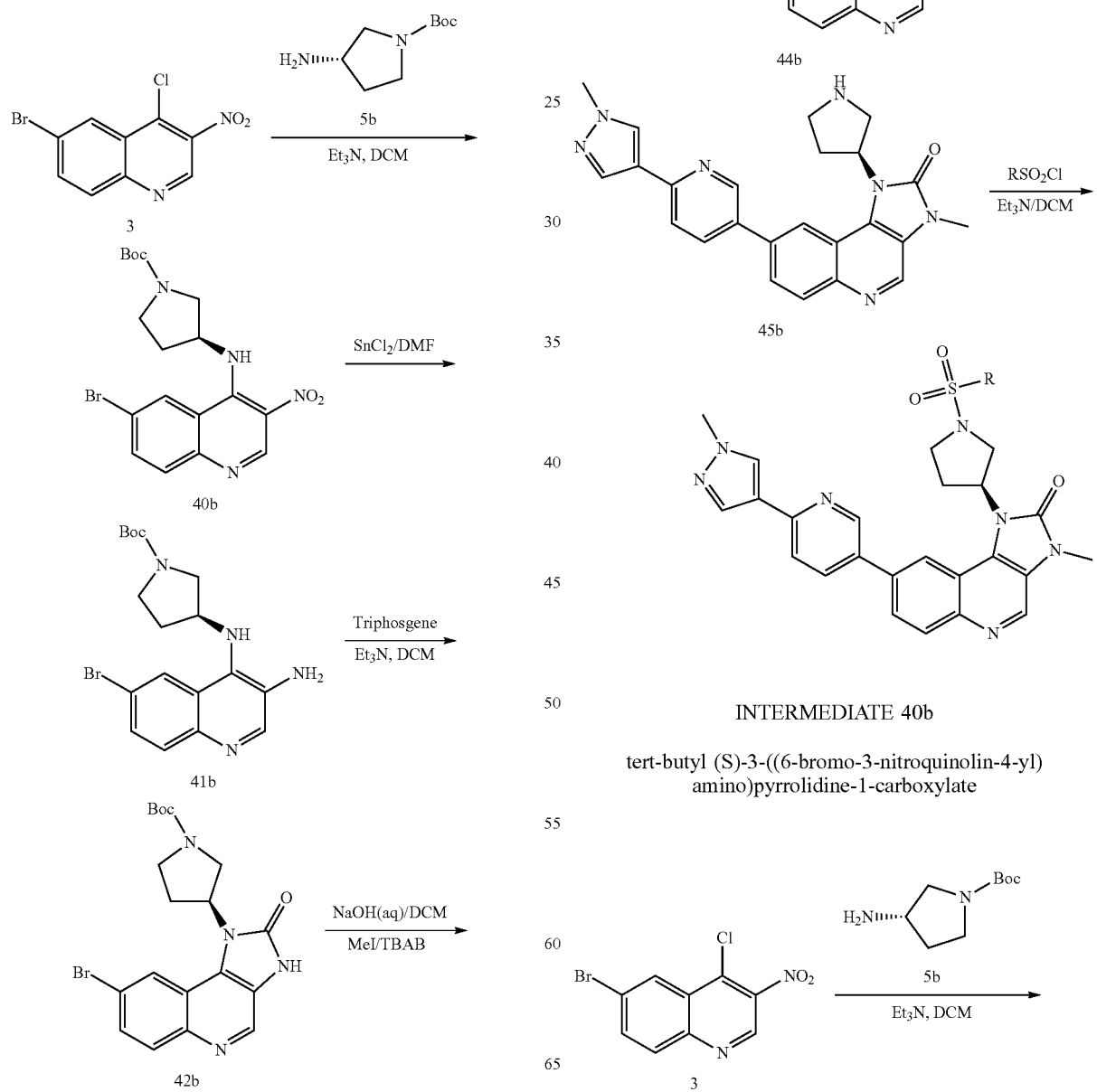

INTERMEDIATE 40b tert-butyl (S)-3-(((6-bromo-3-nitroquinolin-4-yl)amino)pyrrolidine-1-carboxylate

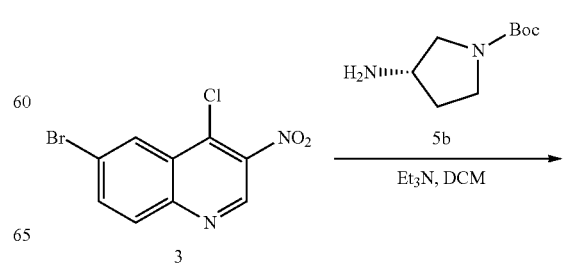

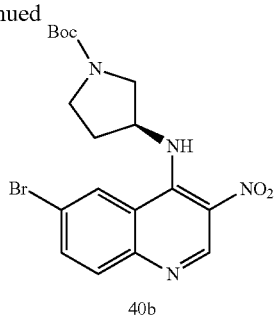

4.28 g (14.9 mmol) of Compound 3 and 5 g (26.8 mmol) of Compound 5a were dissolved in 50 mL of dichloromethane, added with 3.8 g (37.3 mmol) of triethylamine, and stirred at room temperature overnight. The reaction was monitored by TLC. After the reaction was completed, the solvent was rotary evaporated to dryness to afford a crude product. The crude product was purified by silica gel column chromatography (eluent: petroleum ether/ethyl acetate=1/1, V/V) to afford a product (6.5 g) as a yellow powder. Yield: 99.7%. Its identification by TLC coincides with that of the racemic product in the above example.

INTERMEDIATE 41b tert-butyl (S)-3-((3-amino-6-bromoquinolin-4-yl)amino)pyrrolidine-1-carboxylate

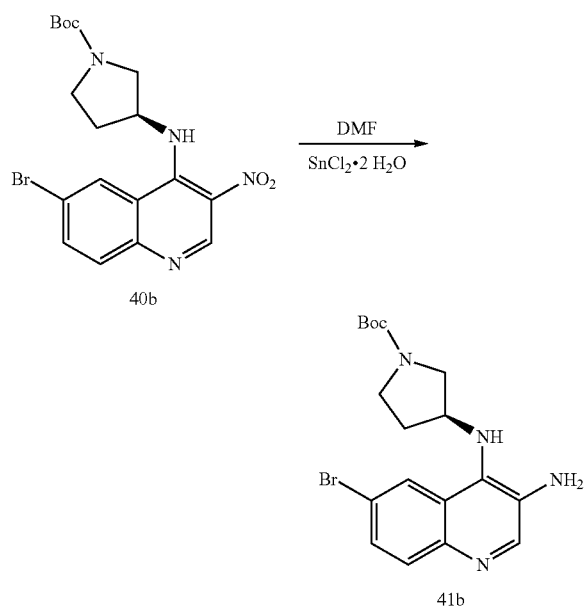

In an ice-water bath, 6.5 g (14.8 mmol) of Intermediate 40b was dissolved in 50 mL of N,N-dimethylformamide 16.8 g (74.2 mmol) of stannous chloride dihydrate was added with in batches over a period of 30 minutes, and stirred at room temperature for 2 h. The reaction was monitored by TLC. After the reaction was completed, 10% of aqueous sodium hydroxide solution was added dropwise to the reaction solution to pH 8-9. The reaction solution was filtered, the filtrate was extracted with dichloromethane, and the filter cake was washed with dichloromethane. The organic phases were combined, washed with water and with brine, dried, and rotary evaporated to dryness to afford a product (6.7 g) as reddish brown oil. Crude yield: 100%. Its identification by TLC coincides with that of the racemic product in the above example.

INTERMEDIATE 42b tert-butyl (S)-3-(8-bromo-2-oxo-2,3-dihydro-1H-imidazo[4,5-c]quinolin-1-yl)pyrrolidine-1-carboxylate

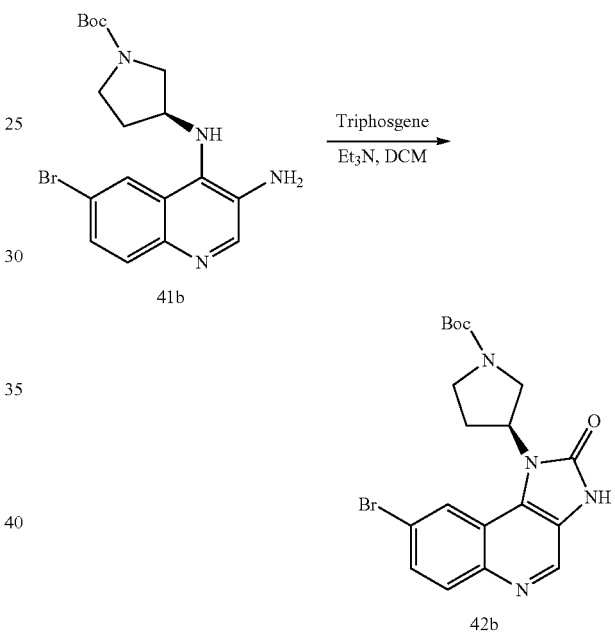

In an ice-water bath, 6.7 g (14.4 mmol) of Intermediate 41b was dissolved in 50 mL of dichloromethane, added with 5.8 g (57.6 mmol) of triethylamine, and stirred for 10 minutes. A solution of 2.6 g (8.64 mmol) of triphosgene was dissolved in 50 mL of dichloromethane was added dropwise, and stirred at 0° C. for 4 h. The reaction was monitored by TLC. After the reaction was completed, 150 mL of saturated sodium bicarbonate solution was added dropwise to the reaction solution to quench the reaction, and stirred for 10 minutes. The organic phase was separated off, and the aqueous phase was extracted with dichloromethane. The organic phases were combined, dried, and rotary evaporated to dryness to afford a crude product. The crude product was purified by silica gel column chromatography (eluent: dichloromethane/methanol=10/1, V/V) to afford a product (4 g) as a brown solid. Yield: 62.5%. Its identification by TLC coincides with that of the racemic product in the above example.

INTERMEDIATE 43b tert-butyl (S)-3-(8-bromo-3-methyl-2-oxo-2,3-di-hydro-1H-imidazo[4,5-c]quinolin-1-yl)pyrrolidine-1-carboxylate

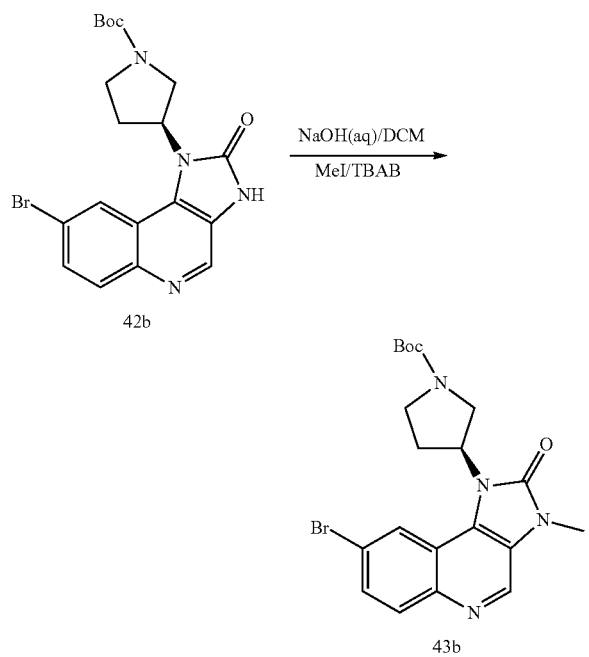

4 g (9 mmol) of Intermediate 42b was dissolved in 80 mL of dichloromethane, added with 0.29 g (0.9 mmol) of tetrabutylammonium bromide and 80 mL of 10% aqueous sodium hydroxide solution, stirred for 10 minutes, then added with 3.46 g (27 mmol) of methyl iodide, and stirred for 4 h. The reaction was monitored by TLC. After the reaction was completed, the reaction solution was allowed to be separated into layers. The organic phase was separated off, and the aqueous phase was extracted with dichloromethane. The organic phases were combined, dried, and rotary evaporated to dryness to afford a product (4.1 g) as a yellow solid. Yield: 100%. Its identification by TLC coincides with that of the racemic product in the above example.

INTERMEDIATE 44b tert-butyl (S)-3-(3-methyl-8-(6-(1-methyl-1H-pyrazol-4-yl)piperidin-3-yl)-2-oxo-2,3-dihydro-1H-imidazo[4,5-c]quinolin-1-yl)pyrrolidine-1-carboxylate

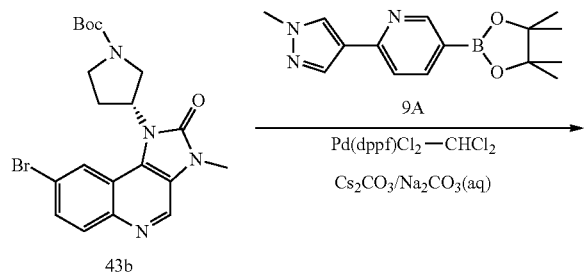

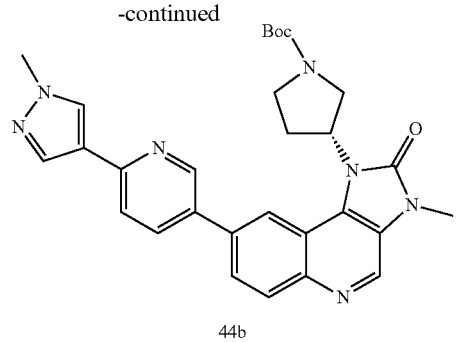

Under the protection of nitrogen, 3 g (6.7 mmol) of Intermediate 43b and 2.85 g (10 mmol) of Intermediate 9A were dissolved in 100 mL of dioxane, added with 10 g (33.5 mmol) of cesium carbonate and 20 mL of 2M aqueous sodium carbonate solution, then added with 0.55 g (0.67 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=20/1, V:V) to afford 1.1 g of the product as a earthy red solid. Yield: 31.4%. Its identification by TLC coincides with that of the racemic product in the above example.

INTERMEDIATE 45b (S)-3-methyl-8-(6-(1-methyl-1H-pyrazol-4-yl)pyridin-3-yl)-1-(pyrrolidin-3-yl)-1H-imidazo[4,5-c]quinolin-2(3H)-one hydrochloride

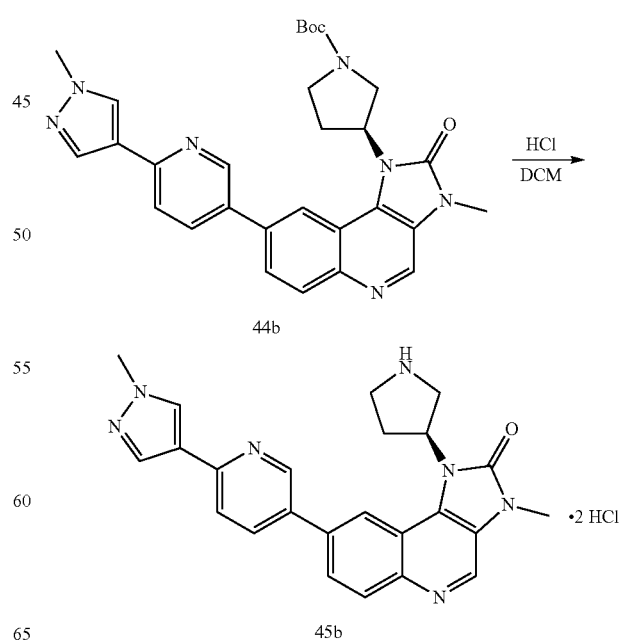

In an ice-water bath, 1.1 g (2.1 mmol) of Intermediate 44b was dissolved in 30 mL of dichloromethane, and hydrogen chloride gas was purged through the reaction solution for 30 minutes. The reaction was monitored by TLC. After the reaction was completed, the reaction solution was filtered, and the solid was washed with dichloromethane, and pumped to dryness under reduced pressure, to afford a product (1.1 g) as a grey white solid. Crude yield: 100%. Its identification by TLC coincides with that of the racemic product in the above example.

EXAMPLE 28

(S)-3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one

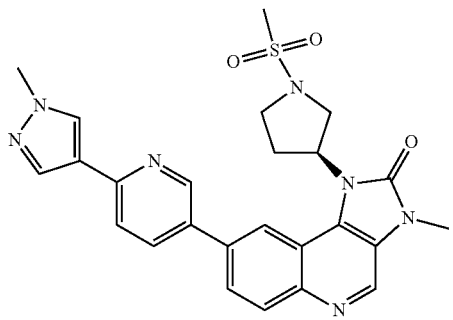 [SMILES: Cn1cc(-c2ccc(-c3ccc4ncc5c(c4c3)n([C@H]3CCN(S(C)(=O)=O)C3)c(=O)n5C)cn2)cn1]

1.1 g (2.1 mmol) of Intermediate 45b was dissolved in 50 mL of dichloromethane, added with 1.07 g (10.5 mmol) of triethylamine, then added with 0.36 g (3.1 mmol) of methanesulfonyl chloride, and stirred at room temperature overnight. The reaction was monitored by TLC. After the reaction was completed, 40 mL of saturated sodium bicarbonate aqueous solution was added, and stirred for 20 minutes. Then the mixture was separated into layers, and the aqueous phase was extracted with dichloromethane. The organic phases were combined, dried, and rotary evaporated to dryness to afford a crude product. The crude product was purified by silica gel column chromatography (dichloromethane/methanol=30/1, V:V) to afford the target compound of Example 28 (0.28 g) as a yellow-white solid. Yield: 25.4%. Its identifications by TLC and HPLC coincide with those of the racemic product in the above example. LC-MS: 504 [M+1]$^+$, $t_R$=1.460 min. $^1$H NMR (400 MHz, CDCl$_3$) δ 8.91 (s, 1H), 8.78 (s, 1H), 8.34 (s, 1H), 8.29 (d, J=8.9 Hz, 1H), 8.10 (s, 1H), 8.04 (s, 2H), 7.93 (d, J=8.6 Hz, 1H), 7.65 (d, J=8.0 Hz, 1H), 5.87-5.72 (m, 1H), 4.11-4.02 (m, 1H), 4.00 (s, 3H), 3.97-3.92 (m, 1H), 3.86-3.81 (m, 1H), 3.63 (s, 3H), 3.61-3.57 (m, 1H), 2.97 (s, 3H), 2.91-2.82 (m, 1H), 2.58-2.44 (m, 1H).

EXAMPLE 29

(S)-1-(1-(ethylsulfonyl)pyrrolidin-3-yl)-3-methyl-8-(6-(1-methyl-1H-pyrazol-4-yl)pyridin-3-yl)-1H-imidazo[4,5-c]quinolin-2(3H)-one

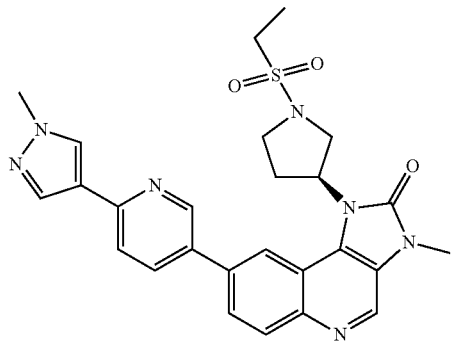 [SMILES: CCS(=O)(=O)N1CC[C@H](n2c(=O)n(C)c3cnc4ccc(-c5ccc(-c6cnn(C)c6)nc5)cc4c32)C1]

0.15 g (0.3 mmol) of Intermediate 45b was dissolved in 25 mL of dichloromethane, added with 0.15 g (1.5 mmol) of triethylamine, then added with 0.058 g (0.45 mmol) of ethylsulfonyl chloride, and stirred at room temperature overnight. The reaction was monitored by TLC. After the reaction was completed, 25 mL of saturated sodium bicarbonate aqueous solution was added, and stirred for 20 minutes. The mixture was separated into layers, and the aqueous phase was extracted with dichloromethane. The organic phases were combined, dried, and rotary evaporated to dryness to afford a crude product. The crude product was purified by silica gel column chromatography (dichloromethane/methanol=30/1, V:V) to afford 0.12 g of the target compound of Example 29, as a off-white solid. Yield: 77.4%. LC-MS: 518 [M+1]$^+$, $t_R$=1.572 min $^1$H NMR (400 MHz, DMSO) δ 9.04 (s, 1H), 8.94 (s, 1H), 8.52 (s, 1H), 8.37 (s, 1H), 8.28 (d, J=8.3 Hz, 1H), 8.17 (d, J=8.8 Hz, 1H), 8.08 (s, 1H), 8.03 (d, J=8.9 Hz, 1H), 7.78 (d, J=8.2 Hz, 1H), 6.03-5.77 (m, 1H), 4.03-3.82 (m, 5H), 3.71 (dd, J=13.3, 8.6 Hz, 1H), 3.63-3.47 (m, 4H), 3.23 (q, J=7.3 Hz, 2H), 2.81-2.67 (m, 1H), 2.48-2.34 (m, 1H), 1.28 (t, J=7.3 Hz, 3H).

(IX) Scheme IX:

Scheme IX

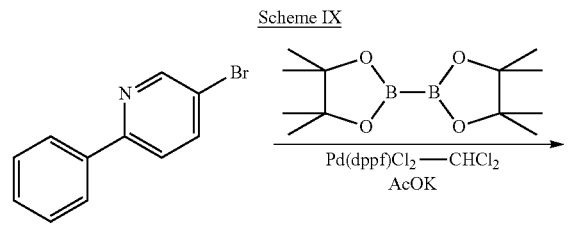

888

INTERMEDIATE 910 tert-butyl (S)-3-(3-methyl-2-oxo-8-(6-phenylpiperidin-3-yl)-2,3-dihydro-1H-imidazo[4,5-c]quinolin-1-yl)pyrrolidine-1-carboxylate

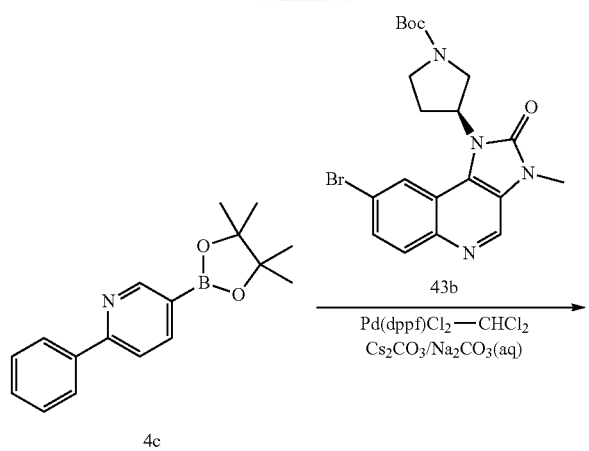

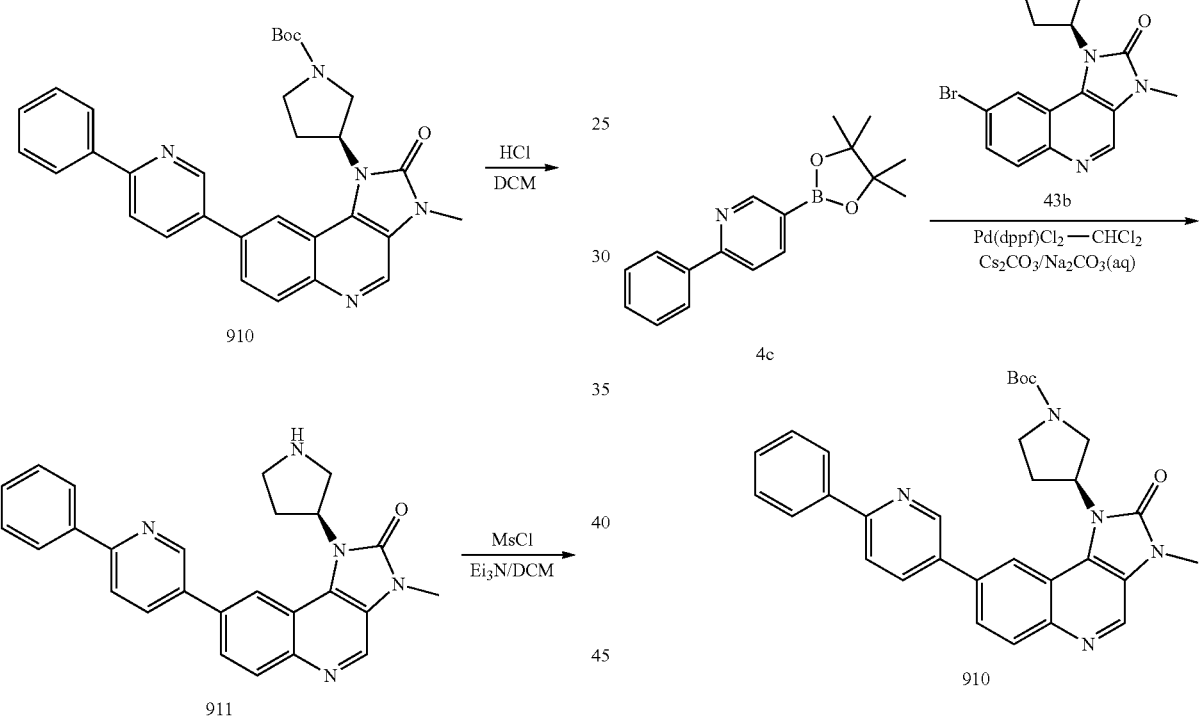

Under the protection of nitrogen, 0.156 g (0.67 mmol) of 5-bromo-2-phenylpyridine, 0.253 g (1 mmol) of bis(pinacolato)diboron, 0.197 g (2.01 mmol) of potassium acetate and 0.044 g (0.05 mmol) of [1,1-bis(di-phenylphosphino)ferrocene]palladium chloride were dissolved in 10 ml of dioxane, and heated at 100° C. for 2 h. The reaction was monitored by TLC. After the reaction was completed, the crude reaction solution was cooled to room temperature, added with 0.2 g (0.45 mmol) of Intermediate 43b, 0.586 g (1.8 mmol) of cesium carbonate, 10 ml of dioxane, 5 ml of 2M sodium carbonate solution and 0.036 g (0.045 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by preparative silica gel plate (dichloromethane/ methanol=10/1, V/V) to afford a product (200 mg), as a brownish yellow solid. Yield: 85.4%. LC-MS: 522 [M+1]⁺, $t_R$=2.446 min.

INTERMEDIATE 911

(S)-3-methyl-8-(6-phenylpiperidin-3-yl)-1-(pyrrolidin-3-yl)-1H-imidazo[4,5-c]quinolin-2(3H)-one hydrochloride

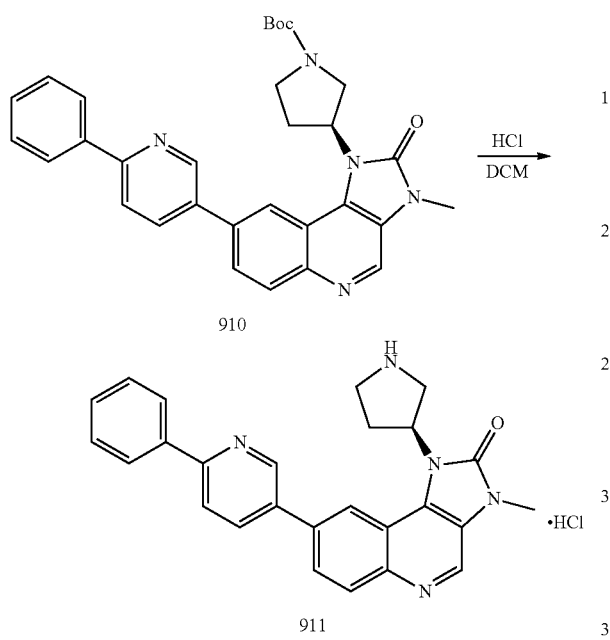

In an ice-water bath, 0.2 g (0.38 mmol) of Intermediate 910 was dissolved in 8 mL of dichloromethane, and hydrogen chloride gas was purged through the reaction solution for 30 minutes. The reaction was monitored by TLC. After the reaction was completed, the reaction solution was filtered, and the solid was washed with dichloromethane, and pumped to dryness under reduced pressure, to afford a product (0.15 g), as an earthy yellow solid. Yield: 93.8%.

EXAMPLE 30

(S)-3-methyl-1-(1-(methanesulfonyl)pyrrolidin-3-yl)-8-(6-phenylpyridin-3-yl)-1H-imidazo[4,5-c]quinolin-2(3H)-one

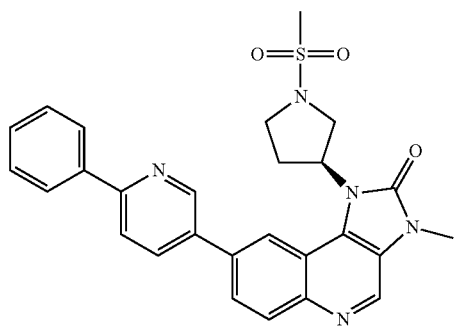 [SMILES: Cn1c(=O)n([C@H]2CCN(S(C)(=O)=O)C2)c2c3cc(-c4ccc(-c5ccccc5)nc4)ccc3ncc21]

0.15 g (0.35 mmol) of Intermediate 911 was dissolved in 25 mL of dichloromethane, added with 0.192 g (1.9 mmol) of triethylamine, then added with 0.062 g (0.57 mmol) of methanesulfonyl chloride, and stirred at room temperature overnight. The reaction was monitored by TLC. After the reaction was completed, 25 mL of saturated sodium bicarbonate aqueous solution was added, and stirred for 20 minutes. The reaction mixture was separated into layers, and the aqueous phase was extracted with dichloromethane. The organic phases were combined, dried, and rotary evaporated to dryness to afford a crude product. The crude product was purified by silica gel column chromatography (dichloromethane/methanol=10/1, V:V) to afford 0.04 g of the target compound of Example 30, as a white solid. Yield: 22.5%. LC-MS: 500 [M+1]⁺, $t_R$=1.929 min.

(X) Scheme X:

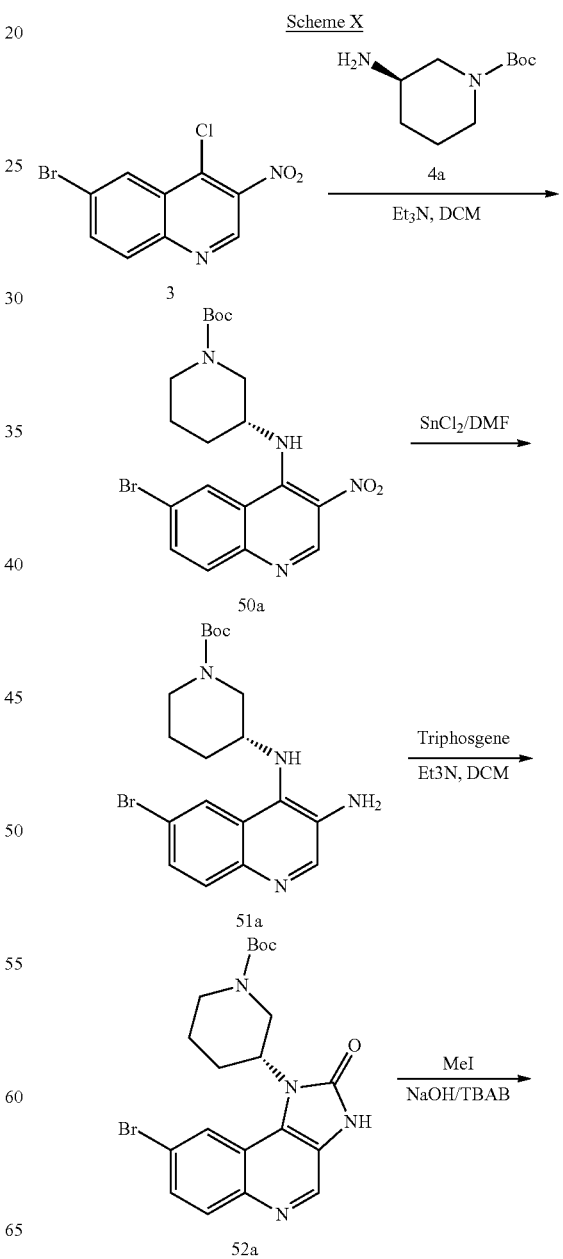

87

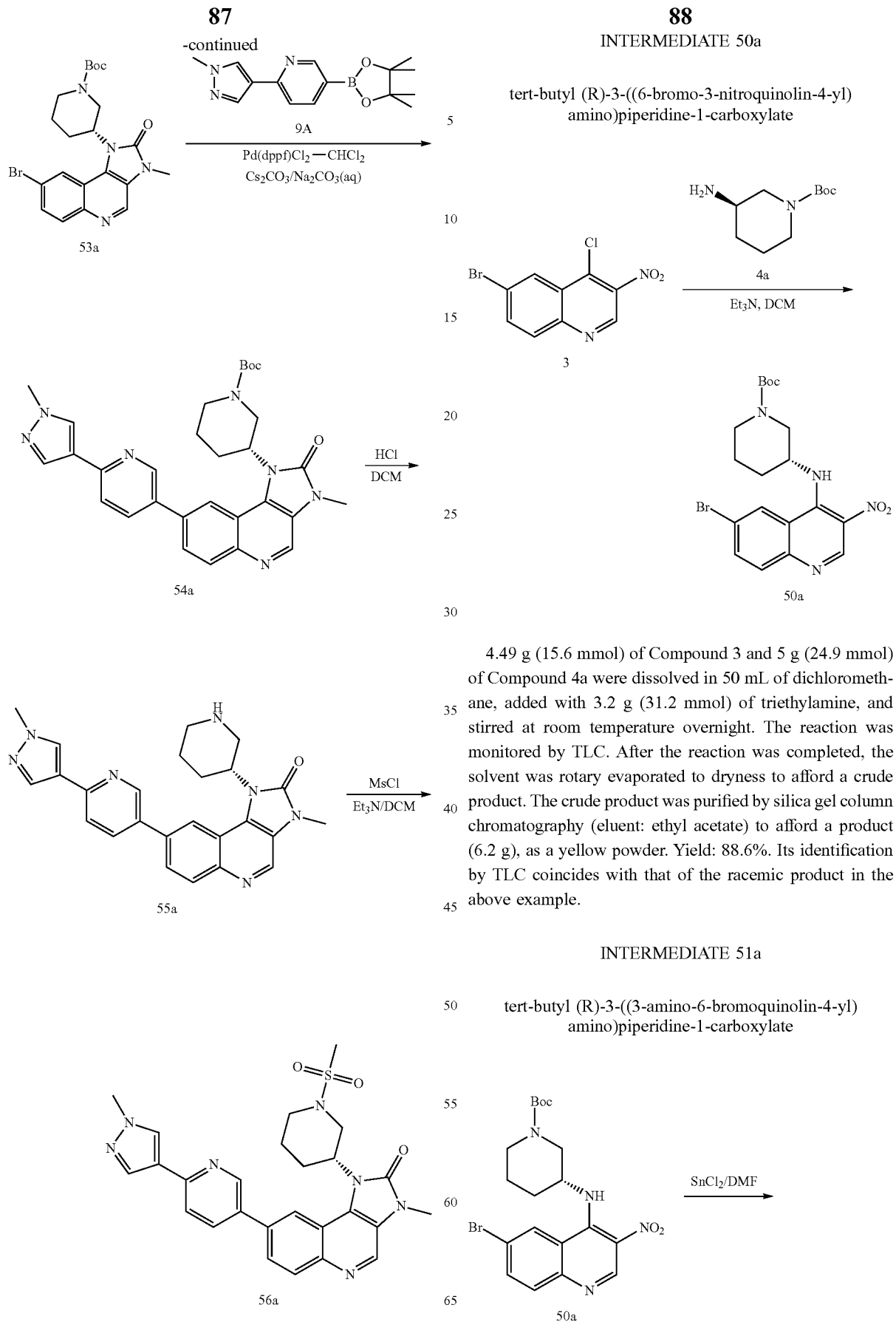

88

INTERMEDIATE 50a tert-butyl (R)-3-((6-bromo-3-nitroquinolin-4-yl)amino)piperidine-1-carboxylate 4.49 g (15.6 mmol) of Compound 3 and 5 g (24.9 mmol) of Compound 4a were dissolved in 50 mL of dichloromethane, added with 3.2 g (31.2 mmol) of triethylamine, and stirred at room temperature overnight. The reaction was monitored by TLC. After the reaction was completed, the solvent was rotary evaporated to dryness to afford a crude product. The crude product was purified by silica gel column chromatography (eluent: ethyl acetate) to afford a product (6.2 g), as a yellow powder. Yield: 88.6%. Its identification by TLC coincides with that of the racemic product in the above example.

INTERMEDIATE 51a tert-butyl (R)-3-((3-amino-6-bromoquinolin-4-yl)amino)piperidine-1-carboxylate

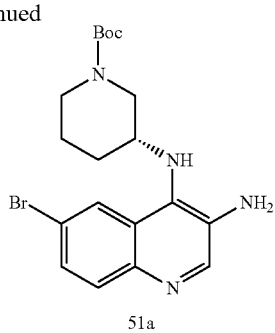

In an ice-water bath, 6.2 g (13.7 mmol) of Intermediate 50a was dissolved in 50 mL of N,N-dimethylformamide 15.5 g (68.6 mmol) of stannous chloride dihydrate was added in batches over a period of 30 minutes, and stirred at room temperature for 2 h. The reaction was monitored by TLC. After the reaction was completed, 10% of aqueous sodium hydroxide solution was added dropwise to the reaction solution to pH 8-9. The reaction solution was filtered, and the filtrate was extracted with dichloromethane, and the filter cake was washed with dichloromethane. The organic phases were combined, washed with water and with brine, dried, rotary evaporated to dryness to afford a product (6.8 g), as reddish brown oil. Crude yield: 100%. Its identification by TLC coincides with that of the racemic product in the above example.

INTERMEDIATE 52a tert-butyl (R)-3-(8-bromo-2-oxo-2,3-dihydro-1H-imidazo[4,5-c]quinolin-1-yl)piperidine-1-carboxylate

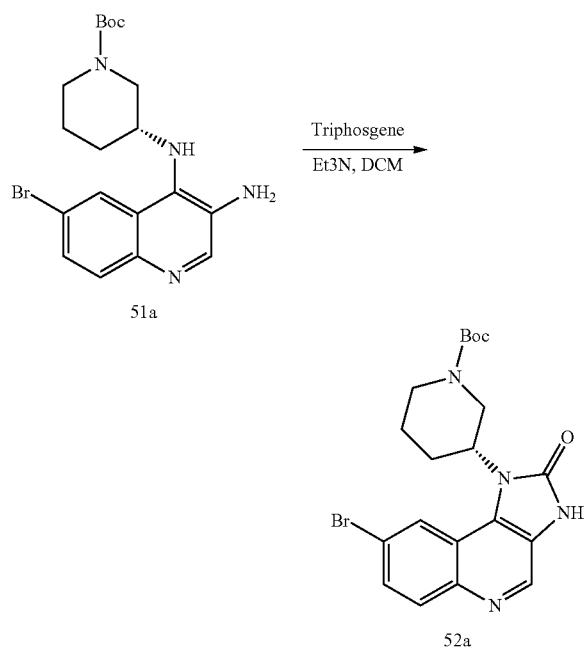

In an ice-water bath, 6.8 g (13.7 mmol) of Intermediate 51a was dissolved in 50 mL of dichloromethane, added with 5.5 g (54.8 mmol) of triethylamine, and stirred for 10 minutes. A solution of 2.4 g (8.22 mmol) of triphosgene dissolved in 50 mL of dichloromethane was added dropwise, and stirred at 0° C. for 4 h. The reaction was monitored by TLC. After the reaction was completed, 150 mL of saturated sodium bicarbonate solution was added dropwise to the reaction solution to quench the reaction, and stirred for 10 minutes. The organic phase was separated off, and the aqueous phase was extracted with dichloromethane. The organic phases were combined, dried, and rotary evaporated to dryness to afford a crude product. The crude product was purified by silica gel column chromatography (eluent: dichloromethane/methanol=10/1, V/V) to afford a product (4.1 g), as a reddish brown solid. Yield: 67.5%. Its identification by TLC coincides with that of the racemic product in the above example.

INTERMEDIATE 53a tert-butyl (R)-3-(8-bromo-3-methyl-2-oxo-2,3-dihydro-1H-imidazo[4,5-c]quinolin-1-yl)piperidine-1-carboxylate

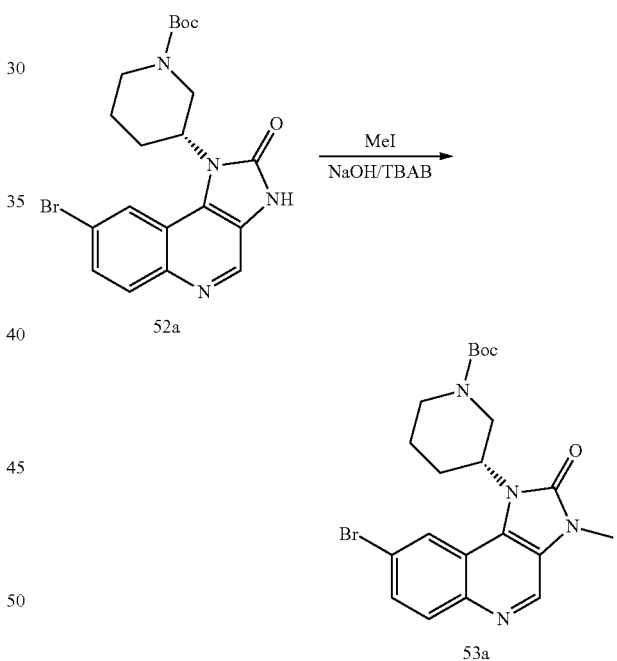

0.6 g (1.34 mmol) of Intermediate 52a was dissolved in 40 mL of dichloromethane, added with 0.044 g (0.134 mmol) of tetrabutylammonium bromide and 40 mL of 10% aqueous sodium hydroxide solution, stirred for 10 minutes, then added with 0.57 g (4 mmol) of methyl iodide, and stirred for 4 h. The reaction was monitored by TLC. After the reaction was completed, the mixture was allowed to be separated into layers. The organic phase was separated off, and the aqueous phase was extracted with dichloromethane. The organic phases were combined, dried, and rotary evaporated to dryness to afford a product (0.7 g), as an orange red solid. Yield: 100%. Its identification by TLC coincides with that of the racemic product in the above example.

INTERMEDIATE 54a tert-butyl (R)-3-(3-methyl-8-(6-(1-methyl-1H-pyrazol-4-yl)pyridin-3-yl)-2-oxo-2,3-dihydro-1H-imidazo[4,5-c]quinolin-1-yl)piperidine-1-carboxylate Under the protection of nitrogen, 0.7 g (1.5 mmol) of Intermediate 53a and 0.65 g (2.3 mmol) of Intermediate 9A were dissolved in 40 mL of dioxane, added with 2.4 g (7.5 mmol) of cesium carbonate and 10 mL of 2M aqueous sodium carbonate solution, then added with 0.12 g (0.15 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=20/1, V:V) to afford 0.7 g of the product as an earthy red solid. Yield: 87.1%. Its identification by TLC coincides with that of the racemic product in the above example.

INTERMEDIATE 55a 3-methyl-8-(6-(1-methyl-1H-pyrazol-4-yl)pyridin-3-yl)-1-(piperidin-3-yl)-1H-imidazo[4,5-c]quinolin-2(3H)-one

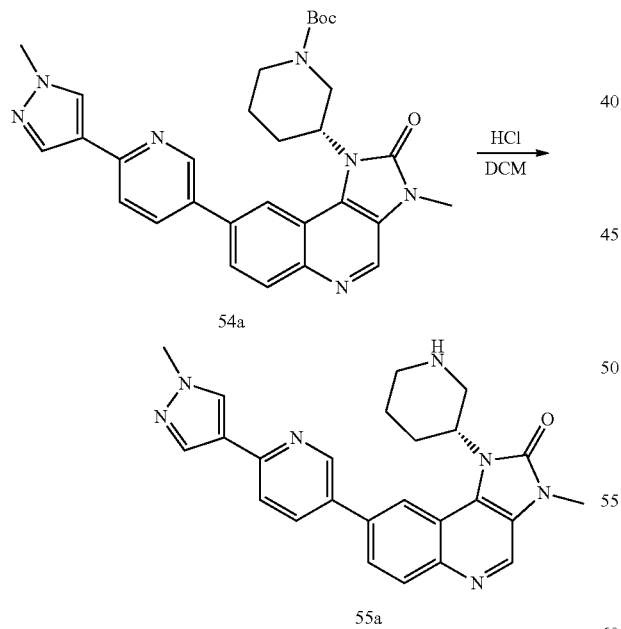

In an ice-water bath, 0.7 g (1.3 mmol) of Intermediate 54a was dissolved in 20 mL of dichloromethane, and hydrogen chloride gas was purged through the reaction solution for 30 minutes. The reaction was monitored by TLC. After the reaction was completed, the reaction solution was filtered, and the solid was washed with dichloromethane, and pumped to dryness under reduced pressure to afford a product (0.5 g), as a dark brown solid. Yield: 71.4%. Its identification by TLC coincides with that of the racemic product in the above example.

EXAMPLE 31

(R)-3-methyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one

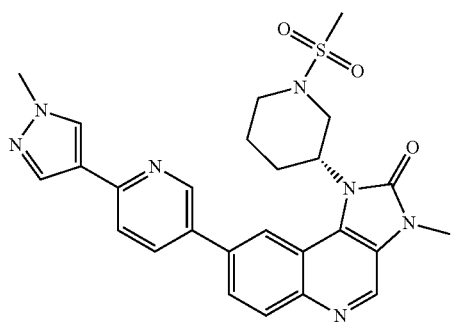 [SMILES: Cn1cc(-c2ccc(-c3ccc4ncc5c(c4c3)n([C@@H]3CCCN(S(C)(=O)=O)C3)c(=O)n5C)cn2)cn1]

0.5 g (0.97 mmol) of Intermediate 55a was dissolved in 20 mL of dichloromethane, added with 0.506 g (5 mmol) of triethylamine, then added with 0.171 g (1.5 mmol) of methanesulfonyl chloride, and stirred at room temperature overnight. The reaction was monitored by TLC. After the reaction was completed, 20 mL of saturated sodium bicarbonate aqueous solution was added, and stirred for 20 minutes. The reaction mixture was separated into layers, and the aqueous phase was extracted with dichloromethane. The organic phases were combined, dried, and rotary evaporated to dryness to afford a crude product. The crude product was purified by silica gel column chromatography (dichloromethane/methanol=10/1, V: V) to afford 0.15 g of the target compound of Example 31, as a yellow-white solid. Yield: 30.4%. Its identifications by TLC and HPLC coincide with those of the racemic product in the above example. LC-MS: 518 [M+1]$^+$, $t_R$=1.509 min $^1$H NMR (400 MHz, CDCl$_3$) δ 8.95 (d, J=2.0 Hz, 1H), 8.76 (s, 1H), 8.44-8.00 (m, 5H), 7.95 (d, J=8.9 Hz, 1H), 7.69 (d, J=7.8 Hz, 1H), 5.15-5.03 (m, 1H), 4.21 (d, J=8.9 Hz, 1H), 4.02 (s, 3H), 4.00-3.80 (m, 2H), 3.62 (s, 3H), 3.02-2.75 (m, 5H), 2.34-1.83 (m, 3H).

(XI) Scheme XI:

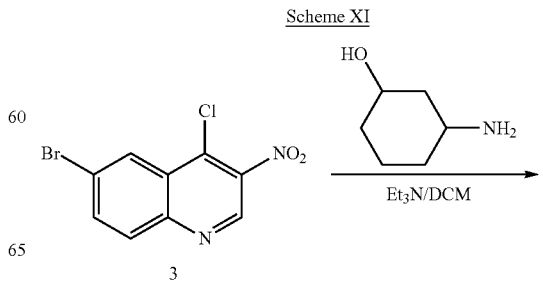

93
-continued

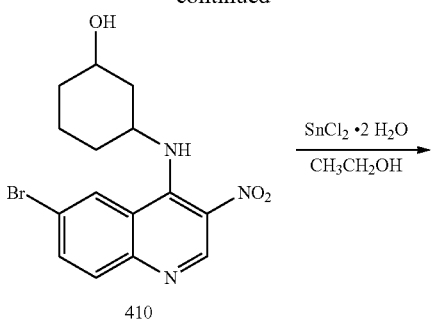
410

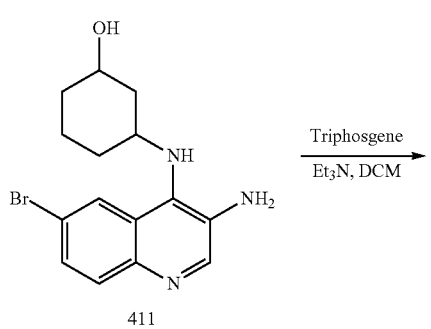
411

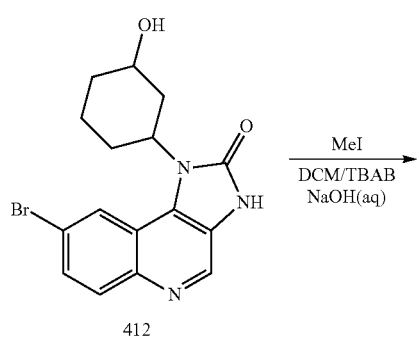
412

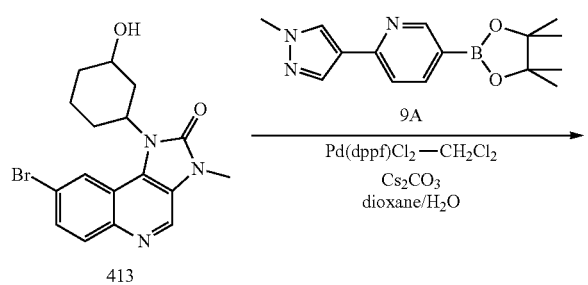
413

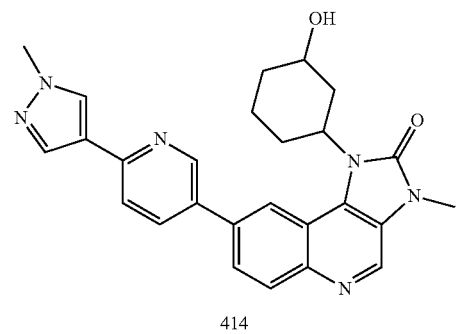 [SMILES: Cn1cc(-c2ccc(-c3ccc4ncc5c(c4c3)n(C3CCCC(O)C3)c(=O)n5C)cn2)cn1]
414

94

INTERMEDIATE 410

3-((6-bromo-3-nitroquinolin-4-yl)amino)cyclohexanol

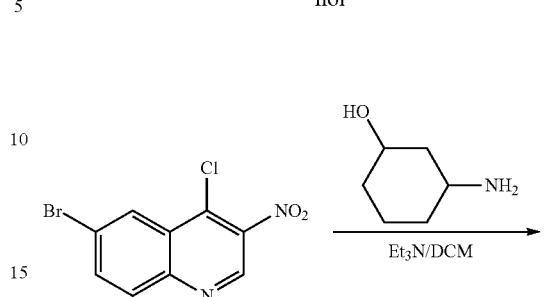

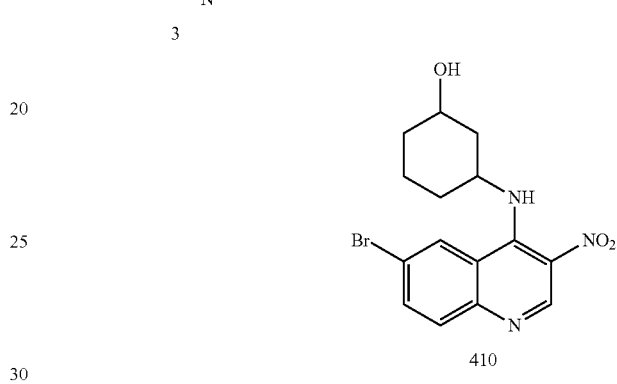
410

1 g (3.48 mmol) of Compound 3 and 0.48 g (4.17 mmol) of 3-aminocyclohexanol (a mixture of cis and trans isomers) were dissolved in 10 ml of dichloromethane, added with 1.46 ml (10.44 mmol) of triethylamine, and stirred at room temperature for 2 h to precipitate out solids. The reaction was completed, filtered, washed with a small amount of dichloromethane, and pumped to dryness to afford a yellow solid (0.4 g). The mother liquor was purified by silica gel column chromatography with an eluent (ethyl acetate:petroleum ether=from 1:10 to 1.5:1) to afford a yellow solid (0.21 g), in total 0.61 g of yellow solid. Yield: 47.89%. LC-MS: 366, 368 [M+1]$^+$, $t_R$=1.978 min.

INTERMEDIATE 411

3-((3-amino-6-bromoquinolin-4-yl)amino)cyclohexanol

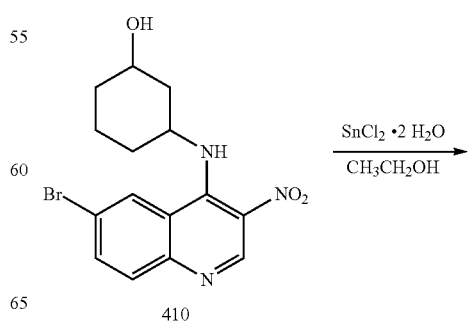
410

-continued

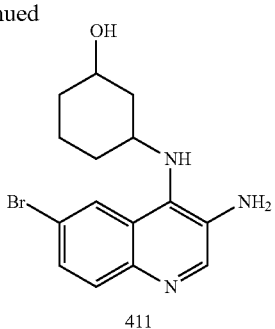

411

0.6 g (1.64 mmol) of Intermediate 410 was dissolved in 12 ml of ethanol, and added with 1.85 g (8.20 mmol) of stannous chloride dihydrate in batches. The reaction was exothermic, and stirred at room temperature overnight. 7 mL of 10% sodium hydroxide solution was added to the reaction system to adjust pH to 8-9, stirred at room temperature for 10 min, and added with 20 ml of dichloromethane and 20 ml of water. Then the reaction mixture was separated into layers, and the aqueous phase was extracted with 80 ml of dichloromethane divided into four times. The organic phases were combined, backwashed with an appropriate amount of saturated saline solution, dried, filtered, rotary evaporated, and pumped to dryness to afford a brown crystal (0.52 g). Yield: 94.30%. LC-MS: 336, 338 $[M+1]^+$, $t_R$=1.509 min.

INTERMEDIATE 412

8-bromo-1-(3-hydroxycyclohexyl)-1H-imidazo[4,5-c]quinolin-2(3H)-one

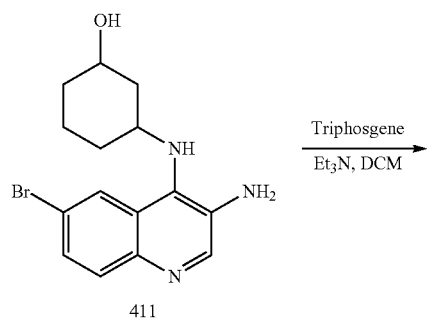

0.51 g (1.52 mmol) of Intermediate 411 was dissolved in 10 ml of dichloromethane, added with 0.64 ml (4.56 mmol) of triethylamine dropwise and then added with 0.226 g (0.76 mmol) of triphosgene dissolved in 5 ml of dichloromethane dropwise under stirring in an ice-water bath, stirred in the ice bath, and reacted overnight. 30 mL of saturated sodium bicarbonate solution was added to quench the reaction, precipitating out solids. The mixture was filtered, and the solid was dissolved with a large amount of dichloromethane and methanol mixture (1:1); the filtrate was separated into two phases, and the aqueous phase was extracted with 120 ml of dichloromethane in four times, and the organic phases were combined, rotary evaporated, followed by azeotropy with the added ethanol to take out the moisture in the solid, and pumped to dryness to afford a brown solid (0.84 g). Crude yield: 100%. LC-MS: 362, 364 $[M+1]^+$, $t_R$=1.509 min.

INTERMEDIATE 413

8-bromo-1-(3-hydroxycyclohexyl)-3-methyl-1H-imidazo[4,5-c]quinolin-2(3H)-one

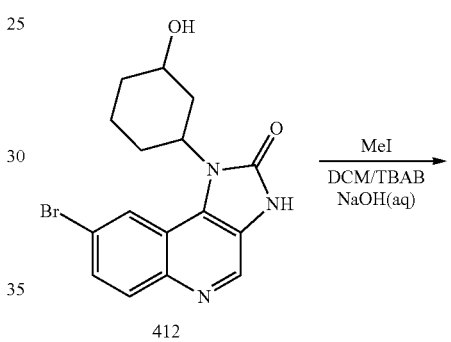

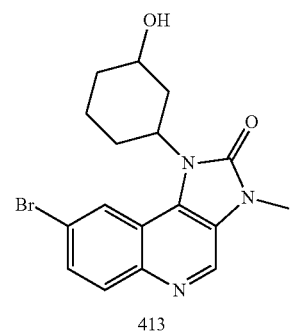

0.84 g (theoretical yield: 0.55 g, 1.52 mmol) of crude Intermediate 412 obtained from the above step was dissolved in 20 ml of dichloromethane, added with 0.049 g (0.152 mmol) of TBAB and 20 ml of 10% sodium hydroxide solution, stirred for 10 min, then added with 0.28 ml (4.56 mmol) of methyl iodide, and stirred at room temperature overnight. After the reaction is complete, the reaction solution was separated into two phases, and the aqueous phase was extracted with 80 ml of dichloromethane in four times. The organic phases were combined, dried, and purified on a silica gel chromatographic column with eluent (methanol:dichloromethane=1:30 to 1:15) to afford a solid (56 mg). Yield: 9.8%. LC-MS: 376, 378 $t_R$=1.603 min.

EXAMPLE 32

1-(3-hydroxycyclohexyl)-3-methyl-8-(6-(1-methyl-1H-pyrazol-4-yl)pyridin-3-yl)-1H-imidazo[4,5-c]quinolin-2(3H)-one

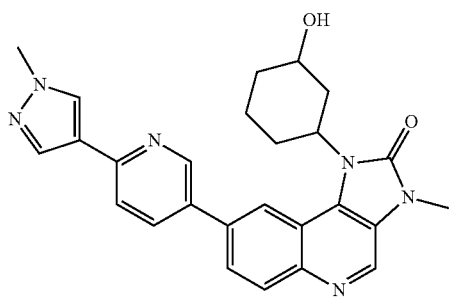 [SMILES: Cn1cc(-c2ccc(-c3ccc4ncc5c(c4c3)n(C3CCCC(O)C3)c(=O)n5C)cn2)cn1]

56 mg (0.149 mmol) of Intermediate 413, 63.7 mg (0.224 mmol) of Compound 9A, 242.7 mg (0.745 mmol) of cesium carbonate, and 0.4 ml of 2M sodium carbonate solution were dissolved in 2 ml of dioxane, purged with nitrogen to remove air, followed by the addition of 24.2 mg (0.0149 mmol) of Pd(dppf)Cl$_2$—CH$_2$Cl$_2$, and then purged with nitrogen to remove air again, reacted at T=110° C. for 4 h under the protection of nitrogen. The raw materials were reacted completely, concentrated by rotary evaporation, added with 10 ml of water and 20 ml of dichloromethane, and separated into two phases. The aqueous phase was extracted with 60 ml of dichloromethane in three times, and the organic phases were combined, and concentrated by rotary evaporation. The solid was dissolved with a small amount of dichloromethane, and purified by TLC preparative plate (methanol:dichloromethane=1:10) to afford the target compound of Example 32, which is a mixture of racemic, cis and trans isomers, as a yellow solid (42 mg). Yield: 62.08%. LC-MS: 455 [M+1]$^+$, t$_R$=1.445 min $^1$H NMR (400 MHz, DMSO) δ 8.99 (d, J=2.3 Hz, 1H), 8.90 (s, 1H), 8.37 (d, J=12.0 Hz, 2H), 8.21 (dd, J=8.3, 2.3 Hz, 1H), 8.17 (d, J=8.8 Hz, 1H), 8.09 (s, 1H), 8.02 (d, J=8.8 Hz, 1H), 7.83 (d, J=8.3 Hz, 1H), 4.96-4.79 (m, 1H), 3.92 (s, 3H), 3.69 (d, J=4.2 Hz, 1H), 3.51 (s, 3H), 3.21-3.07 (m, 1H), 2.44-2.27 (m, 2H), 2.25-2.10 (m, 1H), 2.04-1.72 (m, 3H), 1.66-1.40 (m, 2H), 1.37-1.26 (m, 1H).

(XII) Scheme XII:

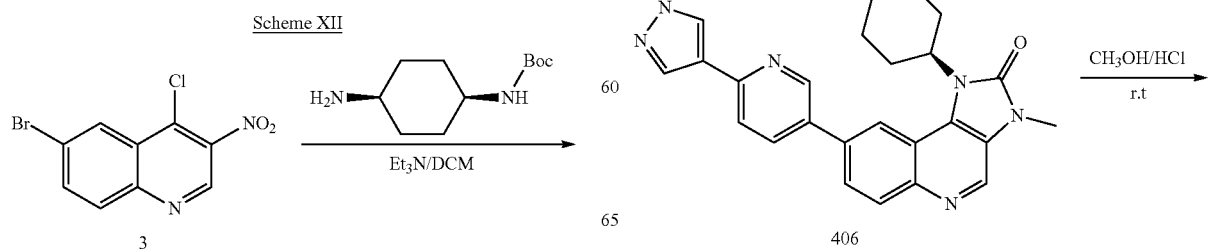

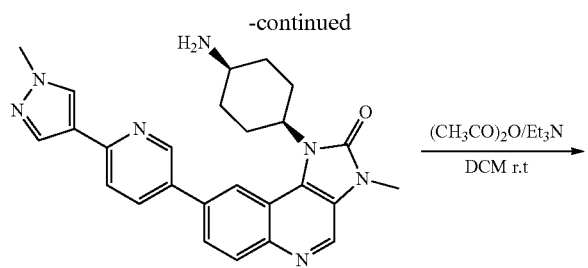

407

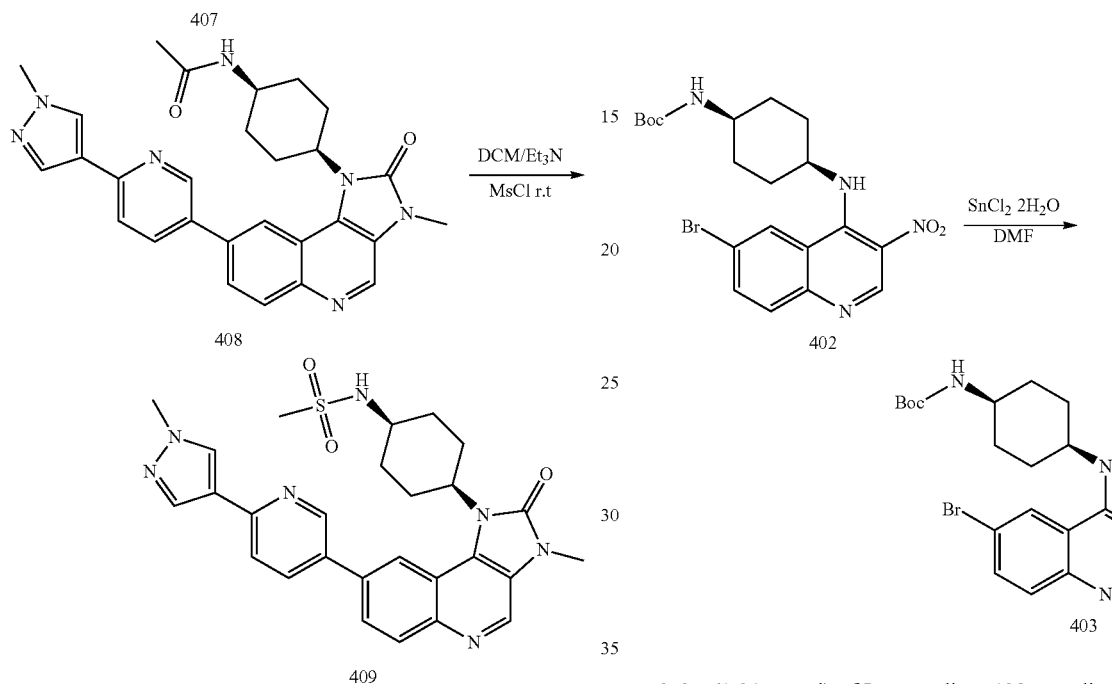

408

409

INTERMEDIATE 402 tert-butyl ((1s,4s)-4-((6-bromo-3-nitroquinolin-4-yl)amino)cyclohexyl)carbamate

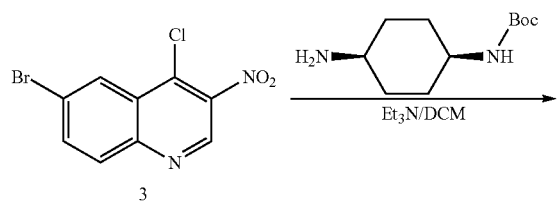

3

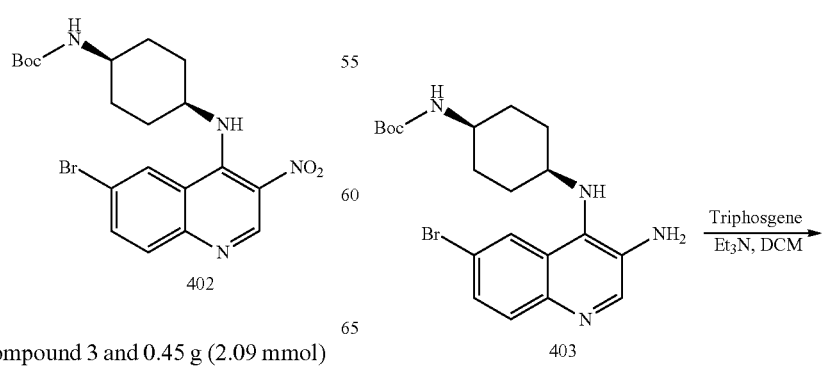

402

0.5 g (1.74 mmol) of Compound 3 and 0.45 g (2.09 mmol) of tert-butyl cis-N-(4-aminocyclohexyl)carbamate were sus- pended in 50 ml of dichloromethane, added with 0.73 ml (5.22 mmol) of triethylamine, and stirred at room temperature for 2.5 h to precipitate out solids. The reaction solution was filtered, washed with a small amount of dichloromethane, and pumped to dryness, to afford a yellow solid (0.6 g). Yield: 74.10%. LC-MS: 465,467 [M+1]$^+$, $t_R$=2.601 min.

INTERMEDIATE 403 tert-butyl ((1s,4s)-4-((6-bromo-3-aminoquinolin-4-yl)amino)cyclohexyl)carbamate

402

403

0.6 g (1.31 mmol) of Intermediate 402 was dissolved in 5 ml of DMF, added with 1.48 g (6.55 mmol) of stannous chloride hydrate in batches, and stirred at room temperature for 1 h. The reaction was quenched with 70 ml of saturated sodium bicarbonate solution, stirred, was allowed to stand, and separated into phases. The aqueous phase was extracted with 70 ml, 50 ml, 30 ml, and 30 ml of ethyl acetate, respectively. The organic phases were combined, and the aqueous phase was adjusted to pH=8~9, dried over anhydrous sodium sulfate, and evaporated to dryness to afford a brown crystal (0.51 g). Yield: 89.42%. LC-MS: 435,437 [M+1]$^+$, $t_R$=1.822 min.

INTERMEDIATE 404 tert-butyl ((1s,4s)-4-(8-bromo-2-carbonyl-2,3-dihydro-1H-imidazo[4,5-c]quinolin-1-yl)cyclohexyl)carbamate

403

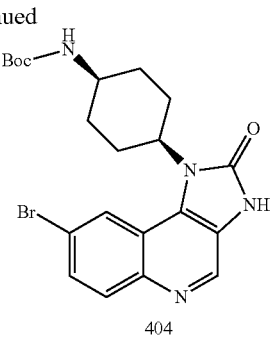

404

0.5 g (1.15 mmol) of Intermediate 403 was dissolved in 10 ml of dichloromethane, added with 0.48 ml (3.45 mmol) dropwise under stirring in an ice-water bath, added with 0.171 g (0.575 mmol) of triphosgene dissolved in 2 ml of dichloromethane, and stirred in the ice-water bath for 2.5 h. 24 ml of saturated sodium hydrogen carbonate was added dropwise to the reaction solution, stirred, was allowed to stand, and separated into phases. The aqueous phase was extracted with 24 ml×2 of dichloromethane, and the organic phases were combined, dried, and rotary evaporated to dryness to afford a crude product. The crude product was purified by chromatography on a silica gel column (eluent: methanol:dichloromethane=1:15) to afford a yellow solid (0.22 g). Yield: 41.47%. LC-MS: 461,463 [M+1]$^+$, $t_R$=2.072 min.

INTERMEDIATE 405 tert-butyl ((1s,4s)-4-(8-bromo-3-methyl-2-carbonyl-2,3-dihydro-1H-imidazo[4,5-c]quinolin-1-yl)cyclohexyl)carbamate

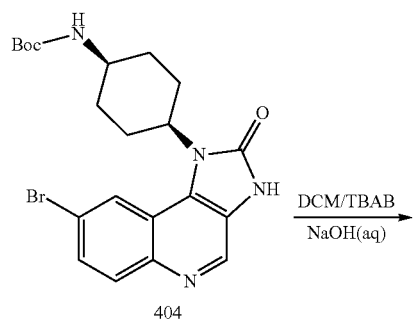

0.22 g (0.48 mmol) of Intermediate 404 was dissolved in 14 ml of dichloromethane, added with 0.015 g (0.048 mmol) of TBAB, then added with 14 ml of 10% NaOH, stirred for 10 min, added with 0.09 ml (1.44 mmol) of methyl iodide, and stirred at room temperature to react overnight (20 h). The reaction solution was allowed to stand, and separated into phases. The aqueous phase was extracted with 14 ml×2 of dichloromethane, and the organic phases were combined, dried, concentrated by rotary evaporation, and pumped to dryness in vacuo, to afford a yellow solid (0.226 g). Yield: 99.04%. LC-MS: 475,477 [M+1]$^+$, $t_R$=2.351 min.

INTERMEDIATE 406 tert-butyl 41s,4s)-4-(8-(6-(1-methyl-1H-pyrazol-4-yl)pyridin-3-yl)-3-methyl-2-carbonyl-2,3-dihydro-1H-imidazo[4,5-c]quinolin-1-yl)cyclohexyl)carbamate

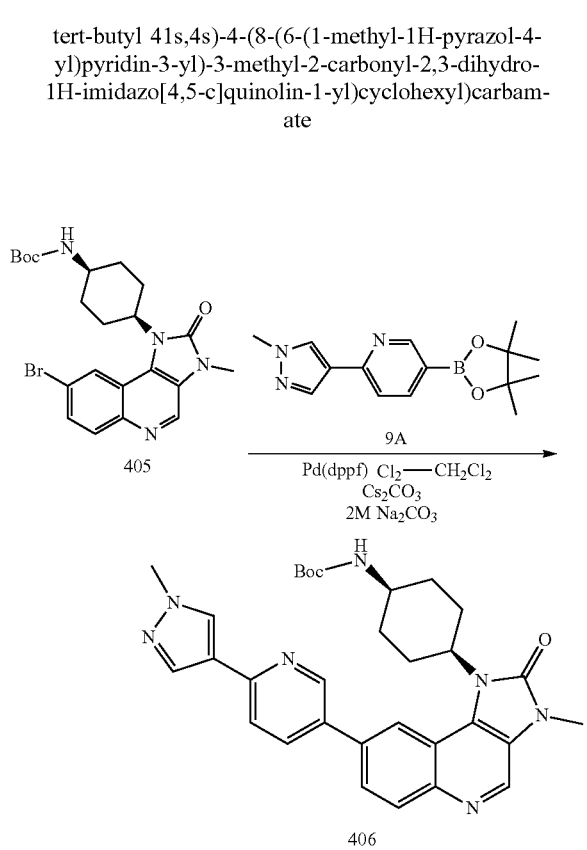

0.226 g (0.48 mmol) of Intermediate 405, 0.205 g (0.72 mmol) of 9A, 0.782 g (2.4 mmol) of cesium carbonate were suspended in 7.5 ml of dioxane, added with 1.5 ml of 2M sodium carbonate, then added with 0.039 g (0.048 mmol) of [1,1'-bis(diphenylphosphino)ferrocene]palladium dichloride dichloromethane complex under the protection of nitrogen, and heated to 110° C. and reacted for 4 h under the protection of nitrogen. 20 mL of water was added, and stirred, and then 20 ml of dichloromethane was added and stirred. The mixture was allowed to stand and separated into two phases. The aqueous phase was extracted with 20 ml×3 of dichloromethane, and the organic phases were combined, dried, and purified by chromatography on silica gel column (eluent: methanol:dichloromethane=1:15) to afford a brownish red solid (0.223 g). Yield: 84.72%. LC-MS: 554,555 [M+1]$^+$, $t_R$=1.884 min.

INTERMEDIATE 407

1-((1s,4s)-4-aminocyclohexyl)-3-methyl-8-(6-(1-methyl-1H-pyrazol-4-yl)pyridin-3-yl)-1H-imidazo[4,5-c]quinolin-2(3H)-one

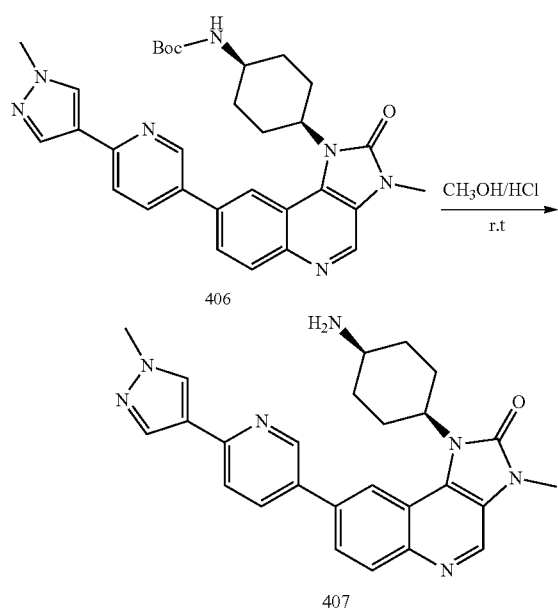

0.2 g (0.36 mmol) of Intermediate 406 and 8 ml of 9.1% solution of hydrogen chloride in methanol were stirred at room temperature overnight to precipitate out solids. The mixture was filtered, washed with 10 ml of dichloromethane, and pumped to dryness to afford a yellow solid (0.12 g). Yield: 63.1%. LC-MS: 227.5 [M/2+1]$^+$, $t_R$=1.322 min.

EXAMPLE 33

N-((1s,4s)-4-(3-methyl-8-(6-(1-methyl-1H-pyrazol-4-yl)pyridin-3-yl)-2-oxo-2,3-dihydro-1H-imidazo[4,5-c]quinolin-1-yl)cyclohexyl)acetamide

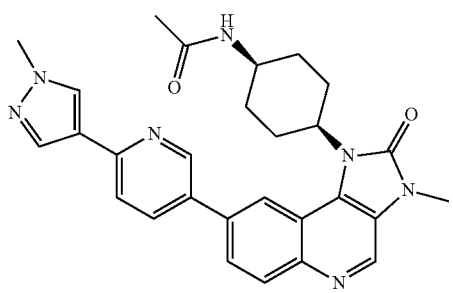 [SMILES: CC(=O)N[C@H]1CC[C@@H](n2c(=O)n(C)c3cnc4ccc(-c5ccc(-c6cnn(C)c6)nc5)cc4c32)CC1]

50 mg (0.095 mmol) of Intermediate 407, and 50 ml of dichloromethane were mixed, then added with 66.2 μl of triethylamine, and stirred for 15 min to dissolve the solid, followed by the addition of 10.7 μl of acetic anhydride, and reacted for 1 h. The reaction solution was rotary evaporated, and purified with TLC preparative plate (dichloromethane:methanol=10:1) to afford the target compound of Example 33, as a white solid (28 mg). Yield: 59.49%. LC-MS: 248.7 [M/2+1]$^+$, $t_R$=1.509 min $^1$H NMR (400 MHz, DMSO) δ 8.99 (d, J=2.3 Hz, 1H), 8.90 (s, 1H), 8.39 (s, 2H), 8.22 (dd, J=8.3, 2.4 Hz, 1H), 8.17 (d, J=8.8 Hz, 1H), 8.10 (s, 1H), 8.02 (d, J=8.8 Hz, 1H), 7.94 (d, J=5.7 Hz, 1H), 7.84 (d, J=8.3 Hz, 1H), 4.88 (t, J=11.9 Hz, 1H), 3.92 (s, 4H), 3.51 (s, 3H), 2.74 (dd, J=24.5, 12.0 Hz, 2H), 2.05-1.66 (m, 10H).

EXAMPLE 34

N-((1s,4s)-4-(3-methyl-8-(6-(1-methyl-1H-pyrazol-4-yl)pyridin-3-yl)-2-oxo-2,3-dihydro-1H-imidazo[4,5-c]quinolin-1-yl)cyclohexyl)methanesulfonamide

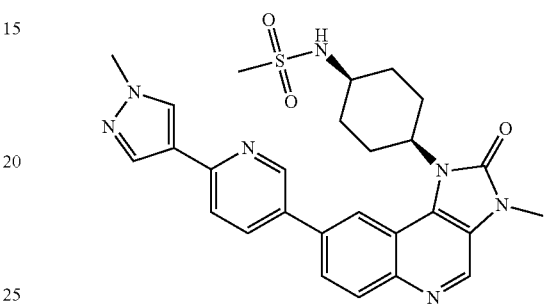

50 mg (0.095 mmol) of Intermediate 407 and 50 ml of dichloromethane were mixed, added with 66.2 μl of triethylamine, stirred for 15 min to dissolve the solid, followed by the addition of 12.8 μl of methanesulfonyl chloride, and reacted for 3 h. 10 mL of saturated sodium bicarbonate solution, 5 ml of dichloromethane and 10 ml of saturated saline solution were added, and separated into two phases. The aqueous phase was extracted with 40 ml of dichloromethane in two times, and the organic phases were combined, dried over anhydrous sodium sulfate, rotary evaporated, and pumped to dryness to afford the target compound of Example 34, as an off-white solid (46 mg). Yield: 91.1%. This compound was dissolved in a mixture of dichloromethane and methanol, adjusted pH to 2 with a solution of hydrogen chloride in methanol, and evaporated to dryness to remove the solvent, to afford the corresponding hydrochloride salt. LC-MS: 266.7 [M/2+1]$^+$, $t_R$=1.510 min $^1$H NMR (400 MHz, DMSO+D$_2$O) δ 9.20 (s, 1H), 9.01 (s, 1H), 8.61-8.43 (m, 3H), 8.36 (s, 2H), 8.20 (s, 1H), 8.07 (d, J=8.4 Hz, 1H), 5.01 (s, 1H), 3.92 (s, 3H), 3.59 (s, 1H), 3.54 (s, 3H), 2.94 (s, 3H), 2.77 (q, J=13.3 Hz, 2H), 2.07-1.69 (m, 6H).

(XIII) Scheme XIII:

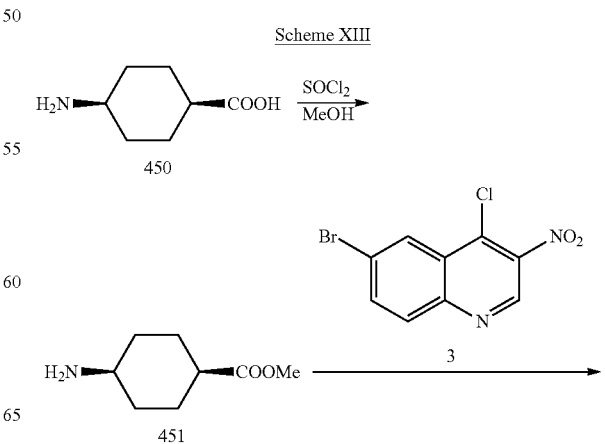

105
-continued

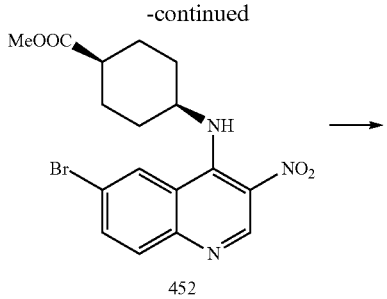
452

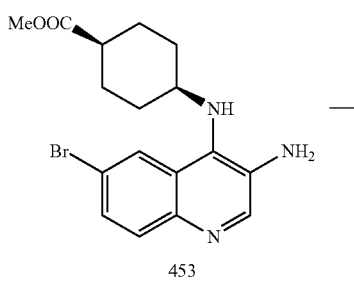
453

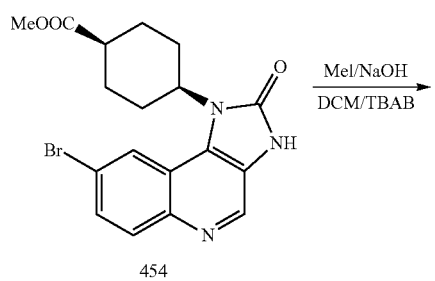
454

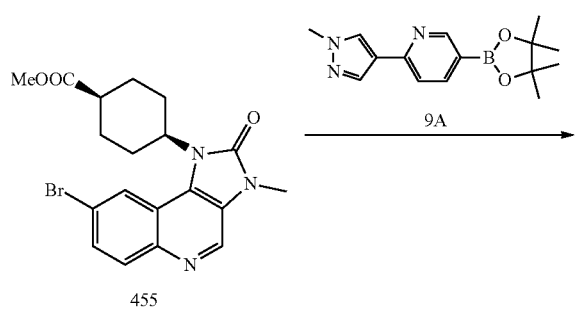
455

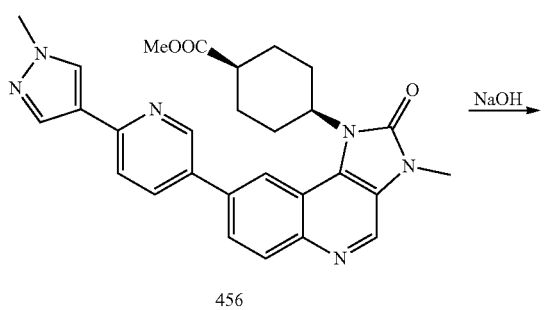
456

106
-continued

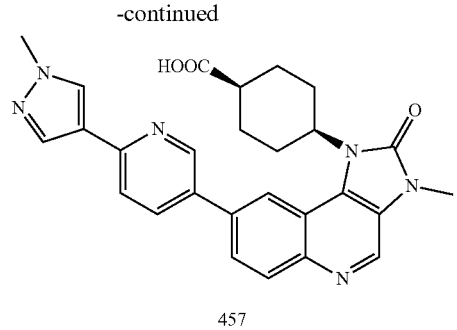
457

INTERMEDIATE 451 methyl (1s,4s)-4-amino-cyclohexanecarboxylate

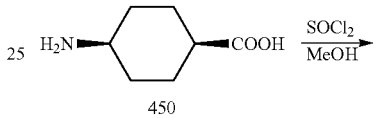
450

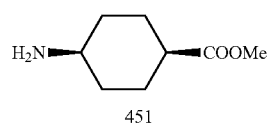
451

At 0° C., to 10 ml of methanol 1.27 ml (17.5 mmol) of sulfoxide chloride was added dropwise, stirred for 30 min, added with 1 g (7 mmol) of Compound 450, heated to room temperature, and stirred for 2 days. The reaction was incomplete, heated to reflux, and reacted for 8 h. Then the reaction was completed. The reaction solution was evaporated to dryness along with dichloromethane and methanol to afford 1.25 g of solid. Crude yield: 100%. LC-MS: 158 [M+1]$^+$, $t_R$=0.485 min.

INTERMEDIATE 452 methyl (1s,4s)-4-((6-bromo-3-nitroquinolin-4-yl)amino)cyclohexanecarboxylate

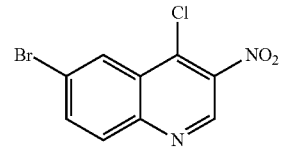
451

-continued

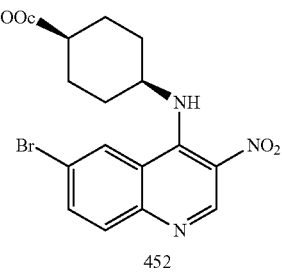

Intermediate 451 (1.25 g, 7 mmol) was dissolved in 10 ml of dichloromethane, added with 1 g (3.5 mmol) of Intermediate 3 and 1.94 ml (14 mmol) of triethylamine, stirred at room temperature for 24 h, and evaporated to dryness to afford a crude product. The crude product was purified by silica gel column chromatography (eluent:ethyl acetate:petroleum ether=1:2), to afford a yellow solid (1.3 g). Yield: 91.0%. LC-MS: 409 [M+1]$^+$, $t_R$=2.481 min.

INTERMEDIATE 453 methyl (1s,4s)-4-((6-bromo-3-aminoquinolin-4-yl)amino)cyclohexanecarboxylate

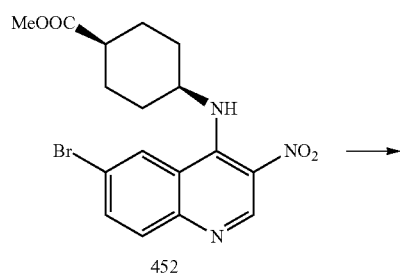

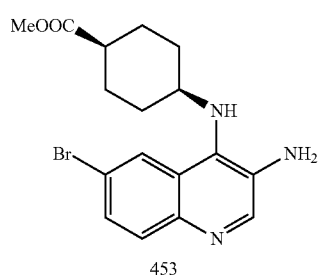

Intermediate 452 (1.3 g, 3.18 mmol) was dissolved in 15 ml of N,N-dimethylformamide, added with 3.59 g (15.9 mmol) of water and stannous chloride in batches, and stirred at room temperature for 2.5 h. The reaction solution was slowly poured into 150 ml of dichloromethane and 150 ml of saturated sodium bicarbonate solution, and separated into two phases. The aqueous phase was extracted with dichloromethane, and the organic phases were combined, washed with equivalent amount of saturated saline solution, dried, and evaporated to dryness to afford a reddish brown solid (1.3 g). Crude yield: 100%.

INTERMEDIATE 454 methyl (1s,4s)-4-(8-bromo-2-oxo-2,3-dihydro-1H-imidazo[4,5-c]quinolin-1-yl)cyclohexanecarboxylate

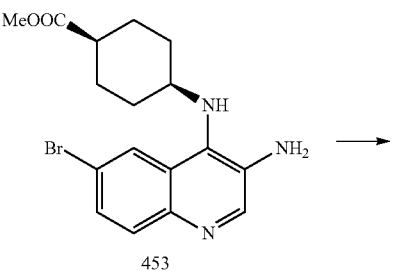

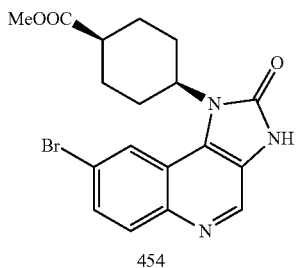

Intermediate 453 (1.3 g, 3.18 mmol) was dissolved in 10 ml of dichloromethane, added with 1.3 ml (9.54 mmol) of triethylamine, then added with a solution of 0.47 g (1.59 mmol) of triphosgene dissolved in 10 ml of dichloromethane dropwise in an ice bath, kept at 0° C. after the dropwise addition was completed, and reacted for 2 h. 20 mL of saturated sodium bicarbonate solution was poured into the reaction solution to quench the reaction. The reaction solution was separated into two phases. The aqueous phase was extracted with dichloromethane, and the organic phases were combined, dried, and evaporated to dryness to afford a crude product. The crude product was purified by silica gel column chromatography (eluent: methanol:dichloromethane=1:20) to afford a yellow solid (0.851 g). Yield: 66.20%. LC-MS: 405 [M+1]$^+$, $t_R$=1.921 min.

INTERMEDIATE 455 methyl (1s,4s)-4-(8-bromo-3-methyl-2-oxo-2,3-dihydro-1H-imidazo[4,5-c]quinolin-1-yl)cyclohexanecarboxylate

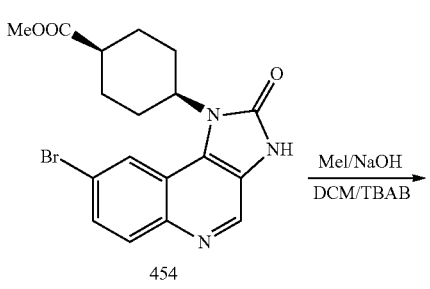

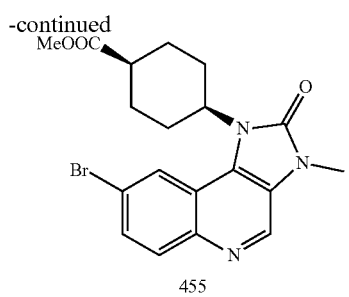

Intermediate 454 (0.851 g, 2.1 mmol) was dissolved in 10 ml of dichloromethane, added with 0.068 g (0.21 mmol) of tetra-n-butyl ammonium bromide, 10 ml of 10% sodium hydroxide solution, and 0.89 ml (6.3 mmol) of methyl iodide, stirred at room temperature overnight, and separated into two phases. The aqueous phase was extracted with dichloromethane, and the organic phases were combined, dried, evaporated to dryness to afford a crude product. The crude product was purified by silica gel column chromatography (eluent: methanol:dichloromethane=1:30) to afford a yellow solid (0.513 g). Yield: 58.43%. LC-MS: 419 [M+1]$^+$, $t_R$=2.102 min.

INTERMEDIATE 456 methyl (1s,4s)-4-(3-methyl-8-(6-(1-methyl-1H-pyrazol-4-yl)pyridin-3-yl)-2-oxo-2,3-dihydro-1H-imidazo[4,5-c]quinolin-1-yl)cyclohexanecarboxylate

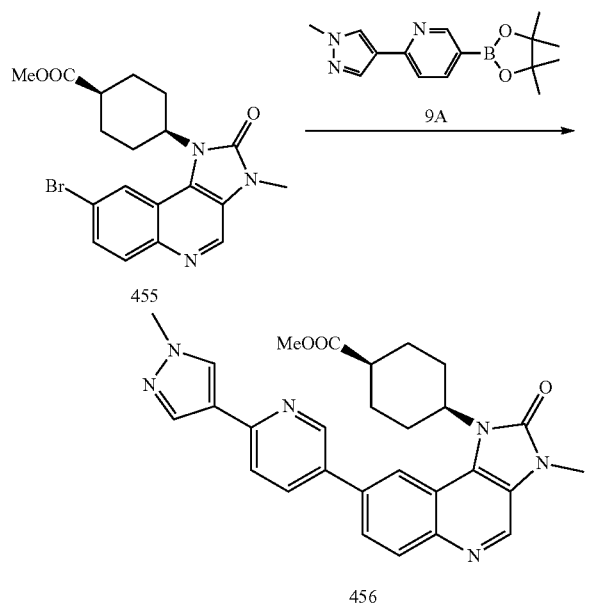

Intermediate 455 (0.513 g, 1.23 mmol) was dissolved in 10 ml of 1,4-dioxane, added with 0.525 g (1.84 mmol) of Intermediate 9A, 1.6 g (4.9 mmol) of cesium carbonate, 0.5 ml of water, and 0.098 g (0.12 mmol) of [1,1-bis(diphenylphosphino)ferrocene]palladium chloride under the protection of nitrogen, heated to 110° C., reacted for 5 h, and cooled to room temperature. The dioxane was removed by evaporation, and the residue was dissolved in 40 ml of water and 40 ml of dichloromethane. The mixture was separated into two phases, the aqueous phase was extracted with dichloromethane, and the organic phases were combined, dried, evaporated to dryness to afford a crude product. The crude product was purified by silica gel column chromatography (eluent: methanol:dichloromethane=1:20) to afford 0.42 g of solid. Yield: 68.73%. LC-MS: 249 [M/2+1]$^+$, $t_R$=1.739 min.

EXAMPLE 35

(1s,4s)-4-(3-methyl-8-(6-(1-methyl-1H-pyrazol-4-yl)pyridin-3-yl)-2-oxo-2,3-dihydro-1H-imidazo[4,5-c]quinolin-1-yl)cyclohexanecarboxylic acid

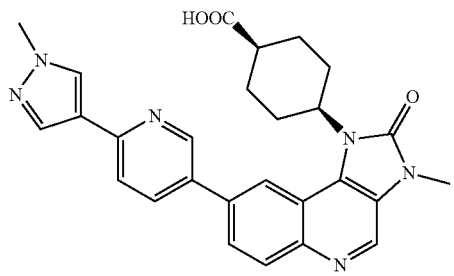 [SMILES: Cn1cc(-c2ccc(-c3ccc4ncc5c(c4c3)n([C@H]3CC[C@@H](C(=O)O)CC3)c(=O)n5C)cn2)cn1]

Intermediate 456 (0.1 g, 0.2 mmol) was dissolved in 10 ml of 1,4-dioxane, added with 2 ml of 10% sodium hydroxide solution, stirred at room temperature for 2 days, added with 100 ml of dichloromethane and 100 ml of water, and separated into two phases. The aqueous phase was adjusted pH to 5 with 1 mol/L of hydrochloric acid, and extracted with methyl tert-butyl ether, and the organic phases were combined, dried, and evaporated to dryness to afford a crude product. The crude product was purified by silica gel column chromatography (eluent: methanol:dichloromethane=1:10) to afford the target compound of Example 35 (0.054 g) as a solid. Yield: 56.25%. LC-MS: 242 [M/2+1]$^+$, $t_R$=1.539 min $^1$H NMR (400 MHz, DMSO) δ 12.31 (s, 1H), 8.99 (s, 1H), 8.87 (s, 1H), 8.38 (s, 2H), 8.29-7.92 (m, 4H), 7.83 (d, J=7.8 Hz, 1H), 4.88 (s, 1H), 3.92 (s, 3H), 3.47 (s, 3H), 2.82-2.55 (m, 3H), 2.28 (d, J=12.0 Hz, 2H), 1.94 (d, J=11.0 Hz, 2H), 1.76 (s, 2H).

(XIV) Scheme XIV:

Scheme XIV

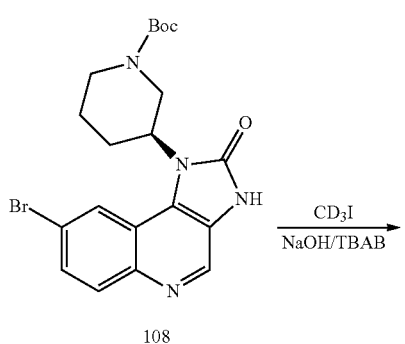

INTERMEDIATE 53b tert-butyl 3-(8-bromo-3-deuteromethyl-2-oxo-2,3-dihydro-1H-imidazo[4,5-c]quinolin-1-yl)piperidine-1-carboxylate

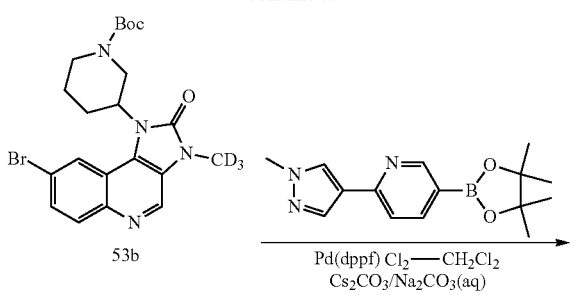

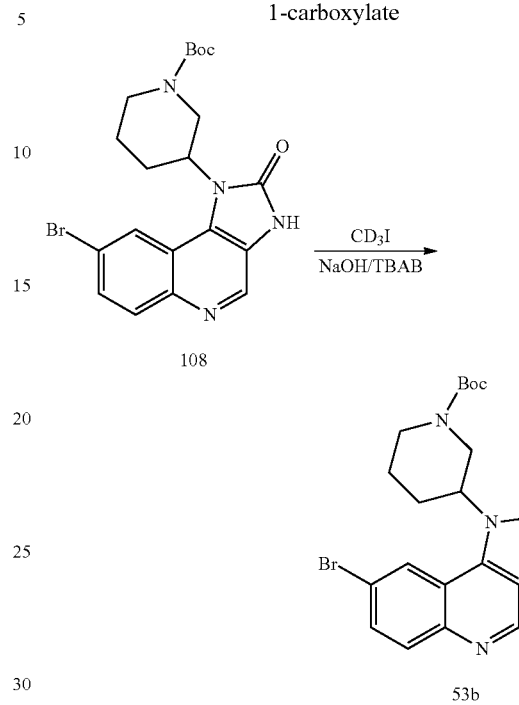

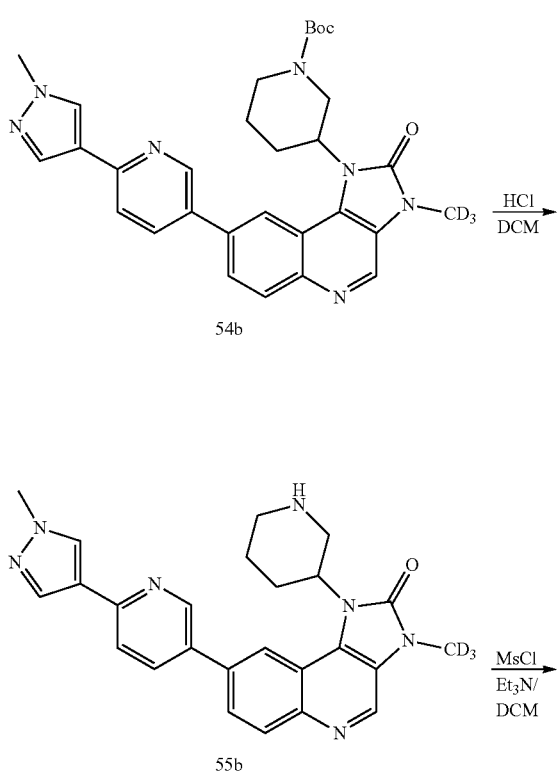

0.6 g (1.34 mmol) of Intermediate 108 was dissolved in 30 mL of dichloromethane, added with 0.044 g (0.134 mmol) of tetrabutylammonium bromide and 30 mL of 10% aqueous sodium hydroxide solution, stirred for 10 minutes, then added with 0.78 g (4 mmol) of deuteromethyl iodide, and stirred for 4 h. The reaction was monitored by TLC. After the reaction was completed, the reaction mixture was allowed to stand and separated into two layers. The organic phase was separated off, and the aqueous phase was extracted with dichloromethane. The organic phases were combined, dried, and rotary evaporated to dryness to afford a crude product. The crude product was purified by silica gel column chromatography (dichloromethane/methanol=50/1, V:V) to afford 0.5 g of the product as a white solid. Yield: 80.5%. LC-MS: 464,466 [M+1]$^+$, $t_R$=2.411 min.

INTERMEDIATE 54b tert-butyl 3-(3-deuteromethyl-8-(6-(1-methyl-1H-pyrazol-4-yl)pyridin-3-yl)-2-oxo-2,3-hydro-1H-imidazo[4,5-c]quinolin-1-yl)piperidine-1-carboxylate

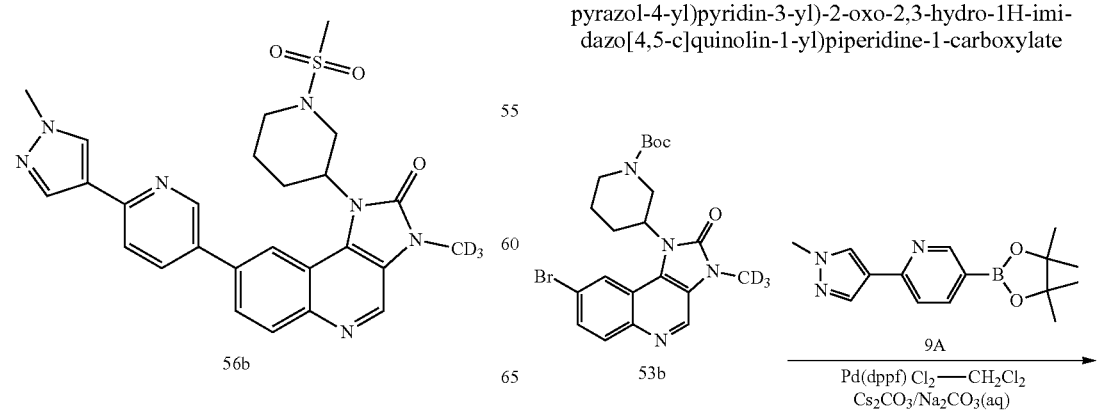

-continued

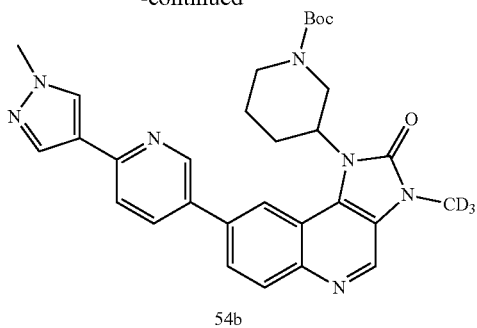

54b

Under the protection of nitrogen, 0.5 g (1.1 mmol) of Intermediate 53b and 0.46 g (1.6 mmol) of Intermediate 9A were dissolved in 40 mL of dioxane, added with 1.8 g (5.5 mmol) of cesium carbonate and 15 mL of 2M aqueous sodium carbonate solution, then added with 0.09 g (0.11 mmol) of [1,1-bis(di-phenylphosphino)ferrocene]palladium chloride, heated at 110° C. for 5 h. The reaction was monitored by TLC. After the reaction was completed, most of dioxanewas removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=30/1, V:V) to afford 0.3 g of the product as a white solid. Yield: 50.3%. LC-MS: 543 [M+1]$^+$, $t_R$=1.931 min.

INTERMEDIATE 55b 3-deuteromethyl-8-(6-(1-methyl-1H-pyrazol-4-yl)pyridin-3-yl)-1-(piperidin-3-yl)-1H-imidazo[4,5-c]quinolin-2(3H)-one

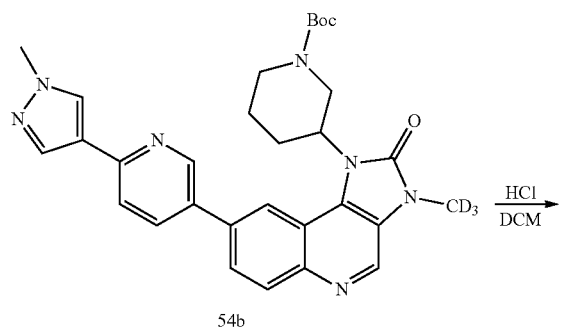

In an ice-water bath, 0.3 g (0.55 mmol) of Intermediate 54b was dissolved in 20 mL of dichloromethane, and hydrogen chloride gas was purged through the reaction solution for 30 minutes. The reaction was monitored by TLC. After the reaction was completed, the reaction solution was filtered, and the solid was washed with dichloromethane, pumped to dryness under a reduced pressure to afford a product (0.3 g) as a dark brown solid. Crude yield: 100%.

EXAMPLE 36

3-deuteromethyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one

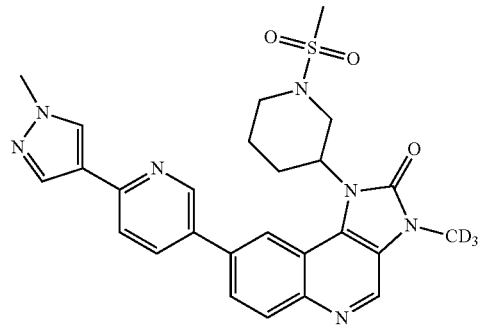 [SMILES: [2H]C([2H])([2H])n1c(=O)n(C2CCCN(S(C)(=O)=O)C2)c2c3cc(-c4ccc(-c5cnn(C)c5)nc4)ccc3ncc21]

0.3 g (0.55 mmol) of Intermediate 55b was dissolved in 40 mL of dichloromethane, added with 0.278 g (2.75 mmol) of triethylamine and then 0.095 g (0.825 mmol) of methylsulfonyl chloride, and stirred at room temperature overnight. The reaction was monitored by TLC. After the reaction was completed, 40 mL of saturated sodium bicarbonate aqueous solution water was added, and stirred for 20 minutes. The mixture was separated into two layers, the aqueous phase was extracted with dichloromethane, and the organic phases were combined, dried, and rotary evaporated to dryness to afford a crude product. The crude product was purified by silica gel column chromatography (dichloromethane/methanol=10/1, V:V) to afford 0.2 g of the target compound of Example 36, as a yellowish white solid. Yield: 69.9%. LC-MS: 521 [M+1]$^+$, $t_R$=1.658 min $^1$H NMR (400 MHz, DMSO) δ 8.99 (d, J=2.3 Hz, 1H), 8.93 (s, 1H), 8.40 (s, 2H), 8.24 (dd, J=8.3, 2.4 Hz, 1H), 8.19 (d, J=8.9 Hz, 1H), 8.09 (s, 1H), 8.05 (d, J=8.9 Hz, 1H), 7.78 (d, J=8.3 Hz, 1H), 5.07 (t, J=11.4 Hz, 1H), 4.01 (d, J=9.1 Hz, 1H), 3.92 (s, 3H), 3.71 (d, J=10.7 Hz, 1H), 3.58 (t, J=11.4 Hz, 1H), 2.99 (s, 3H), 2.89-2.67 (m, 2H), 2.17 (d, J=11.7 Hz, 1H), 1.99 (d, J=13.3 Hz, 1H), 1.79 (q, J=12.5 Hz, 1H).

(XV) Scheme XV:

Scheme XV

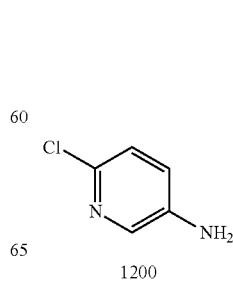  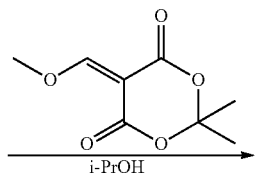

1200

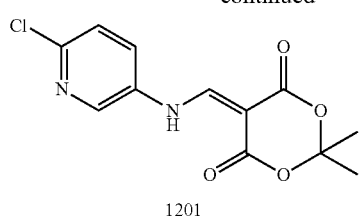
1201
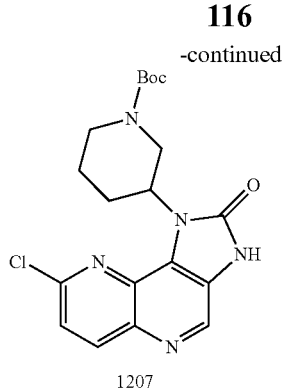
1207
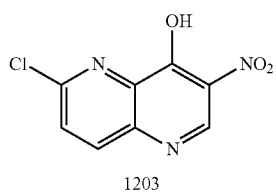
1202
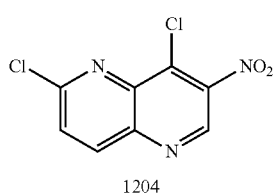
1203
1204
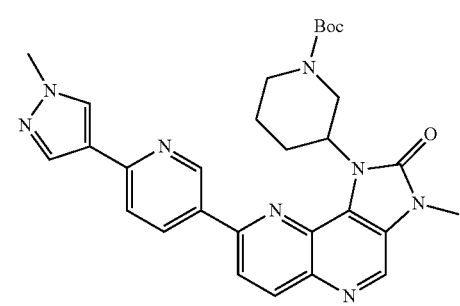
1208
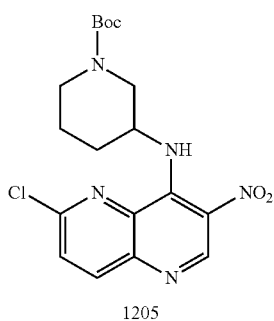
1205
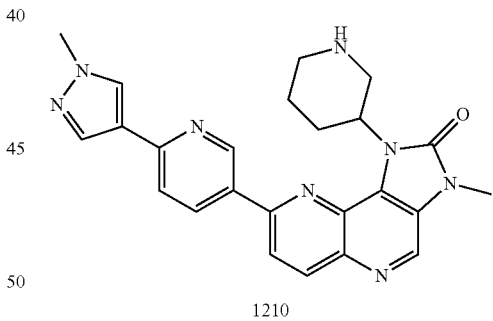
1209
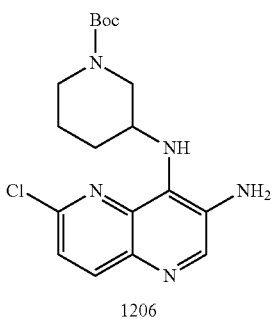
1206
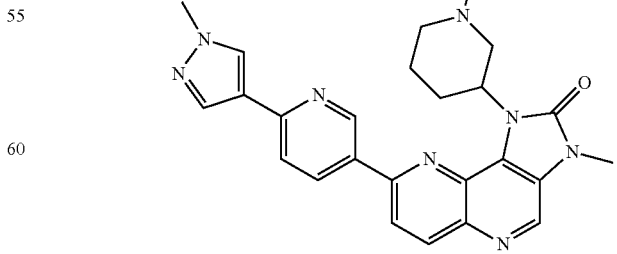
1210
1211

INTERMEDIATE 1201

5-(((6-chloropyridin-3-yl)amino-methylene)-2,2-dimethyl-1,3-dioxan-4,6-dione

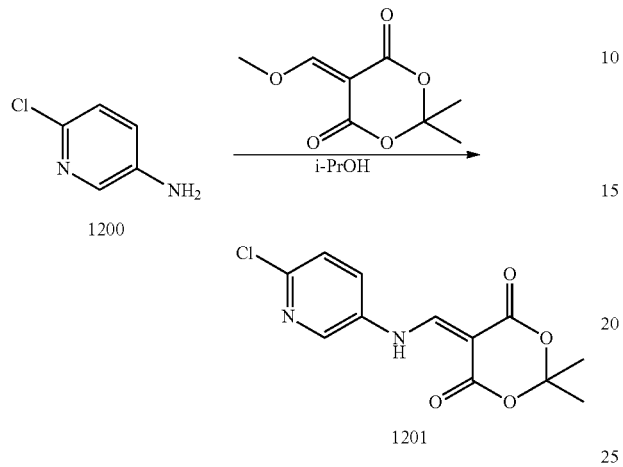

5 g (38.8 mmol) of 2-chloro-5-aminopyridine and 7.2 g (38.8 mmol) of 5-(methoxylmethylene)-2,2-dimethyl-1,3-dioxy-4,6-dione were suspended in 100 mL of isopropanol, and heated to reflux for 2 h. The reaction was monitored by TLC. After the reaction was completed, the solvent was rotary evaporated to dryness to afford a product (10.5 g) as a yellowish white solid. Yield: 95.8%. LC-MS: 283 [M+1]$^+$, $t_R$=1.775 min.

INTERMEDIATE 1202

6-chloro-1,5-naphthyridin-4-ol

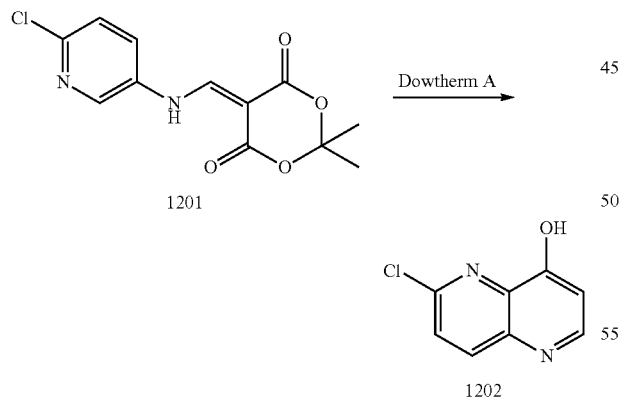

500 ML of diphenyl-diphenyl ether mixture solvent was heated to 220° C., and added with 10.5 g (37.1 mmol) of Intermediate 1201 in batches, and after the addition stirred at 220° C. for 5 minutes. After the reaction was completed, the reaction solution was cooled to room temperature, and 1 L of petroleum ether was added to the reaction solution to precipitate out a large amount of solid. The precipitate was collected via filtration, washed with petroleum ether, and dried under reduced pressure to afford a product (4.9 g) as an earthy yellow solid. Yield: 73.1%. LC-MS: 181 [M+1]$^+$, $t_R$=0.583 min.

INTERMEDIATE 1203

6-chloro-3-nitro-1,5-naphthyridin-4-ol

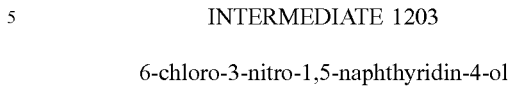

In an ice-water bath, 4.9 g (27.1 mmol) of Intermediate 1202 and 5.5 g (54.2 mmol) of potassium nitrate was slowly added to 40 mL of concentrated sulfuric acid, and reacted at 100° C. for 1 h. The reaction was monitored by TLC. After the reaction was completed, the reaction solution was cooled to room temperature, and slowly poured into ice water to precipitate out a large amount of solid. The precipitate was collected via filtration, and dried under reduced pressure to afford a product (4.2 g) as a yellow solid. Yield: 63.6%. LC-MS: 226 [M+1]$^+$, $t_R$=1.428 min.

INTERMEDIATE 1204

2,8-dichloro-7-nitro-1,5-naphthyridine 4.2 g (17.2 mmol) of Intermediate 1203 was suspended in 15 mL of DMF, added with a solution of 3.5 g (22.4 mmol) of phosphorus oxychloride in 10 ml of DMF dropwise over a period of 3 minutes, followed by stirring at room temperature for 20 h. The reaction solution was poured into ice water, filtered by suction, and dried in an oven to afford a terreous solid (3.8 g). Yield: 90.5%. LC-MS: 244 [M+1]$^+$, $t_R$=2.066 min.

INTERMEDIATE 1205 tert-butyl 3-((6-chloro-3-nitro-1,5-naphthyridin-4-yl)amino)piperidine-1-carboxylate

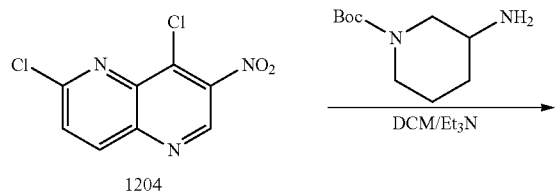

0.9 g (3.7 mmol) of Intermediate 1204 and 1.1 g (5.6 mmol) of the compound of 1-tert-butyloxycarbonyl-3-aminopiperidine were dissolved in 60 mL of dichloromethane, added with 0.75 g (7.4 mmol) of triethylamine, and stirred at room temperature overnight. The reaction was monitored by TLC. After the reaction was completed, the solvent was rotary evaporated to dryness to afford a crude product. The crude product was purified by silica gel column chromatography (eluent: petroleum ether/ethyl acetate=1/1, V/V) to afford a product (1.3 g) as a yellow powder. Yield: 86.6%. LC-MS: 408 [M+1]$^+$, $t_R$=2.603 min.

INTERMEDIATE 1206 tert-butyl 3-((3-amino-6-chloro-1,5-naphthyridin-4-yl)amino)piperidine-1-carboxylate

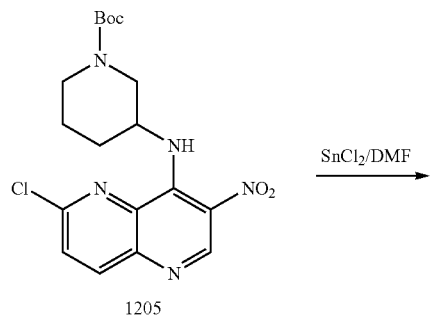

In an ice-water bath, 1.3 g (3.2 mmol) of Intermediate 1205 was dissolved in 15 mL of N,N-dimethylformamide 3.6 g (16 mmol) of stannous chloride dihydrate was added in batches over a period of 30 minutes, and stirred at room temperature for 2 h. The reaction was monitored by TLC. After the reaction was completed, 10% of aqueous sodium hydroxide solution was added dropwise to the reaction solution to pH of 8-9, and filtered. The filtrate was extracted with dichloromethane, and the filter cake was washed with dichloromethane. The organic phases were combined, washed with water and with brine, dried, rotary evaporated to dryness to afford a product (2.5 g) as reddish brown oil. Yield: >100%. LC-MS: 378 [M+1]$^+$, $t_R$=1.758 min.

INTERMEDIATE 1207 tert-butyl 3-(8-chloro-2-oxo-2,3-dihydro-1H-imidazo[4,5-c][1,5]naphthyridin-1-yl)piperidine-1-carboxylate

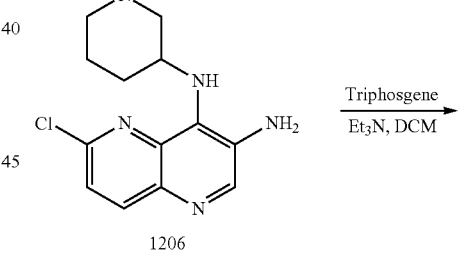

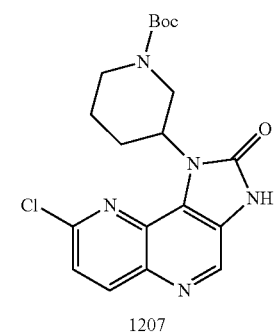

In an ice-water bath, 2.5 g (3.2 mmol) of Intermediate 1206 was dissolved in 10 mL of dichloromethane, added with 1.1 g (11.2 mmol) of triethylamine, and stirred for 10 minutes. A solution of 0.5 g (1.6 mmol) of triphosgene dissolved in 10 mL of dichloromethane was added dropwise, and stirred at 0° C. for 4 h. The reaction was monitored by TLC. After the reaction was completed, 20 mL of saturated sodium bicarbonate solution was added dropwise to the reaction solution to quench the reaction, and stirred for 10 minutes. The organic phase was separated off, and the aqueous phase was extracted with dichloromethane. The organic phases were combined, dried, and rotary evaporated to dryness to afford a crude product. The crude product was purified by silica gel column chromatography (eluent:dichloromethane/methanol=40/1, V/V) to afford a product (0.4 g) as a brownish yellow solid. Yield: 31.8%. LC-MS: 404 [M+1]$^+$, $t_R$=2.252 min.

INTERMEDIATE 1208 tert-butyl 3-(8-bromo-3-methyl-2-oxo-2,3-dihydro-1H-imidazo[4,5-c][1,5]naphthyridin-1-yl)piperidine-1-carboxylate

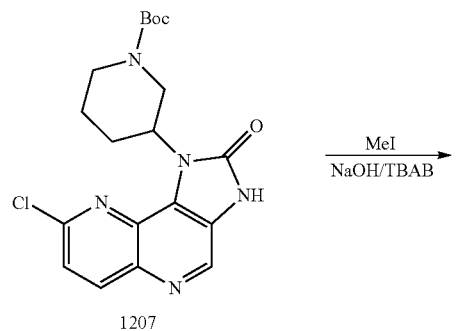

0.4 g (1 mmol) of Intermediate 1207 was dissolved in 30 mL of dichloromethane, added with 0.032 g (0.1 mmol) of tetrabutylammonium bromide and 30 mL of 10% aqueous sodium hydroxide solution, stirred for 10 minutes, then added with 0.4 g (3 mmol) of methyl iodide, and stirred for 4 h. The reaction was monitored by TLC. After the reaction was completed, the reaction mixture was allowed to stand and separated into two layers. The organic phase was separated off, and the aqueous phase was extracted with dichloromethane. The organic phases were combined, dried, and rotary evaporated to dryness to afford a product (0.5 g) as a yellow solid. Crude yield: 100%. LC-MS: 418 [M+1]$^+$, $t_R$=2.425 min.

INTERMEDIATE 1209 tert-butyl 3-(3-methyl-8-(6-(1-methyl-1H-pyrazol-4-yl)pyridin-3-yl)-2-oxo-2,3-dihydro-1H-imidazo[4,5-c][1,5]naphthyridin-1-yl)piperidine-1-carboxylate

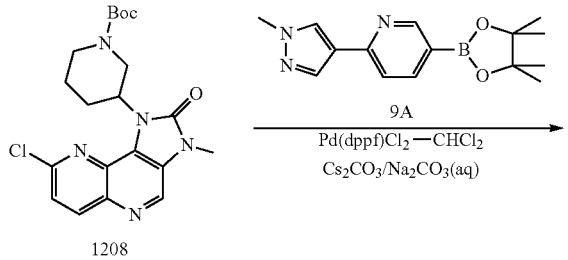

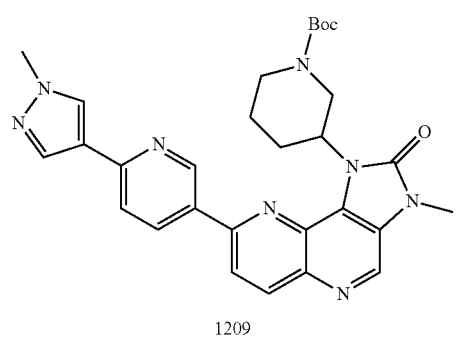

Under the protection of nitrogen, 0.5 g (1.2 mmol) of Intermediate 1208 and 0.5 g (1.8 mmol) of Intermediate 9A were dissolved in 30 mL of dioxane, added with 1.9 g (6 mmol) of cesium carbonate, 10 mL of 2M aqueous sodium carbonate solution, and then 0.1 g (0.12 mmol) of [1,1-bis(di-phenylphosphino)ferrocene]palladium chloride, and heated at 110° C. for 20 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=40/1, V:V) to afford 0.6 g of the product as an earthy yellow solid. Yield: 92.6%. LC-MS: 541 [M+1]$^+$, $t_R$=2.095 min.

INTERMEDIATE 1210

3-methyl-8-(6-(1-methyl-1H-pyrazol-4-yl)pyridin-3-yl)-1-(piperidin-3-yl)-1H-imidazo[4,5-c][1,5]naphthyridin-2(3H)-one

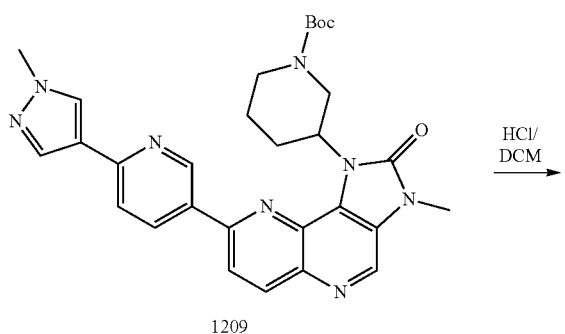

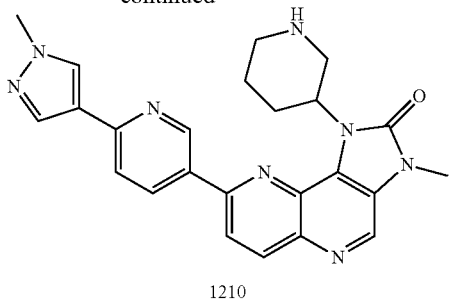

1210

In an ice-water bath, 0.2 g (0.37 mmol) of Intermediate 1209 was dissolved in 5 mL of dichloromethane, and hydrogen chloride gas was purged through the reaction solution for 30 minutes. The reaction was monitored by TLC. After the reaction was completed, the reaction solution was filtered, and the solid was washed with dichloromethane, and pumped to dryness under reduced pressure to afford a product (0.2 g) as an earthy yellow solid. Crude yield: 100%.

EXAMPLE 37

3-methyl-8-(6-(1-methyl-1H-pyrazol-4-yl)pyridin-3-yl)-1-(1-(methanesulfonyl)piperidin-3-yl)-1H-imidazo[4,5-c][1,5]naphthyridin-2(3H)-one

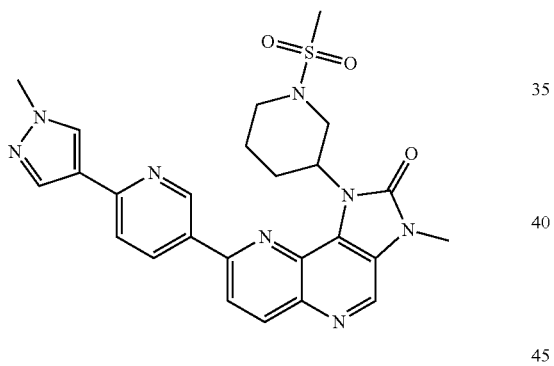

0.2 g (0.37 mmol) of Intermediate 1210 was dissolved in 25 mL of dichloromethane, added with 0.187 g (1.85 mmol) of triethylamine, and then 0.064 g (0.56 mmol) of methylsulfonyl chloride, and stirred at room temperature overnight. The reaction was monitored by TLC. After the reaction was completed, 25 mL of saturated sodium bicarbonate aqueous solution was added, and stirred for 20 minutes. The mixture was separated into layers, the aqueous phase was extracted with dichloromethane, and the organic phases were combined, dried, and rotary evaporated to dryness to afford a crude product. The crude product was purified by silica gel column chromatography (dichloromethane/methanol=10/1, V:V) to afford 0.09 g of the target compound of Example 37, as a yellow solid. Yield: 47.1%. LC-MS: 519 [M+1]$^+$, $t_R$=1.726 min $^1$H NMR (400 MHz, DMSO) δ 9.36 (d, J=1.8 Hz, 1H), 8.99 (s, 1H), 8.59 (d, J=8.1 Hz, 1H), 8.53 (d, J=8.9 Hz, 1H), 8.43 (s, 1H), 8.36 (d, J=8.9 Hz, 1H), 8.11 (s, 1H), 7.81 (d, J=8.4 Hz, 1H), 6.24 (br s, 1H), 3.93 (s, 3H), 3.87 (s, 1H), 3.73 (d, J=11.2 Hz, 2H), 3.55 (s, 3H), 2.97 (s, 3H), 2.84 (t, J=11.9 Hz, 1H), 2.68 (s, 1H), 2.06 (d, J=13.2 Hz, 2H), 1.73 (d, J=12.5 Hz, 1H).

(XVI) Scheme XVI:

Scheme XVI

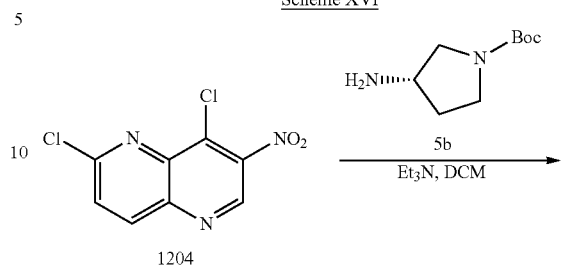

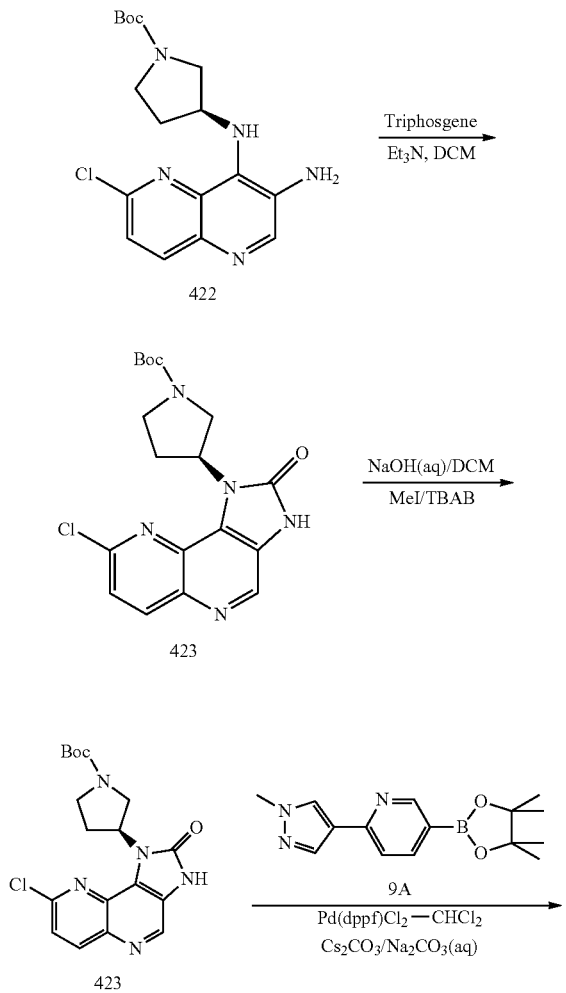

-continued

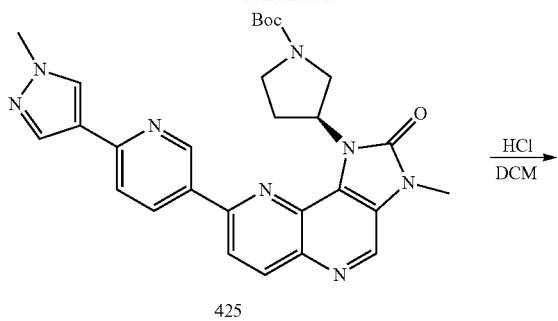
425

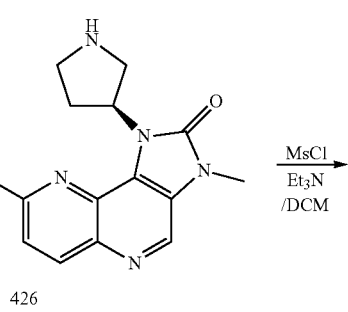
426

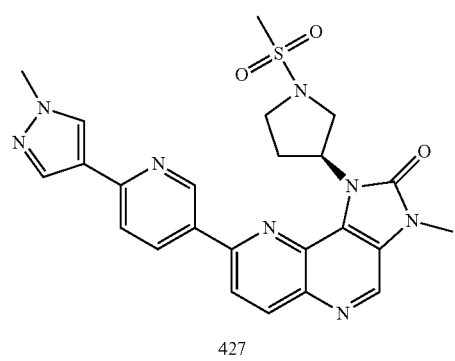
427

INTERMEDIATE 421 tert-butyl (S)-3-((6-chloro-3-nitro-1,5-naphthyridin-4-yl)amino)pyrrolidine-1-carboxylate

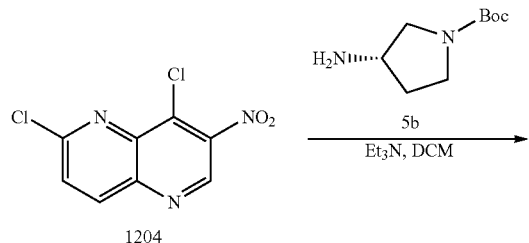

-continued

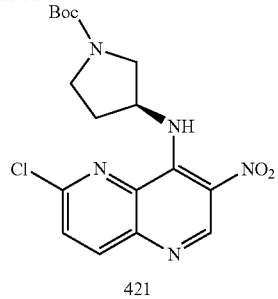
421

0.8 g (3.28 mmol) of Compound 1204, 0.733 g (3.94 mmol) of Compound 5b were dissolved in 15 ml of DMF, stirred for 10 min, added with 0.92 ml of triethylamine, and stirred at room temperature overnight. 75 mL of water was added dropwise to precipitate out a solid, filtered, and the filter cake was rinsed with 20 ml of water, and dried in vacuo to afford a red solid (1.067 g). Yield: 82.6%. LC-MS: 393.9 $[M+1]^+$, $t_R$=2.541 min.

INTERMEDIATE 422 tert-butyl (S)-3-((3-amino-6-chloro-1,5-naphthyridin-4-yl)amino)pyrrolidine-1-carboxylate

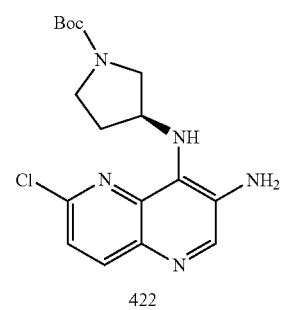
422

1.05 g (2.67 mmol) of Intermediate 421 was dissolved in 20 ml of DMF, added with 3.01 g (13.35 mmol) of stannous chloride dihydrate in batches in an ice-water bath, and stirred overnight. The reaction was completed, added with 10 ml of saturated sodium bicarbonate solution and 8 ml of 10% sodium hydroxide to adjust pH 8~9, and filtered to remove tin salt. The filter cake was washed with 100 ml of dichloromethane in five times until the filtrate had no fluorescence at 365 nm. The filtrate was allowed to stand and separated into two phases. The aqueous phase was extracted with 60 ml of dichloromethane in three times, and the organic phases were combined, and reverse extracted twice with equal volumes of water and saturated saline solution.

The organic phases were dried, rotary evaporated, and pumped to dryness to afford a brown crystal (0.824 g). Yield: 84.82%. LC-MS: 363.9 [M+1]⁺, $t_R$=1.791 min.

INTERMEDIATE 423 tert-butyl (S)-3-(8-chloro-2-oxo-2,3-dihydro-1H-imidazo[4,5-c][1,5]naphthyridin-1-yl)pyrrolidine-1-carboxylate

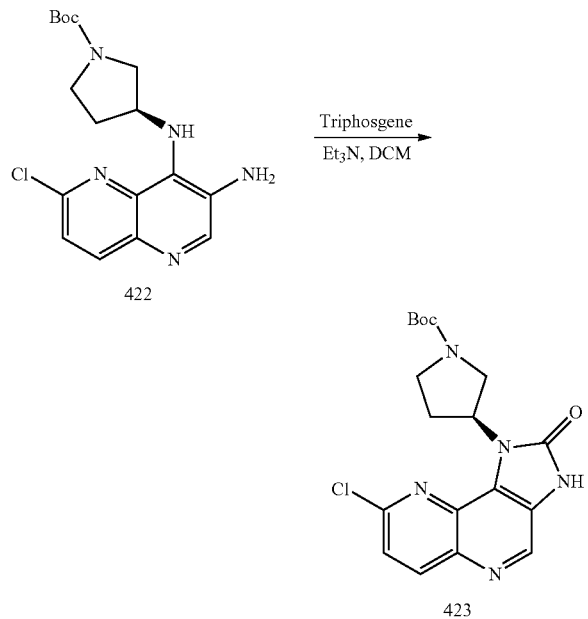

0.82 g (2.25 mmol) of Intermediate 422 was dissolved in 20 ml of dichloromethane, added with 0.94 ml (6.75 mmol) of triethylamine and then 0.335 g (1.13 mmol) of triphosgene dissolved in 10 ml of dichloromethane dropwise with stirring in an ice bath, stirred under ice-bath condition, and reacted overnight. 30 mL of saturated sodium bicarbonate solution was added to quench the reaction, and the reaction solution was separated into two phases, the aqueous phase was extracted with 90 ml of dichloromethane in three times, and the organic phases were combined, dried, and passed through a silica gel chromatographic column (eluent: methanol:dichloromethane=1:30) to afford a brown solid (0.628 g). Yield: 71.6%. LC-MS: 389.9 [M+1]⁺, $t_R$=2.072 min.

INTERMEDIATE 424 tert-butyl (S)-3-(8-chloro-3-methyl-2-oxo-2,3-dihydro-1H-imidazo[4,5-c][1,5]naphthyridin-1-yl)pyrrolidine-1-carboxylate

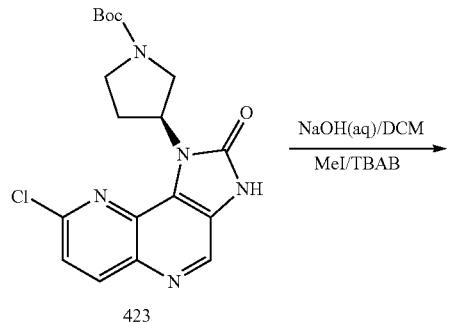

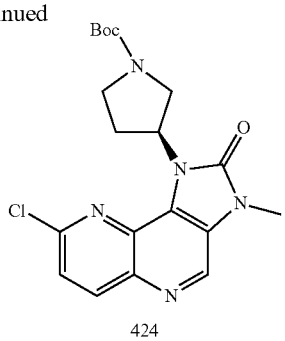

0.62 g (1.59 mmol) of Intermediate 423 was dissolved in 25 ml of dichloromethane, added with 0.053 g (0.159 mmol) of TBAB and then with 25 ml of 10% NaOH, stirred for 10 min, then added with 0.31 ml (4.95 mmol) of methyl iodide, and stirred at room temperature to react overnight. The reaction solution was allowed to stand, and separated into two phases. The aqueous phase was extracted with 25 ml×4 of dichloromethane, and the organic phases were combined, dried, concentrated by rotary evaporation, and pumped to dryness in vacuo, to afford a crude product as a brown solid (0.696 g). Yield: 100%. LC-MS: 403.9 [M+1]⁺, $t_R$=2.320 min.

INTERMEDIATE 425 tert-butyl (S)-3-(3-methyl-8-(6-(1-methyl-1H-pyrazol-4-yl)pyridin-3-yl)-2-oxo-2,3-dihydro-1H-imidazo[4,5-c][1,5]naphthyridin-1-yl)pyrrolidine-1-carboxylate

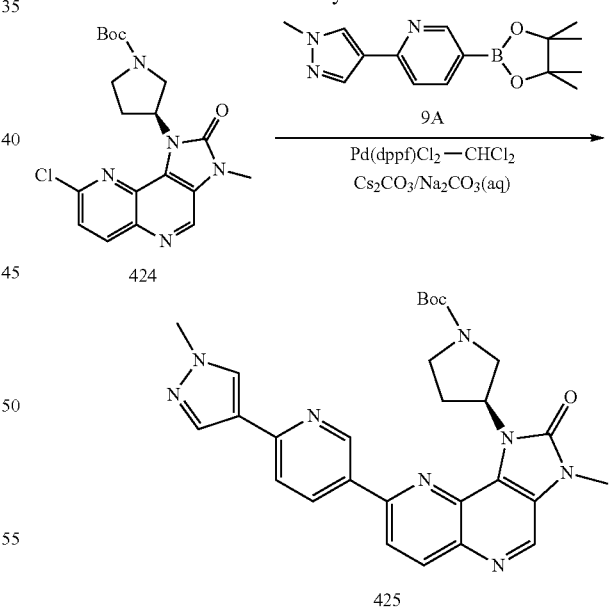

0.2 g (0.495 mmol) of Intermediate 424, 0.22 g (0.77 mmol) of 9A, and 0.836 g (2.565 mmol) of cesium carbonate were suspended in 15 ml of dioxane, added with 3 ml of 2M sodium carbonate, then added with 0.042 g (0.051 mmol) of [1,1'-bis(diphenylphosphino)ferrocene]palladium dichloride dichloromethane complex under the protection of nitrogen, and heated to 110° C. and reacted overnight (15 h) under the protection of nitrogen again. The reaction was completed, concentrated by rotary evaporation, added with 25 ml of water, stirred, then added with 20 ml of dichloromethane and stirred, was allowed to stand and separated into two phases. The aqueous phase was extracted with 20 ml×4 of dichloromethane, and the organic phases were combined, dried, and passed through a silica gel chromatographic column (eluent:methanol:dichloromethane=1:30) to afford a yellow solid (0.252 g). Yield: 96.68%. LC-MS: 526.9 [M+1]$^+$, $t_R$=2.103 min.

INTERMEDIATE 426

(S)-3-methyl-8-(6-(1-methyl-1H-pyrazol-4-yl)pyridin-3-yl)-1-(pyrrolidin-3-yl)-1H-imidazo[4,5-c][1,5]naphthyridin-2(3H)-one

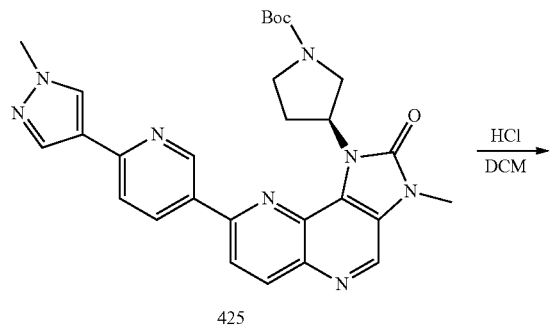

0.25 g (0.47 mmol) of Intermediate 425 was dissolved in 8 ml of DCM, purged with HCl gas in an ice-water bath, stirred and reacted for 1 h to precipitate out solids, filtered, washed with a small amount of DCM, and pumped to dryness in vacuo to afford a brown solid (0.131 g). Yield: 65.31%. LC-MS: 426.9 [M+1]$^+$, $t_R$=1.445 min.

EXAMPLE 38

(S)-3-methyl-8-(6-(1-methyl-1H-pyrazol-4-yl)pyridin-3-yl)-1-(1-(methanesulfonyl)pyrrolidin-3-yl)-1H-imidazol-[4,5-c][1,5]naphthyridin-2(3H)-one

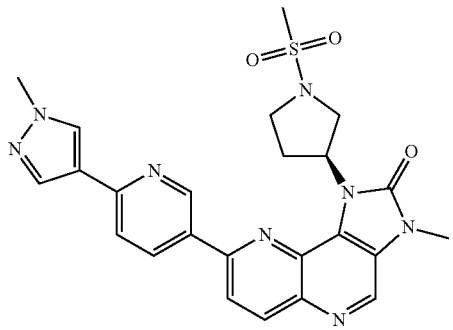 [SMILES: Cn1cc(-c2ccc(-c3ccc4ncc5c(c4n3)n([C@H]3CCN(S(C)(=O)=O)C3)c(=O)n5C)cn2)cn1]

130 mg (0.30 mmol) of Intermediate 426 was added with 25 ml of dichloromethane, then with 1.51 ml of triethylamine, and stirred for 10 min. The solid was not dissolved completely, and 0.08 ml of methylbenzene sulfonyl chloride was added, and reacted overnight. 25 mL of saturated sodium bicarbonate solution was added, and the mixture was separated into two phases. The aqueous phase was extracted with 35 ml×3 of dichloromethane, and the organic phases were combined, dried over anhydrous sodium sulfate, and passed through a TLC preparative plate to afford a light yellow solid (57 mg). Yield: 37.65%. LC-MS: 504.9[M+1]$^+$, $t_R$=1.695 min $^1$H NMR (400 MHz, DMSO) δ 9.37 (s, 1H), 9.01 (s, 1H), 8.63 (d, J=8.3 Hz, 1H), 8.53 (d, J=9.0 Hz, 1H), 8.44-8.32 (m, 2H), 8.09 (s, 1H), 7.82 (d, J=8.3 Hz, 1H), 6.74-6.43 (m, 1H), 4.02-3.94 (m, 1H), 3.92 (s, 3H), 3.83 (t, J=9.3 Hz, 1H), 3.73-3.63 (m, 1H), 3.56 (s, 3H), 3.54-3.48 (m, 1H), 3.06 (s, 3H), 2.97-2.82 (m, 1H), 2.45-2.35 (m, 1H).

(XVII) Scheme XVII:

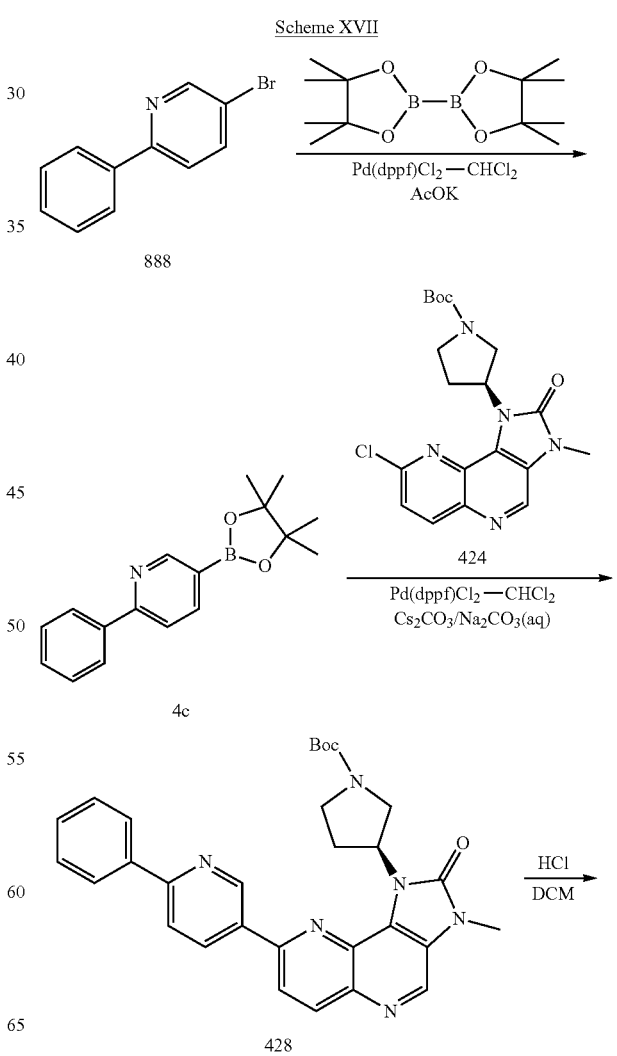

131
-continued

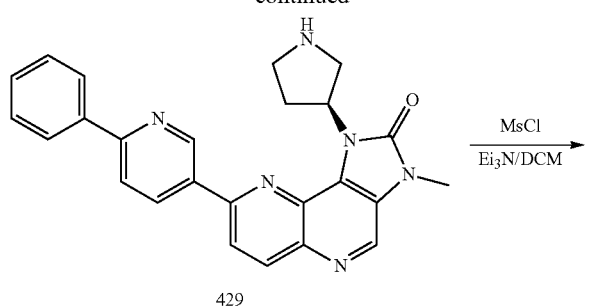

429

→ MsCl
Et₃N/DCM

132
-continued

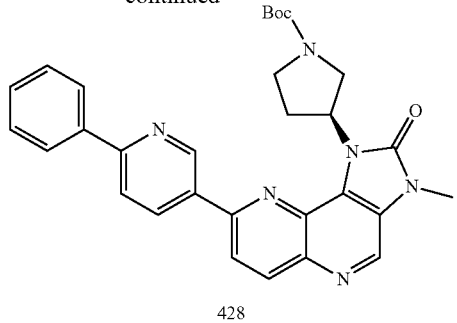

428

156 mg (0.67 mmol) of Compound 888, 253 mg (1 mmol) of diboronate, 197 mg (2.01 mmol) of potassium acetate were dissolved in 10 ml of dioxane, added with 44 mg (0.05 mmol) of [1,1'-bis(diphenylphosphino)ferrocene]palladium dichloride dichloromethane complex under the protection of nitrogen, heated to 100° C. and stirred for 2 h under the protection of nitrogen. The solution was cooled, added with 0.2 g (0.495 mmol) of Intermediate 424, 0.806 g (2.475 mmol) of cesium carbonate, 10 ml of dioxane, and then with 3 ml of 2M sodium carbonate, followed by the addition of 0.041 g (0.050 mmol) of [1,1'-bis(diphenylphosphino)ferrocene]palladium dichloride dichloromethane complex under the protection of nitrogen, heated to 110° C. and reacted overnight. The reaction was completed, concentrated by rotary evaporation, added with 25 ml of water, stirred, then added with 20 ml of dichloromethane, stirred, was allowed to stand and separated into two phases. The aqueous phase was extracted with 20 ml×4 of dichloromethane, and the organic phases were combined, dried, and passed through a silica gel chromatographic column (eluent:methanol:dichloromethane=1:40) to afford a yellow solid (0.286 g). Yield: 100%. LC-MS: 522.9 [M+1]⁺, $t_R$=2.789 min.

INTERMEDIATE 429

(S)-3-methyl-8-(6-phenylpyridin-3-yl)-1-(pyrrolidin-3-yl)-1H-imidazo[4,5-c][1,5]naphthyridin-2(3H)-one

INTERMEDIATE 428 tert-butyl (S)-3-(3-methyl-2-oxo-8-(6-phenylpyridin-3-yl)-2,3-dihydro-1H-imidazo[4,5-c][1,5]naphthyridin-1-yl)pyrrolidine-1-carboxylate

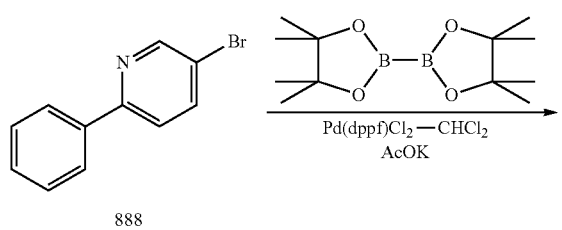

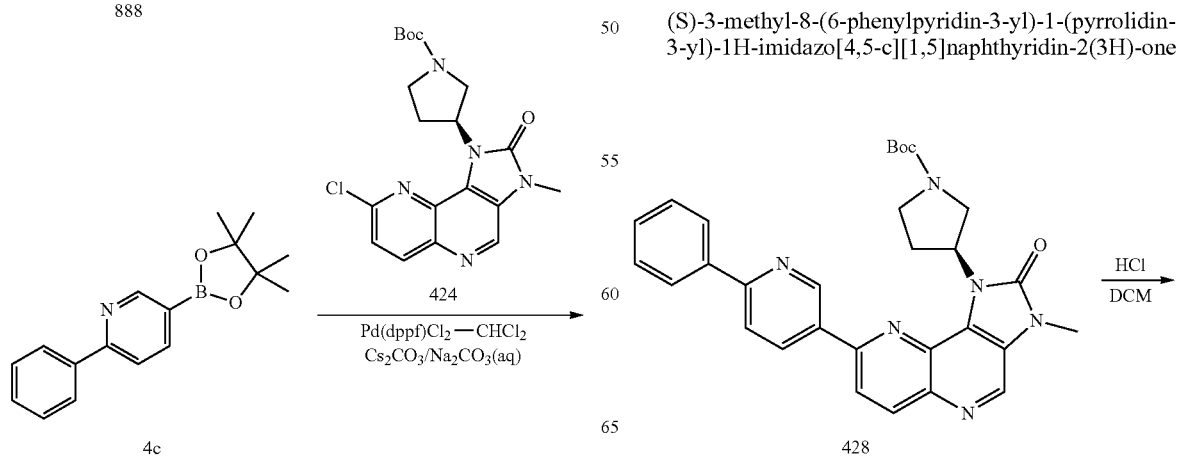

428 → HCl/DCM

133

-continued

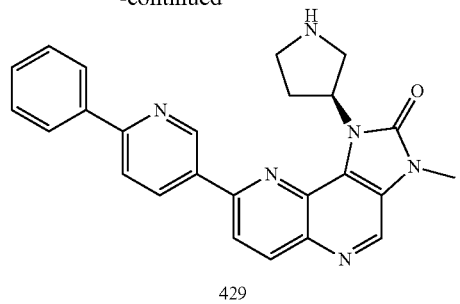

429

0.28 g (0.47 mmol) of Intermediate 428 was dissolved in 8 ml of DCM in an ice-water bath, purged with HCl gas, stirred and reacted for 1 h to precipitate out solids. The reaction was complete, and pumped to dryness in vacuo to afford a crude product as a brown solid (0.342 g). Yield: 100%.

EXAMPLE 39

(S)-3-methyl-1-(1-(methanesulfonyl)pyrrolidin-3-yl)-8-(6-phenylpyridin-3-yl)-1H-imidazo[4,5-c][1,5]naphthyridin-2(3H)-one

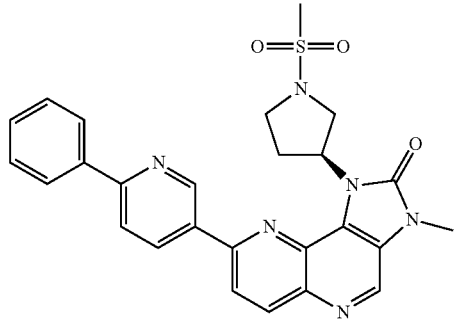 [SMILES: Cn1c(=O)n([C@H]2CCN(S(C)(=O)=O)C2)c2c3nc(-c4ccc(-c5ccccc5)nc4)ccc3ncc21]

226 mg (0.30 mmol) of Intermediate 429 was added with 10 ml of dichloromethane, then with 0.4 ml of triethylamine, stirred for 10 min to obtain a clear solution, then added with 0.06 ml of methylbenzenesulfonyl chloride, and reacted overnight. 10 mL of saturated sodium bicarbonate solution was added, and the mixture was separated into two phases. The aqueous phase was extracted with 20 ml×3 of dichloromethane, and the organic phases were combined, dried over anhydrous sodium sulfate, and passed through a TLC preparative plate to afford a light yellow solid (43 mg). Yield: 16.03%. LC-MS: 500.8 [M+1]$^+$, $t_R$=2.135 min $^1$H NMR (400 MHz, DMSO) δ 9.54 (s, 1H), 9.04 (s, 1H), 8.78 (d, J=6.7 Hz, 1H), 8.57 (d, J=8.9 Hz, 1H), 8.45 (d, J=9.6 Hz, 1H), 8.26-8.13 (m, 3H), 7.63-7.45 (m, 3H), 6.60-6.46 (m, 1H), 4.07-3.64 (m, 3H), 3.57 (s, 3H), 3.55-3.48 (m, 1H), 3.07 (s, 3H), 2.99-2.86 (m, 1H), 2.44-2.30 (m, 1H).

134

(XVIII) Scheme XVIII

Scheme XVIII

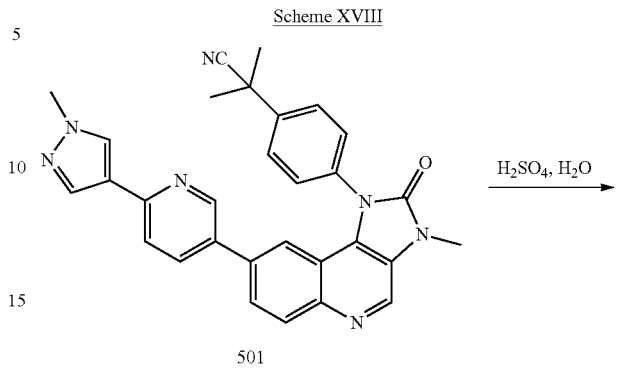

501

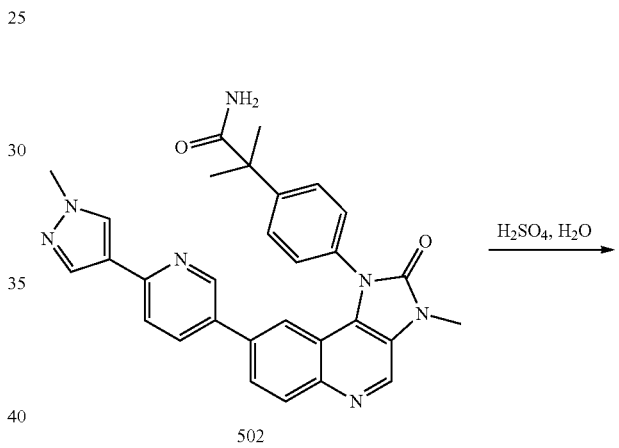

502

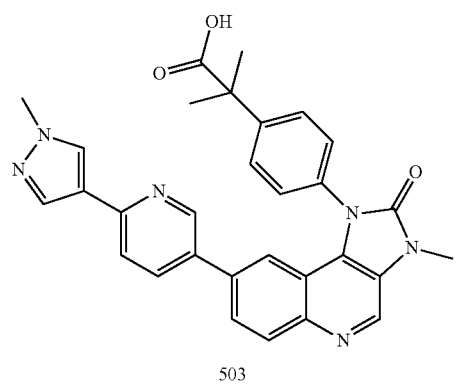

503

EXAMPLE 40

2-methyl-2-(4-(3-methyl-8-(6-(1-methyl-1H-pyrazol-4-yl)pyridin-3-yl)-2-oxo-2,3-dihydro-1H-imidazo[4,5-c]quinolin-1-yl)phenyl)propionamide

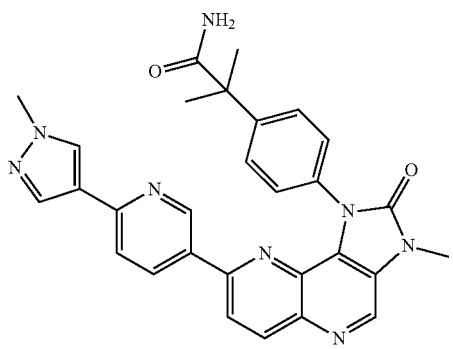 [SMILES: Cn1cc(-c2ccc(-c3ccc4ncc5c(c4n3)n(-c3ccc(C(C)(C)C(N)=O)cc3)c(=O)n5C)cn2)cn1]

100 mg (0.167 mmol) of Intermediate 501 was suspended in 1 ml of water, dropwise added with 1 ml of concentrated sulfuric acid to completely dissolve, heated to 100° C. and stirred for 2 h, cooled to room temperature, and slowly dropwise added to 60 ml of cold saturated NaHCO₃, and extracted with 3×50 ml of a mixture solution of dichloromethane and methanol (DCM:MeOH=10:1). The organic phases were combined, dried over anhydrous sodium sulfate, and evaporated to dryness. The resulting solid was sufficiently stirred with about 15 ml of a mixture solution of dichloromethane and methanol (DCM:MeOH=50:1), and filtered by suction to afford a white solid (about 70 mg), which was purified with a preparative silica gel plate (developing solvent: DCM:MeOH=8:1) to afford a white powder (24 mg). LC-MS: 518.2 [M+1]⁺, $t_R$=1.601 min. ¹H NMR (400 MHz, DMSO) δ 9.01 (s, 1H), 8.47 (d, J=1.9 Hz, 1H), 8.29 (s, 1H), 8.12 (d, J=8.9 Hz, 1H), 8.05-7.94 (m, 2H), 7.65 (dd, J=21.8, 8.5 Hz, 6H), 7.29-7.18 (m, 2H), 7.15 (s, 1H), 3.91 (s, 3H), 3.61 (s, 3H), 1.60 (s, 6H).

EXAMPLE 41

2-methyl-2-(4-(3-methyl-8-(6-(1-methyl-1H-pyrazol-4-yl)pyridin-3-yl)-2-oxo-2,3-dihydro-1H-imidazo[4,5-c]quinolin-1-yl)phenyl)propionic acid

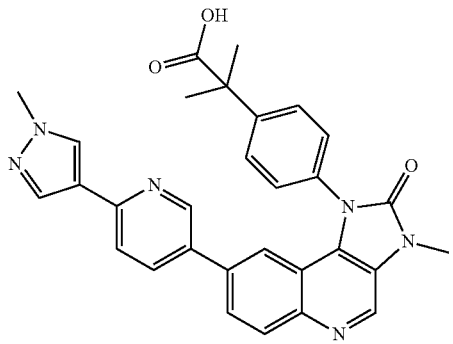 [SMILES: Cn1cc(-c2ccc(-c3ccc4ncc5c(c4c3)n(-c3ccc(C(C)(C)C(=O)O)cc3)c(=O)n5C)cn2)cn1]

100 mg (0.167 mmol) of Intermediate 501 was suspended in 1 ml of water, dropwise added with 1 ml of concentrated sulfuric acid, completely dissolved, heated to 150° C. and stirred for 5 h, cooled to room temperature, slowly dropwise added to 30 ml of saturated NaHCO₃, adjusted pH to 4-5 with hydrochloric acid, and extracted with 4×30 ml of a mixture solvent of dichloromethane and methanol (DCM:MeOH=10:1). The organic phases were combined, dried over anhydrous sodium sulfate, and evaporated to dryness. The resulting solid was purified with a preparative silica gel plate (developing solvent: DCM:MeOH=8:1) to afford a white powder (20 mg). LC-MS: 519.2 [M+1]⁺, $t_R$=1.728 min. ¹H NMR (400 MHz, DMSO) δ 12.53 (s, 1H), 9.02 (s, 1H), 8.54 (s, 1H), 8.28 (s, 1H), 8.13 (d, J=8.9 Hz, 1H), 8.03-7.97 (m, 2H), 7.81-7.51 (m, 6H), 7.19 (d, J=1.9 Hz, 1H), 3.92 (s, 3H), 3.62 (s, 3H), 1.65 (s, 6H).

(XIX) Scheme XIX

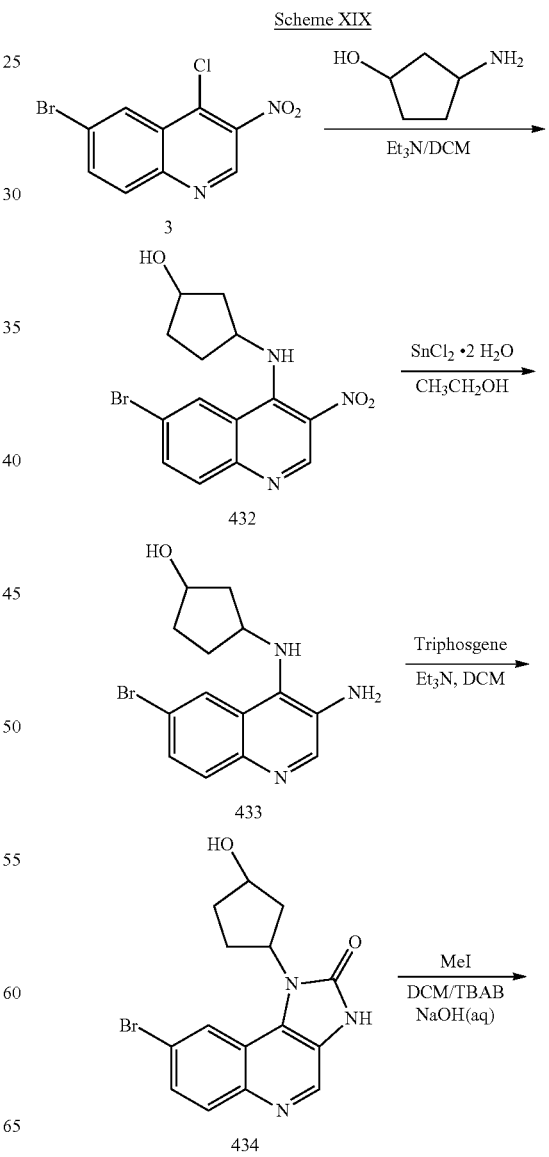

137

-continued

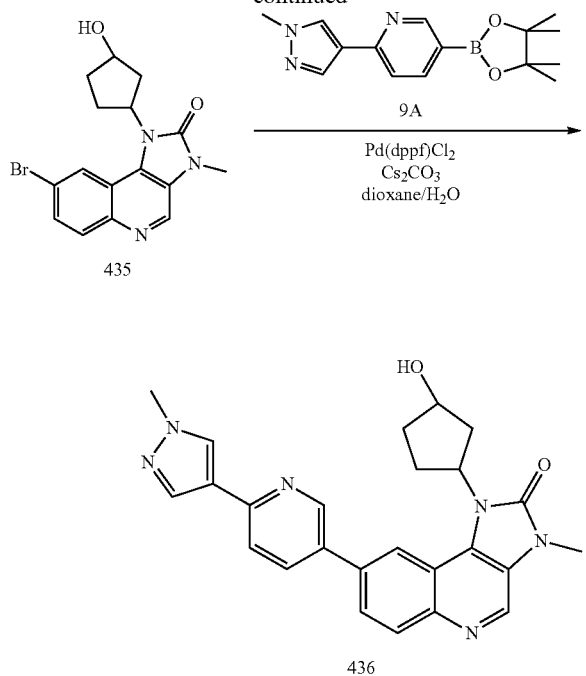

INTERMEDIATE 432

3-(6-bromo-3-nitroquinolin-4-yl)aminocyclopentanol

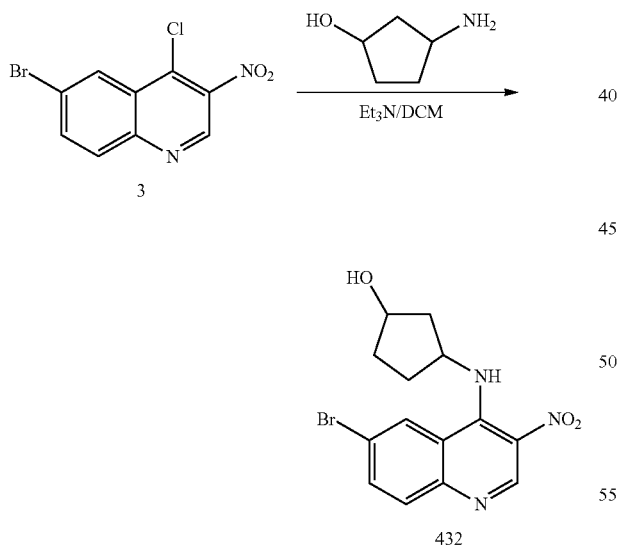

1.69 g (5.9 mmol) of Compound 3 and 1.226 g (8.9 mmol) of 3-aminocyclopentanol hydrochloride (a mixture of cis and trans isomers) were dissolved in 20 ml of dichloromethane, added with 3.3 ml (23.6 mmol) of triethylamine, stirred at room temperature for 2.5 h to precipitate out solids, filtered, washed with a small amount of dichloromethane, and pumped to dryness to afford a yellow solid (2.154 g). Yield: 100%. LC-MS: 351.8, 353.8 [M+1]$^+$, $t_R$=1.822 min.

138

INTERMEDIATE 433

3-(6-bromo-3-aminoquinolin-4-yl)aminocyclopentanol

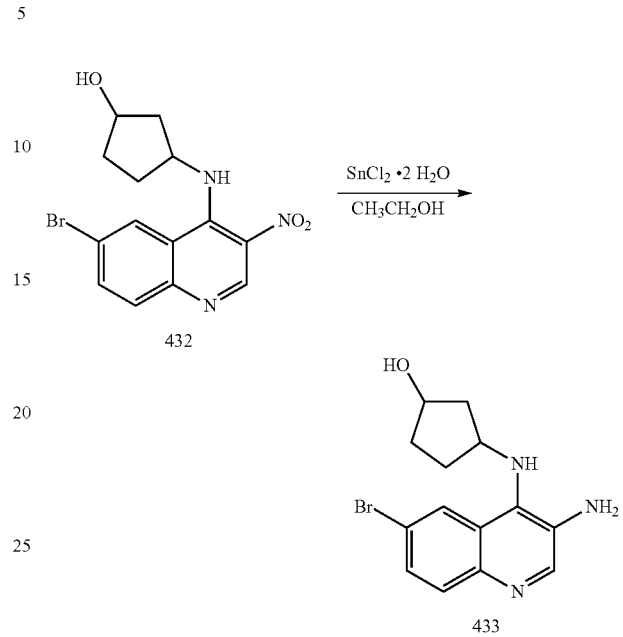

1 g (2.84 mmol) of Intermediate 432 was dissolved in 20 ml of ethanol, added with 3.2 g (14.2 mmol) of stannous chloride dihydrate in batches in an ice-water bath, and stirred overnight. TLC showed that the reaction was completed. 11 mL of 10% sodium hydroxide was added to adjust pH to 8~9, precipitating out a large amount of solid. The solid was filtered off, and the filter cake was washed with 180 ml of ethyl acetate in eight times until the filtrate has no fluorescence. 50 mL of water was supplemented, and the mixture was allowed to stand and separated into two phases. The aqueous phase was extracted with 100 of methyl acetate in twice, and the organic phases were combined, dried, rotary evaporated, and pumped to dryness to afford a brown crystal (0.681 g). Yield: 74.44%. LC-MS: 321.9, 323.9 [M+1]$^+$, $t_R$=1.385 min & 1.478 min (a mixture of cis and trans isomers).

INTERMEDIATE 434

8-bromo-1-(3-hydroxycyclopentyl)-1H-imidazo[4,5-c]quinolin-2(3H)-one

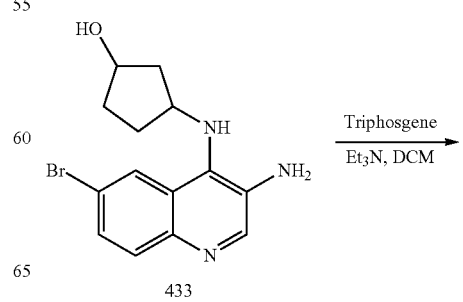

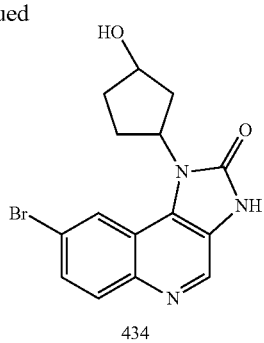

434

0.675 g (2.09 mmol) of Intermediate 433 was dissolved in 20 ml of dichloromethane, and dropwise added with 0.87 ml (6.27 mmol) of triethylamine with stirring in an ice-water bath. After stirring for 10 min, 0.311 g (1.05 mmol) of triphosgene dissolved in 10 ml of dichloromethane was added dropwise, stirred in an ice bath, and reacted for 4 h. 30 mL of saturated sodium bicarbonate solution was added to quench the reaction, and supplemented with 10 ml of methanol to dissolve the solid. The mixture was separated into two phases, the aqueous phase was extracted with 160 ml of dichloromethane in four times, and the organic phases were combined, dried, and passed through a silica gel chromatographic column (eluent: methanol:dichloromethane=1:30) to afford a brown solid (0.455 g). Yield: 62.52%. LC-MS: 347.8, 349.8 [M+1]$^+$, $t_R$=1.385 min & 1.509 min (a mixture of cis and trans isomers).

INTERMEDIATE 435

8-bromo-3-methyl-1-(3-hydroxycyclopentyl)-1H-imidazo[4,5-c]quinolin-2(3H)-one

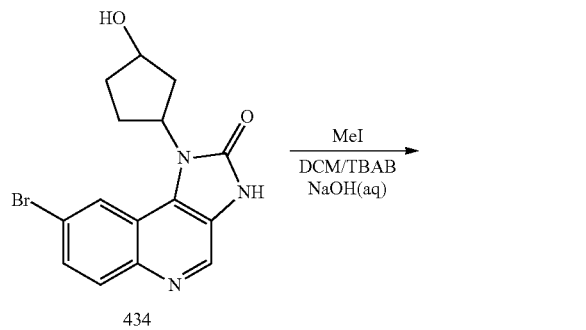

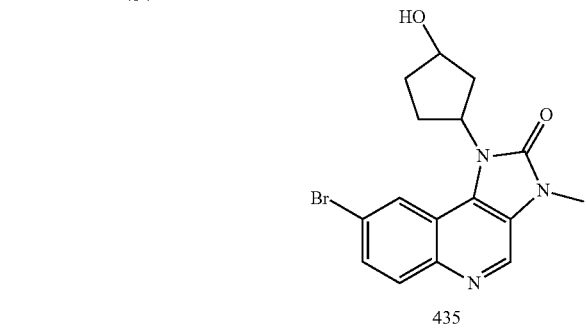

0.45 g (1.29 mmol) of Intermediate 434 was dissolved in 20 ml of dichloromethane, added with 0.042 g (0.129 mmol) of TBAB and then with 20 ml of 10% NaOH, stirred for 10 min, then added with 0.24 ml (3.87 mmol) of methyl iodide, stirred at room temperature and reacted overnight. The reaction solution was allowed to stand, and separated into two phases. The aqueous phase was extracted with 4×20 ml of dichloromethane, and the organic phases were combined, dried, concentrated by rotary evaporation, and pumped to dryness in vacuo, to afford a crude product as a brown solid (0.442 g). Yield: 94.59%. LC-MS: 361.8, 363.8 [M+1]$^+$, $t_R$=1.572 min (a mixture of cis and trans isomers).

EXAMPLE 42

1-(3-hydroxycyclopentyl)-3-methyl-8-(6-(1-methyl-1H-pyrazol-4-yl)pyridin-3-yl)-1H-imidazo[4,5-c]quinolin-2(3H)-one

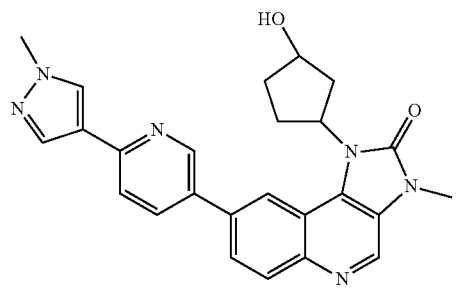 [SMILES: Cn1cc(-c2ccc(-c3ccc4ncc5c(c4c3)n(C3CCC(O)C3)c(=O)n5C)cn2)cn1]

0.44 g (1.21 mmol) of Intermediate 435, 0.519 g (1.82 mmol) of Compound 9A, and 1.971 g (6.05 mmol) of cesium carbonate were suspended in 30 ml of dioxane, added with 6 ml of 2M sodium carbonate, then added with 0.099 g (0.121 mmol) of [1,1'-bis(diphenylphosphino)ferrocene]palladium dichloride dichloromethane complex under the protection of nitrogen, and heated to 110° C. and reacted for 5 h under the protection of nitrogen. The reaction was completed, concentrated by rotary evaporation, added with 30 ml water, stirred, then added with 30 ml of dichloromethane and stirred. The solution was allowed to stand and separated into two phases, the aqueous phase was extracted with 4×30 ml of dichloromethane, and the organic phases were combined, dried, and passed through a silica gel chromatographic column (eluent:methanol:dichloromethane=1:40) to afford Solid a (183 mg), and Solid b (86 mg). Total yield: 50.46%. LC-MS: 441 [M+1]$^+$, $t_R$=1.478 min & 1.416 min (a mixture of cis and trans isomers).

(XX) Scheme XX

Scheme XX

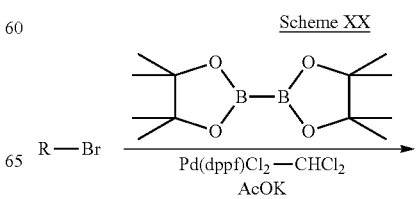

-continued

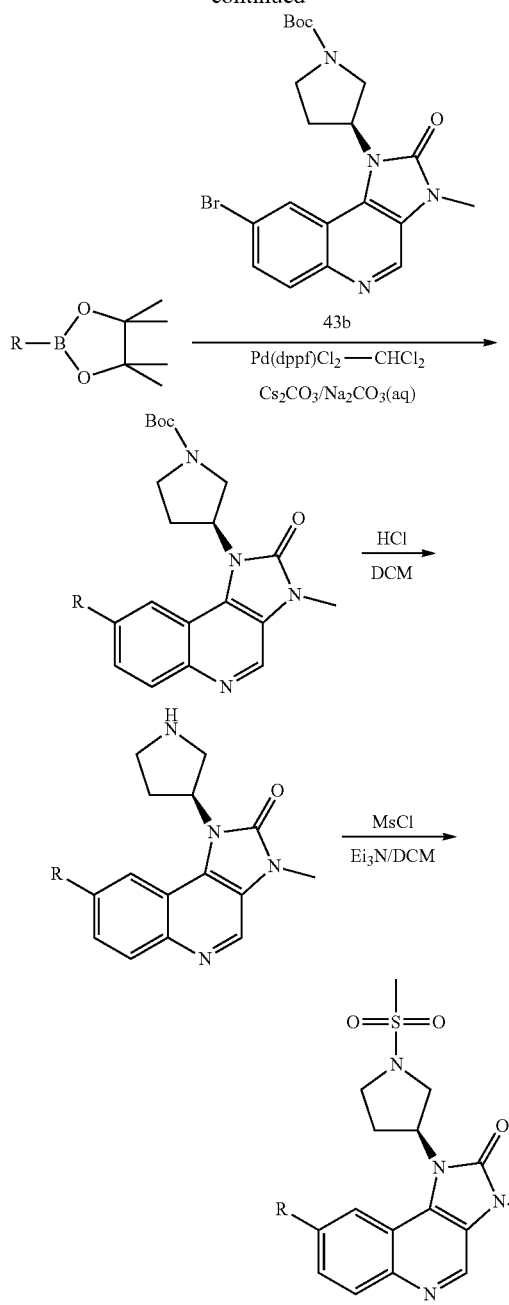

INTERMEDIATE 441

5-bromo-2-(1H-1,2,4-triazol-1-yl)pyridine

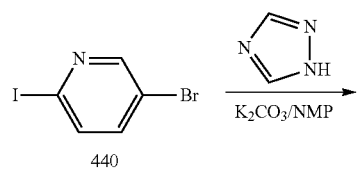

-continued

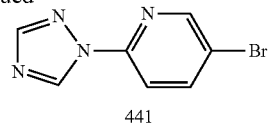

441

4.11 g (14.48 mmol) of Compound 440 and 1.2 g (17.38 mmol) of 1,2,4-triazole were dissolved in 10 ml of NMP, added with 4 g (29 mmol) of potassium carbonate, stirred at T=100° C. overnight. The reaction was reduced to room temperature, and added with 50 ml of ice water to precipitate out solids. The solid was filtered off, washed with a small amount of ice water, and pumped to dryness to afford a crude product as a white solid (3.257 g). The crude product was passed through a silica gel chromatographic column to afford a pure product (1.7 g). LC-MS: 225,227 [M+1]$^+$, $t_R$=1.851 min.

INTERMEDIATE 442

5-(4,4,5,5-tetramethyl-1,3,2-dioxaborolan-2-yl)-2-(1H-1,2,4-triazol-1-yl)pyridine

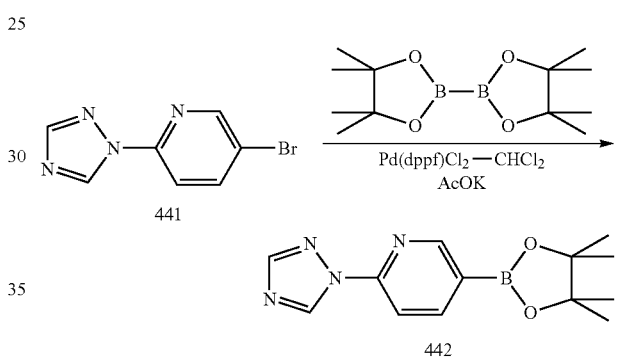

151 mG (0.671 mmol) of Intermediate 441, 256 mg (1.007 mmol) of bis(pinacolato)diboron and 198 mg of potassium acetate (2.01 mmol) were suspended in 10 ml of 1,4-dioxane, added with 44 mg (0.054 mmol) of [1,1′-bis (diphenylphosphino)ferrocene]palladium dichloride dichloromethane complex under the protection of nitrogen, and stirred at T=100° C. and reacted for 2 h. The reaction solution was directly used in the next step.

INTERMEDIATE 444 tert-butyl (S)-3-(3-methyl-8-(6-(1H-1,2,4-triazol-1-yl)pyridin-3-yl)-2-oxo-2,3-dihydro-1H-imidazo[4,5-c]quinolin-1-yl)pyrrolidine-1-carbamate

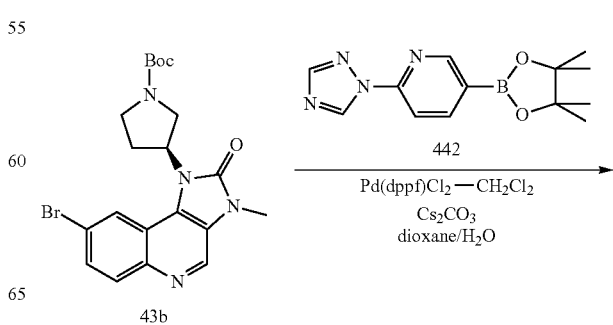

-continued

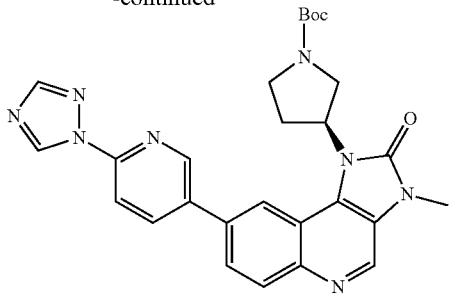

444

0.2 g (0.447 mmol) of Intermediate 43b, 0.183 g (0.671 mmol) of 442, and 0.728 g (2.235 mmol) of cesium carbonate were suspended in 10 ml of dioxane, added with 3 ml of 2M sodium carbonate, then added with 0.037 g (0.045 mmol) of [1, F-bis(diphenylphosphino)ferrocene]palladium dichloride dichloromethane complex under the protection of nitrogen, and heated to 110° C. and reacted for 5 h under the protection of nitrogen again. The reaction was completed, concentrated by rotary evaporation, added with 30 ml of water, stirred, then added with 30 ml of dichloromethane and stirred. The mixture was allowed to stand and separated into two phases, the aqueous phase was extracted with 30 ml×3 of dichloromethane, and the organic phases were combined, dried, and passed through a silica gel chromatographic column (eluent:methanol:dichloromethane=1:40) to afford a brown solid (161 mg). Yield: 70.27%. LC-MS: 512.9 [M+1]$^+$, $t_R$=1.914 min.

INTERMEDIATE 445

(S)-8-(6-(1H-1,2,4-triazol-1-yl)pyridin-3-yl)-3-methyl-1-(pyrrolidin-3-yl)-1H-imidazo[4,5-c]quinolin-2(3H)-one

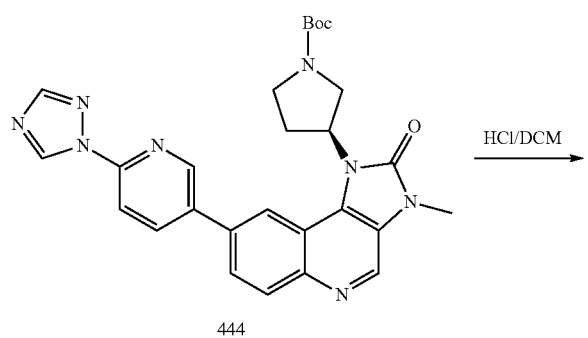

158 mg (0.308 mmol) of Intermediate 444 was dissolved in 5 ml of DCM, purged with dry HCl gas in an ice-water bath, and stirred and reacted for 1 h. The reaction solution was pumped to dryness in vacuo to afford a gray solid (127 mg). Yield: 100%.

EXAMPLE 43

(S)-8-(6-(1H-1,2,4-triazol-1-yl)pyridin-3-yl)-3-methyl-1-(1-(methanesulfonyl)pyrrolidin-3-yl)-1H-imidazo[4,5-c]quinolin-2(3H)-one

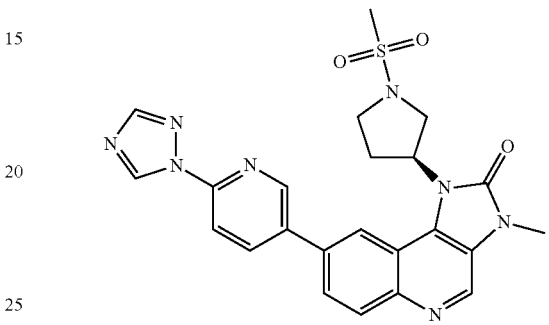

To 127 mg (0.308 mmol) of Intermediate 445, 10 ml of dichloromethane was added, and then 0.7 ml of triethylamine was added. The solution was stirred for 10 min to dissolve, added with 0.046 ml of methylbenzenesulfonyl chloride, and reacted overnight. 10 mL of saturated sodium bicarbonate solution was added, and the mixture was separated into two phases. The aqueous phase was extracted with 20 ml×3 of dichloromethane, and the organic phases were combined, dried over anhydrous sodium sulfate, and purified with a TLC preparative plate to afford a light yellow solid (25 mg). Yield: 16.55%. LC-MS: 490.8 [M+1]$^+$, $t_R$=1.570 min $^1$H NMR (400 MHz, DMSO) δ 9.46 (s, 1H), 9.08 (s, 1H), 8.98 (s, 1H), 8.61 (d, J=12.9 Hz, 2H), 8.37 (s, 1H), 8.22 (d, J=8.8 Hz, 1H), 8.10 (d, J=8.8 Hz, 1H), 8.00 (d, J=8.5 Hz, 1H), 6.04-5.83 (m, 1H), 3.94-3.83 (m, 2H), 3.70 (s, 1H), 3.55 (s, 3H), 3.52-3.46 (m, 1H), 3.06 (s, 3H), 2.75-2.63 (m, 1H), 2.47-2.38 (m, 1H).

INTERMEDIATE 712

2-(1H-pyrazol-1-yl)-5-(4,4,5,5-tetramethyl-1,3,2-dioxaborolan-2-yl)pyridine

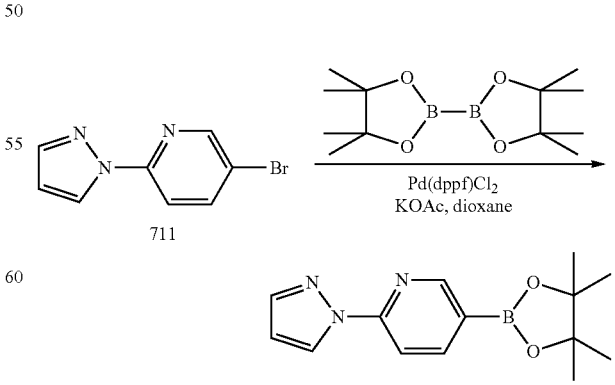

Intermediate 711 (150 mg, 0.67 mmol) was dissolved in 10 ml of 1,4-dioxane, and 253 mg (1 mmol) of bis(pinacolato)diboron, 196 mg (2.01 mmol) of potassium acetate, and 40 mg (0.05 mmol) of [1,1-bis(di-phenylphosphino)ferrocene]palladium chloride were added under the protection of nitrogen. The resulting mixture was heated to 95° C. and reacted for 2 h, and then cooled to room temperature. The reaction solution was used directly in the next step.

INTERMEDIATE 713 tert-butyl (S)-3-(8-(6-(1H-pyrazol-1-yl)pyridin-3-yl)-3-methyl-2-carbonyl-2,3-dihydro-1H-imidazo[4,5-c]quinolin-1-yl)tetrahydropyrrole-1-carboxylate

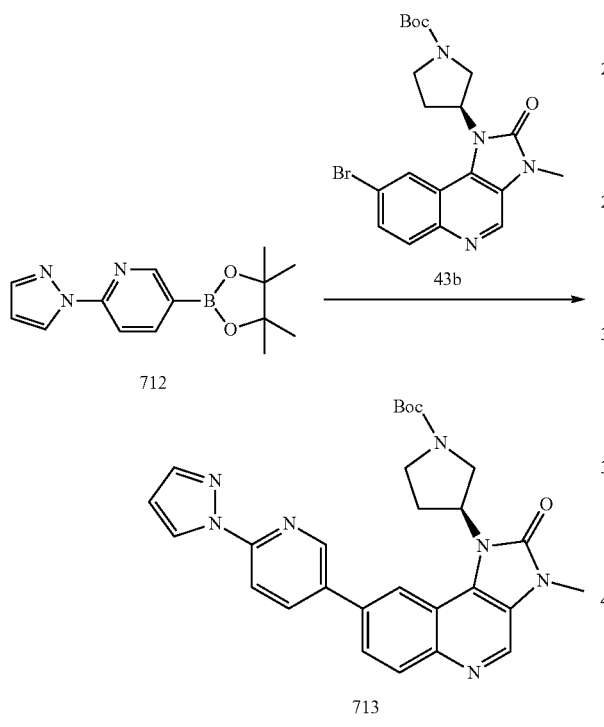

Intermediate 43b (200 mg, 0.45 mmol) was dissolved in 10 ml of 1,4-dioxane, and a crude (0.67 mmol) Intermediate 712, 586 mg (1.8 mmol) of cesium carbonate, 4 ml of 2 mol/L sodium carbonate solution, and 36 mg (0.045 mmol) of [1,1-bis(di-phenylphosphino)ferrocene]palladium chloride dichloromethane complex were added under the protection of nitrogen. The resulting mixture was heated to 110° C. and reacted for 5 h, and then cooled to room temperature. The dioxane was removed by evaporation, and the residue was dissolved in 20 ml of saturated sodium bicarbonate solution and 20 ml of dichloromethane. The mixture was separated into two phases, the aqueous phase was extracted with dichloromethane, and the organic phases were combined, dried, and evaporated to dryness to afford a crude product. The crude product was purified by silica gel column chromatography (eluent:methanol:dichloromethane=1:10) to afford 200 mg of solid. Yield: 86.96%. LC-MS: 511.9 [M+1]$^+$, $t_R$=2.228 min.

INTERMEDIATE 714

(S)-8-(6-(1H-pyrazol-1-yl)pyridin-3-yl)-3-methyl-1-(pyrrol-3-yl)-1H-imidazo[4,5-c]quinolin-2(3H)-one

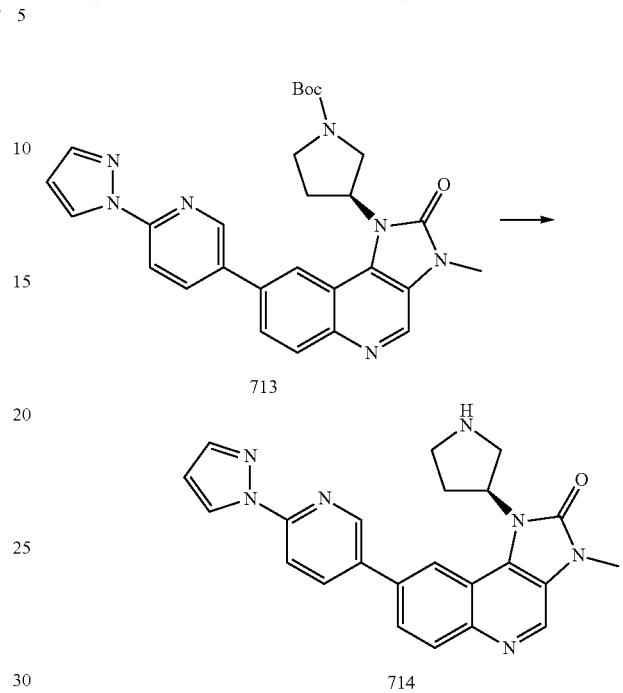

Intermediate 713 (200 mg, 0.39 mmol) was dissolved in 10 ml of dichloromethane, cooled to 0-10° C., purged with hydrogen chloride gas to the reaction system and reacted for 2 h, and then filtered to afford a crude product, which was used directly in the next step.

EXAMPLE 44

(S)-8-(6-(1H-pyrazol-1-yl)pyridin-3-yl)-3-methyl-1-(1-(methanesulfonyl)pyrrolidin-3-yl)-1H-imidazo[4,5-c]quinolin-2(3H)-one

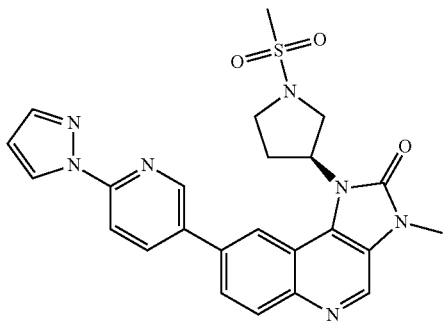 [SMILES: Cn1c(=O)n([C@H]2CCN(S(C)(=O)=O)C2)c2c3cc(-c4ccc(-n5cccn5)nc4)ccc3ncc21]

Intermediate 714 (a crude product) was dissolved in 10 ml of dichloromethane, added with 67 mg (0.585 mmol) of methylsulfonyl chloride and 158 mg (1.56 mmol) of triethylamine, and stirred at room temperature overnight. 30 mL of saturated sodium bicarbonate solution was added, and stirred for 30 min. The resulting solution was separated into two phases, the aqueous phase was extracted with dichloromethane, and the organic phases were combined, dried, and evaporated to dryness to afford a crude product. The crude product was purified by silica gel column chromatography (eluent:methanol:dichloromethane=1:10) to afford the target compound of Example 44 (53 mg). Yield: 27.75%. LC-MS: 489.9 [M+1]$^+$, $t_R$=1.801 min. $^1$H NMR (400 MHz, DMSO) δ 9.03 (d, J=2.3 Hz, 1H), 8.99 (s, 1H), 8.70 (d, J=2.5 Hz, 1H), 8.61-8.51 (m, 2H), 8.22 (d, J=8.9 Hz, 1H), 8.14-8.02 (m, 2H), 7.90 (s, 1H), 6.69-6.62 (m, 1H), 6.03-5.84 (m, 1H), 3.97-3.82 (m, 2H), 3.75-3.67 (m, 1H), 3.56 (s, 3H), 3.55-3.48 (m, 1H), 3.07 (s, 3H), 2.80-2.63 (m, 1H), 2.49-2.29 (m, 1H).

INTERMEDIATE 602

1-methyl-4-(4,4,5,5-tetramethyl-1,3,2-dioxaborolan-2-yl)-1H-1,2,3-triazole

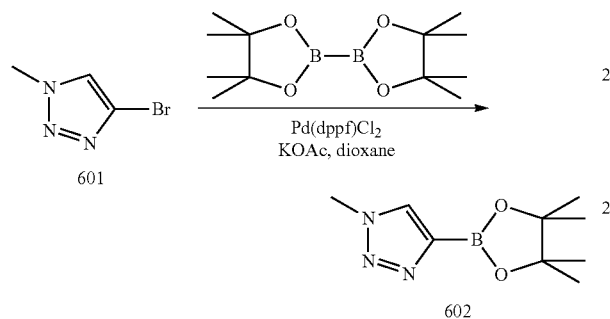

Compound 601 (0.6 g, 3.69 mmol) was dissolved in 15 ml of 1,4-dioxane, added with 1.125 g (4.43 mmol) of bis(pinacolato)diboron, 1.086 g (11.07 mmol) of potassium acetate, and 0.3 g (0.37 mmol) of [1,1-bis(di-phenylphosphino)ferrocene]palladium chloride dichloromethane complex under the protection of nitrogen, heated to 95° C., reacted for 5 h, and then cooled to room temperature. 50 mL of water was added and stirred for 30 min, and filtered to afford 0.35 g of solid. Yield: 45.39%.

INTERMEDIATE 603

5-bromo-2-(1-methyl-1H-1,2,3-triazol-4-yl)pyridine

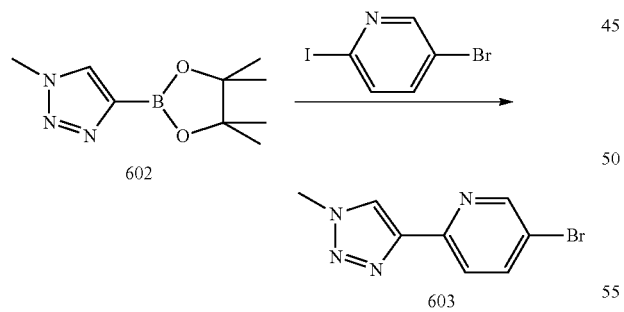

Intermediate 602 (0.1 g, 0.478 mmol) was dissolved in 5 ml of 1,4-dioxane, added with 0.113 g (0.399 mmol) of 5-bromo-2-iodopyridine, 0.39 g (1.197 mmol) of cesium carbonate, 1 ml of water, 0.057 g (0.12 mmol) of 2-dicyclohexylphosphino-2',4',6'-triisopropylbiphenyl, and 0.037 g (0.04 mmol) of tris(dibenzylideneacetone)dipalladium under the protection of nitrogen, heated to 110° C., reacted for 5 h, and cooled to room temperature. The dioxane was removed by evaporation, and the residue was dissolved in 20 ml of saturated sodium bicarbonate solution and 20 ml of dichloromethane. The resulting mixture was separated into two phases, the aqueous phase was extracted with dichloromethane, and the organic phases were combined, dried, and evaporated to dryness to afford a crude product. The crude product was purified by silica gel column chromatography (eluent:ethyl acetate:petroleum ether=5:1) to afford 0.05 g of solid. Yield: 43.48%. LC-MS: 239,241 [M+1]$^+$, $t_R$=3.351 min $^1$H NMR (400 MHz, DMSO) δ 8.73 (s, 1H), 8.60 (s, 1H), 8.14 (d, J=8.5 Hz, 1H), 7.98 (d, J=8.4 Hz, 1H), 4.12 (s, 3H).

INTERMEDIATE 604

2-(1-methyl-1H-1,2,3-triazol-4-yl)-5-(4,4,5,5-tetramethyl-1,3,2-dioxaborolan-2-yl)pyridine

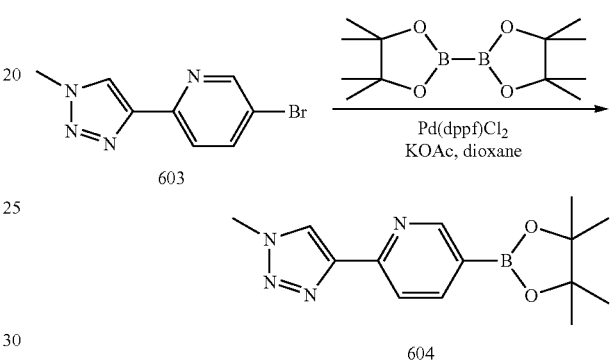

Intermediate 603 (75 mg, 0.31 mmol) was dissolved in 5 ml of 1,4-dioxane, added with 118 mg (0.465 mmol) of diboronate, 91 mg (0.93 mmol) of potassium acetate, and 24 mg (0.03 mmol) of [1,1-bis(di-phenylphosphino)ferrocene] palladium chloride dichloromethane complex under the protection of nitrogen, heated to 95° C., reacted for 2.5 h, and cooled to room temperature. The reaction solution was used directly in the next step.

INTERMEDIATE 605 tert-butyl (S)-3-(3-methyl-8-(6-(1-methyl-1H-1,2,3-triazol-4-yl)pyridin-3-yl)-2-carbonyl-2,3-dihydro-1H-imidazo[4,5-c]quinolin-1-yl)pyrrolidine-1-carboxylate

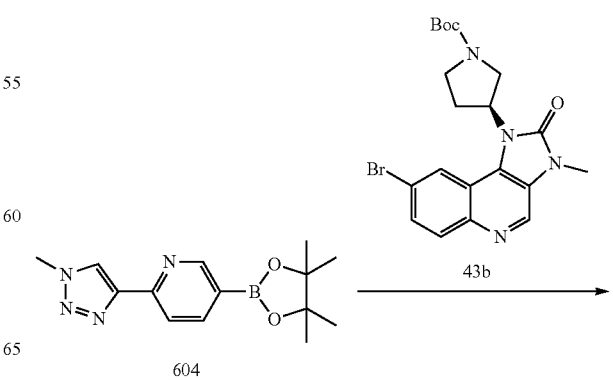

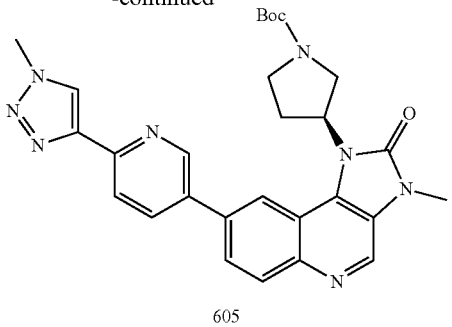

605

Intermediate 43b (115 mg, 0.258 mmol) was dissolved in 10 ml of 1,4-dioxane, added with a crude (0.31 mmol) Intermediate 604, 336 mg (1.032 mmol) of cesium carbonate, 2 ml of mol/L sodium carbonate solution, and 21 mg (0.026 mmol) of [1,1-bis(di-phenylphosphino)ferrocene] palladium chloride under the protection of nitrogen, heated to 110° C., reacted for 5 h, and cooled to room temperature. The dioxane was removed by evaporation, and the residue was dissolved in 20 ml of saturated sodium bicarbonate solution and 20 ml of dichloromethane. The resulting solution was separated into two phases, the aqueous phase was extracted with dichloromethane, and the organic phases were combined, dried, and evaporated to dryness to afford a crude product. The crude product was purified by silica gel column chromatography (eluent:methanol:dichloromethane=1:10) to afford 116 mg of solid. Yield: 85.29%. LC-MS: 526.9 [M+1]$^+$, $t_R$=1.851 min.

INTERMEDIATE 606

(S)-3-methyl-8-(6-(1-methyl-1H-1,2,3-triazol-4-yl)pyridin-3-yl)-1-(pyrrolidin-3-yl)-1H-imidazo[4,5-c]quinolin-2(3H)-one

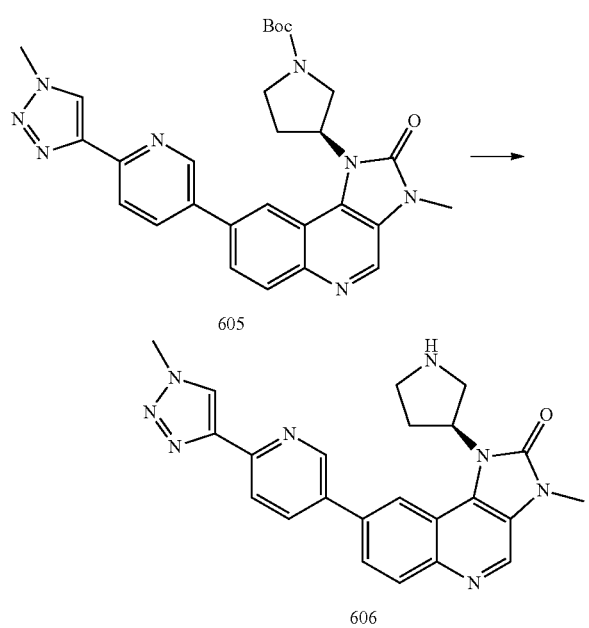

Intermediate 605 (534 mg, 1.014 mmol) was dissolved in 10 ml of dichloromethane, cooled to 0-10° C., to the reaction system purged with hydrogen chloride gas, reacted for 2 h, and filtered to afford 454 mg of solid. Yield: 100%. The reaction solution was directly used in the next step.

EXAMPLE 45

(S)-3-methyl-8-(6-(1-methyl-1H-1,2,3-triazol-4-yl)pyridin-3-yl)-1-(1-(methanesulfonyl)pyrrolidin-3-yl)-1H-imidazo quinolin-2(3H)-one

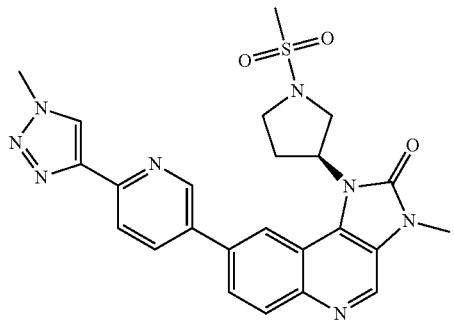 [SMILES: Cn1cc(-c2ccc(-c3ccc4ncc5c(c4c3)n([C@H]3CCN(S(C)(=O)=O)C3)c(=O)n5C)cn2)nn1]

Intermediate 606 (a crude product) was dissolved in 20 ml of dichloromethane, added with 174 mg (1.521 mmol) of methanesulfonyl chloride and 410 mg (4.056 mmol) of triethylamine, and stirred at room temperature for 3 h. 50 mL of saturated sodium bicarbonate solution was added, and stirred for 30 min. The resulting solution was separated into two phases, the aqueous phase was extracted with dichloromethane, and the organic phases were combined, dried, and evaporated to dryness to afford a crude product. The crude product was purified by silica gel chromatography (eluent:methanol:dichloromethane=1:30) to afford 183 mg of the target compound of Example 45. Yield: 35.67%. LC-MS: 505.2 [M+1]$^+$, $t_R$=1.510 min $^1$H NMR (400 MHz, DMSO) δ 9.15 (s, 1H), 8.98 (s, 1H), 8.65 (s, 1H), 8.59 (s, 1H), 8.51-8.42 (m, 1H), 8.19 (dd, J=17.1, 8.5 Hz, 2H), 8.10 (d, J=8.9 Hz, 1H), 6.06-5.83 (m, 1H), 4.16 (s, 3H), 3.97-3.84 (m, 2H), 3.76-3.65 (m, 1H), 3.56 (s, 3H), 3.54-3.48 (m, 1H), 3.06 (s, 3H), 2.77-2.66 (m, 1H), 2.47-2.31 (m, 1H).

INTERMEDIATE 448

5-bromo-2-(1H-1,2,3-triazol-1-yl)pyridine

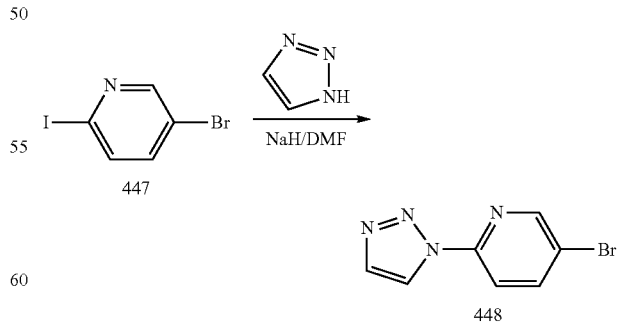

0.695 g (17.38 mmol) of NaH was added to 20 ml of DMF, added with 1.2 g (17.38 mmol) of 1,2,3-triazole in batches and stirred at room temperature for 1 h, then added with 4.11 g (14.48 mmol) of Compound 447 and stirred to dissolve, heated to T=120° C. and stirred overnight. The reaction was reduced to room temperature, added with 50 ml of ice water to precipitate out solids, filtered, washed with a small amount of ice water, and pumped to dryness to afford a crude product as a white solid (3.0 g). 2 g of the crude product was taken and passed through a silica gel chromatographic column to afford a pure product (167 mg). LC-MS: 225,227 [M+1]⁺, $t_R$=1.728 min.

INTERMEDIATE 449

5-(4,4,5,5-tetramethyl-1,3,2-dioxaborolan-2-yl)-2-(1H-1,2,3-triazol-1-yl)

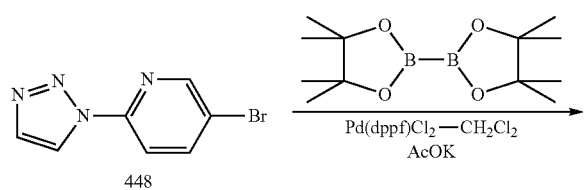

448

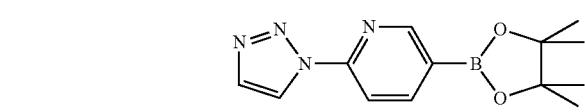

449

160 mg (0.71 mmol) of Intermediate 448, 269 mg (1.06 mmol) of bis(pinacolato)diboron and 209 mg (2.13 mmol) of potassium acetate were suspended in 10 ml of 1,4-dioxane, added with 46 mg (0.057 mmol) of [1,1'-bis(diphenylphosphino)ferrocene]palladium dichloride dichloromethane complex under the protection of nitrogen, stirred at T=100° C. and reacted for 2 h. The reaction solution was directly used in the next step.

INTERMEDIATE 451a tert-butyl (S)-3-(3-methyl-8-(6-(1H-1,2,3-triazol-1-yl)pyridin-3-yl)-2-oxy-2,3-dihydro-1H-imidazo[4,5-c]quinolin-1-yl)pyrrolidine-1-carbamate

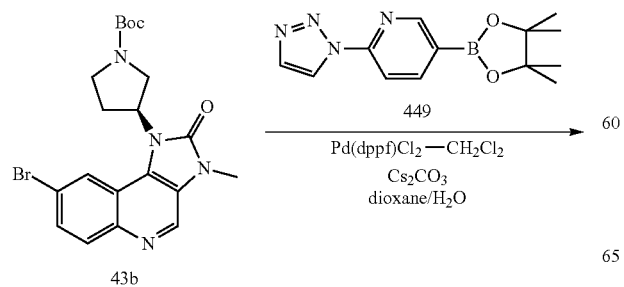

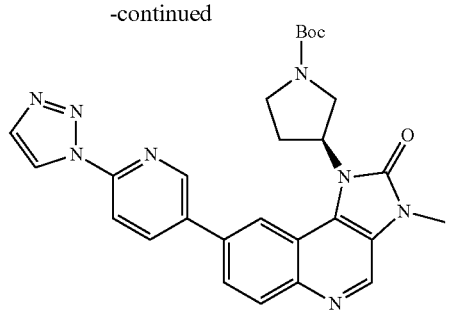

451a 0.15 g (0.34 mmol) of Intermediate 43b, 0.193 g (0.71 mmol) of Intermediate 449, and 0.554 g (1.7 mmol) of cesium carbonate were suspended in 10 ml of dioxane, added with 2 ml of 2M sodium carbonate, then added with 0.028 g (0.034 mmol) of [1, F-bis(diphenylphosphino)ferrocene]palladium dichloride dichloromethane complex under the protection of nitrogen, and heated to 110° C. and reacted for 5 h under the protection of nitrogen again. The reaction was completed, concentrated by rotary evaporation, added with 25 ml of water and stirred, then added with 25 ml of dichloromethane and stirred. The resulting solution was allowed to stand and separated into two phases, the aqueous phase was extracted with 25 ml×3 of dichloromethane, and the organic phases were combined, dried, and purified with a TLC preparative plate (developing solution: methanol:dichloromethane=1:15) to afford a brown solid (0.15 g). Yield: 86.07%. LC-MS: 512.9 [M+1]⁺, $t_R$=2.007 min.

INTERMEDIATE 452a (S)-8-(6-(1H-1,2,3-triazol-1-yl)pyridin-3-yl)-3-methyl-1-(pyrrolidin-3-yl)-1H-imidazo[4,5-c]quinolin-2(3H)-one 150 mg (0.29 mmol) of Intermediate 451a was dissolved in 5 ml of DCM, purged with HCl gas in an ice-water bath, stirred and reacted for 1 h. The reaction solution was pumped to dryness in vacuo to afford a grey solid (120 mg). Yield: 100%.

EXAMPLE 46

(S)-8-(6-(1H-1,2,3-triazol-1-yl)pyridin-3-yl)-3-methyl-1-(1-(methanesulfonyl)pyrrolidin-3-yl)-1H-imidazo[4,5-c]quinolin-2(3H)-one

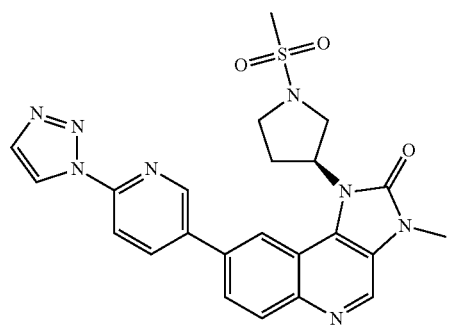 [SMILES: Cn1c(=O)n([C@H]2CCN(S(C)(=O)=O)C2)c2c3cc(-c4ccc(-n5ccnn5)nc4)ccc3ncc21]

120 mg (0.29 mmol) of Intermediate 452a was added to 8 ml of dichloromethane, added with 0.6 ml of triethylamine and stirred for 10 min to dissolve, then added with 0.034 ml of methylbenzenesulfonyl chloride, and reacted for 2 h. 10 mL of saturated sodium bicarbonate solution was added, and separated into two phases. The aqueous phase was extracted with 20 ml×3 of dichloromethane, and the organic phases were combined, dried over anhydrous sodium sulfate, and purified with a TLC preparative plate (developing solution: methanol:dichloromethane=1:10) to afford an off-white powder (32 mg). Yield: 22.49%. LC-MS: 490.9 [M+1]$^+$, $t_R$=1.603 min $^1$H NMR (400 MHz, DMSO) δ 9.15 (s, 1H), 8.99 (s, 1H), 8.94 (s, 1H), 8.71-8.58 (m, 2H), 8.30-8.19 (m, 2H), 8.12 (d, J=8.7 Hz, 1H), 8.06 (s, 1H), 6.08-5.81 (m, 1H), 3.95-3.82 (m, 2H), 3.75-3.67 (m, 1H), 3.55 (s, 3H), 3.53-3.45 (m, 1H), 3.06 (s, 3H), 2.77-2.64 (m, 1H), 2.47-2.37 (m, 1H).

INTERMEDIATE 702

1-methyl-3-(4,4,5,5-tetramethyl-1,3,2-dioxaborolan-2-yl)-1H-pyrazole

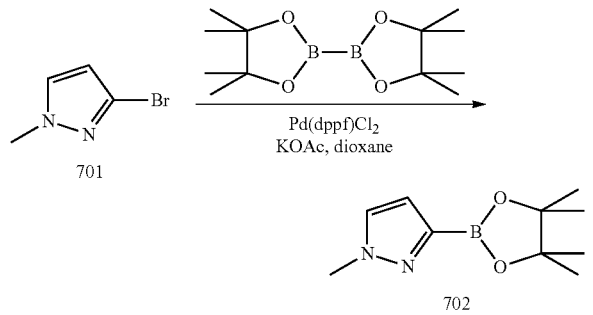

Compound 701 (0.2 g, 1.24 mmol) was dissolved in 5 ml of 1,4-dioxane, added with 0.378 g (1.49 mmol) of bis(pinacolato)diboron, 0.365 g (3.72 mmol) of potassium acetate, and 0.11 g (0.124 mmol) of [1,1-bis(di-phenylphosphino)ferrocene]palladium chloride dichloromethane complex under the protection of nitrogen, heated to 95° C. and reacted for 5 h, and then cooled to room temperature. 15 mL of water was added, stirred for 1 h, and filtered to afford 0.114 g of solid. Yield: 44.19%.

INTERMEDIATE 703

5-bromo-2-(1-methyl-1H-pyrazol-3-yl)pyridine

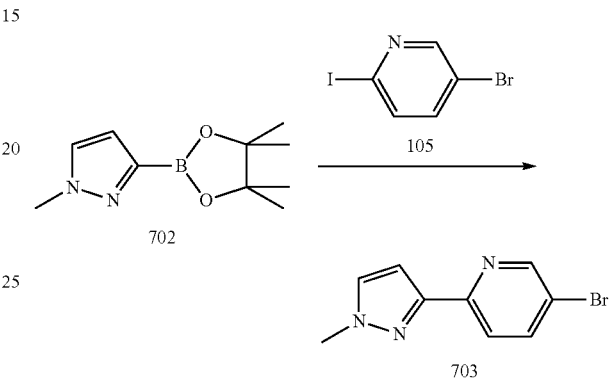

Intermediate 702 (0.114 g, 0.548 mmol) was dissolved in 5 ml of 1,4-dioxane, added with 0.130 g (0.457 mmol) of Compound 105, 0.447 g (1.371 mmol) of cesium carbonate, 1 ml of water and 0.027 g (0.023 mmol) of tetrakis(triphenylphosphine)palladium under the protection of nitrogen, heated to 110° C. and reacted for 5 h, and then cooled to room temperature. The dioxane was removed by evaporation, and the residue was dissolved in 20 ml of saturated sodium bicarbonate solution and 20 ml of dichloromethane, and the resulting solution was separated into two phases. The aqueous phase was extracted with dichloromethane, and the organic phases were combined, dried, evaporated to dryness to afford a crude product. The crude product was purified by silica gel column chromatography (eluent:ethyl acetate:petroleum ether=3:1) to afford 0.022 g of solid. Yield: 20.18%. LC-MS: 238,240 [M+1]$^+$, $t_R$=1.866 min.

INTERMEDIATE 704

2-(1-methyl-1H-pyrazol-3-yl)-5-(4,4,5,5-tetramethyl-1,3,2-dioxaborolan-2-yl)pyridine

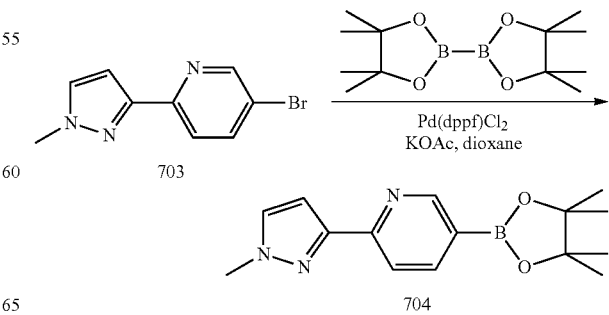

Intermediate 703 (88 mg, 0.37 mmol) was dissolved in 5 ml of 1,4-dioxane, added with 141 mg (0.465 mmol) of bis(pinacolato)diboron, 109 mg (1.11 mmol) of potassium acetate, and mg (0.037 mmol) of [1,1-bis(di-phenylphosphino)ferrocene]palladium chloride dichloromethane complex under the protection of nitrogen, heated to 95° C. and reacted for 2.5 h, and then cooled to room temperature. The reaction solution was used directly in the next step.

INTERMEDIATE 705 tert-butyl (S)-3-(3-methyl-8-(6-(1-methyl-1H-pyrazol-3-yl)pyridin-3-yl)-2-carbonyl-2,3-dihydro-1H-imidazo[4,5-c]quinolin-1-yl)pyrrolidine-1-carboxylate

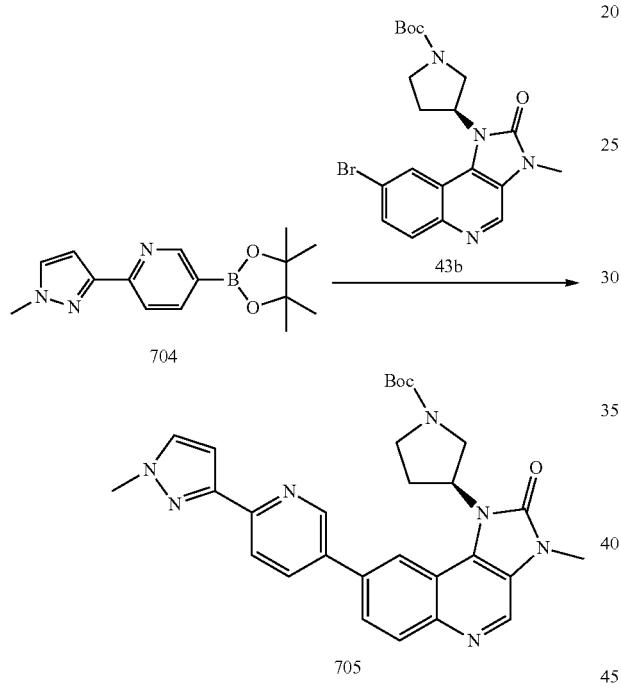

Intermediate 43b (110 mg, 0.247 mmol) was dissolved in 10 ml of 1,4-dioxane, added with a crude (0.37 mmol) Intermediate 704, 322 mg (0.988 mmol) of cesium carbonate, 2 ml of water, and 21 mg (0.025 mmol) of [1,1-bis(diphenylphosphino)ferrocene]palladium chloride dichloromethane complex under the protection of nitrogen, heated to 110° C. and reacted for 5 h, and then cooled to room temperature. The dioxane was removed by evaporation, and the residue was dissolved in 20 ml of saturated sodium bicarbonate solution and 20 ml of dichloromethane. The resulting solution was separated into two phases, the aqueous phase was extracted with dichloromethane, and the organic phases were combined, dried, and evaporated to dryness to afford a crude product. The crude product was purified by silica gel column chromatography (eluent: methanol:dichloromethane=1:10) to afford 97 mg of solid. Yield: 74.62%. LC-MS: 526.2 [M+1]$^+$, $t_R$=1.923 min.

INTERMEDIATE 706

(S)-3-methyl-8-(6-(1-methyl-1H-pyrazol-3-yl)pyridin-3-yl)-1-(pyrrolidin-3-yl)-1H-imidazo[4,5-c]quinolin-2(3H)-one

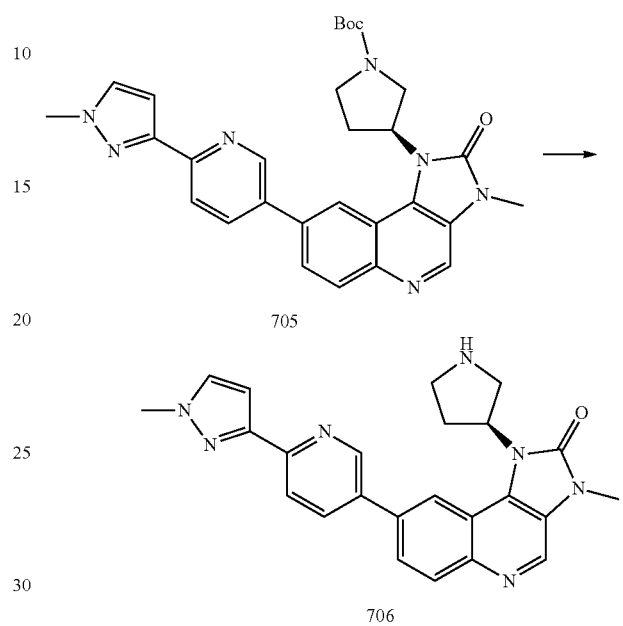

Intermediate 705 (97 mg, 0.18 mmol) was dissolved in 5 ml of dichloromethane, cooled to 0-10° C., to the reaction system purged with hydrogen chloride gas, reacted for 2 h, and filtered to afford a crude product, which was directly used in the next step.

EXAMPLE 47

(S)-3-methyl-8-(6-(1-methyl-1H-pyrazol-3-yl)pyridin-3-yl)-1-(1-(methanesulfonyl)pyrrolidin-3-yl)-1H-imidazo[4,5-c]quinolin-2(3H)-one

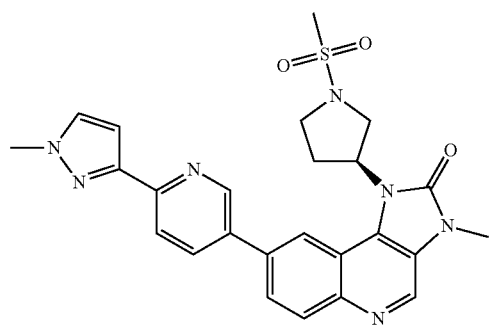

Intermediate 706 (a crude product) was dissolved in 5 ml of dichloromethane, added with 31 mg (0.27 mmol) of methylsulfonyl chloride and 73 mg (0.72 mmol) of triethylamine, and stirred at room temperature overnight. 20 mL of saturated sodium bicarbonate solution was added, and stirred for 30 min. The resulting solution was separated into two phases, the aqueous phase was extracted with dichloromethane, and the organic phases were combined, dried, evaporated to dryness to afford a crude product. The crude product was purified by silica gel chromatography (eluent: methanol:dichloromethane=1:10) to afford the target compound of Example 47 (23 mg). Yield: 25.38%. LC-MS: 504.2 [M+1]$^+$, $t_R$=1.539 min $^1$H NMR (400 MHz, DMSO) δ 9.11 (s, 1H), 8.97 (s, 1H), 8.57 (s, 1H), 8.37 (d, J=8.1 Hz, 1H), 8.20 (d, J=8.8 Hz, 1H), 8.06 (dd, J=17.2, 8.3 Hz, 2H), 7.82 (s, 1H), 6.87 (s, 1H), 6.00-5.87 (m, 1H), 3.95 (s, 3H), 3.93-3.82 (m, 2H), 3.73-3.66 (m, 1H), 3.55 (s, 3H), 3.53-3.47 (m, 1H), 3.06 (s, 3H), 2.67 (s, 1H), 2.46-2.39 (m, 1H).

INTERMEDIATE 471

5-bromo-N'-methylpyridineiminehydrazide

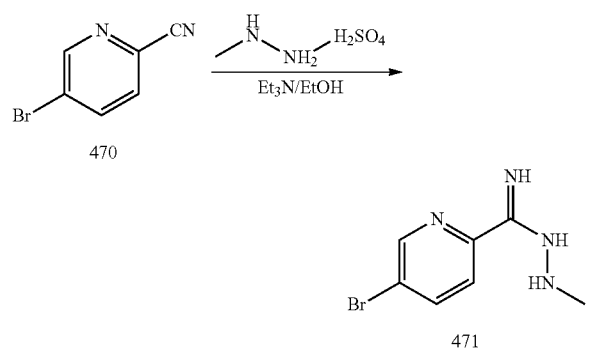

0.788 g (5.46 mmol) of methylhydrazine sulfate was added to 20 ml of ethanol, then added with 1.42 g (10.92 mmol) of N,N-diisopropylethylamine in batches, stirred for 30 min, then added with 1 g (5.46 mmol) of Compound 470, heated to reflux and stirred overnight. 20 mL of water was added to quench the reaction, adjusted to pH=2~3, and extracted with 20 ml×3 of methyl tert-butyl ether. The organic phases were combined, dried, filtered, concentrated by rotary evaporation, and pumped to dryness in vacuo to afford 0.279 g of yellow solid. Yield: 22.31%. LC-MS: 229,231 [M+1]$^+$, $t_R$=0.604 min.

INTERMEDIATE 472

5-bromo-2-(1-methyl-1H-1,2,4-triazol-3-yl)pyridine

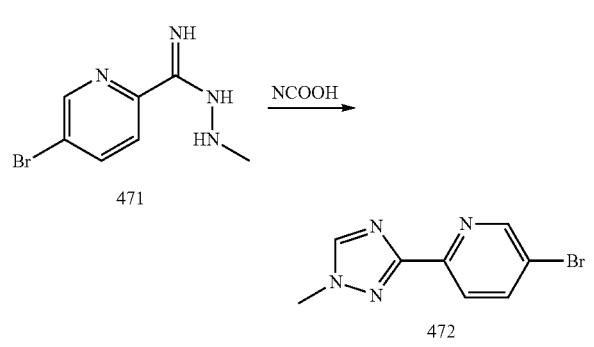

In an ice-water bath, 0.5 g (2.18 mmol) of Intermediate 471 was added to 5 ml (130.8 mmol) of formic acid, naturally warming to room temperature, and heated in an oil bath and refluxed for 2 h. 10 mL of saturated sodium carbonate was added to quench the reaction, and the organic phase was extracted with 20 ml×3 of DCM, and the organic phases were combined, dried over an appropriate amount of anhydrous sodium sulfate, filtered, rotary evaporated and pumped to dryness in vacuo to afford a crude product. The crude product was passed through a silica gel chromatographic column (eluent:methanol:dichloromethane=1:30) to afford a brown solid (101 mg). Yield: 19.38%. LC-MS: 239,241 [M+1]$^+$, $t_R$=1.601 min.

INTERMEDIATE 473

5-(4,4,5,5-tetramethyl-1,3,2-dioxaborolan-2-yl)-2-(1-methyl-1H-1,2,4-triazol-3-yl)pyridine

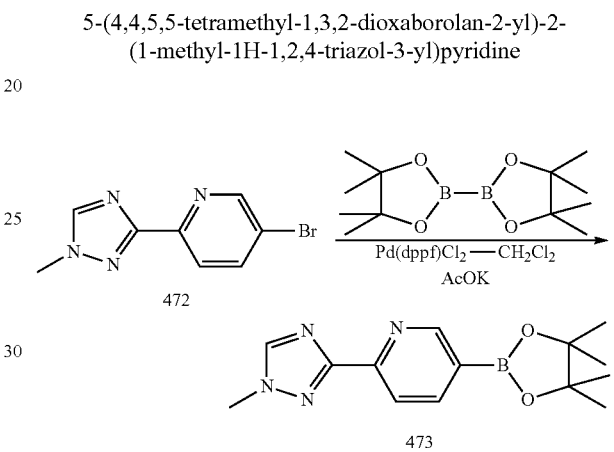

100 mg (0.42 mmol) of Intermediate 472, 160 mg (0.63 mmol) of diboronate and 124 mg (1.26 mmol) of potassium acetate were suspended in 5 ml of 1,4-dioxane, added with 38 mg (0.046 mmol) of [1,1'-bis(diphenylphosphino)ferrocene]palladium dichloride dichloromethane complex under the protection of nitrogen, stirred at T=100° C. and reacted for 2 h. The reaction solution was directly used in the next step.

INTERMEDIATE 475 tert-butyl (S)-3-(3-methyl-8-(6-(1-methyl-1H-1,2,4-triazol-3-yl)pyridin-3-yl)-2-oxy-2,3-dihydro-1H-imidazo[4,5-c]quinolin-1-yl)pyrrolidine-1-carbamate

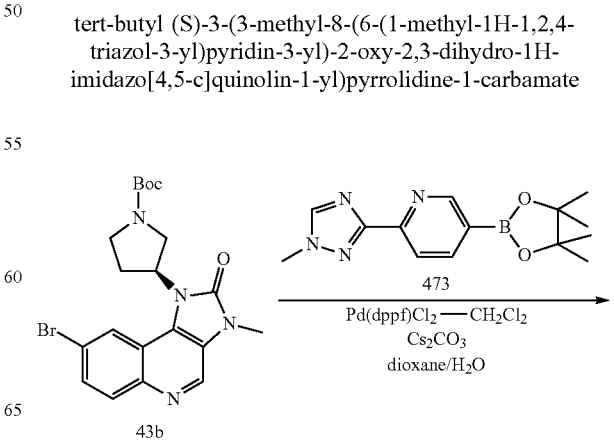

-continued

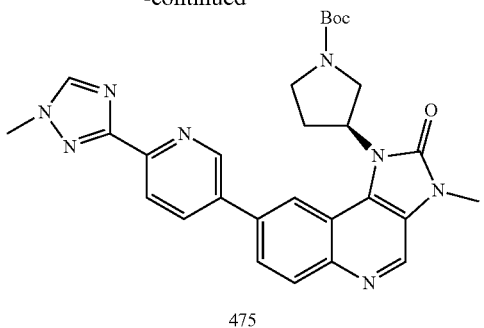

475

0.125 g (0.28 mmol) of Intermediate 43b, 0.120 g (0.42 mmol) of Intermediate 473, and 0.456 g (1.4 mmol) of cesium carbonate were suspended in 5 ml of dioxane, added with 1 ml of 2M sodium carbonate, then added with 0.023 g (0.028 mmol) of [1, F-bis(diphenylphosphino)ferrocene] palladium dichloride dichloromethane complex under the protection of nitrogen, and reacted at T=110° C. for 5 h under the protection of nitrogen again. The reaction was completed, concentrated by rotary evaporation, added with 20 ml of water and stirred, then added with 20 ml of dichloromethane and stirred, allowed to stand and separated into two phases. The aqueous phase was extracted with 20 ml×3 of dichloromethane, and the organic phases were combined, dried, and purified with a TLC preparative plate (developing solution:methanol:dichloromethane=1:10) to afford a brown solid (0.056 g). Yield: 37.98%. LC-MS: 527 [M+1]$^+$, $t_R$=1.726 min.

INTERMEDIATE 476

(S)-8-(6-(1-methyl-1H-1,2,4-triazol-3-yl)pyridin-3-yl)-3-methyl-1-(pyrrolidin-3-yl)-1H-imidazo[4,5-c]quinolin-2(3H)-one

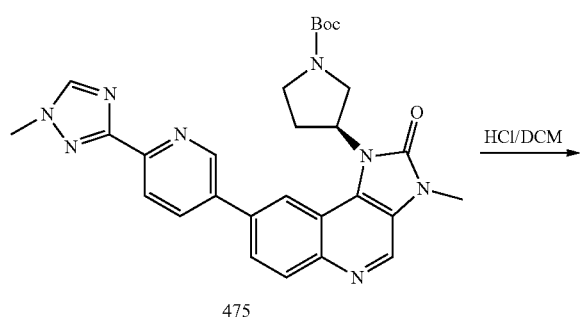

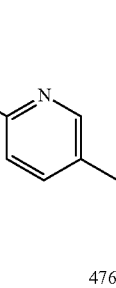

476

56 mg (0.106 mmol) of Intermediate 475 was dissolved in 4 ml of DCM, purged with HCl gas in an ice-water bath, stirred and reacted for 1 h. The reaction solution was pumped to dryness in vacuo to afford a grey solid (45 mg). Yield: 100%.

EXAMPLE 48

(S)-3-methyl-8-(6-(1-methyl-1H-1,2,4-triazol-3-yl)pyridin-3-yl)-1-(1-(methanesulfonyl)pyrrolidin-3-yl)-1H-imidazo[4,5-c]quinolin-2(3H)-one

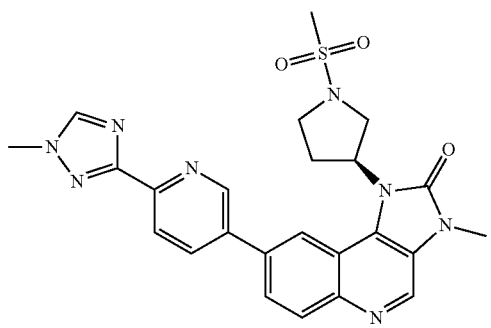

45 mg (0.106 mmol) of Intermediate 476 was added to 5 ml of dichloromethane, then added with 0.074 ml of triethylamine, stirred for 10 min to dissolve, and then added with 0.013 ml of methylsulfonyl chloride, and stirred overnight. 6 mL of saturated sodium bicarbonate aqueous solution was added, and the resulting mixture was separated into two phases. The aqueous phase was extracted with 6 ml×4 of dichloromethane, and the organic phases were combined, dried over anhydrous sodium sulfate, and purified with a TLC preparative plate (developing solution:methanol:dichloromethane=1:15), to afford an off-white powder (39 mg). Yield: 72.92%. LC-MS: 505 [M+1]$^+$, $t_R$=1.478 min $^1$H NMR (400 MHz, DMSO) δ 9.18 (s, 1H), 8.97 (s, 1H), 8.60 (d, J=10.8 Hz, 2H), 8.45 (dd, J=8.3, 2.1 Hz, 1H), 8.19 (dd, J=15.0, 8.5 Hz, 2H), 8.11 (d, J=8.8 Hz, 1H), 6.03-5.80 (m, 1H), 3.99 (s, 3H), 3.96-3.81 (m, 2H), 3.74-3.66 (m, 1H), 3.55 (s, 3H), 3.54-3.47 (m, 1H), 3.06 (s, 3H), 2.76-2.63 (m, 1H), 2.47-2.38 (m, 1H).

(XXI) Scheme XXI

SCHEME XXI

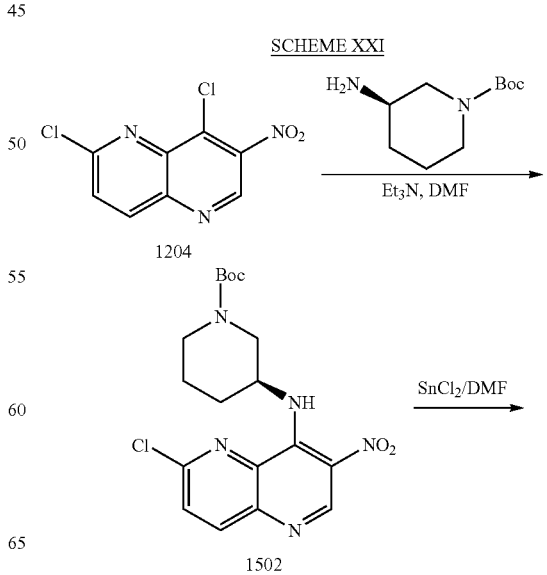

-continued

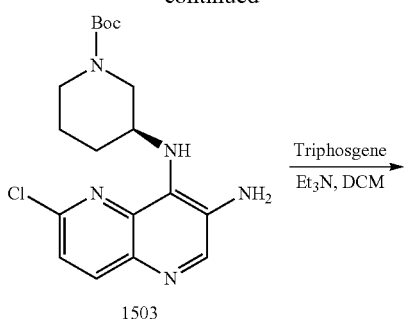
1503

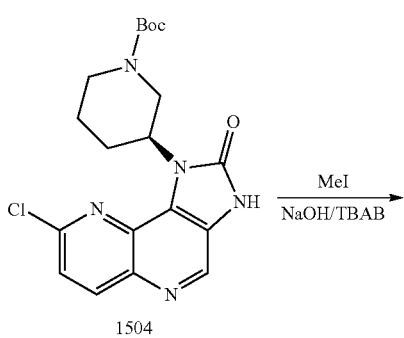
1504

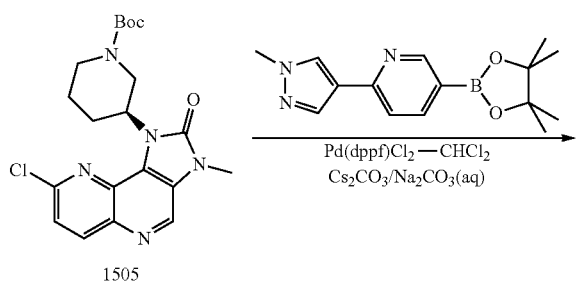
1505

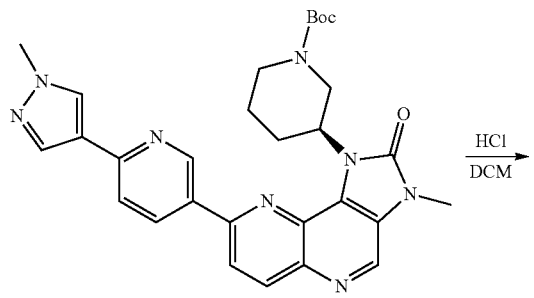
1506

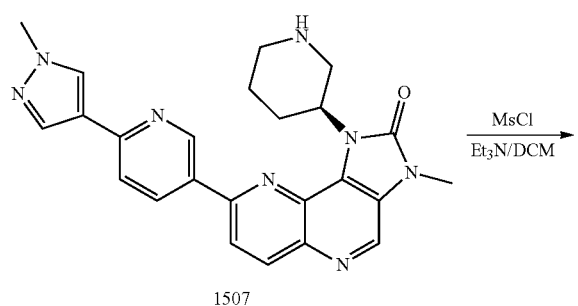
1507

-continued

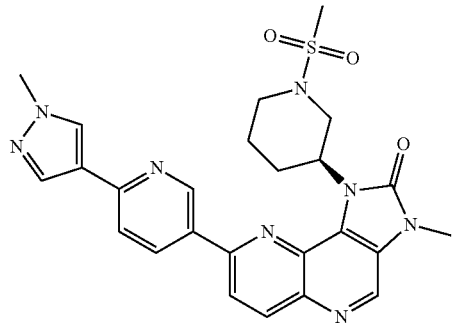
1508

INTERMEDIATE 1502 tert-butyl (R)-3-((6-chloro-3-nitro-1,5-naphthyridin-4-yl)amino)piperidine-1-carboxylate

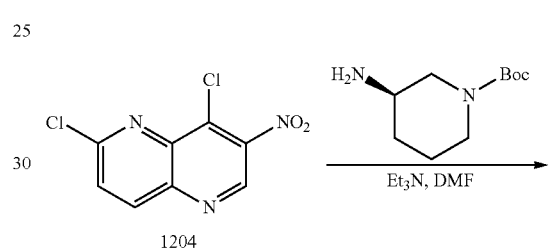
1204

1502

3 g (12.3 mmol) of Intermediate 1204 and 2.9 g (14.7 mmol) of the compound, (R)-1-tert-butyloxycarbonyl-3-aminopiperidine were dissolved in 20 mL of N,N-dimethylformamide, added with 3.7 g (36.9 mmol) of triethylamine, and stirred at room temperature for 3 h. The reaction was monitored by TLC. After the reaction was completed, 100 mL water was added, and stirred for 30 minutes, filtered, washed, and dried to afford a product (4.3 g) as a yellow solid. Yield: 86%. TLC showed that the product was identical with the racemic compound in Scheme XV.

INTERMEDIATE 1503 tert-butyl (R)-3-((3-amino-6-chloro-1,5-naphthyridin-4-yl)amino)piperidine-1-carboxylate

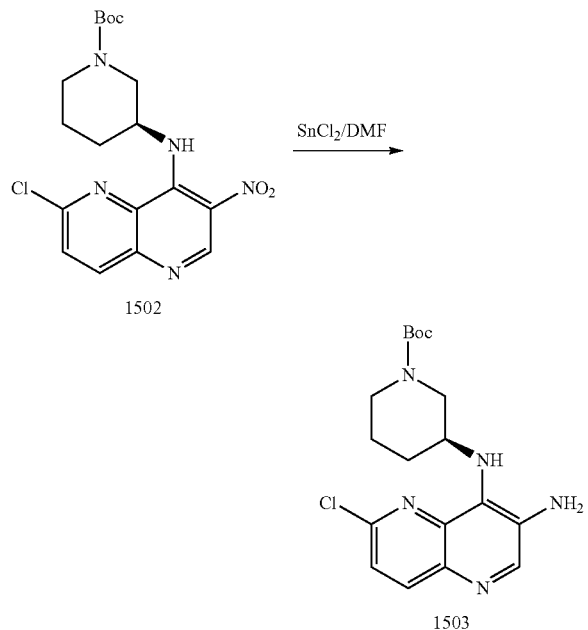

In an ice-water bath, 4.3 g (10.5 mmol) of Intermediate 1502 was dissolved in 50 mL of N,N-dimethylformamide 11.9 g (52.7 mmol) of stannous chloride dihydrate was added in batches over a period of 30 minutes, and stirred at room temperature for 3 h. The reaction was monitored by TLC. After the reaction was completed, to the reaction solution, 10% aqueous sodium hydroxide solution was added dropwise to pH 8-9, and filtered. The filtrate was extracted with dichloromethane, and the filter cake was washed with dichloromethane. The organic phases were combined, washed with water and with brine, dried, rotary evaporated to dryness to afford a product (4.4 g) as a reddish brown solid. Yield: 100%. TLC showed that the product was identical with the racemic compound in Scheme XV.

INTERMEDIATE 1504 tert-butyl (R)-3-(8-chloro-2-oxo-2,3-dihydro-1H-imidazo[4,5-c][1,5]naphthyridin-1-yl)piperidine-1-carboxylate

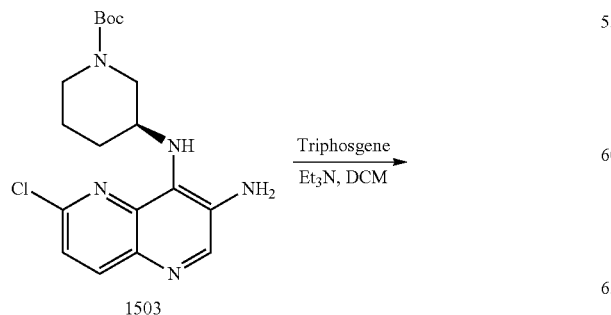

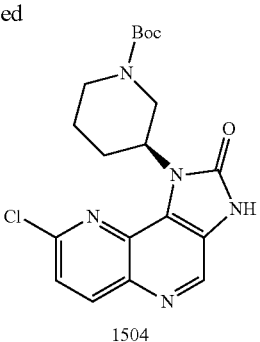

In an ice-water bath, 4.4 g (10.5 mmol) of Intermediate 1503 was dissolved in 50 mL of dichloromethane, added with 4.2 g (42 mmol) of triethylamine, and stirred for 10 minutes. A solution of 1.56 g (5.25 mmol) of triphosgene dissolved in 30 ml of dichloromethane was added dropwise, and stirred at 0° C. for 4 h. The reaction was monitored by TLC. After the reaction was completed, to the reaction solution, 100 mL of saturated sodium bicarbonate solution was added dropwise to quench the reaction, and stirred for 10 minutes. The organic phase was separated off, and the aqueous phase was extracted with dichloromethane. The organic phases were combined, dried, and rotary evaporated to dryness to afford a crude product. The crude product was purified by silica gel column chromatography (eluent:dichloromethane/methanol=40/1, V/V) to afford a product (2.6 g) as an earthy yellow solid. Yield: 61.9%. TLC showed that the product was identical with the racemic compound in Scheme XV.

INTERMEDIATE 1505 tert-butyl (R)-3-(8-bromo-3-methyl-2-oxo-2,3-dihydro-1H-imidazo[4,5-c][1,5]naphthyridin-1-yl)piperidine-1-carboxylate

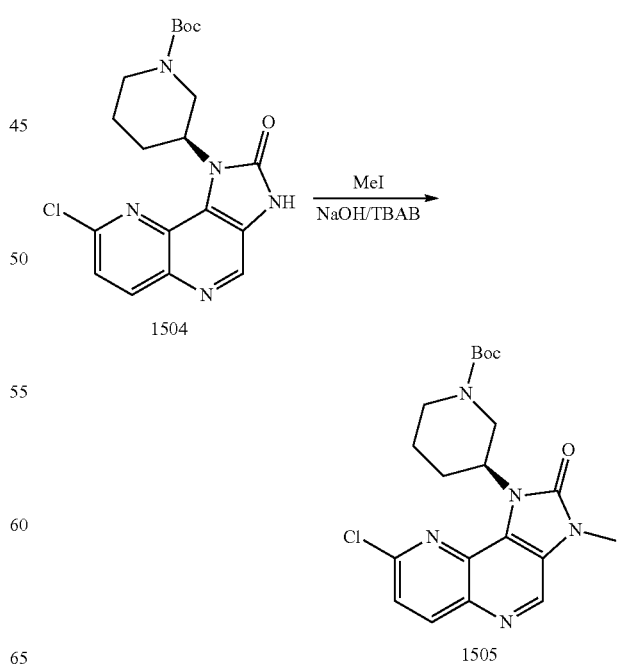

2.6 g (6.4 mmol) of Intermediate 1504 was dissolved in 50 ml of dichloromethane, added with 0.2 g (0.64 mmol) of tetrabutylammonium bromide and 50 mL of 10% aqueous sodium hydroxide solution, stirred for 10 minutes, then added with 2.7 g (19.3 mmol) of methyl iodide, and stirred at room temperature overnight. The reaction was monitored by TLC. After the reaction was completed, the reaction mixture was allowed to stand and separated into two layers. The organic phase was separated off, and the aqueous phase was extracted with dichloromethane. The organic phases were combined, dried, and rotary evaporated to dryness, to afford a product (3.3 g) as an earthy yellow solid. Yield: 100%. TLC showed that the product was identical with the racemic compound in Scheme XV.

INTERMEDIATE 1506 tert-butyl (R)-3-(3-methyl-8-(6-(1-methyl-1H-pyrazol-4-yl)pyridin-3-yl)-2-oxo-2,3-dihydro-1H-imidazo[4,5-c][1,5]naphthyridin-1-yl)piperidine-1-carboxylate

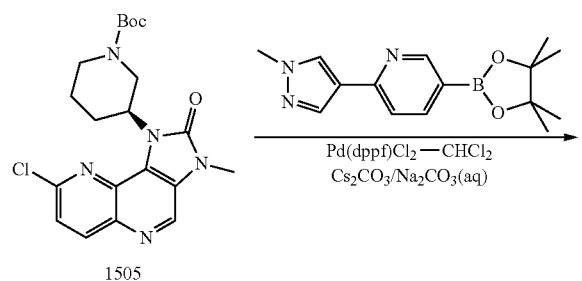

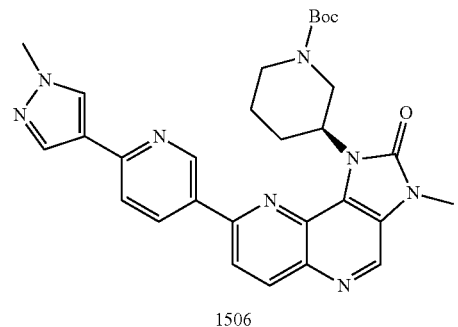

Under the protection of nitrogen, 1.8 g (4.3 mmol) of Intermediate 1505 and 1.8 g (6.45 mmol) of Intermediate 9A were dissolved in 50 mL of dioxane, added with 7.0 g (21.5 mmol) of cesium carbonate and 10 mL of 2M aqueous sodium carbonate solution, then added with 0.35 g (0.43 mmol) of [1,1-bis(di-phenylphosphino)ferrocene]palladium chloride, and heated at 110° C. for 20 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=40/1, V:V) to afford 1.6 g of the product as an earthy yellow solid. Yield: 69.6%. TLC showed that the product was identical with the racemic compound in Scheme XV.

INTERMEDIATE 1507

(R)-3-methyl-8-(6-(1-methyl-1H-pyrazol-4-yl)pyridin-3-yl)-1-(piperidin-3-yl)-1H-imidazo[4,5-c][1,5]naphthyridin-2(3H)-one

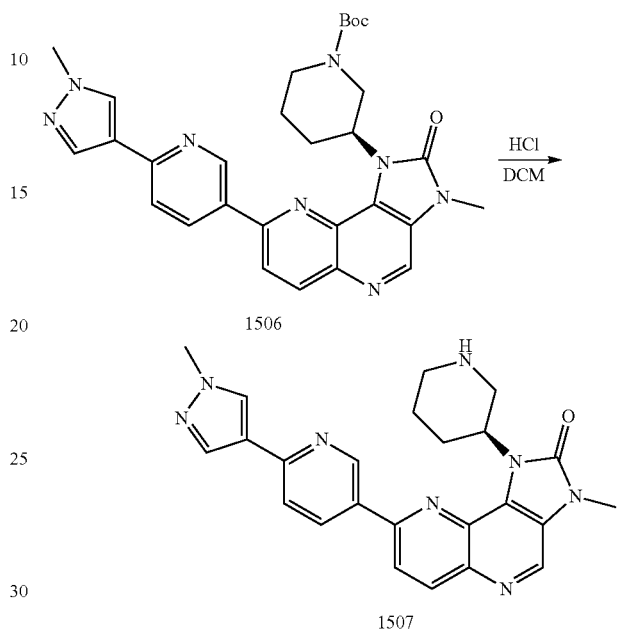

In an ice-water bath, 1.6 g (2.9 mmol) of Intermediate 1506 was dissolved in 20 ml of dichloromethane, and hydrogen chloride gas was purged to the reaction solution for 30 minutes. The reaction was monitored by TLC. After the reaction was completed, the reaction solution was filtered, and the solid was washed with dichloromethane, and pumped to dryness under reduced pressure to afford a product (1.5 g) as an earthy yellow solid, Yield: 100%. TLC showed that the product was identical with the racemic compound in Scheme XV.

EXAMPLE 49

(R)-3-methyl-8-(6-(1-methyl-1H-pyrazol-4-yl)pyridin-3-yl)-1-(1-(methanesulfonyl)piperidin-3-yl)-1H-imidazo[4,5-c][1,5]naphthyridin-2(3H)-one

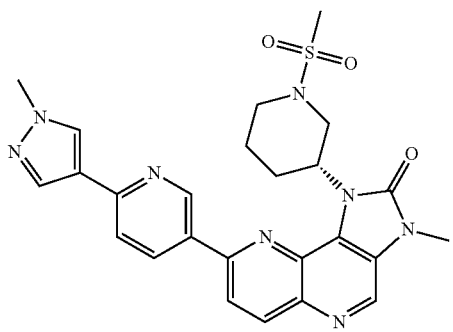 [SMILES: Cn1cc(-c2ccc(-c3ccc4ncc5c(c4n3)n([C@@H]3CCCN(S(C)(=O)=O)C3)c(=O)n5C)cn2)cn1]

1.5 g (2.9 mmol) of Intermediate 1507 was dissolved in 60 ml of dichloromethane, added with 1.5 g (14.5 mmol) of triethylamine, and then with 0.5 g (4.4 mmol) of methylsulfonyl chloride, and stirred at room temperature overnight. The reaction was monitored by TLC. After the reaction was completed, 100 mL of saturated sodium bicarbonate aqueous solution was added, and stirred for 20 minutes. The mixture was separated into layers, the aqueous phase was extracted with dichloromethane, and the organic phases were combined, dried, and rotary evaporated to dryness to afford a crude product. The crude product was purified by silica gel column chromatography (dichloromethane/methanol=10/1, V:V) to afford 1.0 g of the product as a yellowish white solid. Yield: 66.7%. TLC showed that the product was identical with the racemic compound in Scheme XV. LC-MS: 519.2 [M+1]$^+$, $t_R$=1.728 min.

(XXII) Scheme XXII

Scheme XXII

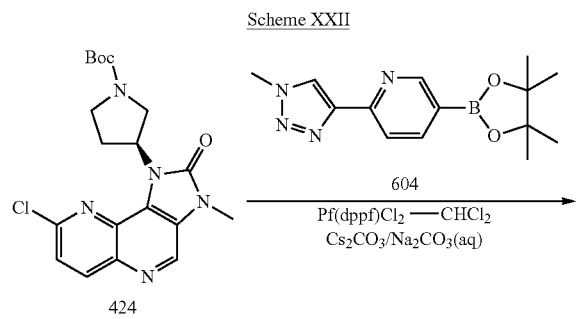

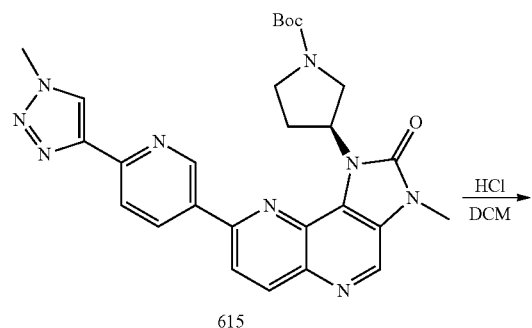

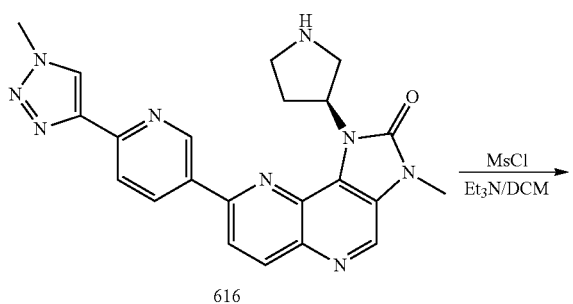

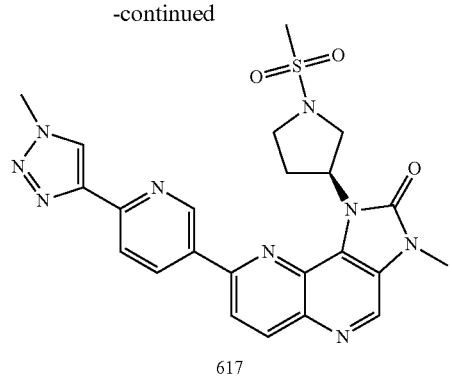

617

INTERMEDIATE 615 tert-butyl (S)-3-(3-methyl-8-(6-(1-methyl-1H-1,2,3-triazol-4-yl)pyridin-3-yl)-2-carbonyl-2,3-dihydro-1H-imidazo[4,5-c][1,5]naphthyridin-1-yl)pyrrolidine-1-carboxylate

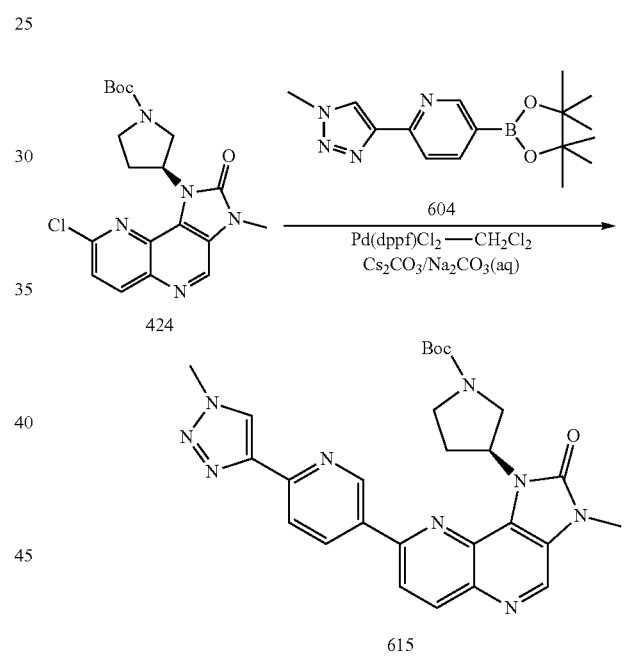

Intermediate 424 (165 mg, 0.408 mmol) was dissolved in 10 ml of 1,4-dioxane, added with crude (0.49 mmol) Intermediate 604, 424 mg (1.63 mmol) of cesium carbonate, 2 ml of 2 mol/L sodium carbonate solution, and 33 mg (0.041 mmol) of [1,1-bis(di-phenylphosphino)ferrocene]palladium chloride dichloromethane complex under the protection of nitrogen, heated to 110° C. and reacted for 5 h, and then cooled to room temperature. The dioxane was removed by evaporation, and the residue was dissolved in 20 ml of saturated sodium bicarbonate solution and 20 ml of dichloromethane. The solution was separated into two phases, the aqueous phase was extracted with dichloromethane, and the organic phases were combined, dried, and evaporated to dryness to afford a crude product. The crude product was purified by silica gel column chromatography (eluent: methanol:dichloromethane=1:10), to afford 124 mg of solid. Yield: 57.7%. LC-MS: 528.3 [M+1]$^+$, $t_R$=2.009 min.

INTERMEDIATE 616

(S)-3-methyl-8-(6-(1-methyl-1H-1,2,3-triazol-4-yl)pyridin-3-yl)-1-(pyrrolidin-3-yl)-1H-imidazo[4,5-c][1,5]naphthyridin-2(3H)-one

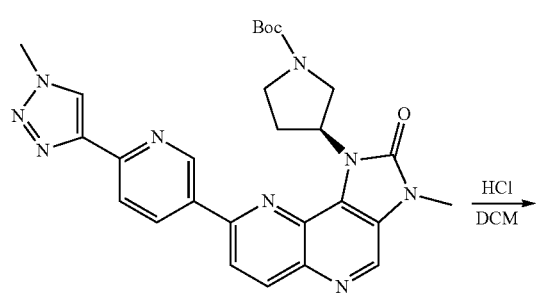

Intermediate 615 (124 mg, 0.235 mmol) was dissolved in 10 ml of dichloromethane, cooled to 0-10° C., to the reaction system purged with hydrogen chloride gas, reacted for 2 h, and filtered to afford a crude product, which was directly used in the next step.

EXAMPLE 50

(S)-3-methyl-8-(6-(1-methyl-1H-1,2,3-triazol-4-yl)pyridin-3-yl)-1-(1-(methanesulfonyl)pyrrolidin-3-yl)-1H-imidazo[4,5-c][1,5]naphthyridin-2(3H)-one

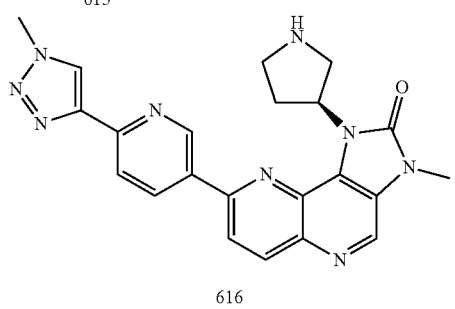

Intermediate 616 (a crude product) was dissolved in 10 ml of dichloromethane, added with 40 mg (0.353 mmol) of methylsulfonyl chloride and 95 mg (0.94 mmol) of triethylamine, and stirred at room temperature for 3 h. 30 mL of saturated sodium bicarbonate solution was added, and stirred for 30 min. The resulting solution was separated into two phases, the aqueous phase was extracted with dichloromethane, and the organic phases were combined, dried, evaporated to dryness to afford a crude product. The crude product was purified by silica gel chromatography (eluent: methanol:dichloromethane=1:10) to afford 32 mg. Yield: 26.89%. LC-MS: 506.2 [M+1]$^+$, $t_R$=1.664 min $^1$H NMR (400 MHz, DMSO) δ 9.47 (s, 1H), 9.11 (s, 1H), 8.85 (d, J=8.6 Hz, 1H), 8.68 (s, 1H), 8.62 (d, J=8.9 Hz, 1H), 8.50 (d, J=8.8 Hz, 1H), 8.27 (d, J=8.1 Hz, 1H), 6.58-6.45 (m, 1H), 5.42-5.28 (m, 1H), 4.17 (s, 3H), 4.06-3.97 (m, 1H), 3.59 (s, 3H), 3.07 (s, 3H), 3.03-2.87 (m, 1H), 2.10-1.91 (m, 3H).

The following compounds were obtained in accordance with Scheme IV.

INTERMEDIATE 604

2-(1-methyl-1H-1,2,3-triazol-4-yl)-5-(4,4,5,5-tetramethyl-1,3,2-dioxaborolan-2-yl)pyridine

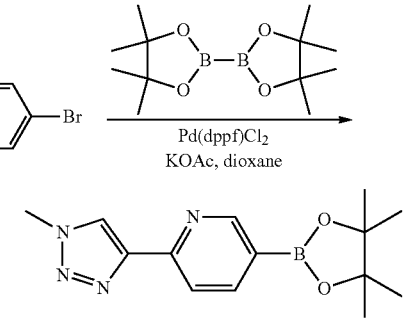

76 mg (0.32 mmol) of Intermediate 603, 122 mg (0.48 mmol) of bis(pinacolato)diboron and 94 mg (0.96 mmol) of potassium acetate were suspended in 6 ml of 1,4-dioxane, added with 26 mg (0.032 mmol) of [1,1'-bis(diphenylphosphino)ferrocene]palladium dichloride dichloromethane complex under the protection of nitrogen, stirred and reacted for 3 h at T=95° C. The reaction solution was directly used in the next step.

EXAMPLE 51

1-((1s,4s)-4-hydroxycyclohexyl)-3-methyl-8-(6-(1-methyl-1H-1,2,3-triazol-4-yl)pyridin-3-yl)-1H-imidazo[4,5-c]quinolin-2(3H)-one

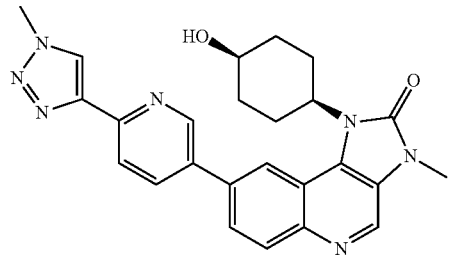 [SMILES: Cn1cc(-c2ccc(-c3ccc4ncc5c(c4c3)n([C@H]3CC[C@@H](O)CC3)c(=O)n5C)cn2)nn1]

100 mg (0.266 mmol) of Intermediate 208, 92 mg (0.320 mmol) of 604, and 347 mg (1.064 mmol) of cesium carbonate were suspended in 6 ml of 1,4-dioxane, then added with 2 ml of 2 M aqueous sodium carbonate solution, and added with 22 mg (0.0266 mmol) of [1, F-bis(diphenylphosphino)ferrocene]palladium dichloride dichloromethane complex under the protection of nitrogen, and heated to 110° C. and reacted for 5 h under the protection of nitrogen again. The reaction solution was concentrated by rotary evaporation, added with 20 ml of water and stirred, then added with 20 ml of dichloromethane and stirred, allowed to stand and separated into two phases. The aqueous phase was extracted with 20 ml×3 of dichloromethane, and the organic phases were combined, dried, and purified with a TLC silica gel preparative plate (eluent:methanol:dichloromethane=1:10) to afford a light yellow solid (14 mg). Yield: 11.6%. LC-MS: 456 [M+1]$^+$, $t_R$=1.523 min $^1$H NMR (400 MHz, DMSO+D$_2$O) δ 9.33 (s, 1H), 9.12 (s, 1H), 8.68 (s, 1H), 8.54-8.34 (m, 3H), 8.25 (d, J=8.1 Hz, 1H), 5.08-4.92 (s, 1H), 4.16 (s, 3H), 3.98 (s, 1H), 3.60 (s, 3H), 2.95-2.65 (m, 2H), 2.04-1.61 (m, 6H).

The following compounds were obtained in accordance with Scheme X.

EXAMPLE 52

(R)-1-(1-(ethylsulfonyl)piperidin-3-yl)-3-methyl-8-(6-(1-methyl-1H-pyrazol-4-yl)pyridin-3-yl)-1H-imidazo[4,5-c]quinolin-2(3H)-one

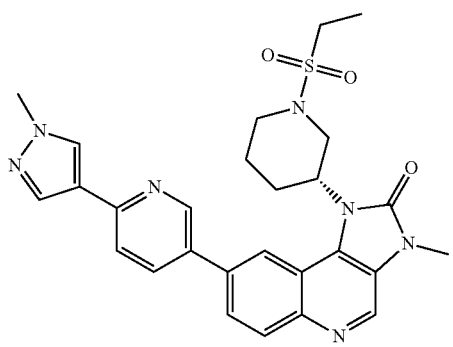 [SMILES: CCS(=O)(=O)N1CCC[C@@H](n2c(=O)n(C)c3cnc4ccc(-c5ccc(-c6cnn(C)c6)nc5)cc4c32)C1]

Intermediate 55a (75 mg, 0.17 mmol) was dissolved in 10 ml of dichloromethane, added with 33 mg (0.26 mmol) of ethylsulfonyl chloride and 69 mg (0.68 mmol) of triethylamine, and stirred at room temperature for 1.5 h. 15 mL of saturated sodium bicarbonate solution was added, stirred for 30 min, and separated into two phases. The aqueous phase was extracted with dichloromethane, and the organic phases were combined, dried, and evaporated to dryness to afford a crude product. The crude product was purified by silica gel chromatography (eluent: methanol:dichloromethane=1:10) to afford the target compound of Example 52 (20 mg). Yield: 22.09%. LC-MS: 532 [M+1]$^+$, $t_R$=3.384 min $^1$H NMR (400 MHz, DMSO) δ 8.99 (s, 1H), 8.92 (s, 1H), 8.40 (d, J=13.9 Hz, 2H), 8.21 (dd, J=21.4, 7.4 Hz, 2H), 8.12-7.97 (m, 2H), 7.76 (d, J=8.3 Hz, 1H), 5.10-4.98 (m, 1H), 4.02 (d, J=10.5 Hz, 1H), 3.91 (s, 3H), 3.79-3.62 (m, 2H), 3.51 (s, 3H), 3.21-3.06 (m, 2H), 2.96-2.68 (m, J=11.1 Hz, 2H), 2.16 (d, J=12.1 Hz, 1H), 1.96 (d, J=13.1 Hz, 1H), 1.85-1.66 (m, 1H), 1.19 (t, J=7.4 Hz, 3H).

EXAMPLE 53

(R)-1-(1-(cyclopropylsulfonyl)piperidin-3-yl)-3-methyl-8-(6-(1-methyl-1H-pyrazol-4-yl)pyridin-3-yl)-1H-imidazo[4,5-c]quinolin-2(3H)-one

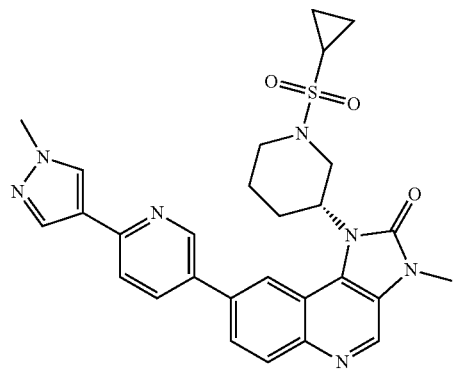 [SMILES: Cn1cc(-c2ccc(-c3ccc4ncc5c(c4c3)n([C@@H]3CCCN(S(=O)(=O)C4CC4)C3)c(=O)n5C)cn2)cn1]

Intermediate 55a (75 mg, 0.17 mmol) was dissolved in 10 ml of dichloromethane, added with 37 mg (0.26 mmol) of cyclopropylsulfonyl chloride and 69 mg (0.68 mmol) of triethylamine, and stirred at room temperature for 1.5 h. 15 mL of saturated sodium bicarbonate solution was added, stirred for 30 min, and separated into two phases. The aqueous phase was extracted with dichloromethane, and the organic phases were combined, dried, and evaporated to dryness to afford a crude product. The crude product was purified by silica gel chromatography (eluent:methanol:dichloromethane=1:10) to afford 27 mg of the target compound. Yield: 29.16%. LC-MS: 544 [M+1]$^+$, $t_R$=3.459 min $^1$H NMR (400 MHz, DMSO) δ 8.98 (s, 1H), 8.92 (s, 1H), 8.38 (d, J=5.6 Hz, 2H), 8.27-8.13 (m, 2H), 8.12-7.97 (m, 2H), 7.76 (d, J=8.2 Hz, 1H), 5.12-4.96 (m, 1H), 4.04 (d, J=10.2 Hz, 1H), 3.91 (s, 3H), 3.80-3.61 (m, 2H), 3.51 (s, 3H), 2.91 (t, J=11.6 Hz, 1H), 2.85-2.62 (m, 2H), 2.16 (d, J=10.8 Hz, 1H), 1.99 (d, J=14.1 Hz, 1H), 1.87-1.69 (m, 1H), 1.06-0.85 (m, 4H).

EXAMPLE 54

(R)-3-(3-methyl-8-(6-(1-methyl-1H-pyrazol-4-yl)pyridin-3-yl)-2-oxo-2,3-dihydro-1H-imidazo[4,5-c]quinolin-1-yl)piperidine-1-sulfamide

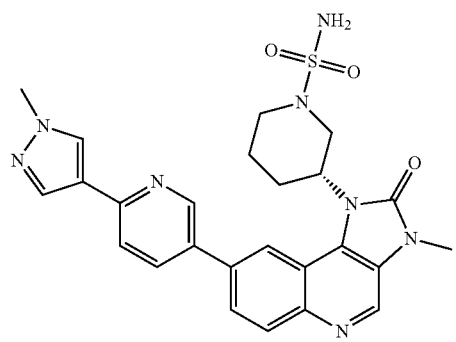 [SMILES: Cn1cc(-c2ccc(-c3ccc4ncc5c(c4c3)n([C@@H]3CCCN(S(N)(=O)=O)C3)c(=O)n5C)cn2)cn1]

100 mg (0.195 mmol) of Intermediate 55a was added with 10 ml dioxane, and then with 136 μl of triethylamine, stirred for 15 min, then added with 56 mg of sulfamide, refluxed and reacted at T=100° C. overnight. The solvent was removed by rotary evaporation, and the residue was added with 20 ml of water to quench the reaction, then added with 20 ml of dichloromethane and stirred, allowed to stand and separated into two phases. The aqueous phase was extracted with 3×20 ml of dichloromethane, and the organic phases were combined, dried, and purified with a silica gel preparative plate (methanol:dichloromethane=1:10) to afford a solid (12 mg). Yield: 11.87%. LC-MS: 519 [M+1]$^+$, $t_R$=3.226 min $^1$H NMR (400 MHz, DMSO) δ 9.40 (s, 1H), 9.07 (s, 1H), 8.68-8.38 (m, 5H), 8.27 (s, 1H), 8.03 (d, J=7.8 Hz, 1H), 6.98 (s, 2H), 5.38-5.15 (m, 1H), 3.94 (s, 3H), 3.67-3.48 (m, 2H), 3.57 (s, 3H), 2.72-2.55 (m, 2H), 2.27-2.13 (m, 1H), 2.05-1.78 (m, 3H).

EXAMPLE 55

(R)—N-ethyl-3-(3-methyl-8-(6-(1-methyl-1H-pyrazol-4-yl)pyridin-3-yl)-2-oxo-2,3-dihydro-1H-imidazo[4,5-c]quinolin-1-yl)piperidine-1-formamide

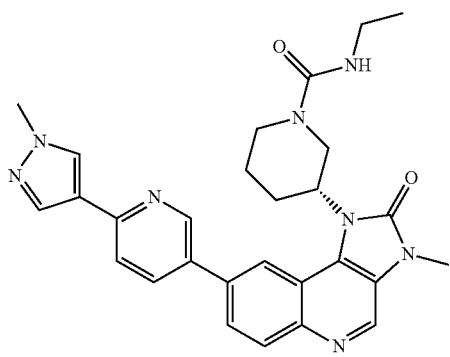 [SMILES: CCNC(=O)N1CCC[C@@H](n2c(=O)n(C)c3cnc4ccc(-c5ccc(-c6cnn(C)c6)nc5)cc4c32)C1]

50 mg (0.098 mmol) of Intermediate 55a was added with 5 ml of dioxane, and then with 28 μl of triethylamine, stirred for 30 min, then added with 9 μl of ethyl isocyanate, and reacted under reflux at T=110° C. for 1 h. The reaction solution was rotary evaporated to remove the solvent, added with 10 ml of water to quench the reaction, then added with 10 ml of dichloromethane and stirred, allowed to stand and separated into two phases. The aqueous phase was extracted with 3×10 ml of dichloromethane, and the organic phases were combined, dried, and purified with a silica gel preparative plate (methanol:dichloromethane=1:10) to afford a solid (21 mg). Yield: 41.97%. LC-MS: 511 [M+1]$^+$, $t_R$=3.228 min $^1$H NMR (400 MHz, DMSO) δ 9.42 (s, 1H), 9.09 (s, 1H), 8.88 (s, 1H), 8.65 (s, 2H), 8.59 (d, J=8.9 Hz, 1H), 8.42 (d, J=8.7 Hz, 1H), 8.33 (s, 1H), 8.06 (d, J=8.0 Hz, 1H), 6.79 (s, 1H), 5.10-4.94 (m, 1H), 4.47 (d, J=12.1 Hz, 1H), 3.96 (s, 3H), 3.58 (s, 3H), 3.40 (t, J=11.9 Hz, 1H), 3.15-3.00 (m, 2H), 2.99-2.77 (m, 2H), 2.16-1.43 (m, 4H), 0.93 (t, J=7.0 Hz, 3H).

EXAMPLE 56

(R)-3-methyl-8-(6-(1-methyl-1H-pyrazol-4-yl)pyridin-3-yl)-1-(1-((trifluoromethyl)sulfonyl)piperidin-3-yl)-1H-imidazo[4,5-c]quinolin-2(3H)-one

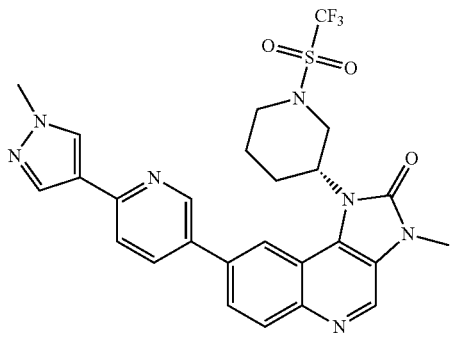 [SMILES: Cn1cc(-c2ccc(-c3ccc4ncc5c(c4c3)n([C@@H]3CCCN(S(=O)(=O)C(F)(F)F)C3)c(=O)n5C)cn2)cn1]

100 mg (0.195 mmol) of Intermediate 55a was dissolved in 10 ml of dichloromethane, added with 136 μl of triethylamine, stirred for 10 min, and then added with 40 μl of trifluoromethyl sulfonic anhydride. The reaction system turned red, and stirred and reacted for 2 h at room temperature. 10 mL of saturated sodium bicarbonate solution was added to quench the reaction, stirred, allowed to stand and separated into two phases. The aqueous phase was extracted with 3×10 ml of dichloromethane, and the organic phases were combined, dried, and purified with a silica gel preparative plate (methanol:dichloromethane=1:10) to afford a red solid (50 mg). Yield: 44.86%. LC-MS: 572 [M+1]$^+$, $t_R$=3.884 min.

(XXIII) Scheme XXIII

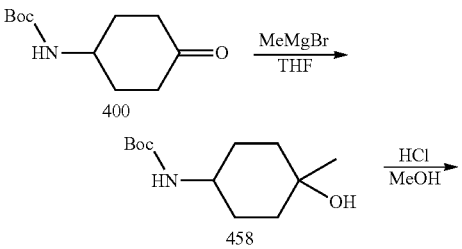

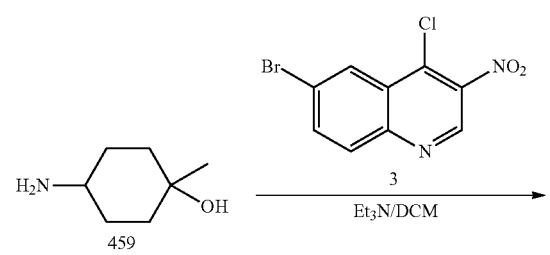

-continued

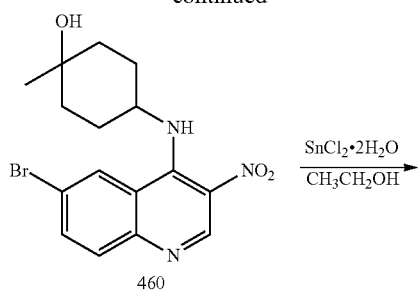

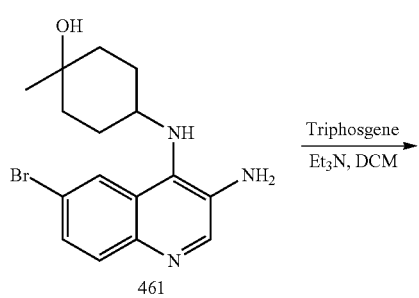

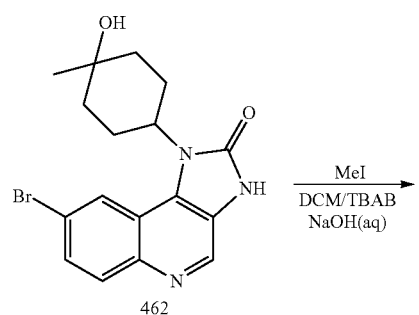

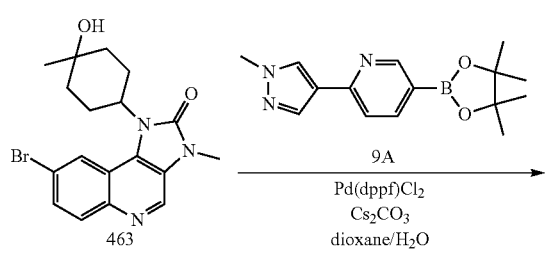

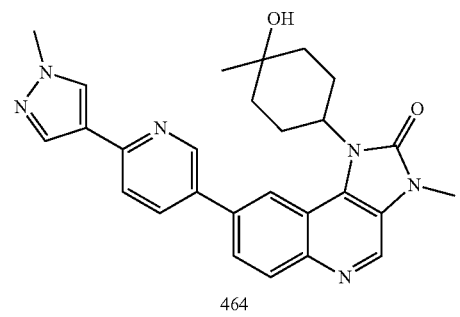 [SMILES: Cn1cc(-c2ccc(-c3ccc4ncc5c(c4c3)n(C3CCC(C)(O)CC3)c(=O)n5C)cn2)cn1]

INTERMEDIATE 458 tert-butyl (4-hydroxy-4-methylcyclohexyl)carbamate

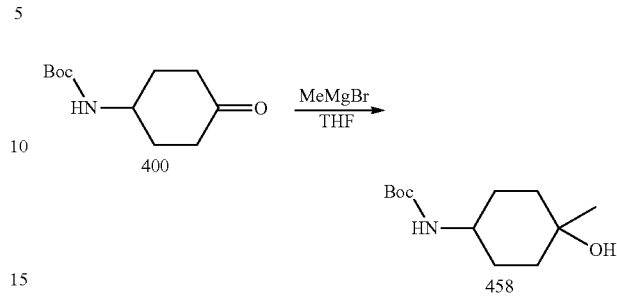

Under the protection of nitrogen, 2 g (9.3 mmol) of Compound 400 was dissolved in 40 ml of THF, cooled to −78° C., and added with 10 ml of methyl magnesium bromide (3 M) dropwise. After the dropwise addition was completed, the solution was rised to room temperature and stirred at overnight. 200 mL of saturated ammonium chloride aqueous solution was used to quench the reaction, and the resulting mixture was separated into two phases. The aqueous phase was extracted three times with equal volume of dichloromethane, and the organic phases were combined, dried, filtered, and evaporated to dryness to afford yellow oil (0.6 g). LC-MS: 174 [M+1−56]$^+$, $t_R$=1.759 min.

INTERMEDIATE 459

4-amino-1-methylcyclohexanol

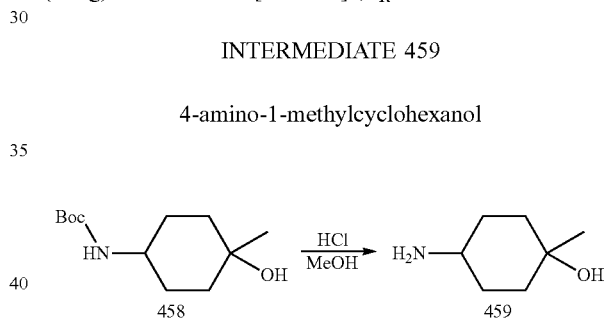

0.6 g of Intermediate 458 was dissolved in 70 ml of HCl/MeOH (10%), and stirred at room temperature for 7 h. The reaction solution was evaporated to dryness, and dried along with 3×20 ml of dichloromethane to afford a dark brown solid (0.5 g).

INTERMEDIATE 460

4-((6-bromo-3-nitroquinolin-4-yl)amino)-1-methyl-cyclohexanol

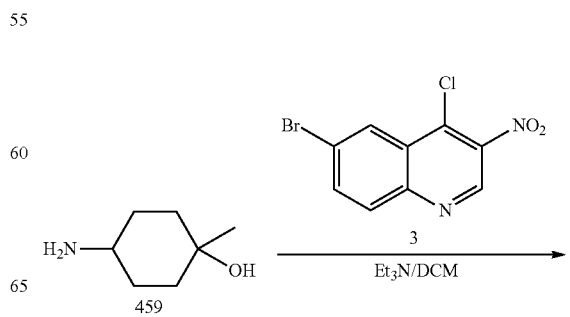

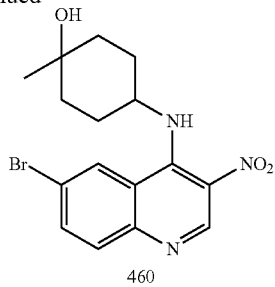

0.5 g (2.6 mmol) of Intermediate 459 and 0.86 g (8.5 mmol) of triethylamine were added into 20 ml of dichloromethane, stirred for 10 min, and then added with 0.5 g (1.7 mmol) of Intermediate 3, and stirred at room temperature overnight. The reaction solution was evaporated to dryness and purified by passing through a silica gel column, and collected two product fractions, to afford 170 mg of yellow solid (a mixture of cis and trans isomers). LC-MS: 380,382 [M+1]$^+$, $t_R$=2.036&2.107 min.

INTERMEDIATE 461

4-((3-amino-6-bromo-4-yl)amino)-1-methylcyclohexanol

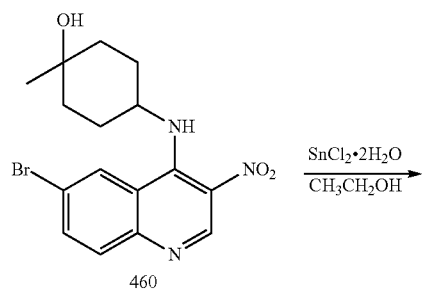

170 mg (0.447 mmol) of Intermediate 460 was dissolved in 30 ml of EtOH, added with 505 mg (2.24 mmol) of stannous chloride hydrate in batches, and stirred at room temperature overnight. The reaction solution was concentrated by rotary evaporation, and the concentrate was adjusted with total 20 ml of 10% sodium hydroxide solution and saturated sodium bicarbonate solution to pH=8~9, added with 20 ml of DCM and stirred, allowed to stand, and separated into two phases. The aqueous phase was extracted with 30 ml×3 of DCM, and the organic phases were combined and dried over anhydrous sodium sulfate, and evaporated to dryness to afford a brown crystal (156 mg) (a mixture of cis and trans isomers). Yield: 100%. LC-MS: 350,352 [M+1]$^+$, $t_R$=1.353&1.478 min.

INTERMEDIATE 462

8-bromo-1-(4-methyl-4-hydroxycyclohexyl)-1H-imidazo[4,5-c]quinolin-2(3H)-one

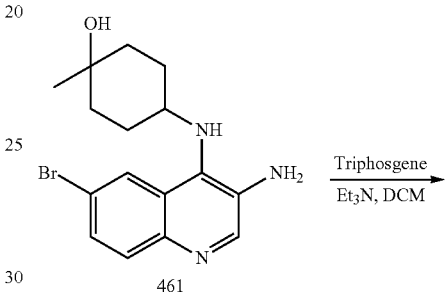

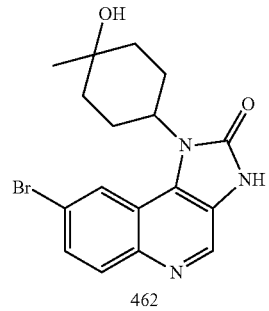

156 mg (0.447 mmol) of Intermediate 461 was dissolved in 10 ml of dichloromethane, added with 0.2 ml (1.34 mmol) of triethylamine and dropwise added with 67 mg (0.224 mmol) of triphosgene dissolved in 10 ml of dichloromethane under stirring in an ice-water bath, and stirred in the ice-water bath for 4 h. To the reaction solution 20 ml of saturated sodium hydrogen carbonate was added dropwise, stirred, allowed to stand, and separated into two phases. The aqueous phase was extracted with 20 ml×4 of dichloromethane, and the organic phases were combined, dried, and rotary evaporated solvent to dryness to afford a crude product. The crude product and passed through a silica gel chromatographic column (eluent:methanol:dichloromethane=1:30) to afford 29 mg of brown solid (a mixture of cis and trans isomers). Yield: 17.24%. LC-MS: 376,378 [M+1]$^+$, $t_R$=1.531& 1.629 min.

INTERMEDIATE 463

8-bromo-3-methyl-1-(4-methyl-4-hydroxycyclohexyl)-1H-imidazo[4,5-c]quinolin-2(3H)-one

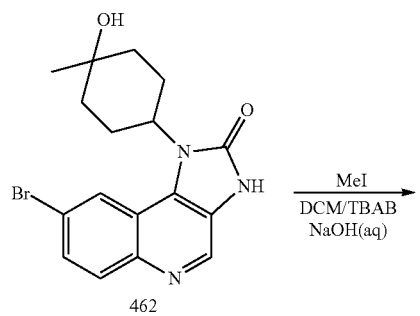

29 mg (0.077 mmol) of Intermediate 462 was dissolved in 2 ml of dichloromethane, added with 3 mg (0.0077 mmol) of TBAB, then with 2 ml of 10% NaOH and stirred for 10 min, then added with 14 μl (0.231 mmol) of methyl iodide, and stirred and reacted at room temperature overnight. The reaction solution was allowed to stand, and separated into two phases. The aqueous phase was extracted with 3 ml×6 of dichloromethane, and the organic phases were combined, dried, filtered, concentrated by rotary evaporation, and pumped to dryness in vacuo, to afford a yellow solid (30 mg) (a mixture of cis and trans isomers). Yield: 100%. LC-MS: 390,392 [M+1]$^+$, $t_R$=1.664&1.757 min.

EXAMPLE 57

1-(4-hydroxy-4-methylcyclohexyl)-3-methyl-8-(6-(1-methyl-1H-pyrazol-4-yl)pyridin-3-yl)-1H-imidazo[4,5-c]quinolin-2(3H)-one

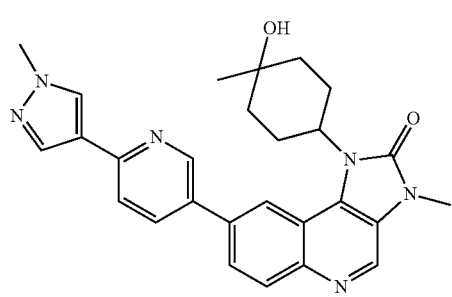 [SMILES: Cn1cc(-c2ccc(-c3ccc4ncc5c(c4c3)n(C3CCC(C)(O)CC3)c(=O)n5C)cn2)cn1]

30 mg (0.077 mmol) of Intermediate 463, 33 mg (0.116 mmol) of Intermediate 9A, and 126 mg (0.385 mmol) of cesium carbonate were suspended in 5 ml of dioxane, then added with 1 ml of 2M sodium carbonate solution, and then with 7 mg (0.0077 mmol) of [1, F-bis(diphenylphosphino)ferrocene]palladium dichloride dichloromethane complex under the protection of nitrogen, and heated to 110° C. and reacted for 5 h under the protection of nitrogen again. 2 mL of water was added and stirred, and then 3 ml of dichloromethane was added and stirred. The resulting mixture was allowed to stand and separated into two phases. The aqueous phase was extracted with 3 ml×6 of dichloromethane, and the organic phases were combined, dried, and purified with a TLC silica gel preparative plate (eluent:methanol:dichloromethane=1:15) to afford a brownish red solid (18 mg) (a mixture of cis and trans isomers). Yield: 49.89%. LC-MS: 469 [M+1]$^+$, $t_R$=1.508&1.539 min.

(XXIV) Scheme XXIV

Scheme XXIV

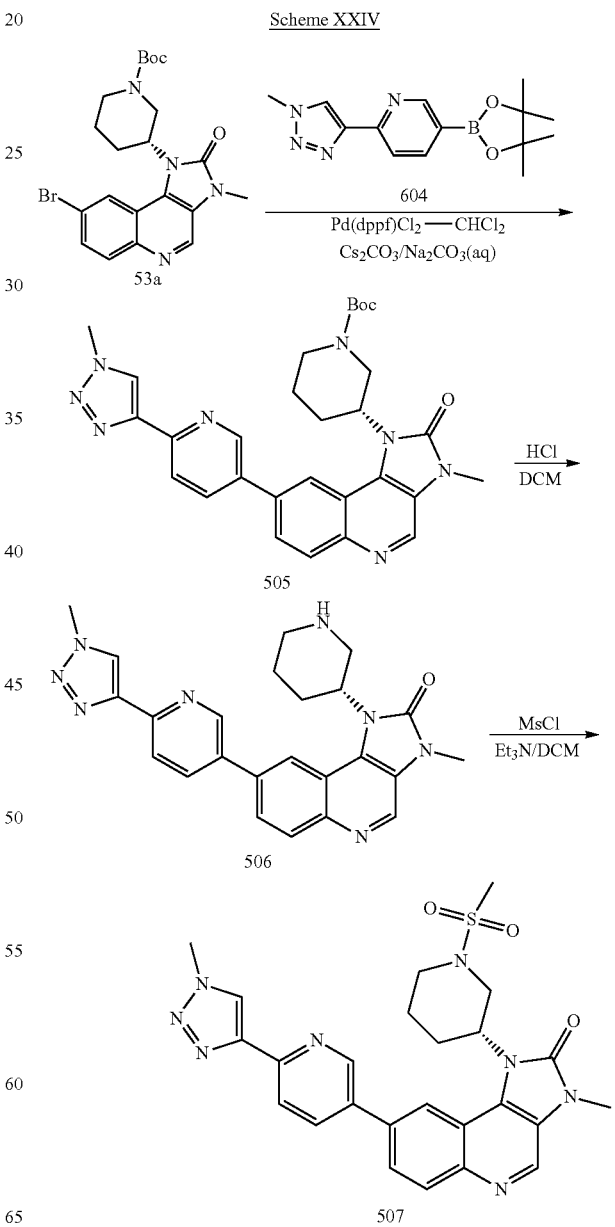

INTERMEDIATE 505 tert-butyl (R)-3-(3-methyl-8-(6-(1-methyl-1H-1,2,3-triazol-4-yl)pyridin-3-yl)-2-carbonyl-2,3-dihydro-1H-imidazo[4,5-c]quinolin-1-yl)piperidine-1-formate

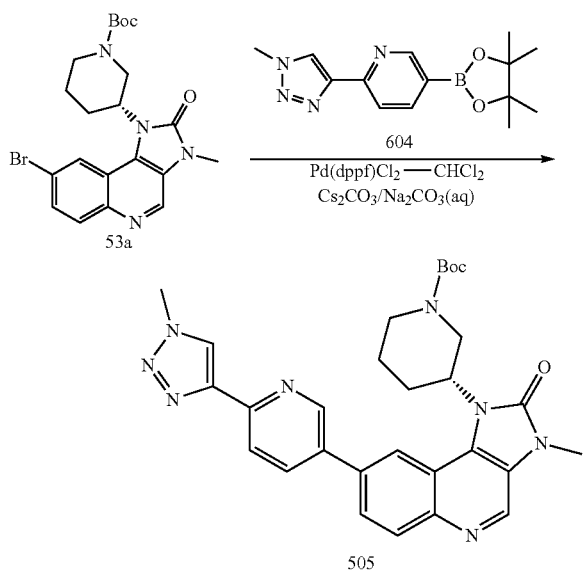

0.125 g (0.27 mmol) of Intermediate 53a, 0.093 g (0.324 mmol) of Intermediate 604, and 0.352 g (1.08 mmol) of cesium carbonate were suspended in 5 ml of dioxane, then added with 2 ml of 2M sodium carbonate, then added with 0.022 g (0.027 mmol) of [1,1'-bis(diphenylphosphino)ferrocene]palladium dichloride dichloromethane complex under the protection of nitrogen, and heated to T=110° C. and reacted for 5 h under the protection of nitrogen again. The solvent was removed by rotary evaporation, and the residue was added with 20 ml of water and 20 ml of dichloromethane, stirred, allowed to stand and separated into two phases. The aqueous phase was extracted with 20 ml×3 of dichloromethane, and the organic phases were combined, dried, and purified with a silica gel preparative plate (eluent: methanol:dichloromethane=1:10) to afford a light yellow solid (0.036 g). Yield: 24.66%. LC-MS: 541.2 [M+1]$^{30}$, $t_R$=1.998 min.

INTERMEDIATE 506

(R)-3-methyl-8-(6-(1-methyl-1H-1,2,3-triazol-4-yl)pyridin-3-yl)-1-(piperidin-3-yl)-1H-imidazo[4,5-c]quinolin-2(3H)-one

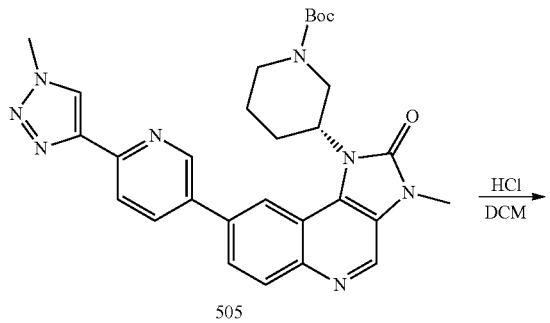

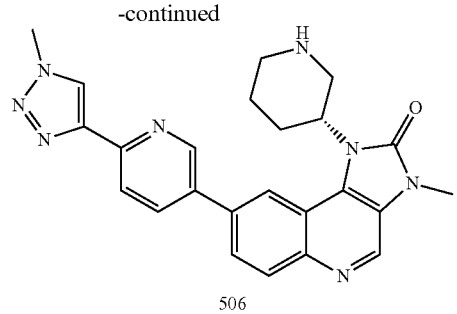

0.036 g (0.067 mmol) of Intermediate 505 was dissolved in 5 ml of dichloromethane, continually purged with HCl gas under an ice-water bath condition, and stirred and reacted for 2 h. The reaction solution was pumped to dryness to afford a solid (0.03 g). Yield: 100%.

EXAMPLE 58

(R)-3-methyl-8-(6-(1-methyl-1H-1,2,3-triazol-4-yl)pyridin-3-yl)-1-(1-(methanesulfonyl)piperidin-3-yl)-1H-imidazo[4,5-c]quinolin-2(3H)-one

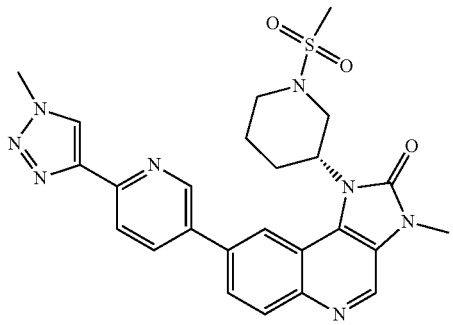 [SMILES: Cn1cc(-c2ccc(-c3ccc4ncc5c(c4c3)n([C@@H]3CCCN(S(C)(=O)=O)C3)c(=O)n5C)cn2)nn1]

30 mg (0.067 mmol) of Intermediate 506 was suspended in 10 ml of dichloromethane, then added with 46 μl of triethylamine, and stirred for 15 min. When the solid is dissolved, 8 μl of methylsulfonyl chloride was added, stirred and reacted at room temperature overnight. 10 mL of saturated sodium bicarbonate solution was added to quench the reaction, stirred, allowed to stand and separated into two phases. The aqueous phase was extracted with 3×10 ml of dichloromethane, and the organic phases were combined, dried, and purified with a silica gel preparative plate (methanol:dichloromethane=1:10) to afford a light yellow solid (26 mg). Yield: 75.28%. LC-MS: 519 [M+1]$^+$, $t_R$=1.465 min $^1$H NMR (400 MHz, DMSO+D$_2$O) δ 9.35 (s, 1H), 9.14 (s, 1H), 8.69 (s, 1H), 8.62 (s, 1H), 8.53-8.38 (m, 3H), 8.19 (d, J=8.2 Hz, 1H), 5.31-5.16 (m, 1H), 4.16 (s, 3H), 4.10 (d, J=10.1 Hz, 1H), 3.82-3.68 (m, 2H), 3.57 (s, 3H), 3.53-3.48 (m, 1H), 2.98 (s, 3H), 2.91-2.67 (m, 2H), 2.29-2.16 (m, 1H), 2.07-1.93 (m, 1H), 1.91-1.71 (m, 1H).

(XXV) Scheme XXV

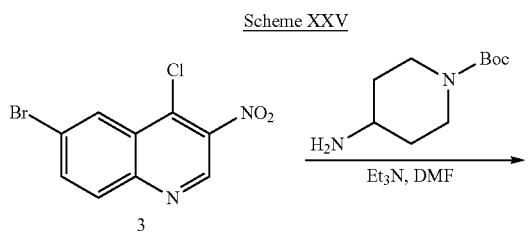

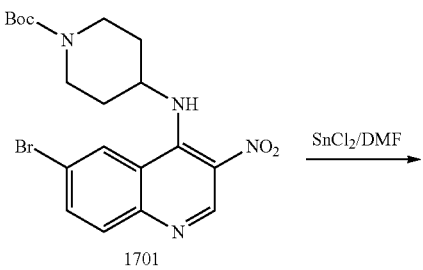

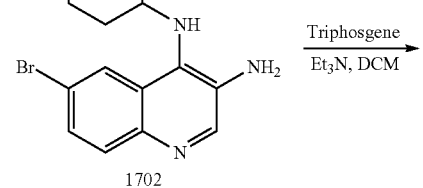

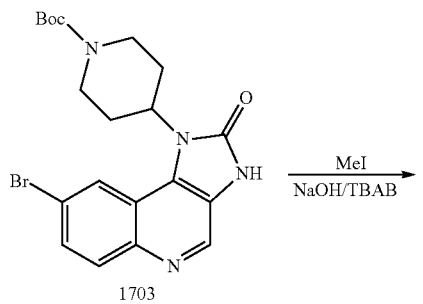

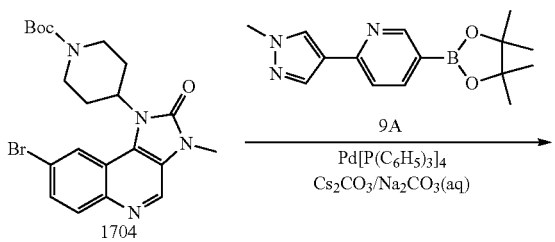

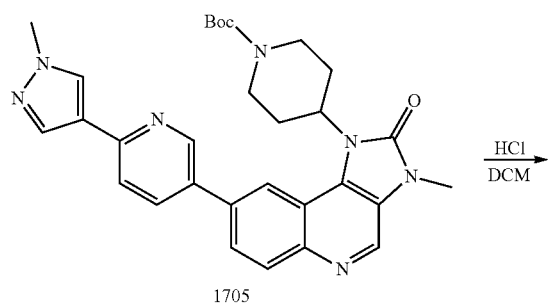

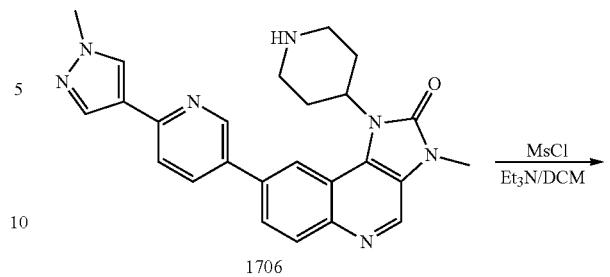

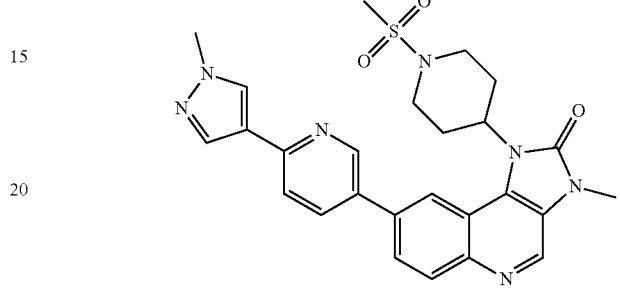

INTERMEDIATE 1701 tert-butyl 4-((6-bromo-3-nitroquinolin-4-yl)amino)piperidine-1-carboxylate

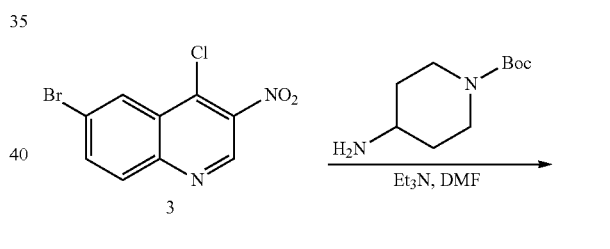

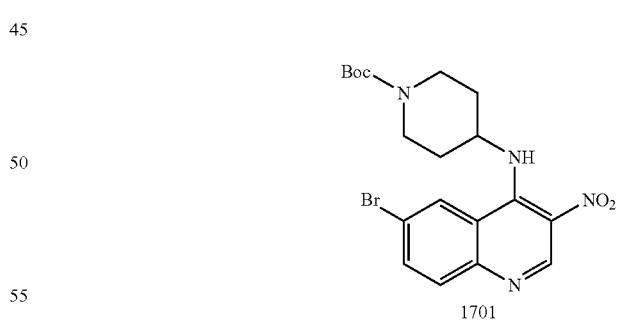

1.3 g (4.5 mmol) of Compound 3 and 1 g (5 mmol) of N-Boc-4-amino-piperidine were dissolved in 10 mL of N,N-dimethylformamide, added with 0.9 g (9 mmol) of triethylamine, and stirred at room temperature for 3 h. The reaction was monitored by TLC. After the reaction was completed, 60 mL of water was added, and stirred for 20 minutes. Then the solution was filtered, and the filter cake was washed with water to afford a product (1.1 g) as a yellow powder. Yield: 55.1%. LC-MS: 451,453 $[M+1]^+$, $t_R$=2.671 min.

INTERMEDIATE 1702 tert-butyl 4-((3-amino-6-bromoquinolin-4-yl)amino)piperidine-1-carboxylate

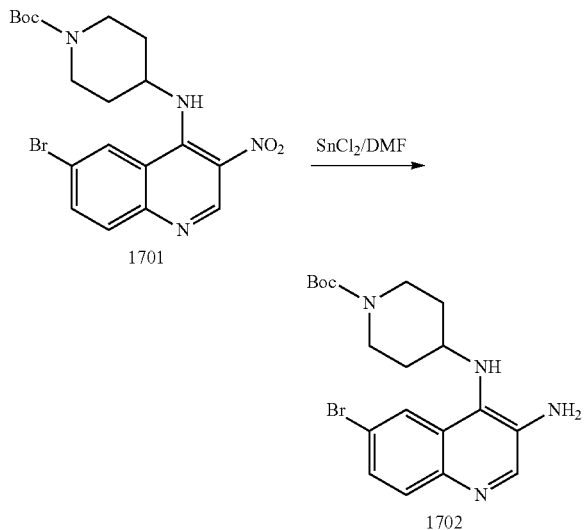

In an ice-water bath, 1.1 g (2.4 mmol) of Intermediate 1701 was dissolved in 10 mL of N,N-dimethylformamide 2.7 g (12.2 mmol) of stannous chloride dihydrate was added in batches over a period of 30 minutes, and stirred at room temperature for 2 h. The reaction was monitored by TLC. After the reaction was completed, to the reaction solution, 10% aqueous sodium hydroxide solution was added dropwise to a pH value of 8-9, and filtered. The filtrate was extracted with dichloromethane, and the filter cake was washed with dichloromethane. The organic phases were combined, washed with water and with brine, dried, and rotary evaporated to dryness to afford a product (1.1 g) as a brownish yellow solid. Yield: 100%. LC-MS: 421,423 [M+1]$^+$, $t_R$=1.981 min.

INTERMEDIATE 1703 tert-butyl 4-(8-bromo-2-oxo-2,3-dihydro-1H-imidazo[4,5-c]quinolin-1-yl)piperidine-1-carboxylate

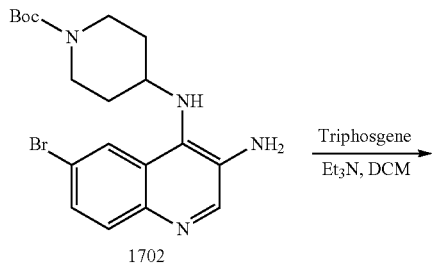

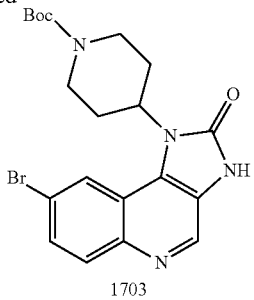

In an ice-water bath, 1.1 g (2.4 mmol) of Intermediate 1702 was dissolved in 10 ml of dichloromethane, added with 0.97 g (9.6 mmol) of triethylamine, and stirred for 10 minutes. A solution of 0.4 g (1.44 mmol) of triphosgene dissolved in 10 ml of dichloromethane was added dropwise and stirred at 0° C. for 4 h. The reaction was monitored by TLC. After the reaction was completed, to the reaction solution 20 mL of saturated sodium bicarbonate solution was added dropwise to quench the reaction, stirred for 10 minutes, and separated off the organic phase. The aqueous phase was extracted with dichloromethane, and the organic phases were combined, dried, and rotary evaporated to dryness to afford a crude product. The crude product was purified by silica gel column chromatography (eluent: dichloromethane/methanol=10/1, V/V) to afford a product (0.6 g) as a yellow-white solid. Yield: 55.8%. LC-MS: 447,449 [M+1]$^+$, $t_R$=2.199 min.

INTERMEDIATE 1704 tert-butyl 4-(8-bromo-3-methyl-2-oxo-2,3-dihydro-1H-imidazo[4,5-c]quinolin-1-yl)piperidine-1-carboxylate

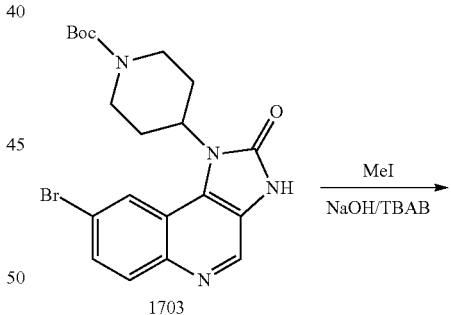

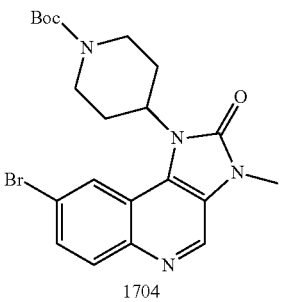

0.6 g (1.34 mmol) of Intermediate 1703 was dissolved in 30 ml of dichloromethane, added with 0.044 g (0.134 mmol) of tetrabutylammonium bromide and 30 mL of 10% aqueous sodium hydroxide solution, stirred for 10 minutes, then added with 0.57 g (4 mmol) of methyl iodide, and stirred for 4 h. The reaction was monitored by TLC. After the reaction was completed, the reaction mixture was allowed to stand and separated into two layers. The organic phase was separated off, and the aqueous phase was extracted with dichloromethane. The organic phases were combined dried, and rotary evaporated to dryness to afford a product (0.6 g) as a yellow solid. Yield: 100%. LC-MS: 461,463 [M+1]$^+$, $t_R$=2.364 min.

INTERMEDIATE 1705 tert-butyl 4-(3-methyl-8-(6-(1-methyl-1H-pyrazol-4-yl)pyridin-3-yl)-2-oxo-2,3-dihydro-1H-imidazo[4,5-c]quinolin-1-yl)piperidine-1-carboxylate

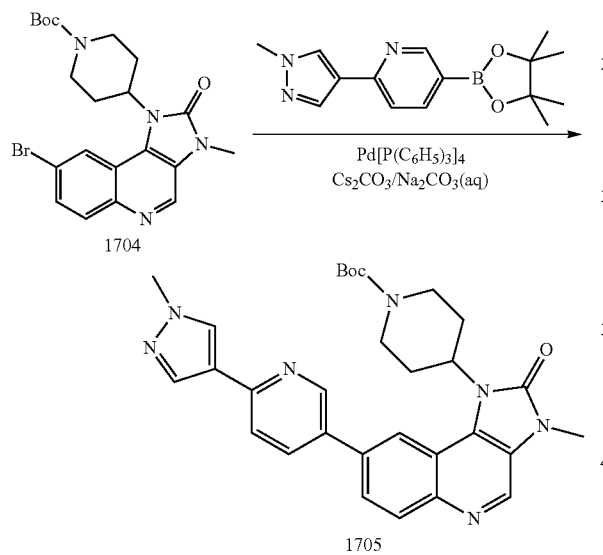

Under the protection of nitrogen, 0.1 g (0.22 mmol) of Intermediate 1704 and 0.092 g (0.32 mmol) of Intermediate 9A were dissolved in 10 mL of dioxane, added with 0.358 g (7.5 mmol) of cesium carbonate and 2 mL of 2M aqueous sodium carbonate solution, then with 0.025 g (0.022 mmol) of tetrakis(triphenylphosphine)palladium, and heated at 110° C. for 5 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=20/1, V:V) to afford 0.02 g of the product as a white solid. Yield: 16.8%. LC-MS: 484 [M-56+1]$^+$, $t_R$=3.995 min.

INTERMEDIATE 1706

3-methyl-8-(6-(1-methyl-1H-pyrazol-4-yl)pyridin-3-yl)-1-(piperidin-4-yl)-1H-imidazo[4,5-c]quinolin-2(3H)-one

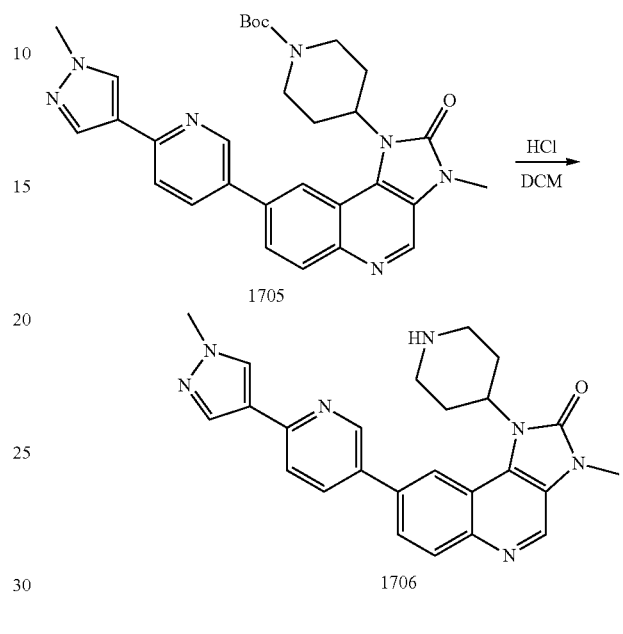

In an ice-water bath, 0.02 g (0.037 mmol) of Intermediate 1705 was dissolved in 5 ml of dichloromethane, and hydrogen chloride gas was purged through the reaction solution for 30 minutes. The reaction was monitored by TLC. After the reaction was completed, the reaction solution was filtered, and the solid was washed with dichloromethane, and pumped to dryness under reduced pressure to afford a product (0.02 g) as a dark brown solid. Yield: 100%.

EXAMPLE 59

3-methyl-8-(6-(1-methyl-1H-pyrazol-4-yl)pyridin-3-yl)-1-(1-(methanesulfonyl)piperidin-4-yl)-1H-imidazo[4,5-c]quinolin-2(3H)-one

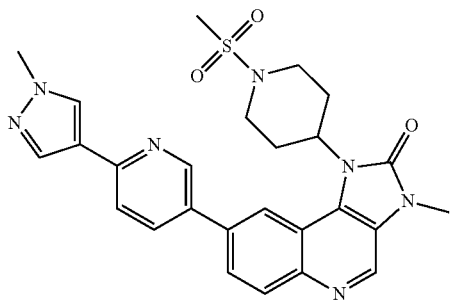 [SMILES: Cn1cc(-c2ccc(-c3ccc4ncc5c(c4c3)n(C3CCN(S(C)(=O)=O)CC3)c(=O)n5C)cn2)cn1]

0.02 g (0.037 mmol) of Intermediate 1706 was dissolved in 5 ml of dichloromethane, added with 0.018 g (0.185 mmol) of triethylamine, then with 0.006 g (0.056 mmol) of methylsulfonyl chloride, and stirred at room temperature overnight. The reaction was monitored by TLC. After the reaction was completed, 10 mL of saturated sodium bicarbonate aqueous solution was added, stirred for 20 minutes, and separated into layers. The aqueous phase was extracted with dichloromethane, and the organic phases were combined, dried, and rotary evaporated to dryness to afford a crude product. The crude product was purified by silica gel column chromatography (dichloromethane/methanol=10/1, V:V) to afford 0.01 g of the product as a white solid. Yield: 52.3%. LC-MS: 518 [M+1]$^+$, $t_R$=3.245 min.

(XXVI) Scheme XXVI

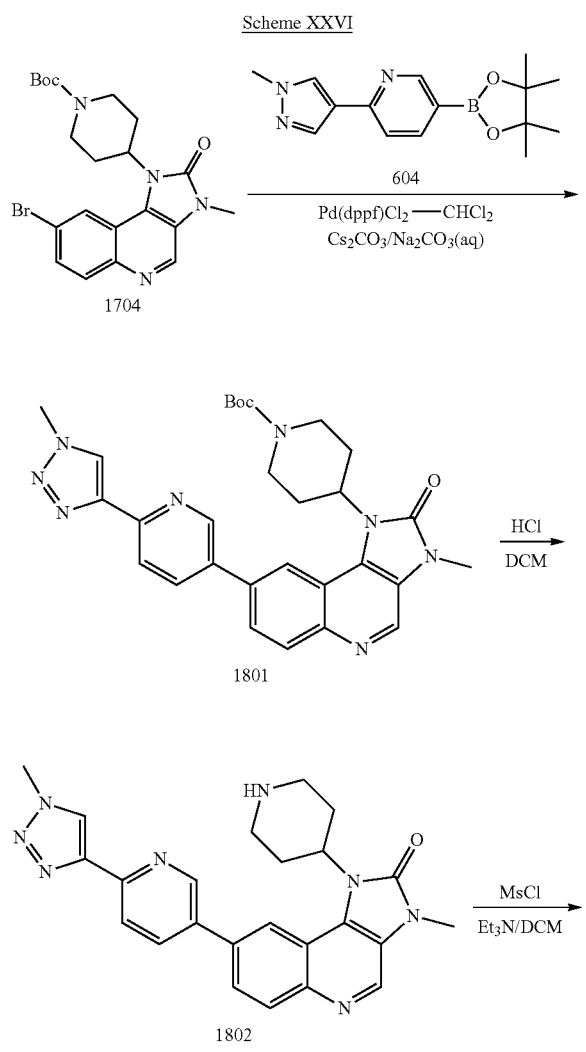

INTERMEDIATE 1801 tert-butyl 4-(3-methyl-8-(6-(1-methyl-1H-1,2,3-triazol-4-yl)pyridin-3-yl)-2-oxo-2,3-dihydro-1H-imidazo[4,5-c]quinolin-1-yl)piperidine-1-carboxylate

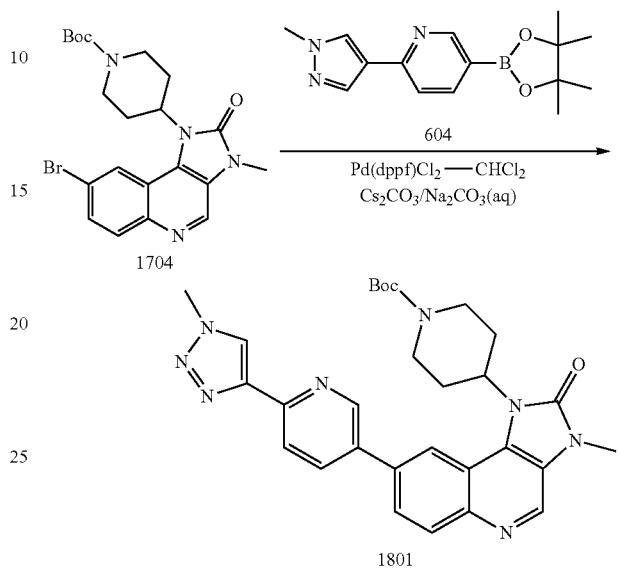

Under the protection of nitrogen, 0.25 g (0.54 mmol) of Intermediate 1704 and 0.186 g (0.65 mmol) of Intermediate 604 were dissolved in 5 mL of dioxane, added with 0.527 g (1.62 mmol) of cesium carbonate and 3 mL of 2M aqueous sodium carbonate solution, and then with 0.044 g (0.054 mmol) of [1,1-bis(di-phenylphosphino)ferrocene]palladium chloride, and heated at 110° C. for 5 h. The reaction was monitored by TLC. After the reaction was completed, most of dioxane was removed from the reaction solution, and the residue was added with water and extracted with dichloromethane. The organic phases were combined, dried, and rotary evaporated to dryness to afford a crude product. The crude product was purified by silica gel column chromatography (dichloromethane/methanol=20/1, V:V) to afford 0.16 g of the product as an earthy yellow solid. Yield: 54.9%. LC-MS: 541.3 [M+1]$^+$, $t_R$=1.964 min.

INTERMEDIATE 1802

3-methyl-8-(6-(1-methyl-1H-1,2,3-triazol-4-yl)pyridin-3-yl)-1-(piperidin-4-yl)-1H-imidazo[4,5-c]quinolin-2(3H)-one

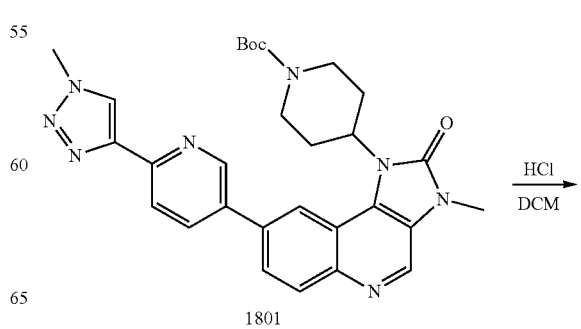

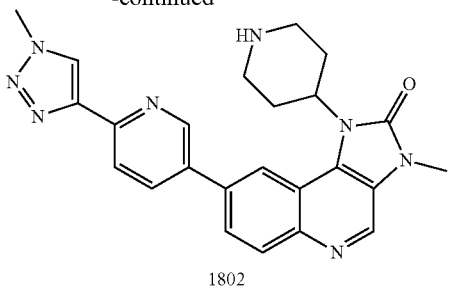

1802

In an ice-water bath, 0.16 g (0.29 mmol) of Intermediate 1801 was dissolved in 8 ml of dichloromethane, and hydrogen chloride gas was purged through the reaction solution for 30 minutes. The reaction was monitored by TLC. After the reaction was completed, the reaction solution was filtered, and the solid was washed with dichloromethane, and pumped to dryness under reduced pressure to afford a product (0.12 g) as a dark brown solid. Yield: 74.5%.

EXAMPLE 60

3-methyl-8-(6-(1-methyl-1H-1,2,3-triazol-4-yl)pyridin-3-yl)-1-(1-(methanesulfonyl)piperidin-4-yl)-1H-imidazo[4,5-c]quinolin-2(3H)-one

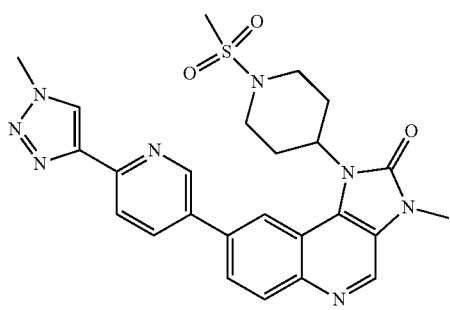 [SMILES: Cn1cc(-c2ccc(-c3ccc4ncc5c(c4c3)n(C3CCN(S(C)(=O)=O)CC3)c(=O)n5C)cn2)nn1]

0.06 g (0.12 mmol) of Intermediate 1802 was dissolved in 5 ml of dichloromethane, added with 0.06 g (0.18 mmol) of triethylamine and then with 0.02 g (0.18 mmol) of methylsulfonyl chloride, and stirred at room temperature overnight. The reaction was monitored by TLC. After the reaction was completed, 10 mL of saturated sodium bicarbonate aqueous solution was added, stirred for 20 minutes, and separated into layers. The aqueous phase was extracted with dichloromethane, and the organic phases were combined, dried, and rotary evaporated to dryness to afford a crude product. The crude product was purified by silica gel column chromatography (dichloromethane/methanol=10/1, V:V) to afford 0.02 g of the product as a white solid. Yield: 31.7%. LC-MS: 519.2 [M+1]$^+$, $t_R$=1.648 min $^1$H NMR (400 MHz, DMSO) δ 9.13 (s, 1H), 8.95 (s, 1H), 8.65 (s, 1H), 8.55 (s, 1H), 8.39 (d, J=6.1 Hz, 1H), 8.21 (dd, J=8.5, 2.9 Hz, 2H), 8.09 (d, J=8.3 Hz, 1H), 5.14-5.00 (m, 1H), 4.15 (s, 3H), 3.81 (d, J=9.0 Hz, 2H), 3.53 (s, 3H), 3.08 (t, J=11.4 Hz, 2H), 2.99 (s, 3H), 2.84-2.63 (m, 3H), 2.12 (d, J=11.7 Hz, 2H).

(XXVII) Scheme XXVII

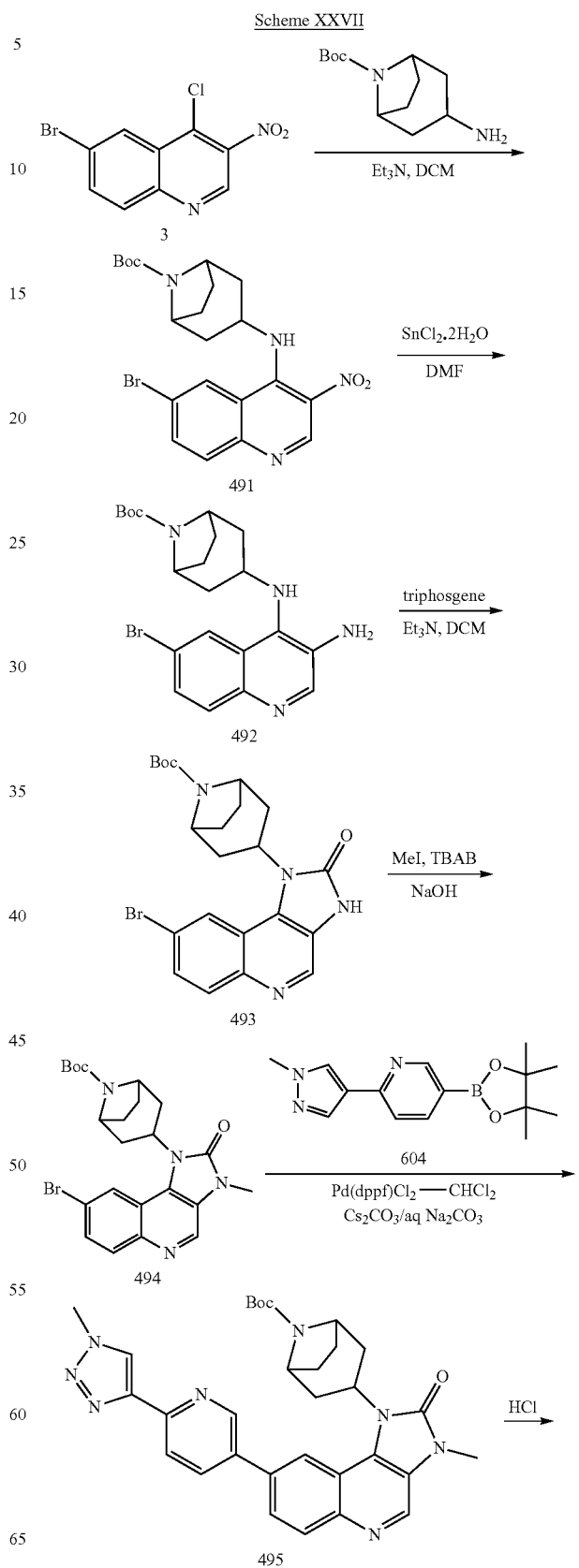

-continued

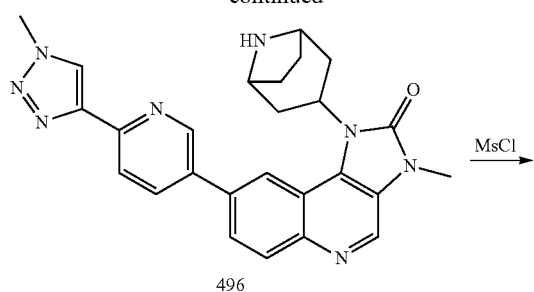

496

497

INTERMEDIATE 491 tert-butyl 3-((6-bromo-3-nitroquinolin-4-yl)amino)-8-azabicyclo[3.2.1]octane-8-carboxylate

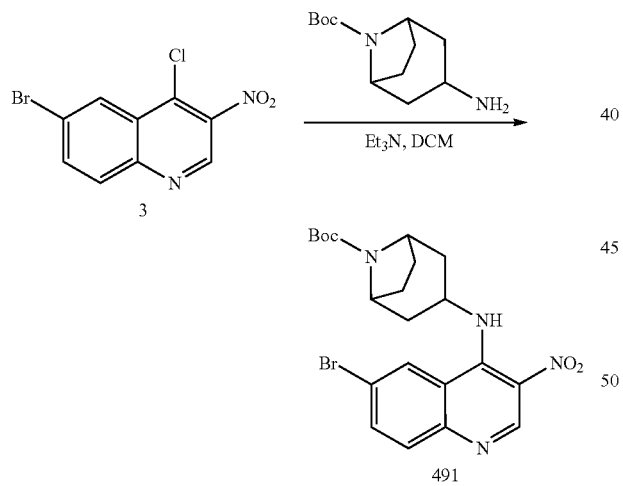

491

0.316 g of (1.10 mmol) Compound 3 and 0.3 g (1.33 mmol) of tert-butyl 3-amino-8-azabicyclo[3.2.1]octane-8-formate (endo configuration) were dissolved in 10 ml of dichloromethane, added with 0.31 ml (2.20 mmol) of triethylamine, and stirred at room temperature for 5 h, precipitating out solids. The solid was filtered off, washed with a small amount of dichloromethane, and pumped to dryness; the filtrate was passed through a silica gel chromatographic column (from PE: EA=2:1 to EA) to afford a yellow solid (0.419 g in total). Yield: 79.80%. LC-MS: 477,479 [M+1]$^+$, $t_R$=2.820 min.

INTERMEDIATE 492 tert-butyl 3-((6-bromo-3-aminoquinolin-4-yl)amino)-8-azabicyclo[3.2.1]octane-8-formate

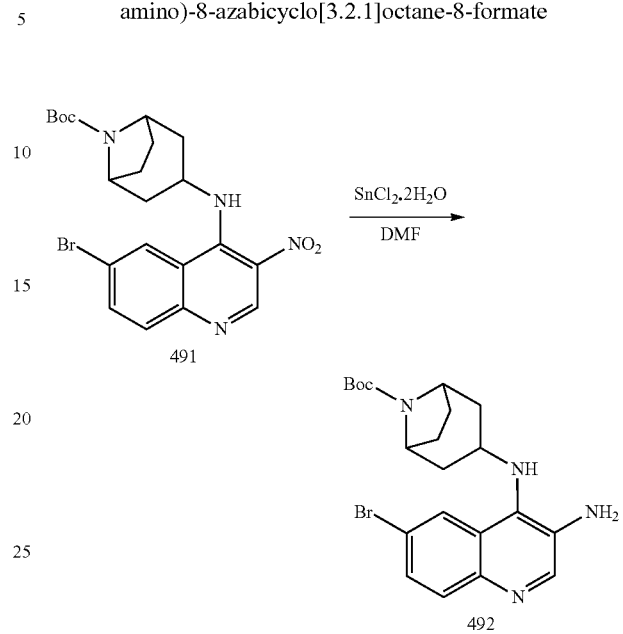

492

0.419 g (0.878 mmol) of Intermediate 491 was dissolved in 10 ml of DMF, added with 0.99 g (4.39 mmol) of stannous chloride hydrate in batches, and stirred at room temperature for 2 h. 10% Sodium hydroxide solution was added to adjust pH to 8-9 to quench the reaction, added with 100 ml of water and 100 ml of dichloromethane, stirred, allowed to stand, and separated into phases. The aqueous phase was extracted with 3×80 ml of dichloromethane, and the organic phases were combined, dried over anhydrous sodium sulfate, and evaporated to dryness to afford a brown solid (0.392 g). Yield: 100%. LC-MS: 447,449 [M+1]$^+$, $t_R$=2.103 min.

INTERMEDIATE 493 tert-butyl 3-(8-bromo-2-carbonyl-2,3-dihydro-1H-imidazo[4,5-c]quinolin-1-yl)-8-azabicyclo[3.2.1]octane-8-carboxylate

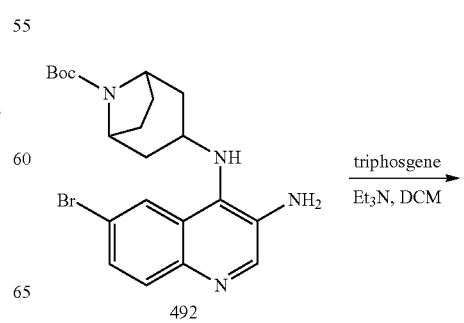

492

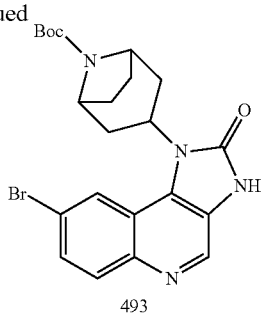

0.392 g (0.878 mmol) of Intermediate 492 was dissolved in 10 ml of dichloromethane, dropwise added with 0.37 ml (2.634 mmol) of triethylamine and added with 0.131 g (0.439 mmol) of triphosgene dissolved in 7 ml of dichloromethane under stirring and ice-water bath conditions, and stirred in the ice-water bath for 5.5 h. To the reaction solution 20 ml of saturated sodium hydrogen carbonate was added dropwise to quench the reaction, stirred, allowed to stand, and separated into phases. The aqueous phase was extracted with 3×20 ml of dichloromethane, and the organic phases were combined, dried, and rotary evaporated to dryness to afford a crude product. The crude product was passed through a silica gel chromatographic column (eluent: methanol:dichloromethane=1:20) to afford a brown solid (0.129 g). Yield: 31.04%. LC-MS: 473,475 [M+1]$^+$, $t_R$=2.382 min.

INTERMEDIATE 494 tert-butyl 3-(8-bromo-2-carbonyl-3-methyl-2,3-dihydro-1H-imidazo[4,5-c]quinolin-1-yl)-8-azabicyclo[3.2.1]octane-8-carboxylate

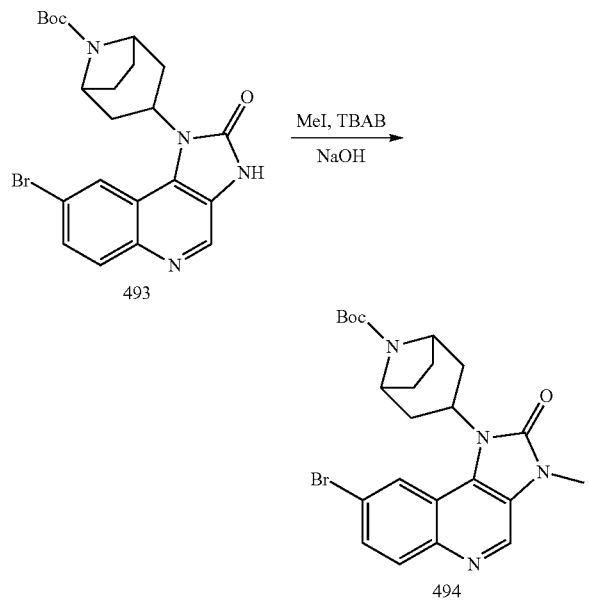

0.129 g (0.27 mmol) of Intermediate 493 was dissolved in 5 ml of dichloromethane, then added with 0.009 g (0.027 mmol) of TBAB and then with 5 ml of 10% NaOH, stirred for 10 min, then added with 0.051 ml (0.82 mmol) methyl iodide, and stirred and reacted at room temperature overnight (20 h). The reaction solution was allowed to stand, and separated into phases. The aqueous phase was extracted with 3×5 ml of dichloromethane, and the organic phases were combined, dried, concentrated by rotary evaporation, and pumped to dryness to afford a brownish red solid (0.131 g). Yield: 100%. LC-MS: 487,489 [M+1]$^+$, $t_R$=2.632 min.

INTERMEDIATE 495 tert-butyl 3-(8-(6-(1-methyl-1H-1,2,3-triazol-4-yl)pyridin-3-yl)-3-methyl-2-oxo-2,3-dihydro-1H-imidazo[4,5-c]quinolin-1-yl)-8-azabicyclo[3.2.1]octane-8-formate

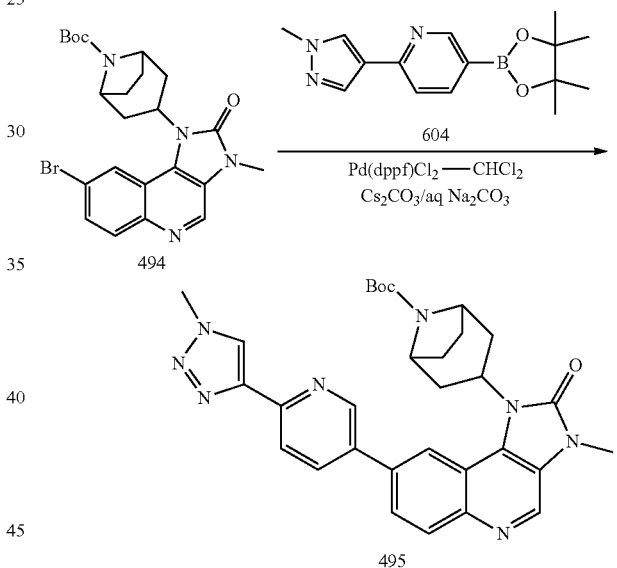

0.131 g (0.27 mmol) of Intermediate 494, 0.093 g (0.324 mmol) of Intermediate 604, and 0.352 g (1.08 mmol) of cesium carbonate were suspended in 8 ml of dioxane, then added with 2 ml of 2M sodium carbonate, added with 0.038 g (0.048 mmol) of [1,1'-bis(diphenylphosphino)ferrocene] palladium dichloride dichloromethane complex under the protection of nitrogen, and heated to T=110° C. and reacted for 5 h under the protection of nitrogen again. 20 mL of water was added and stirred, and then 20 ml of dichloromethane was added and stirred. The solution was allowed to stand and separated into layers. The aqueous phase was extracted with 20 ml×3 of dichloromethane, and the organic phases were combined, dried, and passed through a silica gel preparative plate (eluent:methanol:dichloromethane=1:10) to afford a brown solid (0.032 g). Yield: 22.88%. LC-MS: 256 [(M-56)/2+1]$^+$, $t_R$=2.048 min.

INTERMEDIATE 496

1-(8-azabicyclo[3.2.1]octan-3-yl)-3-methyl-8-(6-(1-methyl-1H-1,2,3-triazol-4-yl)pyridin-3-yl)-1H-imidazo[4,5-c]quinolin-2(3H)-one

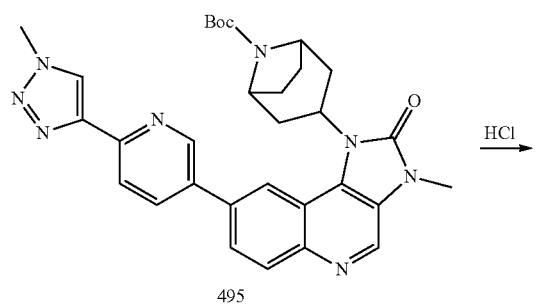

0.032 g (0.056 mmol) of Intermediate 495 was dissolved in 3 ml of dichloromethane, continually purged with HCl gas under an ice-water bath condition, and stirred and reacted for 1 h. The reaction solution was pumped to dryness to afford a solid (0.026 g). Yield: 100%.

EXAMPLE 61

3-methyl-8-(6-(1-methyl-1H-1,2,3-triazol-4-yl)pyridin-3-yl)-1-(8-(methanesulfonyl)-8-azabicyclo[3.2.1]octan-3-yl)-1H-imidazo[4,5-c]quinolin-2(3H)-one

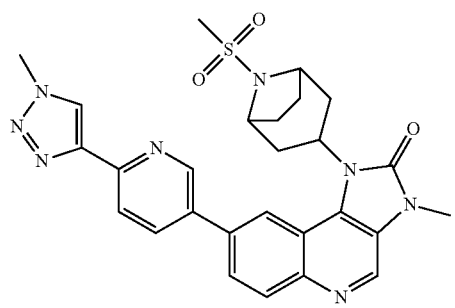 [SMILES: Cn1cc(-c2ccc(-c3ccc4ncc5c(c4c3)n(C3CC4CCC(C3)N4S(C)(=O)=O)c(=O)n5C)cn2)nn1]

26 mg (0.056 mmol) of Intermediate 496 was added with 5 ml of dichloromethane, and then with 78 μl of triethylamine, and stirred for 15 min. The solid was dissolved, and then 14 μl of methylsulfonyl chloride was added, and reacted overnight. 6 mL of saturated sodium bicarbonate solution was added to quench the reaction, and stirred. The reaction solution was allowed to stand and separated into layers. The aqueous phase was extracted with 3×6 ml of dichloromethane, and the organic phases were combined, dried, and purified with a silica gel preparative plate (methanol:dichloromethane=1:10) to afford an off-white solid (30 mg). Yield: 100%. LC-MS: 545 [M+1]$^+$, $t_R$=1.728 min.

(XXVIII) Scheme XXVIII

Scheme XXVIII

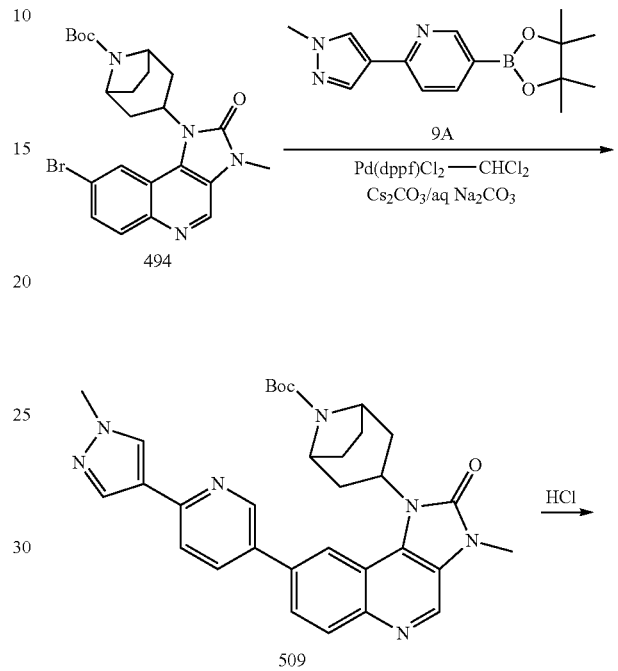

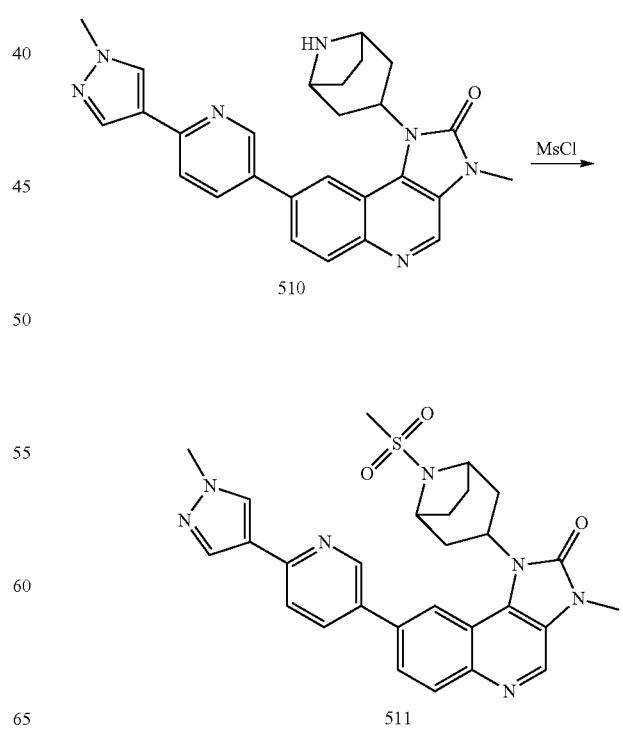

INTERMEDIATE 509 tert-butyl 3-(8-(6-(1-methyl-1H-pyrazol-4-yl)pyridin-3-yl)-3-methyl-2-carbonyl-2,3-dihydro-1H-imidazo[4,5-c]quinolin-1-yl)-8-azabicyclo[3.2.1]octane-8-carboxylate

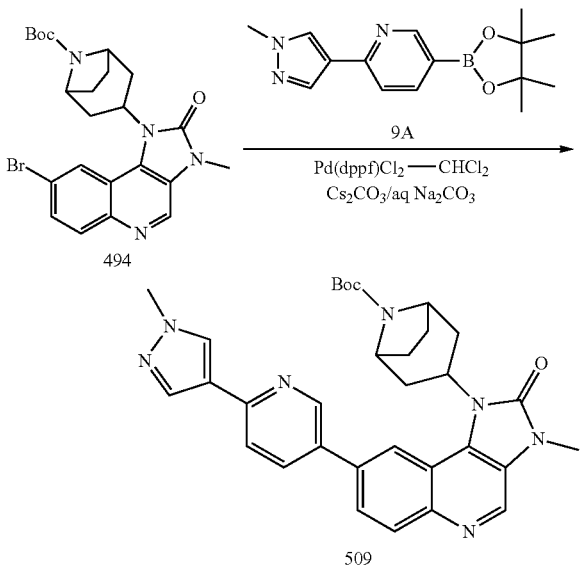

0.050 g (0.103 mmol) of Intermediate 494, 0.044 g (0.155 mmol) of 9A, and 0.168 g (0.515 mmol) of cesium carbonate were suspended in 6 ml of dioxane, added with 1 ml of 2M sodium carbonate, then added with 0.009 g (0.0103 mmol) of [1,1'-bis(diphenylphosphino)ferrocene]palladium dichloride dichloromethane complex under the protection of nitrogen, and heated to T=110° C. and reacted for 5 h under the protection of nitrogen again. The solvent was removed by rotary evaporation, and 10 ml of water and 10 ml of dichloromethane were added and stirred. The solution was allowed to stand and separated into two phases. The aqueous phase was extracted with 10 ml×3 of dichloromethane, and the organic phases were combined, dried, and purified with a silica gel preparative plate (eluent: methanol:dichloromethane=1:10) to afford a solid (0.019 g). Yield: 32.61%. LC-MS: 565.9 [M+1]$^+$, $t_R$=2.853 min.

INTERMEDIATE 510

1-(8-azabicyclo[3.2.1]octan-3-yl)-3-methyl-8-(6-(1-methyl-1H-pyrazol-4-yl)pyridin-3-yl)-1H-imidazo[4,5-c]quinolin-2(3H)-one

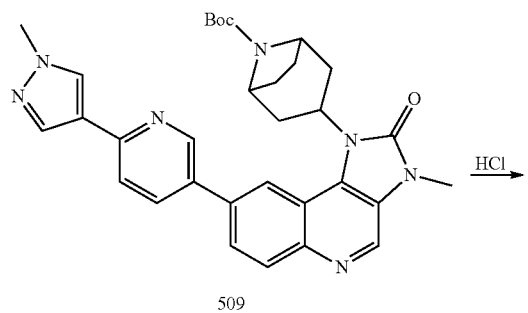

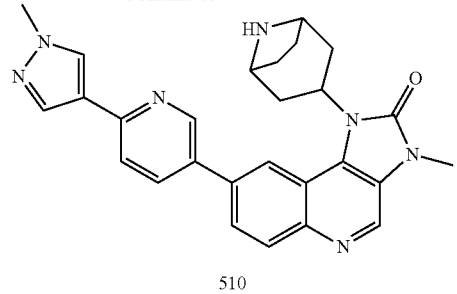

0.019 g (0.034 mmol) of Intermediate 509 was dissolved in 5 ml of dichloromethane, continually purged with HCl gas under a ice-water bath condition, and stirred and reacted for 2 h. The reaction solution was pumped to dryness to afford a solid (0.015 g). Yield: 100%.

EXAMPLE 62

3-methyl-8-(6-(1-methyl-1H-pyrazol-4-yl)pyridin-3-yl)-1-(8-(methanesulfonyl)-8-azabicyclo[3.2.1]octan-3-yl)-1H-imidazo[4,5-c]quinolin-2(3H)-one

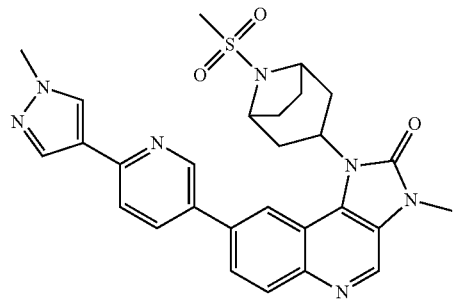 [SMILES: Cn1cc(-c2ccc(-c3ccc4ncc5c(c4c3)n(C3CC4CCC(C3)N4S(C)(=O)=O)c(=O)n5C)cn2)cn1]

16 mg (0.034 mmol) of Intermediate 510 was added with 5 ml of dichloromethane, then with 24 μl of triethylamine, and stirred for 10 min. The solid was dissolved, and 5 drops of methylsulfonyl chloride were added, and stirred and reacted at room temperature for 3 h. 5 mL of saturated sodium bicarbonate solution was added to quench the reaction, and stirred. The reaction solution was allowed to stand and separated into two phases. The aqueous phase was extracted with 3×5 ml of dichloromethane, and the organic phases were combined, dried, and purified with a silica gel preparative plate (methanol:dichloromethane=1:10) to afford an off-white solid (18 mg). Yield: 100%. LC-MS: 544 [M+1]$^+$, $t_R$=3.353 min.

(XXIX) Scheme XXIX

Scheme XXIX

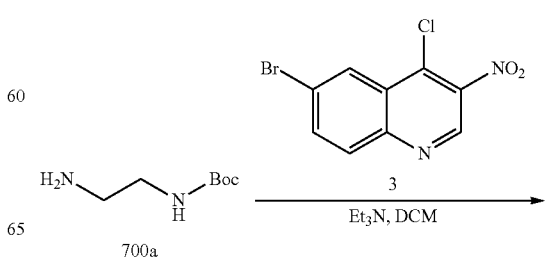

201
-continued
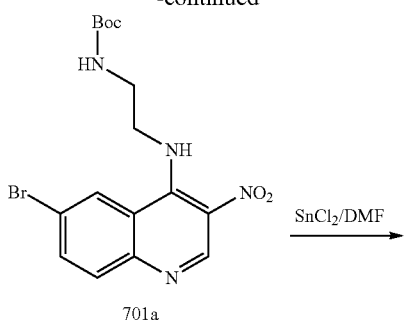
701a
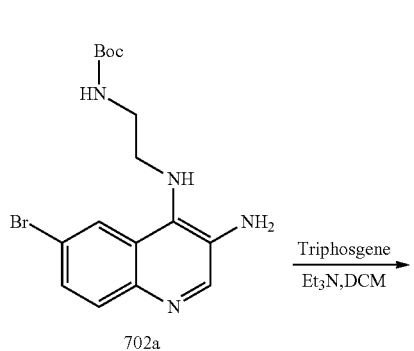
202
-continued
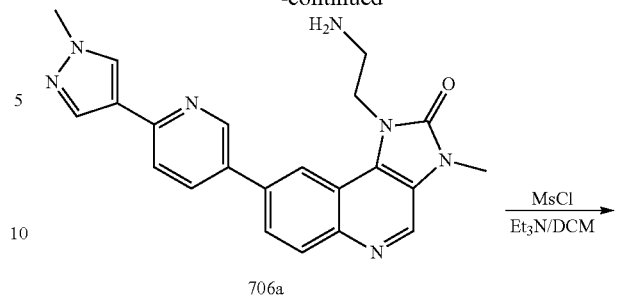
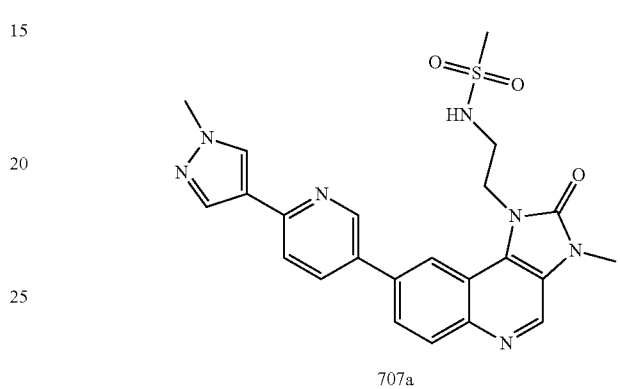
INTERMEDIATE 701a
tert-butyl 2-((6-bromo-3-nitroquinolin-4-yl)amino)ethylcarbamate
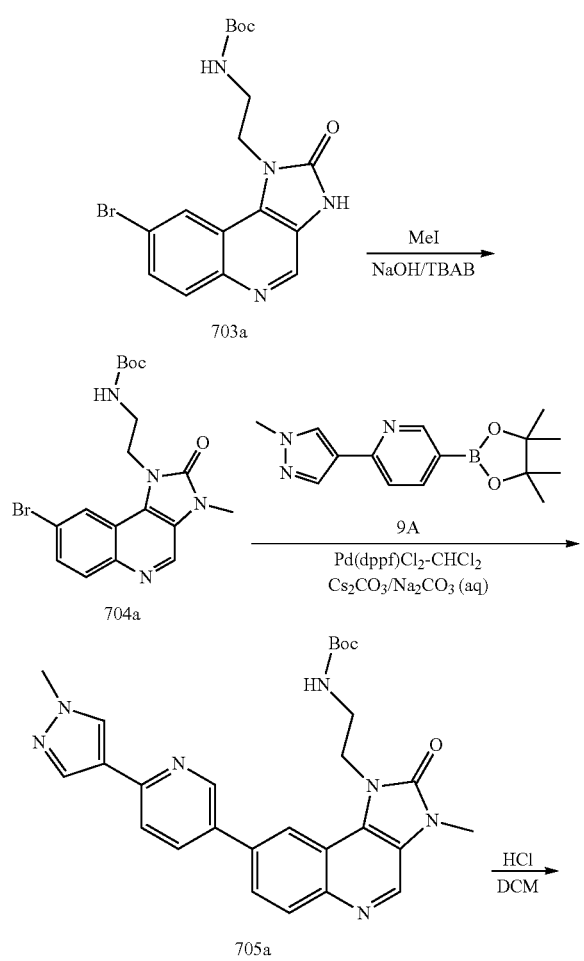
Intermediate 700a (0.836 g, 5.22 mmol) was dissolved in 10 ml of dichloromethane, added with 1.06 g (10.44 mmol) of triethylamine and 1 g (3.48 mmol) of Intermediate 3, stirred at room temperature for 3 h, filtered, and pumped to dryness to afford a yellow solid (1.007 g). Yield: 70.37%.

INTERMEDIATE 702a tert-butyl 2-((3-amino-6-bromoquinolin-4-yl)amino)ethylcarbamate

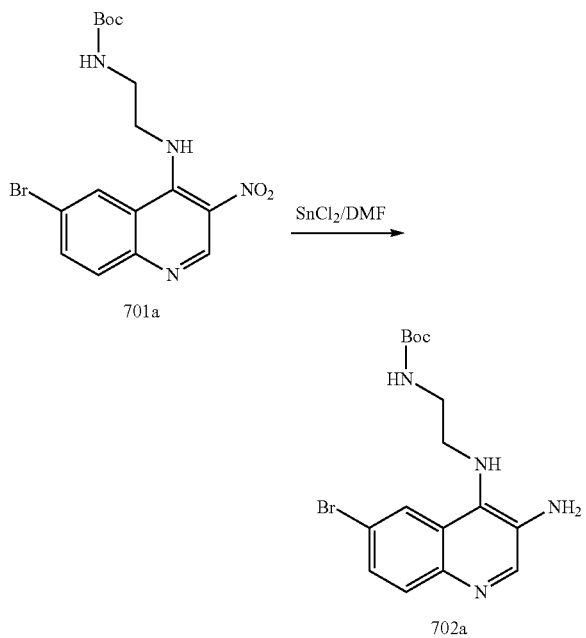

Intermediate 701a (580 mg, 1.41 mmol) was dissolved in 5 ml of N,N-dimethylformamide, added with 1.591 g (7.05 mmol) stannous chloride hydrate in batches, and stirred at room temperature for 3 h. The reaction solution was slowly poured into 50 ml of saturated sodium bicarbonate solution and 50 ml of dichloromethane, and separated into two phases. The aqueous phase was extracted with dichloromethane, and the organic phases were combined, washed with equal volumes of saturated saline solution, dried, and evaporated to dryness to afford 1.627 g of reddish brown liquid. LC-MS: 381,383 [M+1]$^+$, $t_R$=3.366 min.

INTERMEDIATE 703a tert-butyl 2-(8-bromo-2-oxo-2,3-dihydro-1H-imidazo[4,5-c]quinolin-1-yl)ethylcarbamate

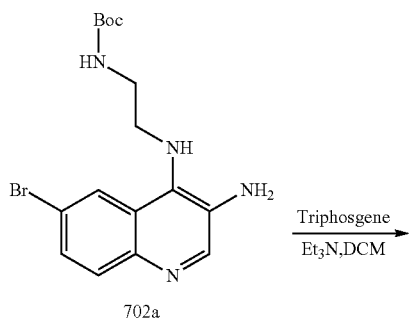

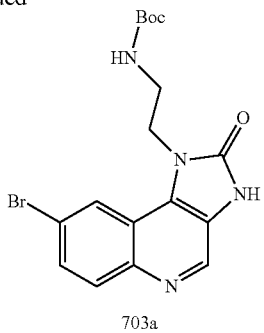

Intermediate 702a (1.627 g, crude) was dissolved in 5 ml of dichloromethane, added with 0.57 g (5.64 mmol) of triethylamine, and then added with a solution of 0.209 g (0.705 mmol) of triphosgene dissolved in 5 ml of dichloromethane dropwise under the cooling of an ice bath. After the dropwise addition was completed, the reaction solution was kept at 0° C. and reacted for 3 h. 20 mL of saturated sodium bicarbonate solution was added dropwise, and the reaction solution was separated into two phases. The aqueous phase was extracted with dichloromethane, and the organic phases were combined, dried, and evaporated to dryness to afford a crude product. The crude product was purified by silica gel column chromatography (eluent: methanol:dichloromethane=1:10) to afford a yellow solid (0.14 g). Yield: 24.39%. LC-MS: 407,409 [M+1]$^+$, $t_R$=4.163 min.

INTERMEDIATE 704a tert-butyl 2-(8-bromo-3-methyl-2-oxo-2,3-dihydro-1H-imidazo[4,5-c]quinolin-1-yl)ethylcarbamate

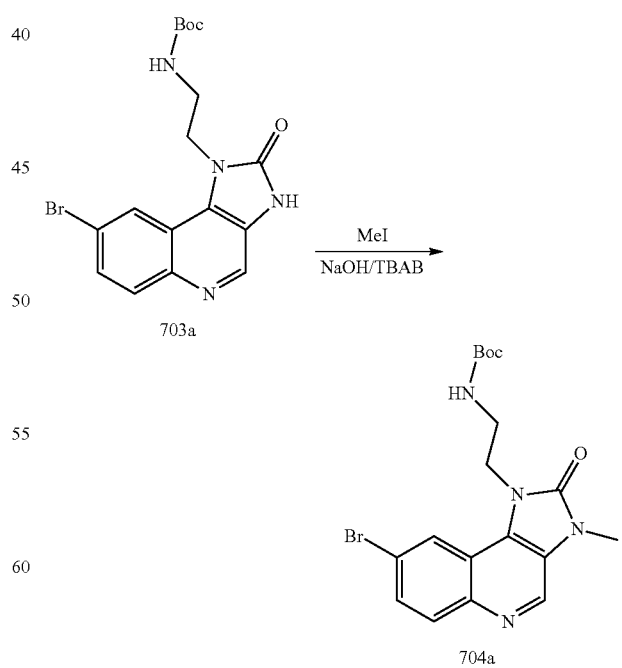

Intermediate 703a (0.14 g, 0.34 mmol) was dissolved in 5 ml of dichloromethane, added with 0.011 g (0.034 mmol)

of tetra-n-butyl ammonium bromide, 5 ml of 10% sodium hydroxide solution, and 0.145 g (1.02 mmol) of methyl iodide, stirred at room temperature overnight, and separated into two phases. The aqueous phase was extracted with dichloromethane, and the organic phases were combined, dried, and evaporated to dryness to afford a yellow solid (0.17 g).

INTERMEDIATE 705a tert-butyl 2-(3-methyl-8-(6-(1-methyl-1H-pyrazol-4-yl)pyridin-3-yl)-2-oxo-2,3-dihydro-1H-imidazo[4,5-c]quinolin-1-yl)ethylcarbamate

INTERMEDIATE 706a 1-(2-aminoethyl)-3-methyl-8-(6-(1-methyl-1H-pyrazol-4-yl)pyridin-3-yl)-1H-imidazo[4,5-c]quinolin-2(3H)-one

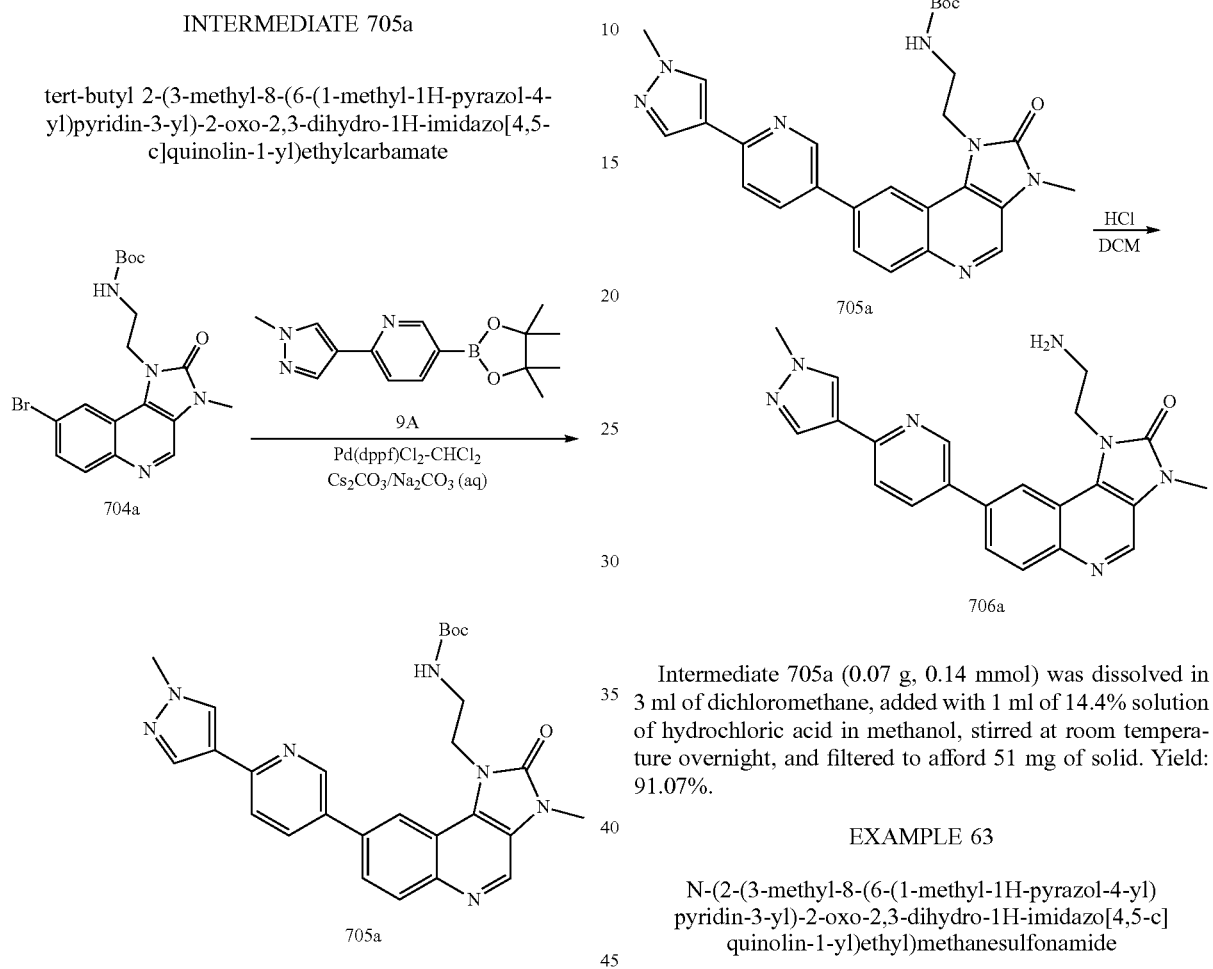

Intermediate 704a (0.17 g, crude) was dissolved in 5 ml of 1,4-dioxane, added with 0.145 g (0.51 mmol) of Intermediate 9A, 0.332 g (1.02 mmol) of cesium carbonate, 1 ml of 2 mol/L sodium carbonate solution and 0.028 g (0.034 mmol) of [1,1-bis(di-phenylphosphino)ferrocene]palladium chloride dichloromethane complex under the protection of nitrogen, heated to 110° C. and reacted for 5 h, and then cooled to room temperature. The dioxane was removed by evaporation, and the residue was dissolved in 10 ml of saturated sodium bicarbonate solution and 10 ml of dichloromethane, and separated into two phases. The aqueous phase was extracted with dichloromethane, and the organic phases were combined, dried, and evaporated to dryness to afford a crude product. The crude product was purified by silica gel column chromatography (eluent:methanol:dichloromethane=1:30) to afford 0.07 g of solid. Yield: 41.18%. LC-MS: 500.2 [M+1]$^+$, $t_R$=2.205 min.

Intermediate 705a (0.07 g, 0.14 mmol) was dissolved in 3 ml of dichloromethane, added with 1 ml of 14.4% solution of hydrochloric acid in methanol, stirred at room temperature overnight, and filtered to afford 51 mg of solid. Yield: 91.07%.

EXAMPLE 63

N-(2-(3-methyl-8-(6-(1-methyl-1H-pyrazol-4-yl)pyridin-3-yl)-2-oxo-2,3-dihydro-1H-imidazo[4,5-c]quinolin-1-yl)ethyl)methanesulfonamide Intermediate 706a (40 mg, 0.1 mmol) was dissolved in 3 ml of dichloromethane, added with 17 mg (0.15 mmol) of methylsulfonyl chloride and 40 mg (0.4 mmol) of triethylamine, and stirred at room temperature for 3 h. 10 mL of saturated sodium bicarbonate solution was added, and stirred for 30 min. The reaction solution was separated into two phases. The aqueous phase was extracted with dichloromethane, and the organic phases were combined, dried, evaporated to dryness to afford a crude product. The crude product was purified by silica gel chromatography (eluent: methanol:dichloromethane=1:10) to afford 20 mg of the target compound. Yield: 41.88%. LC-MS: 478.2 [M+1]$^+$, $t_R$=1.565 min $^1$H NMR (400 MHz, DMSO) δ 9.05 (d, J=1.9 Hz, 2H), 8.54 (s, 1H), 8.39 (s, 1H), 8.31 (dd, J=8.3, 2.3 Hz, 1H), 8.22 (d, J=9.1 Hz, 1H), 8.16-8.11 (m, 1H), 8.10 (s, 1H), 7.80 (d, J=8.2 Hz, 1H), 7.44 (t, J=6.3 Hz, 1H), 4.58 (t, J=6.6 Hz, 2H), 3.92 (s, 3H), 3.58 (s, 3H), 3.13-3.04 (m, 2H), 2.89 (s, 3H).

(XXX) Scheme XXX

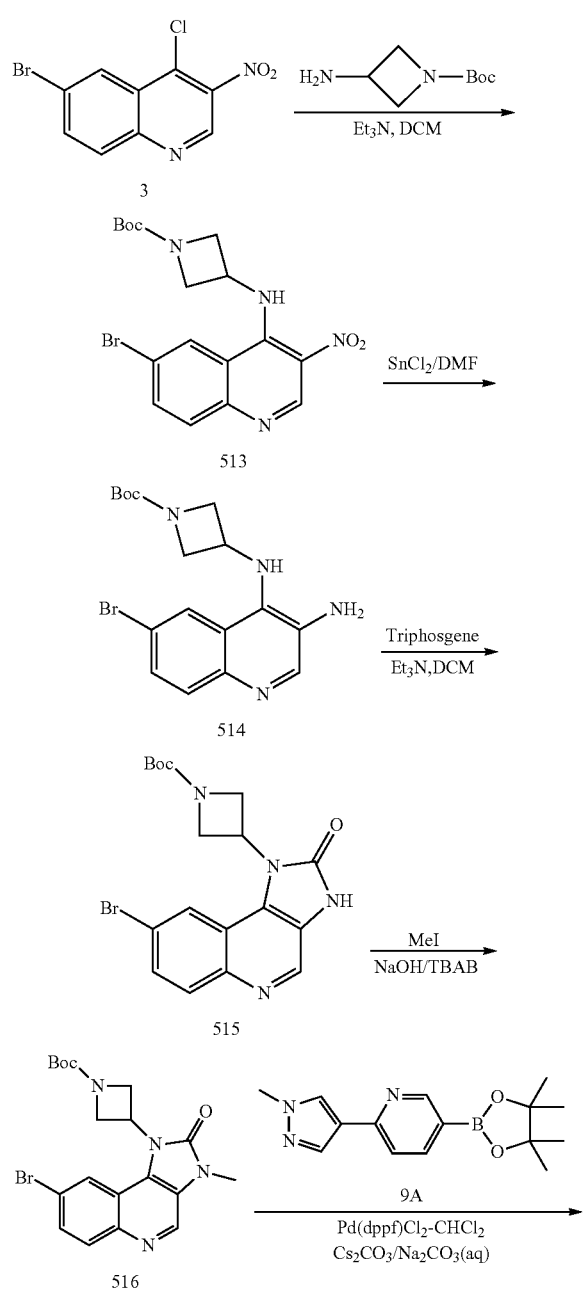

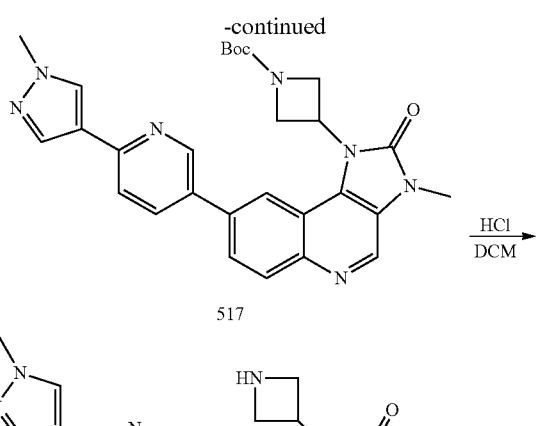

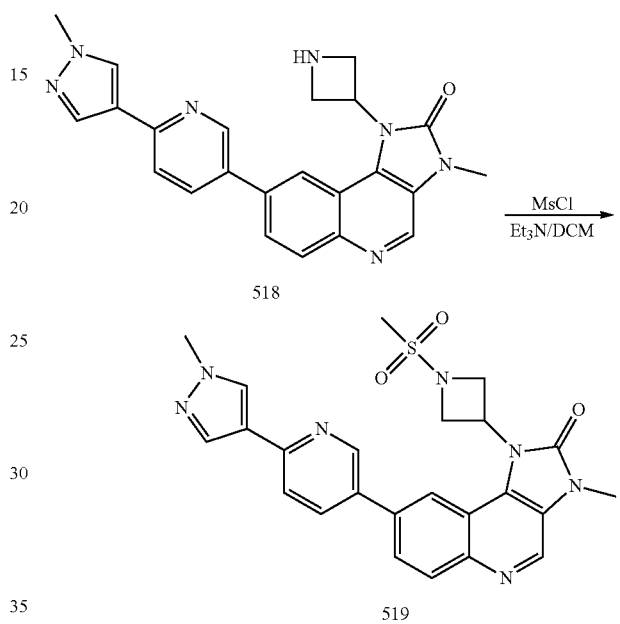

INTERMEDIATE 513 tert-butyl 3-((6-bromo-3-nitroquinolin-4-yl)amino)azetidine-1-formate

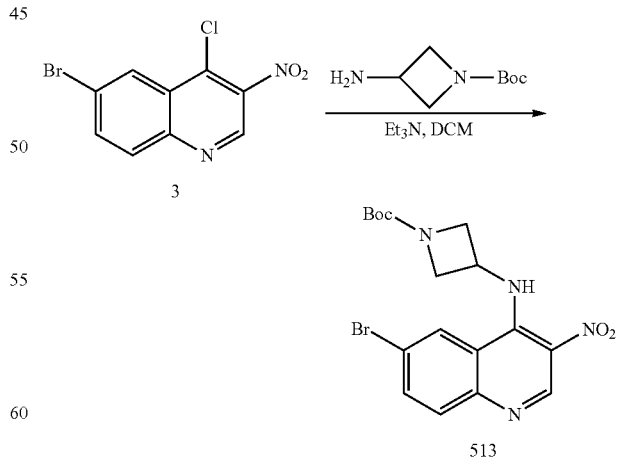

0.279 g (0.97 mmol) of Compound 3 and 0.217 g (1.26 mmol) of tert-butyl 3-aminoazetidine-1-formate were dissolved in 15 ml of dichloromethane, added with 0.27 ml (1.94 mmol) of triethylamine, and stirred at room temperature overnight. 30 mL of water was added and stirred, allowed to stand, and separated into phases. The aqueous phase was extracted with 3×20 ml of dichloromethane, and the organic phases were combined, dried over anhydrous sodium sulfate, filtered, rotary evaporated, and pumped to dryness to afford a brown solid (0.374 g). Yield: 91.09%. LC-MS: 423,425 [M+1]$^+$, $t_R$=7.008 min.

INTERMEDIATE 514 tert-butyl 3-((6-bromo-3-aminoquinolin-4-yl)amino)azetidine-1-formate

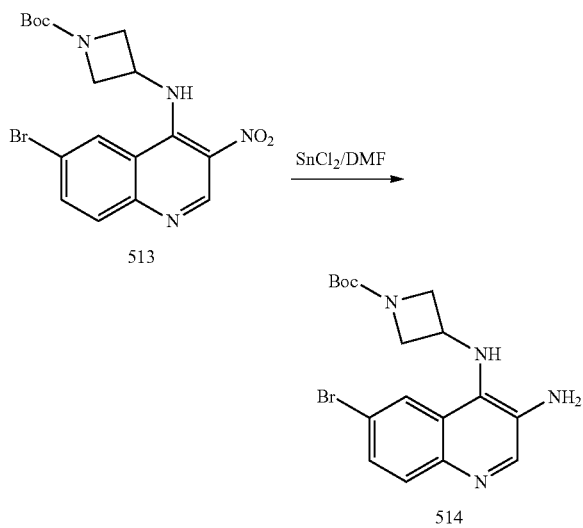

0.370 g (0.87 mmol) of Intermediate 513 was dissolved in 10 ml of DMF, added with 0.986 g (4.37 mmol) of stannous chloride in batches, and stirred at room temperature overnight. 10% Of sodium hydroxide solution was used to adjust pH to 8~9 to quench the reaction, added with 80 ml of water and 20 ml of dichloromethane, stirred, allowed to stand, and separated into phases. The aqueous phase was extracted with 3×20 ml of dichloromethane, and the organic phases were combined, backwashed with 80 ml of saturated saline solution, dried over anhydrous sodium sulfate, filtered, rotary evaporated, and pumped to dryness. The crude product was passed through a silica gel chromatographic column (eluent: ethyl acetate:petroleum ether=3:1) to afford an oil (0.106 g). Yield: 30.98%. LC-MS: 393,395 [M+1]$^+$, $t_R$=3.571 min.

INTERMEDIATE 515 tert-butyl 3-(8-bromo-2-carbonyl-2,3-dihydro-1H-imidazo[4,5-c]quinolin-1-yl)azetidine-1-formate

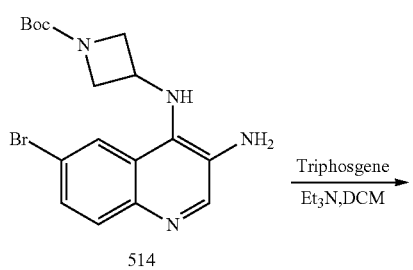

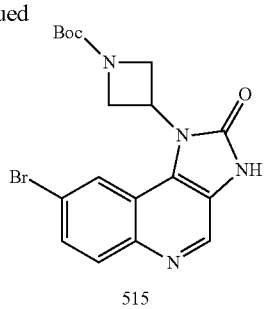

0.106 g (0.27 mmol) of Intermediate 514 was dissolved in 5 ml of dichloromethane, dropwise added with 0.113 ml (0.81 mmol) of triethylamine and added with 0.040 g (0.135 mmol) of triphosgene dissolved in 5 ml of dichloromethane under stirring and ice-water bath conditions, and stirred in the ice-water bath for 2.5 h. To the reaction solution, 10 ml of saturated sodium hydrogen carbonate was added dropwise to quench the reaction, and stirred. The reaction solution was allowed to stand and separated into phases. The aqueous phase was extracted with 3×10 ml of dichloromethane, and the organic phases were combined, dried, and rotary evaporated to dryness to afford a crude product. The crude product was passed through a silica gel chromatographic column (eluent:methanol:dichloromethane=1:20) to afford a brown solid (0.046 g). Yield: 40.64%. LC-MS: 419,421 [M+1]$^+$, $t_R$=4.477 min.

INTERMEDIATE 516 tert-butyl 3-(8-bromo-3-methyl-2-carbonyl-2,3-dihydro-1H-imidazo[4,5-c]quinolin-1-yl)azetidine-1-formate

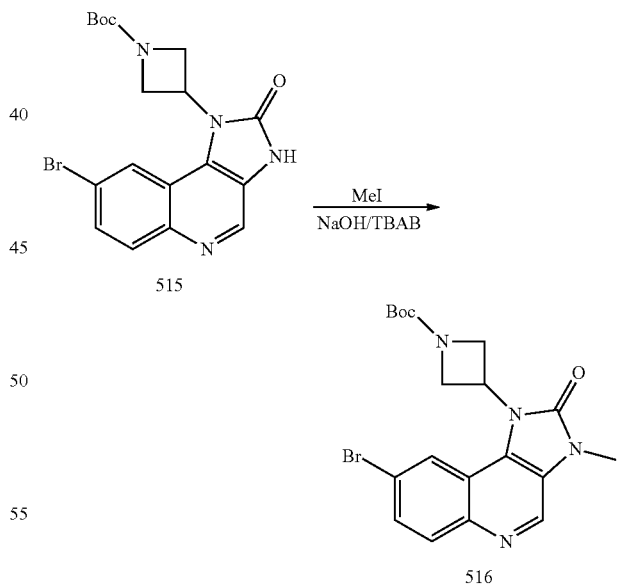

0.044 g (0.105 mmol) of Intermediate 515 was dissolved in 5 ml of dichloromethane, added with 0.004 g (0.0105 mmol) of TBAB, then with 5 ml of 10% NaOH, stirred for 10 min, and then with 0.020 ml (0.315 mmol) of methyl iodide, and stirred and reacted at room temperature for 3 h. The reaction solution was allowed to stand, and separated into phases. The aqueous phase was extracted with 3×5 ml of dichloromethane, and the organic phases were combined, dried, rotary evaporated, and pumped to dryness to afford a yellow solid (0.045 g). Yield: 100%. LC-MS: 433,435 [M+1]$^+$, $t_R$=3.353 min.

INTERMEDIATE 517 tert-butyl 3-(3-methyl-8-(6-(1-methyl-1H-pyrazol-4-yl)pyridin-3-yl)-2-carbonyl-2,3-dihydro-1H-imidazo[4,5-c]quinolin-1-yl)azetidine-1-formate

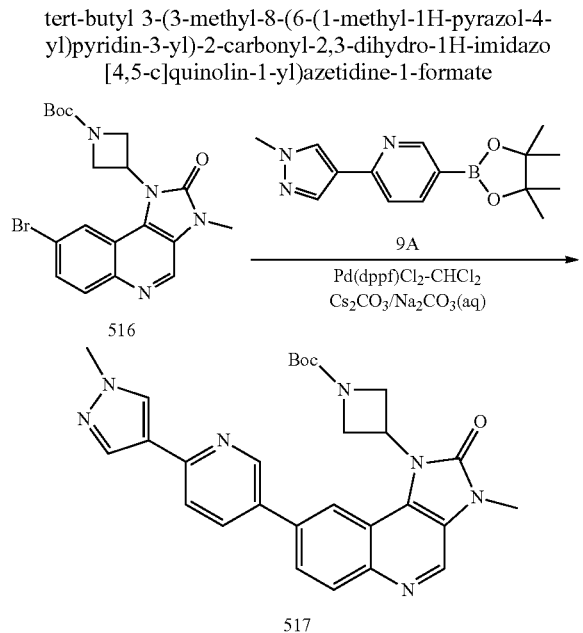

0.045 g (0.105 mmol) of Intermediate 516, 0.045 g (0.158 mmol) of 9A, and 0.171 g (0.525 mmol) of cesium carbonate were suspended in 6 ml of dioxane, then added with 12 ml of 2M sodium carbonate, added with 0.009 g (0.0105 mmol) of [1,1'-bis(diphenylphosphino)ferrocene]palladium dichloride dichloromethane complex under the protection of nitrogen, and heated to T=110° C. and reacted for 5 h under the protection of nitrogen again. The solvent was removed by rotary evaporation, and the residue was added with 10 ml of water and 10 ml of dichloromethane, and stirred. The resulting solution was allowed to stand, and separated into phases. The aqueous phase was extracted with 10 ml×2 of dichloromethane, and the organic phases were combined, dried, and passed through a silica gel preparative plate (eluent:methanol:dichloromethane=1:10) to afford a brown solid (0.043 g). Yield: 80.05%. LC-MS: 512 [M+1]$^+$, $t_R$=3.757 min.

INTERMEDIATE 518

1-(azetidin-3-yl)-3-methyl-8-(6-(1-methyl-1H-pyrazol-4-yl)pyridin-3-yl)-1H-imidazo[4,5-c]quinolin-2(3H)-one

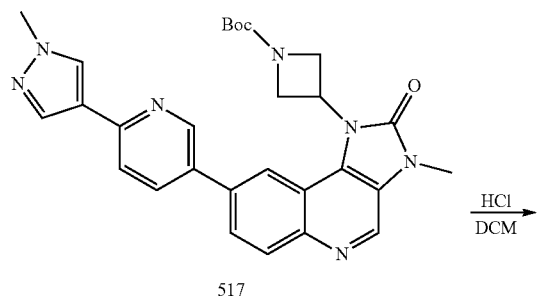

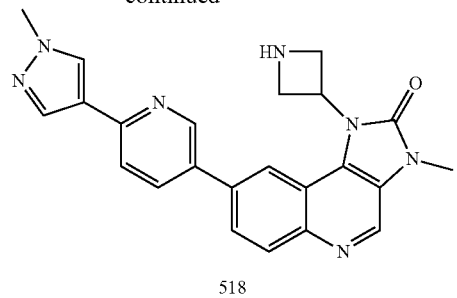

0.043 g (0.084 mmol) of Intermediate 517 was dissolved in 5 ml of dichloromethane, purged with HCl gas continually under a ice-water bath condition, and stirred and reacted for 2 h. The reaction solution was pumped to dryness to afford a solid (0.035 g). Yield: 100%.

EXAMPLE 64

3-methyl-8-(6-(1-methyl-1H-pyrazol-4-yl)pyridin-3-yl)-1-(1-(methanesulfonyl)azetidin-3-yl)-1H-imidazo[4,5-c]quinolin-2(3H)-one

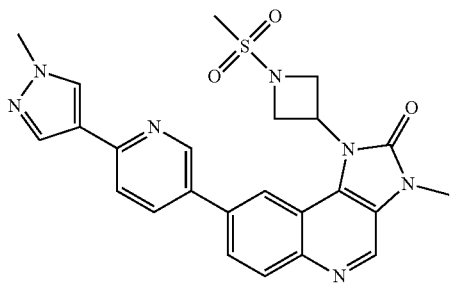 [SMILES: Cn1cc(-c2ccc(-c3ccc4ncc5c(c4c3)n(C3CN(S(C)(=O)=O)C3)c(=O)n5C)cn2)cn1]

35 mg (0.084 mmol) of Intermediate 518 was added with 5 ml of dichloromethane, then with 59 μl of triethylamine, and stirred for 15 min. The solid was dissolved, and 10 μl of methylsulfonyl chloride was added, and reacted overnight. 10 mL of saturated sodium bicarbonate solution was added to quench the reaction, and stirred. The resulting solution was allowed to stand and separated into phases. The aqueous phase was extracted with 3×10 ml of dichloromethane, and the organic phases were combined, dried, and passed through a silica gel preparative plate (methanol:dichloromethane=1:10) to afford a light yellow solid powder (16 mg). Yield: 38.91%. LC-MS: 490 [M+1]$^+$, $t_R$=1.925 min.

Biological Activity Assays

The compounds of the invention were detected for biological activity hereinafter:

1. mTOR Kinase Activity Assay: The inhibition of the mTOR protein kinase activity by the compounds was determined by the enzymatic activity assay in vitro. The detection kit supplied by Invitrogen was used to detect the inhibition of the activity of the mTOR protease. The principle of the assay was as follows: mTOR kinase, fluorescein-labeled substrate and ATP were mixed, and after the reaction, EDTA and terbium-labeled first antibody were added. During the chemical reaction process of the mTOR kinase, the antibody recognized the phosphorylated and fluorescein-labeled substrate, and then the "time-resolved fluorescence resonance energy transfer" (TR-FRET) effect was enhanced. TR-FRET effect was calculated as the ratio of signals from the acceptor fluorescein to signals from the donor terbium. The amount of the antibody bound to the tracer was directly proportional to the amount of the phosphorylated substrate after the reaction. In this way, the kinase activity can be detected. In this assay, the substrate of the mTOR kinase was green fluorescent protein-coupled 4E binding protein 1 (GFP-4EBP1).

1.1 Materials and Instruments:

4-Hydroxyethylpiperazine ethanesulfonic acid (HEPES, Sigma, Cat# SH3375), ethylene glycol-bis-(2-aminoethylether)-tetraacetic acid (EGTA, Sigma, Cat# E3889), manganese chloride (MnCl2, Sigma, Cat# M1787), Tween-20 (Tween-20, Amresco), 1,4-dithiothreitol (DTT, Merck, CB233155), Adenosine triphosphate (ATP, sigma, A7699), Mammalian Target Of Rapamycin (mTOR, Invitrogen, Cat# PV4753), Anti-4E binding protein 1 phosphorylated at Thr46-antibody (LanthaScreen™ Tb-anti-p4E-BP1 (pThr46) Antibody, Invitrogen, Cat# PV4757), Green fluorescent protein-coupled 4E binding protein 1 (GFP-4E-BP1, Invitrogen, Cat# PV4759), TR-FRET Dilution Buffer (Invitrogen, Cat# PV3574), ProxiPlate, Black (PerkinElmer, Detection Plate), 384-well plates (Corning, Dilution Plate), Nunc PP plate (Corning, Dilution Plate), Envision-2104 Reader (Perkin Elmer).

1.2 Preparation of Solutions and Reagents:

1.2.1 1×Detection Buffer Stock Solution: 50 mM HEPES pH 7.5, 1 mM EGTA, 0.01% Tween-20, 10 mM MnCl$_2$, mM DTT.

1.2.2 Substrate Working Solution: 4 mL 2.5×Substrate (1000 reactions): 3.8 mL 1×Detection Solution, 191 μL GFP-4E-BP1 (20.96 μM, Stock Solution), 10 μL ATP (10 mM). Final Concentration: 0.4 μM GFP-4E-BP1; 10 M ATP.

1.2.3 mTOR Working Solution: 4 mL 2.5×mTOR (1000 reactions): 4 mL.

1.2.4 1×Detection Solution; 7.5 μL mTOR (0.4 mg/mL, Stock Solution), Final Concentration: 0.3 μg/mL.

1.2.5 Detection Working Solution: 10 mL 2×Detection Buffer (1000 reactions): 9.6 mL TR-FRET Dilution Solution, 11.5 μL Tb-anti-p4E-BP1 Antibody (stock 3.49 μM), 400 μL EDTA (stock 500 mM), Final Concentration: 2 nM Tb-anti-p4E-BP1 antibody, 10 mM EDTA.

1.3 Test Procedures:

1.3.1 50 μL of each compound of the invention diluted with dimethyl sulfoxide (DMSO) at a concentration of 100 μM were added to the 38-well dilution plate.

1.3.2 The compounds were diluted with dimethyl sulfoxide (DMSO) in a ratio of 1:3 (10 diluted concentrations plus 1 zero-concentration).

1.3.3 2.5 μL of the diluted compounds (the compounds in Table 1) were transferred to their respective wells (containing 47.5 μL of detection solution/well), and shaked for several seconds.

1.3.4 4 μL of the mTOR working solution was added to the 384-well, black Proxiplate.

1.3.5 2 μL of the diluted compounds were added to the detection plate (3 wells for each concentration).

1.3.6 The plate was incubated at room temperature for 15 minutes.

1.3.7 4 μL of the substrate working solution was added.

1.3.8 The final mTOR reaction concentrations were: 0.3 μg/mL mTOR, 0.4 μM GFP-4E-BP1, 10 μM adenosine triphosphate (ATP). The compounds were diluted with 1% dimethyl sulfoxide (DMSO) to the following concentrations of: 1 μM, 0.33 μM, 0.11 μM, 0.037 μM, 0.0123 μM, 0.00411 μM, 0.00137 μM, 0.000457 μM, 0.000152 μM, 0.000051 μM, and 0 μM.

1.3.9 The plate was incubated at room temperature for 30 minutes.

1.3.10 10 μL of the detection solution was added, and the final working concentrations were: Tb-anti-p4E-BP1 Antibody 2 nM, EDTA 10 mM.

1.3.11 The plate was incubated at room temperature for 30 minutes.

1.3.12 The reading values of TR-FRET were detected by using Envision Reader. The excitation light was at 340 nm, the emitting light 1 was at 495 nm, and the emitting light 2 was at 520 nm Ratio=520 nm/495 nm was as the TR-FRET value.

1.3.13 The data was analyzed and the 50% Inhibition rate (IC50) was calculated:

50% Inhibition rate was calculated using a nonlinear regression equation:

Y=Bottom+(Top−Bottom)/(1+10^((Log IC50−X)*HillSlope)), X: Concentrations of the compounds (denary logarithm), Y: TR-FRET value (ratio of 520 nm to 495 nm), Top and Bottom: Plateaus in same units as Y, 50% Inhibition (log IC50): same log units as X. The inhibitory activity for the mTOR enzyme is shown in Table 1.

2. CTG Cell Survival Assay:

ATP is necessarily produced during the metabolic activities of viable cells, and there is a linear relationship between the content of ATP and the number of viable cells. Cell viability assay by CTG chemiluminescence is a general method for detecting the number of viable cells in the culture cells based on this principle. The addition of the CellTiter-Glo (CTG) reagent may induce cell lysis and produce chemiluminescent signals directly proportional to the amount of ATP in the well-plate, and thereby the cell proliferation activity in the well-plate can be measured by the reading values from the chemiluminescence.

2.1 Experimental Materials and Instruments:

2.1.1 Experimental Materials: compounds to be tested, cell basal culture medium, RPMI Medium 1640 (Invitrogen, Cat#11875-093), fetal calf serum (FBS): Hyclone FETAL BOVINE SERUM DEFINED (Invitrogen, Cat#SH30070.03), antibiotics: Penicilin Streptomycin (Invitrogen, Cat#15140-122), phosphate buffer (Corning Cellgro, Cat#R21-040-CV), cell digestive solution: 0.25% Trypsin-EDTA (Invitrogen, Cat#25200-056), CTG detection kit: Promega, Cat#G7571, flat-bottom 96-well black bottom plate: NUNC, Cat#165305, T25 culture flask: NUNC, Cat#156367, T75 culture flask: NUNC, Cat#156439

2.2 Experimental Instruments: Carbon Dioxide Incubator, SANYO-MCO-20AIC, Biosafe Cabinet: BSC-1360-LIIA2, Table-Top High-Speed Refrigerated Centrifuge: SorvallST 16R, Microplate Rapid Oscillator: QB-9001, M3 Reader: SpectraMax M3, Microscope: OLYMPUS-CKX41/CKX31.

2.3 Preparation of Solutions and Reagents: Formulation of cell growth medium: RPMI Medium 1640+10% FBS+ antibiotics, others: trypsin digestive solution, phosphate buffer (PBS), DMSO, CTG detection kit.

2.4 Experimental Procedure:

1.4.1 Cell Thawing: Cryogenic vials were removed from the liquid nitrogen container, directly immersed in a water bath at 37° C., and shaked from time to time to thaw. The cryogenic vials were removed from the water bath at 37° C., and transferred to the biosafe cabinet. Their lids were opened, and the cell suspensions were aspirated with pipettes, added to centrifuge tubes, and then added with more than 10 volumes of culture solution, mixed well; centrifuged for 5 min at 1000 rpm; the supernatant was discarded, and medium containing cell growth was added to resuspend cells. All cell suspensions were seeded to the T25 culture flasks and static cultured in an incubator at 37° C.; the culture solution were changed once on the next day, and continued to be cultured.

2.4.2 Cell Passaging: After cells were grown to logarithmic phase and were 80%-90% confluent, cells were removed and placed in the biosafe cabinet, the old culture solution was discarded, and the cells were wetted and washed with PBS once or twice. An appropriate amount of 0.25% Trypsin-EDTA solution was added to the culture flasks. The flasks were placed in the carbon dioxide incubator at 37° C. for 2-5 min. An appropriate amount of cell growth medium containing 10% PBS was added to terminate the digestion, lightly swished, and transferred to the centrifuge tubes and centrifuged for 5 min at 1000 rpm. The cells were prepare (into cell suspensions for passaging and experimental use.

2.4.3 Cell Plating
- 2.4.3.1 A cell suspension was prepared: After cells were grown to logarithmic phase and were 80%-90% confluent, the cells were removed to the biosafe cabinet, and the old culture solution was discarded, then the cells were wetted and washed with PBS once or twice. An appropriate amount of 0.25% Trypsin-EDTA solution was added to the culture flask. The flask was placed in a carbon dioxide incubator at 37° C. for 2-5 min. An appropriate amount of the cell growth medium containing 10% PBS was added to terminate digestion, and was lightly swished. The solution was transferred to a centrifuge tube, centrifuged for 5 min at 1000 rpm, and counted. The final concentration of the cell suspension was adjusted to the proper concentration (Cell viability should be greater than 90%).
- 2.4.3.2 The cell suspension with the adjusted final concentration was added at 100 ul/well to the 96-well plate.
- 2.4.3.3 The plate was cultured in the incubator at 37° C., 5% CO2 for 24 h.

2.4.4 Drug Treatment
- 2.4.4.1 Preparation of stock solutions of the compounds to be tested: powders of compounds to be tested were dissolved in DMSO at a concentration of 10 mM.
- 2.4.4.2 Preparation of gradient dilution solutions of the compounds to be tested: Firstly, 1 ul of stock solution of compound to be tested was taken and added to 499 ul of cell growth medium containing 10% FBS; at this point, the maximum concentration of compounds to be tested was 20 uM, and the concentration of DMSO was 0.2%. Secondly, 20 uM of the compound to be tested was diluted with the cell growth medium containing 0.2% DMSO in 3-fold dilution to obtain 9 concentrations, and there were 10 concentration gradients in total.
- 2.4.4.3 Addition of the compounds to be tested: the prepared gradient dilution solutions of compounds to be tested were taken and added to the cell culture plate at 100 ul/well; at this point, the maximum concentration of compounds to be tested was 10 uM, and the concentration of DMSO was 0.1%. Two wells were set for each of the concentration gradienta and blank control wells (with addition of only 0.1% DMSO in cell growth medium without cells) and negative control wells (with addition of cells and 0.1% DMSO-containing cell growth medium) were set.
- 2.4.4.4 After the addition of the compounds to be tested, the plate was incubated in the incubator at 37° C., 5% CO2 for one doubling time.

2.4.5 Detection and Data Analysis
- 2.4.5.1 Dection: the cell culture plate was taken out, and 100 ul of the culture solution was removed from each well to be discarded, then the prepared CTG substrate solution was added to the culture plate at 50 ul/well. After addition, the plate was oscillated in the Microplate Rapid Oscillator for 2 min, and then was allowed to stand under light-tight condition for 10 min. The luminescent signals were equilibrated, and read by using the M3 Reader.
- 2.4.5.2 Data Analysis: GraphPad software was used for statistical analysis of the data.

3. PI3K-alpha Enzyme Activity Assay: PI3K alpha-ADP Glo Assay was employed. In the determination of PI3K enzyme activity, the detection kit supplied by Promega (Promega, Cat #: V9101) was used to detect the inhibition effect of the compounds on the activity of PI3K enzyme. The adenosine diphosphate produced during the whole enzymic reactions was quantified. The resulting values were used to calculate the activity of PI3K (Table 1).

3.1 Detection reagents: PIK3CA/PIK3R1 purchased from Invitrogen (Cat #: PV4788): The active kinase was diluted with kinase diluent III; and mixed with bovine serum albumin (BSA) in a ratio of 1:4 (5×dilution). The final BSA concentration was 50 ng/ml; and the compositions of Kinase Detection Solution I were: 25 mM MOPS, pH7.2, 12.5 mM β-glycerophosphate, 25 mM magnesium chloride, 5 mM EGTA, and 2 mM EDTA. Before use, 0.25 mM DTT was added to Kinase Detection Solution I; 250 μM adenosine triphosphate (ATP) Detection solution: 0.55 mg of ATP was dissolved in 4 ml of Kinase Detection Solution I, subdivided in 200 μl/vial and stored at −20° C. Substrate: Phosphatidylinositol (4,5) bis-phosphate; this substrate was diluted with Kinase Detection Solution I to a concentration of 125 μM. Final concentrations were: 10 μM PIP2, 10 μM ATP, 1% DMSO, and 0.0005-10 μM compounds.

a) Experimental Procedure:
- 3.2.1 50 μL of the compounds diluted with dimethyl sulfoxide (DMSO) at a concentration of 100 μM were added to the 384-well dilution plate. The compounds were diluted with dimethyl sulfo de (DMSO) in a ratio of 1:3 (10 dilution concentrations plus 1 zero concentration).
- 3.2.2 5 μL of the diluted compounds were transferred to the corresponding 384-well black Proxi plate (containing 47.5 μL of detection solution/well), and shaked for several seconds.
- 3.2.3 2 μL of 2.5×PI3K working solution was added to 384-well black Proxi plate.
- 3.2.4 2 μL of the diluted compounds were added to the detection plate (3 wells for each concentration).
- 3.2.5 The plate was incubated at room temperature for 2 h.
- 3.2.6 5 μL of ADP Glo Reagent was added.
- 3.2.7 The plate was incubated at room temperature for 40 minutes.
- 3.2.8 10 μL of the kinase detection reagent was added.
- 3.2.9 The plate was incubated at room temperature for 40 minutes.
- 3.2.10 The activity was detected by using Envision Reader.

3.3 Data Analysis and Calculation of 50% Inhibition (IC50): $IC_{50}$ was calculated by using Prism5 Software. The result shows that the compounds of the invention had an inhibiting effect on the activity of the mTOR protease. The inhibition of the mTOR protease activity by the compounds ranges in 0.5 to several hundreds nanomoles, see Table 1. The determined activity of inhibiting PI3K enzyme is shown in Table 2. The determined data of inhibiting tumor cell lines is shown in Table 1. These data show that the compounds of the invention have an activity of inhibiting mTOR and PI3K proteases, and also have anti-tumor activity.

TABLE 1

Cellular activity and mTOR protease activity of the compounds of the invention

| Example | Enzyme (mTOR) $IC_{50}$ nM | PC-3 ($EC_{50}$ nM) | MV-4-11 ($EC_{50}$ nM) | SK-BR3/BT474 ($EC_{50}$ nM) |
|---|---|---|---|---|
| 1 | 10-100 | <200 | <1000 | <500 |
| 2 | 100-1000 | ND | ND | ND |
| 3 | <10 | <50 | <200 | <100 |
| 4 | 10-100 | <200 | <500 | <500 |
| 5 | <10 | <500 | <500 | <200 |
| 6 | <10 | <50 | <200 | <50 |
| 7 | 100-1000 | <1000 | ND | <1000 |
| 9 | 100-1000 | <100 | ND | <1000 |
| 10 | 100-1000 | <200 | <1000 | <1000 |
| 11 | 100-1000 | <1000 | ND | <1000 |
| 12 | 100-1000 | <500 | ND | <1000 |
| 13 | 100-1000 | <1000 | ND | <500 |
| 14 | 100-1000 | <1000 | ND | <200 |
| 15 | 100-1000 | <500 | ND | <1000 |
| 16 | 100-1000 | <1000 | ND | ND |
| 17 | <10 | <100 | <500 | <200 |
| 18 | <10 | <50 | <100 | <50 |
| 19 | <10 | <50 | <200 | <100 |
| 20 | 10-100 | <200 | <200 | <500 |
| 21 | 10-100 | <500 | <200 | <500 |
| 22 | 10-100 | <200 | <200 | <200 |
| 23 | 10-100 | <200 | <500 | <500 |
| 24 | 10-100 | <200 | <500 | <500 |
| 25 | 25 | <100 | <500 | <500 |
| 26 | <10 | ND | <50 | <200 |
| 27 | 100-1000 | ND | ND | <1000 |
| 28 | <10 | <50 | <100 | <50 |
| 29 | <10 | ND | <100 | <100 |
| 30 | <10 | ND | <100 | <100 |
| 31 | <10 | 19 | <100 | <100 |
| 32 | <10 | <50 | <200 | <100 |
| 33 | <10 | <200 | <500 | <100 |
| 34 | <10 | <100 | <200 | <50 |
| 35 | <10 | ND | <500 | <200 |
| 36 | <10 | ND | <200 | <500 |
| 37 | <10 | ND | <50 | <50 |
| 38 | <10 | 21 | ND | ND |
| 39 | <10 | 37 | ND | ND |
| 40 | ND | 10 | 30 | 25 |
| 41 | ND | ND | 100 | ND |
| 44 | ND | <50 | 40 | 90 |
| 45 | ND | <10 | <20 | <20 |
| 46 | ND | ND | ND | 400 |
| 47 | ND | 30 | <100 | 40 |
| 48 | ND | ND | ND | <100 |
| 49 | ND | 10 | <20 | 20 |
| 50 | ND | 20 | <30 | 30 |
| 51 | ND | <10 | <20 | 10 |
| 52 | ND | <30 | <30 | 50 |
| 53 | ND | <20 | ND | 100 |
| 54 | ND | ND | ND | 70 |
| 55 | ND | 300 | 800 | 300 |
| 56 | ND | <30 | 60 | 70 |
| 58 | ND | ND | 60 | ND |
| 59 | ND | 30 | 100 | <100 |
| 60 | ND | <30 | <100 | 40 |
| 61 | ND | <10 | <20 | <10 |
| 62 | ND | <10 | <20 | <20 |
| 63 | ND | ND | ND | 300 |
| 64 | ND | ND | ND | 200 |

TABLE 2

Activity of inhibiting PI3K enzyme of the compounds

| Example | IC50 (nM) |
|---|---|
| 3 | <10 |
| 27 | <10 |
| 28 | <10 |
| 31 | <10 |
| 18 | <10 |

4. Pharmacokinetic Characteristics:

4.1 Animal Test

The compounds to be tested were administrated orally to the murine to determine the bioavailability and pharmacokinetic profiles of the compounds in plasma of the murine.

4.2 Test Method:

Routes of administration: intragastric administration (PO), administration dosage: 10 mg/kg, final concentration of administration: 1 mg/mL, volume of administration: 10 mL/kg.

4.3 Collection of whole blood sample: Blood was sampled from the animals at 300 μL each time. Blood was sampled before the administration and at 0.25 h, 0.5 h, 1 h, 2 h, 4 h, 6 h, 8 h, and 24 h after the administration. The collected blood samples were centrifuged at 4° C., 2000 rpm for 5 min, and the resulting plasma were transferred to polyethylene microcentrifuge tubes, and kept in a refrigerator at −80° C. for storage.

4.4 Biological Sample Analysis Method

LC/MS/MS biological sample analysis method was used.

4.5 Test Results

The maximum concentrations and half-lifes of the compounds in the animal body and the concentrations in blood and AUC of the compounds over six hours were tested (Table 3).

TABLE 3

Pharmacokinetic data in murine (10 mg/kg, oral administration)

| Example | Animal | Cmax (ng/mL) | $T_{1/2}$ (h) | AUC (h * ng/mL) | 6 h concentration (μM) |
|---|---|---|---|---|---|
| 18 | Balb/c mice | 5000-10000 | 1-4 | 10000-100000 | 1-10 |
| 28 | SD rat | 800-4000 | 4-10 | 10000-100000 | 1-10 |
| 31 | SD rat | 800-4000 | 4-10 | 10000-100000 | 1-10 |

5. Solubility Test:

TABLE 4

Examples of the solubility of the compounds of the invention in the common aqueous vehicles (25° C., pH = 3):

| Example | Vehicles | Solubility |
|---|---|---|
| 1 | water | >1 mg/ml |
| 18 | water | >5 mg/ml |
| 19 | 30% hydroxypropyl-β-cyclodextrin | >1 mg/ml |
| 28 | 30% sulfobutyl-β-cyclodextrin | >3 mg/ml |
| 31 | water | >5 mg/ml |
| 52 | water | >1 mg/ml |

What is claimed is:
1. A compound represented by formula I:

$$\text{Formula I}$$

wherein,
Ring A is selected from pyrazolyl, triazolyl, and phenyl;
Ring B is pyridyl;
Ring C is a saturated monocyclic carbocycle containing 5 or 6 ring atoms, or Ring C is a saturated heterocycle containing 4 to 8 ring atoms;
when Ring C is a saturated monocyclic carbocycle, $R_1$ is hydroxy;
when Ring C is a saturated heterocycle, one of the ring atoms in the saturated heteocycle is an N atom, and $R_1$ is $R_6SO_2$— attached to the N atom, wherein $R_6$ is selected from the group consisting of $C_{1-6}$ alkyl, monocyclic cycloalkyl, —$NH_2$, and trifluoromethyl;
$R_2$ is $C_{1-6}$ alkyl;
$R_3$ is H;
$R_4$ is at least one group attached to Ring A, which is independently selected from H and $C_{1-6}$ alkyl;
X is CH; and
pharmaceutically acceptable salts, stereoisomers, isotopical labels, solvates, polymorphs and prodrugs thereof.
2. The compound according to claim 1, wherein:
Ring A is pyrazolyl;
Ring C is a saturated monocyclic carbocycle containing 5 or 6 ring atoms, or Ring C is a saturated monocyclic heterocycle containing 5 or 6 ring atoms;
when Ring C is a saturated monocyclic carbocycle, $R_1$ is hydroxy;
when Ring C is a saturated heterocycle, one of the ring atoms in the saturated heteocycle is an N atom, and $R_1$ is $R_6SO_2$— attached to the N atom, wherein $R_6$ is of $C_{1-6}$ alkyl;
or pharmaceutically acceptable salts, stereoisomers, isotopical labels, solvates, polymorphs or prodrugs thereof.
3. The compound according to claim 1, wherein Ring C is selected from the group consisting of pyrrolidinyl, cyclohexyl, 3-piperidinyl, 4-piperidinyl, and 2-piperidinyl; or pharmaceutically acceptable salts, stereoisomers, isotopical labels, solvates, polymorphs or prodrugs thereof.
4. The compound according to claim 1, wherein the compound is selected from the group consisting of:
3-methyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one;
3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one;
3-(3-methyl-8-(6-(1-methyl-1H-pyrazol-4-yl)pyridin-3-yl)-2-oxo-2,3-dihydro-1H-imidazo[4,5-c]quinolin-1-yl)pyrrolidine-1-sulfamide;
1-((1r,4r)-4-hydroxycyclohexyl)-3-methyl-8-(6-(1-methyl-1H-pyrazol-4-yl)pyridin-3-yl)-1H-imidazo[4,5-c]quinolin-2(3H)-one;
1-((1s,4s)-4-hydroxycyclohexyl)-3-methyl-8-(6-(1-methyl-1H-pyrazol-4-yl)pyridin-3-yl)-1H-imidazo[4,5-c]quinolin-2(3H)-one;
1-((1s,4s)-4-hydroxycyclohexyl)-3-methyl-8-(6-phenylpyridin-3-yl)-1H-imidazo[4,5-c]quinolin-2(3H)-one;
1-((1r,4-hydroxycyclohexyl)-3-methyl-8-(6-phenylpyridin-3-yl)-1H-imidazo[4,5-c]quinolin-2(3H)-one;
(R)-3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one;
(S)-3-methyl-8-(6-(1-methyl-1H-pyrazol-4-yl)pyridin-3-yl)-1-(1-(methanesulfonyl)pyrrolidin-3-yl)-1H-imidazo[4,5-c]quinolin-2(3H)-one;
(S)-1-(1-(ethylsulfonyl)pyrrolidin-3-yl)-3-methyl-8-(6-(1-methyl-1H-pyrazol-4-yl)pyridin-3-yl)-1H-imidazo[4,5-c]quinolin-2(3H)-one;
(S)-3-methyl-1-(1-(methanesulfonyl)pyrrolidin-3-yl)-8-(6-phenylpyridin-3-yl)-1H-imidazo[4,5-c]quinolin-2(3H)-one;
(R)-3-methyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one;
1-(3-hydroxycyclohexyl)-3-methyl-8-(6-(1-methyl-1H-pyrazol-4-yl)pyridin-3-yl)-1H-imidazo[4,5-c]quinolin-2(3H)-one;
3-deuteromethyl-8-(6-(1-methyl-1H-pyrazol-4-yl)pyridin-3-yl)-1-(1-(methanesulfonyl)piperidin-3-yl)-1H-imidazo[4,5-c]quinolin-2(3H)-one;
1-(3-hydroxycyclopentyl)-3-methyl-8-(6-(1-methyl-1H-pyrazol-4-yl)pyridin-3-yl)-1H-imidazo[4,5-c]quinolin-2(3H)-one;
(S)-8-(6-(1H-1,2,4-triazol-1-yl)pyridin-3-yl)-3-methyl-1-(1-(methanesulfonyl)pyrrolidin-3-yl)-1H-imidazo[4,5-c]quinolin-2(3H)-one;
(S)-8-(6-(1H-pyrazol-1-yl)pyridin-3-yl)-3-methyl-1-(1-(methanesulfonyl)pyrrolidin-3-yl)-1H-imidazo[4,5-c]quinolin-2(3H)-one;
(S)-3-methyl-8-(6-(1-methyl-1H-1,2,3-triazol-4-yl)pyridin-3-yl)-1-(1-(methanesulfonyl)pyrrolidin-3-yl)-1H-imidazo[4,5-c]quinolin-2(3H)-one;
(S)-8-(6-(1H-1,2,3-triazol-1-yl)pyridin-3-yl)-3-methyl-1-(1-(methanesulfonyl)pyrrolidin-3-yl)-1H-imidazo[4,5-c]quinolin-2(3H)-one;
(S)-3-methyl-8-(6-(1-methyl-1H-pyrazol-3-yl)pyridin-3-yl)-1-(1-(methanesulfonyl)pyrrolidin-3-yl)-1H-imidazo[4,5-c]quinolin-2(3H)-one;
(S)-3-methyl-8-(6-(1-methyl-1H-1,2,4-triazol-3-yl)pyridin-3-yl)-1-(1-(methanesulfonyl)pyrrolidin-3-yl)-1H-imidazo[4,5-c]quinolin-2(3H)-one;
1-((1s,4s)-4-hydroxycyclohexyl)-3-methyl-8-(6-(1-methyl-1H-1,2,3-triazol-4-yl)pyridin-3-yl)-1H-imidazo[4,5-c]quinolin-2(3H)-one;
(R)-1-(1-(ethylsulfonyl)piperidin-3-yl)-3-methyl-8-(6-(1-methyl-1H-pyrazol-4-yl)pyridin-3-yl)-1H-imidazo[4,5-c]quinolin-2(3H)-one;
(R)-1-(1-(cyclopropylsulfonyl)piperidin-3-yl)-3-methyl-8-(6-(1-methyl-1H-pyrazol-4-yl)pyridin-3-yl)-1H-imidazo[4,5-c]quinolin-2(3H)-one;
(R)-3-(3-methyl-8-(6-(1-methyl-1H-pyrazol-4-yl)pyridin-3-yl)-2-oxo-2,3-dihydro-1H-imidazo[4,5-c]quinolin-1-yl)piperidine-1-sulfamide;

(R)-3-methyl-8-(6-(1-methyl-1H-pyrazol-4-yl)pyridin-3-yl)-1-(1-((trifluoromethyl)sulfonyl)piperidin-3-yl)-1H-imidazo[4,5-c]quinolin-2(3H)-one;

1-(4-hydroxy-4-methylcyclohexyl)-3-methyl-8-(6-(1-methyl-1H-pyrazol-4-yl)pyridin-3-yl)-1H-imidazo[4,5-c]quinolin-2(3H)-one;

(R)-3-methyl-8-(6-(1-methyl-1H-1,2,3-triazol-4-yl)pyridin-3-yl)-1-(1-(methanesulfonyl)piperidin-3-yl)-1H-imidazo[4,5-c]quinolin-2(3H)-one;

3-methyl-8-(6-(1-methyl-1H-pyrazol-4-yl)pyridin-3-yl)-1-(1-(methanesulfonyl)piperidin-4-yl)-1H-imidazo[4,5-c]quinolin-2(3H)-one;

3-methyl-8-(6-(1-methyl-1H-1,2,3-triazol-4-yl)pyridin-3-yl)-1-(1-(methanesulfonyl)piperidin-4-yl)-1H-imidazo[4,5-c]quinolin-2(3H)-one;

3-methyl-8-(6-(1-methyl-1H-1,2,3-triazol-4-yl)pyridin-3-yl)-1-(8-(methanesulfonyl)-8-azabicyclo[3.2.1]octan-3-yl)-1H-imidazo[4,5-c]quinolin-2(3H)-one;

3-methyl-8-(6-(1-methyl-1H-pyrazol-4-yl)pyridin-3-yl)-1-(8-(methanesulfonyl)-8-azabicyclo[3.2.1]octan-3-yl)-1H-imidazo[4,5-c]quinolin-2(3H)-one; and 3-methyl-8-(6-(1-methyl-1H-pyrazol-4-yl)pyridin-3-yl)-1-(1-(methanesulfonyl)azetidin-3-yl)-1H-imidazo[4,5-c]quinolin-2(3H)-one, or pharmaceutically acceptable salts, stereoisomers, isotopical labels, solvates, polymorphs or prodrugs thereof.

5. A pharmaceutical composition comprising the compound according to claim 1, or pharmaceutically acceptable salts, stereoisomers, isotopical labels, solvates, polymorphs or prodrugs thereof as well as pharmaceutically acceptable carriers.

6. The compound according to claim 1, wherein Ring A is pyrazolyl.

7. The compound according to claim 6, wherein Ring C is selected from piperidinyl, pyrrolidinyl, and cyclohexyl.

8. The compound according to claim 1, wherein the compound is selected from the group consisting of:

(Example 3)

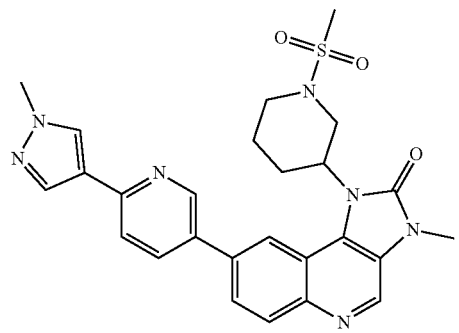

(Exanmple 17)

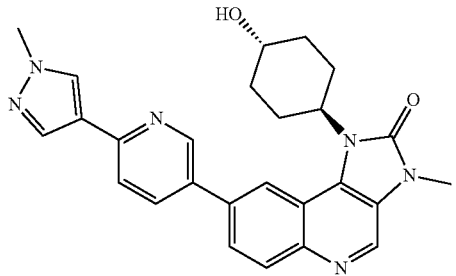

(Example 18)

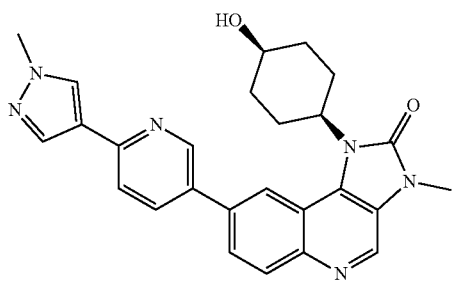

(Example 28)

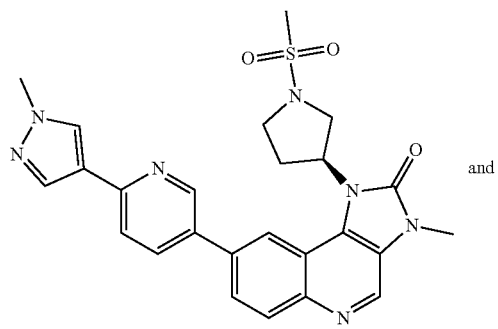

and (Example 31)

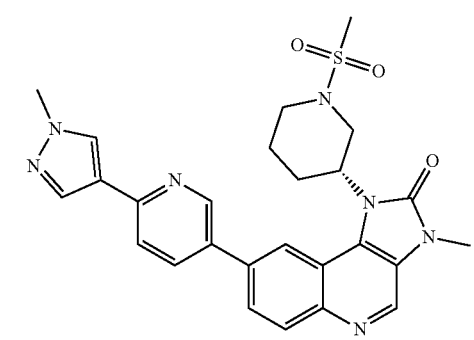

;

or pharmaceutically acceptable salts, stereoisomers, isotopical labels, solvates, polymorphs or prodrugs thereof.

* * * * *